(12) United States Patent
Broughton et al.

(10) Patent No.: US 7,745,438 B2
(45) Date of Patent: Jun. 29, 2010

(54) 3-(2-ACYLAMINO-1-HYDROXYETHYL)-MORPHOLINE DERIVATIVES AND THEIR USE AS BACE INHIBITORS

(75) Inventors: Howard Barff Broughton, Alcobendas (ES); Robert Dean Dally, Zionsville, IN (US); Timothy Barrett Durham, Indianapolis, IN (US); Maria Rosario Gonzalez-Garcia, Alcobendas (ES); Patric James Hahn, Indianapolis, IN (US); Kenneth James Henry, Jr., Carmel, IN (US); Todd Jonathan Kohn, San Mateo, IN (US); James Ray McCarthy, Zionsville, IN (US); Timothy Alan Shepherd, Indianapolis, IN (US); Jon Andre Erickson, Carmel, IN (US); Ana Belen Bueno Melendo, Alcobendas (ES)

(73) Assignee: Eli Lilly and Company, Indianapolis, IN (US)

( * ) Notice: Subject to any disclaimer, the term of this patent is extended or adjusted under 35 U.S.C. 154(b) by 588 days.

(21) Appl. No.: 11/574,989

(22) PCT Filed: Sep. 20, 2005

(86) PCT No.: PCT/US2005/033277

§ 371 (c)(1),
(2), (4) Date: Mar. 9, 2007

(87) PCT Pub. No.: WO2006/034093

PCT Pub. Date: Mar. 30, 2006

(65) Prior Publication Data

US 2007/0225267 A1    Sep. 27, 2007

Related U.S. Application Data

(60) Provisional application No. 60/611,718, filed on Sep. 21, 2004.

(51) Int. Cl.
*C07D 265/32* (2006.01)
*A61K 31/5377* (2006.01)

(52) U.S. Cl. .................................. 514/237.8; 544/168

(58) Field of Classification Search ................ 544/58.1, 544/59, 168, 169
See application file for complete search history.

(56) References Cited

U.S. PATENT DOCUMENTS 7,388,007 B2 *    6/2008    Thompson et al. ....... 514/237.2

FOREIGN PATENT DOCUMENTS

| WO | WO 89/03842 | 5/1989 |
|----|----|----|
| WO | WO03/006021 A1 | 1/2003 |
| WO | WO2004/024081 A2 | 3/2004 |
| WO | WO2004/043916 A1 | 5/2004 |
| WO | WO2005/001450 A1 | 2/2005 |
| WO | WO2005/016876 A2 | 2/2005 |
| WO | WO2005/108358 A2 | 11/2005 |
| WO | WO2005/108391 A1 | 11/2005 |

OTHER PUBLICATIONS

Scholz, Dieter et al., Backbone stabilized peptidomimetics containing statine-like structural elements: diastereospecific synthesis of trisubstituted cyclic ureas and 1,4-diazepan-2-ones, *Monatshefte Fuer Chemie*, 1999, XP002371889, p. 1295, 130(10).

* cited by examiner

*Primary Examiner*—Rebecca L Anderson
*Assistant Examiner*—Matthew P Coughlin
(74) *Attorney, Agent, or Firm*—Robert D. Titus; Elizabeth Dingess-Hammond

(57) ABSTRACT

The present invention provides BACE inhibitors of Formula (I); methods for their use and preparation, and intermediates useful for their preparation.

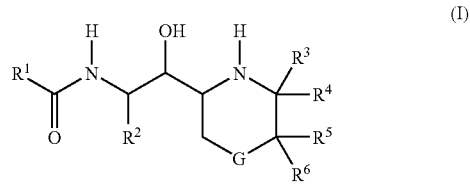

4 Claims, No Drawings

3-(2-ACYLAMINO-1-HYDROXYETHYL)-MORPHOLINE DERIVATIVES AND THEIR USE AS BACE INHIBITORS

This application is a United States national phase entry, pursuant to 35 U.S.C. 371, of PCT/US2005/033277, filed Sep. 20, 2005 which claims the benefit of U.S. provisional patent application Ser. No. 60/611,718, filed Sep. 21, 2004.

Alzheimer's disease, characterized by cognitive and behavioral deterioration in its latter stages, has emerged as a significant social and financial concern. With a prevalence approaching 5.5% in the population above the age of 60, the cost for care of Alzheimer's disease patients has been estimated to be in excess of $100 billion annually. Although cholinesterase inhibitors are somewhat effective in reducing the symptoms of Alzheimer's disease, particularly when the disease is in its early phases, they are not at all effective in slowing or stopping the progression of the disease.

Neurofibrillary tangles and neuritic plaques are generally found in the brain regions associated with memory and cognition, of those afflicted with Alzheimer's disease. These plaques are also found in the brains of individuals with Down's syndrome, Hereditary Cerebral Hemorrhage of the Dutch-Type, and other neurodegenerative disorders. The neuritic plaques are comprised primarily of amyloid β (Aβ) peptide, a neurotoxic and highly aggregatory peptide segment of amyloid precursor protein (APP). Aβ peptide is formed by the proteolytic cleavage of APP by β-secretase (BACE) followed by at least one subsequent C-terminal cleavage by γ-secretase. As such, inhibition of BACE is an attractive target for the treatment or prevention of Alzheimer's disease as well as other diseases characterized pathologically by amyloid plaques.

BACE is a member of the pepsin sub-family of mammalian aspartyl proteases and, like its substrate APP, is a type I transmembrane protein. BACE has been disclosed in the literature and is referred to also as "β-site APP-cleaving enzyme", "membrane aspartic protease of the pepsin family", "Asp-2", "β-secretase", "membrane-bound aspartic protease" and "Memapsin 2" (See: Ghosh, et al., *Current Medicinal Chemistry*, 9(11), 1135-1144 (2002)). Two isoforms of BACE have been identified in humans, designated BACE1 and BACE2. It is believed that the BACE1 inhibitory activity is most important to inhibition of amyloid β (Aβ) peptide (Roggo, *Current Topics in Medicinal Chemistry*, 2, 359-370 (2002)). Currently described BACE inhibitors are peptidomimetic transition state analogs, typically containing a hydroxyethyl moiety. Although many of these compounds are potent inhibitors of BACE, their high molecular weights and low membrane permeability make them poor drug candidates. (See: Park and Lee, *Journal of the American Chemical Society*, 125(52), 16416-16422 (2003)).

Additional compounds described as BACE inhibitors are disclosed in WO 03/040096, WO 04/024081, WO 04/0039034, and WO 04/043916. Additional BACE inhibitors are necessary to provide treatments for A-β peptide mediated disorders such as Alzheimer's disease. The present invention provides new inhibitors of BACE.

The present invention provides compounds of Formula I:

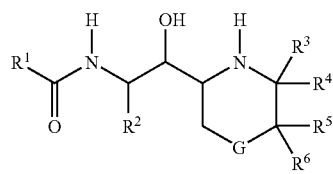

I where:

$R^1$ is $C_1$-$C_{10}$ alkyl optionally substituted with $C_3$-$C_8$ cycloalkyl, phenyl, or furyl; $C_2$-$C_8$ alkenyl optionally substituted with $C_3$-$C_8$ cycloalkyl, phenyl, or furyl; $C_2$-$C_8$ alkynyl optionally substituted with $C_3$-$C_8$ cycloalkyl, phenyl, or furyl; or $C_3$-$C_8$ cycloalkyl; each optionally substituted up to six times with fluoro, or with up to four substituents independently selected from the group consisting of halo, cyano, methyl optionally substituted with up to three fluoro atoms, trifluoromethoxy, $C_1$-$C_6$ alkoxy, $C_3$-$C_7$ cycloalkoxy, oxo, $NR^7R^8$, and $C(O)NR^7R^7$; or $R^1$ is hydrogen; furyl optionally substituted with $C(O)NR^7R^7$ or up to two times with $C_1$-$C_6$ alkyl; thienyl; tetrahydrofuryl; $NR^7R^8$; or $C_1$-$C_6$ alkoxy;

$R^2$ is $C_1$-$C_3$ alkyl optionally substituted with $C_3$-$C_6$ cycloalkyl; benzyl optionally monosubstituted in the phenyl ring with a substituent selected from the group consisting of halo, hydroxy, thiol, benzyloxy, $C_1$-$C_6$ alkyl optionally substituted in the alkyl chain up to three times with fluoro or with $C_3$-$C_6$ cycloalkyl optionally substituted with $C_1$-$C_3$ alkyl, $C_1$-$C_6$ alkoxy optionally substituted in the alkyl chain up to three times with fluoro or with $C_3$-$C_6$ cycloalkyl optionally substituted with $C_1$-$C_3$ alkyl, $C_2$-$C_6$ alkenyloxy, $C_1$-$C_6$ alkylthio optionally substituted in the alkyl chain up to three times with fluoro or with $C_3$-$C_6$ cycloalkyl optionally substituted with $C_1$-$C_3$ alkyl, $C_3$-$C_8$ cycloalkoxy, phenyl optionally substituted with $C_1$-$C_6$ alkyl or $C_1$-$C_6$ alkoxy, and phenylthio; benzyl disubstituted in the phenyl ring with a first substituent selected from the group consisting of halo, trifluoromethoxy, and $C_1$-$C_6$ alkyl optionally substituted in the alkyl chain up to three times with fluoro or with $C_3$-$C_6$ cycloalkyl optionally substituted with $C_1$-$C_3$ alkyl, and a second substituent selected from the group consisting of halo, $C_1$-$C_6$ alkyl optionally substituted in the alkyl chain up to three times with fluoro or with $C_3$-$C_6$ cycloalkyl optionally substituted with $C_1$-$C_3$ alkyl, $C_1$-$C_6$ alkoxy optionally substituted in the alkyl chain up to three times with fluoro or with $C_3$-$C_6$ cycloalkyl optionally substituted with $C_1$-$C_3$ alkyl, $C_2$-$C_6$ alkenyloxy, $C_1$-$C_6$ alkylthio optionally substituted in the alkyl chain up to three times with fluoro or with $C_3$-$C_6$ cycloalkyl optionally substituted with $C_1$-$C_3$ alkyl, $C_3$-$C_8$ cycloalkoxy, phenyl optionally substituted with $C_1$-$C_6$ alkyl or $C_1$-$C_6$ alkoxy, and phenylthio; or benzyl trisubstituted in the phenyl ring with three substituents independently selected from halo or two substituents independently selected from halo and a third substituent selected from $C_1$-$C_6$ alkyl;

$R^3$ is hydrogen or $C_1$-$C_6$ alkyl optionally substituted with $C_3$-$C_8$ cycloalkyl or up to three times with fluoro and $R^4$ is hydrogen or $C_1$-$C_6$ alkyl; or $R^3$ and $R^4$ taken together with the carbon atom to which they are attached form a $C_3$-$C_6$ cycloalkyl ring;

$R^5$ is hydrogen; $R^9$; or —$(CH_2)_{0-2}$—$OR^9$;

$R^6$ is hydrogen or phenyl;

G is O;

$R^7$ is selected independently at each occurrence from the group consisting of hydrogen, $C_1$-$C_6$ alkyl, and phenyl;

$R^8$ is hydrogen; $C_1$-$C_6$ alkyl; phenyl; —$C(O)(C_1$-$C_6$ alkyl); or —$SO_2(C_1$-$C_6$ alkyl);

$R^9$ is hydrogen; $C_1$-$C_{10}$ alkyl optionally substituted with 1-6 fluorine atoms or tri-($C_1$-$C_6$ alkyl)silyl; $C_2$-$C_{10}$ acyl; $C_2$-$C_6$ alkenyl; or —$(CH_2)_{0-4}$—$R^{10}$;

$R^{10}$ is $C_3$-$C_8$ cycloalkyl; $C_3$-$C_8$ cycloalkanonyl; tetrahydrofuryl; tetrahydropyranyl; or phenyl each optionally substituted with one substituent selected from the group consisting of $C_3$-$C_8$ cycloalkyl, phenyl, and benzyl, up to four times with fluoro, or with one or two substitutents independently selected from the group consisting of halo, $C_1$-$C_6$ alkyl optionally substituted up to three times with fluoro, $C_2$-$C_6$ acyl, $C_1$-$C_6$ alkoxy, hydroxy, and trifluoromethoxy; or $R^{10}$ is adamantyl; or a pharmaceutically acceptable salt thereof.

The present invention also provides a method of treating Alzheimer's disease in a mammal comprising administering to a mammal in need of such treatment an effective amount of a compound of Formula I.

The present invention further provides a method of preventing the progression of mild cognitive impairment to Alzheimer's disease in a mammal comprising administering to a mammal in need of such treatment an effective amount of a compound of Formula I.

The present invention also provides a method of inhibiting BACE in a mammal comprising administering to a mammal in need of such treatment an effective amount of a compound of Formula I.

The present invention also provides a method for inhibiting β-secretase mediated cleavage of amyloid precursor protein comprising administering to a mammal in need of such treatment an effective amount of a compound of Formula I.

The present invention further provides a method for the inhibition of production of A-β peptide comprising administering to a mammal in need of such treatment an effective amount of a compound of Formula I.

The present invention also provides a pharmaceutical formulation comprising a compound of Formula I, in combination with a pharmaceutically acceptable carrier, diluent, or excipient.

Another embodiment of the present invention is a compound of Formula I for use as a pharmaceutical. Furthermore, this invention provides the use of a compound of Formula I for the manufacture of a medicament for the treatment of Alzheimer's disease. This invention also provides the use of a compound of Formula I for the manufacture of a medicament for the prevention of the progression of mild cognitive impairment to Alzheimer's disease. The invention also provides the use of a compound of Formula I for the manufacture of a medicament for the inhibition of BACE. The present invention also provides the use of a compound of Formula I for the manufacture of a medicament for the inhibition of β-secretase mediated cleavage of amyloid precursor protein. The invention further provides the use of a compound of Formula I for the manufacture of a medicament for the inhibition of production of A-β peptide.

Additionally, this invention provides a pharmaceutical formulation adapted for the treatment of Alzheimer's disease. Furthermore, this invention provides a pharmaceutical formulation adapted for the prevention of the progression of mild cognitive impairment to Alzheimer's disease. This invention also provides a pharmaceutical formulation adapted for the inhibition of BACE.

Furthermore the present invention provides a pharmaceutical formulation adapted for the inhibition of β-secretase mediated cleavage of amyloid precursor protein. The present invention also provides a pharmaceutical formulation adapted for the treatment of conditions resulting from excessive levels of A-β peptide comprising a compound of Formula I or a pharmaceutically acceptable salt thereof in combination with one or more pharmaceutically acceptable excipients, carriers, or diluents.

This invention also provides intermediates of Formula II:

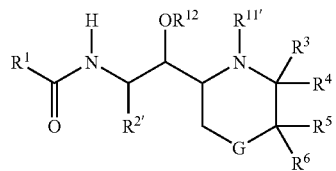

II where:

$R^1$ is $C_1$-$C_{10}$ alkyl optionally substituted with $C_3$-$C_8$ cycloalkyl, phenyl, or furyl; $C_2$-$C_8$ alkenyl optionally substituted with $C_3$-$C_8$ cycloalkyl, phenyl, or furyl; $C_2$-$C_8$ alkynyl optionally substituted with $C_3$-$C_8$ cycloalkyl, phenyl, or furyl; or $C_3$-$C_8$ cycloalkyl; each optionally substituted up to six times with fluoro, or with up to four substituents independently selected from the group consisting of halo, cyano, methyl optionally substituted with up to three fluoro atoms, trifluoromethoxy, $C_1$-$C_6$ alkoxy, $C_3$-$C_7$ cycloalkoxy, oxo, $NR^7R^8$, and $C(O)NR^7R^7$; or $R^1$ is hydrogen; furyl optionally substituted with $C(O)NR^7R^7$ or up to two times with $C_1$-$C_6$ alkyl; thienyl; tetrahydrofuryl; $NR^7R^8$; or $C_1$-$C_6$ alkoxy;

$R^{2'}$ is $C_1$-$C_3$ alkyl optionally substituted with $C_3$-$C_6$ cycloalkyl; benzyl optionally monosubstituted in the phenyl ring with a substituent selected from the group consisting of halo, —$OR^{12}$, thiol, $C_1$-$C_6$ alkyl optionally substituted in the alkyl chain up to three times with fluoro or with $C_3$-$C_6$ cycloalkyl optionally substituted with $C_1$-$C_3$ alkyl, $C_1$-$C_6$ alkoxy optionally substituted in the alkyl chain up to three times with fluoro or with $C_3$-$C_6$ cycloalkyl optionally substituted with $C_1$-$C_3$ alkyl, $C_2$-$C_6$ alkenyloxy, $C_1$-$C_6$ alkylthio optionally substituted in the alkyl chain up to three times with fluoro or with $C_3$-$C_6$ cycloalkyl optionally substituted with $C_1$-$C_3$ alkyl, $C_3$-$C_8$ cycloalkoxy, phenyl optionally substituted with $C_1$-$C_6$ alkyl or $C_1$-$C_6$ alkoxy, and phenylthio; benzyl disubstituted in the phenyl ring with a first substituent selected from the group consisting of halo, trifluoromethoxy, and $C_1$-$C_6$ alkyl optionally substituted in the alkyl chain up to three times with fluoro or with $C_3$-$C_6$ cycloalkyl optionally substituted with $C_1$-$C_3$ alkyl, and a second substituent selected from the group consisting of halo, —$OR^{12}$, thiol, $C_1$-$C_6$ alkyl optionally substituted in the alkyl chain up to three times with fluoro or with $C_3$-$C_6$ cycloalkyl optionally substituted with $C_1$-$C_3$ alkyl, $C_1$-$C_6$ alkoxy optionally substituted in the alkyl chain up to three times with fluoro or with $C_3$-$C_6$ cycloalkyl optionally substituted with $C_1$-$C_3$ alkyl, $C_2$-$C_6$ alkenyloxy, $C_1$-$C_6$ alkylthio optionally substituted in the alkyl chain up to three times with fluoro or with $C_3$-$C_6$ cycloalkyl optionally substituted with $C_1$-$C_3$ alkyl $C_3$-$C_8$ cycloalkoxy, phenyl optionally substituted with $C_1$-$C_6$ alkyl or $C_1$-$C_6$ alkoxy, and phenylthio; or benzyl trisubstituted in the phenyl ring with three substituents independently selected from halo or two substituents independently selected from halo and a third substituent selected from $C_1$-$C_6$ alkyl;

$R^3$ is hydrogen or $C_1$-$C_6$ alkyl optionally substituted with $C_3$-$C_8$ cycloalkyl or up to three times with fluoro and $R^4$ is hydrogen or $C_1$-$C_6$ alkyl; or $R^3$ and $R^4$ taken together with the carbon atom to which they are attached form a $C_3$-$C_6$ cycloalkyl ring;

$R^5$ is $R^9$; or —$(CH_2)_{0-2}$—$OR^9$;

$R^6$ is hydrogen or phenyl;

G is O;

$R^7$ is selected independently at each occurrence from the group consisting of hydrogen, $C_1$-$C_6$ alkyl, and phenyl;

$R^8$ is hydrogen; $C_1$-$C_6$ alkyl; phenyl; —$C(O)(C_1$-$C_6$ alkyl); or —$SO_2(C_1$-$C_6$ alkyl);

$R^9$ is hydrogen; $C_1$-$C_{10}$ alkyl optionally substituted with 1-6 fluorine atoms or tri-($C_1$-$C_6$ alkyl)silyl; $C_2$-$C_{10}$ acyl; $C_2$-$C_6$ alkenyl; or —$(CH_2)_{0-4}$—$R^{11}$;

$R^{10}$ is $C_3$-$C_8$ cycloalkyl; $C_3$-$C_8$ cycloalkanonyl; tetrahydrofuryl; tetrahydropyranyl; or phenyl each optionally substituted with one substitutent selected from the group consisting of $C_3$-$C_8$ cycloalkyl, phenyl, and benzyl, up to four times with fluoro, or with one or two substitutents independently selected from the group consisting of halo, $C_1$-$C_6$ alkyl optionally substituted up to three times with fluoro, $C_2$-$C_6$ acyl, $C_1$-$C_6$ alkoxy, hydroxy, and trifluoromethoxy; or $R^{10}$ is adamantyl;

$R^{11'}$ hydrogen or a nitrogen protecting group;

$R^{12}$ is hydrogen or an oxygen protecting group; or an acid addition salt thereof provided that at least one of $R^{11'}$ and $R^{12}$ is other than hydrogen.

Additionally, the present invention provides intermediates of Formula III:

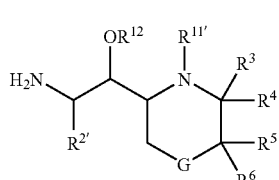

III where:

$R^{2'}$ is $C_1$-$C_3$ alkyl optionally substituted with $C_3$-$C_6$ cycloalkyl; benzyl optionally monosubstituted in the phenyl ring with a substituent selected from the group consisting of halo, —$OR^{12}$, thiol, $C_1$-$C_6$ alkyl optionally substituted in the alkyl chain up to three times with fluoro or with $C_3$-$C_6$ cycloalkyl optionally substituted with $C_1$-$C_3$ alkyl, $C_1$-$C_6$ alkoxy optionally substituted in the alkyl chain up to three times with fluoro or with $C_3$-$C_6$ cycloalkyl optionally substituted with $C_1$-$C_3$ alkyl, $C_2$-$C_6$ alkenyloxy, $C_1$-$C_6$ alkylthio optionally substituted in the alkyl chain up to three times with fluoro or with $C_3$-$C_6$ cycloalkyl optionally substituted with $C_1$-$C_3$ alkyl, $C_3$-$C_8$ cycloalkoxy, phenyl optionally substituted with $C_1$-$C_6$ alkyl or $C_1$-$C_6$ alkoxy, and phenylthio; benzyl disubstituted in the phenyl ring with a first substituent selected from the group consisting of halo, trifluoromethoxy, and $C_1$-$C_6$ alkyl optionally substituted in the alkyl chain up to three times with fluoro or with $C_3$-$C_6$ cycloalkyl optionally substituted with $C_1$-$C_3$ alkyl, and a second substituent selected from the group consisting of halo, —$OR^{12}$, thiol, $C_1$-$C_6$ alkyl optionally substituted in the alkyl chain up to three times with fluoro or with $C_3$-$C_6$ cycloalkyl optionally substituted with $C_1$-$C_3$ alkyl, $C_1$-$C_6$ alkoxy optionally substituted in the alkyl chain up to three times with fluoro or with $C_3$-$C_6$ cycloalkyl optionally substituted with $C_1$-$C_3$ alkyl, $C_2$-$C_6$ alkenyloxy, $C_1$-$C_6$ alkylthio optionally substituted in the alkyl chain up to three times with fluoro or with $C_3$-$C_6$ cycloalkyl optionally substituted with $C_1$-$C_3$ alkyl $C_3$-$C_8$ cycloalkoxy, phenyl optionally substituted with $C_1$-$C_6$ alkyl or $C_1$-$C_6$ alkoxy, and phenylthio; or benzyl trisubstituted in the phenyl ring with three substituents independently selected from halo or two substituents independently selected from halo and a third substituent selected from $C_1$-$C_6$ alkyl;

$R^3$ is hydrogen or $C_1$-$C_6$ alkyl optionally substituted with $C_3$-$C_8$ cycloalkyl or up to three times with fluoro and $R^4$ is hydrogen or $C_1$-$C_6$ alkyl; or $R^3$ and $R^4$ taken together with the carbon atom to which they are attached form a $C_3$-$C_6$ cycloalkyl ring;

$R^5$ is $R^9$; or —$(CH_2)_{0-2}$—$OR^9$;

$R^6$ is hydrogen or phenyl;

G is O;

$R^9$ is hydrogen; $C_1$-$C_{10}$ alkyl optionally substituted with 1-6 fluorine atoms or tri-($C_1$-$C_6$ alkyl)silyl; $C_1$-$C_{10}$ acyl; $C_2$-$C_6$ alkenyl; or —$(CH_2)_{0-4}$—$R^{10}$;

$R^{10}$ is $C_3$-$C_8$ cycloalkyl; $C_3$-$C_8$ cycloalkanonyl; tetrahydrofuryl; tetrahydropyranyl; or phenyl each optionally substituted with one substitutent selected from the group consisting of $C_3$-$C_8$ cycloalkyl, phenyl, and benzyl, up to four times with fluoro, or one or two substitutents independently selected from the group consisting of halo, $C_1$-$C_6$ alkyl optionally substituted up to three times with fluoro, $C_2$-$C_6$ acyl, $C_1$-$C_6$ alkoxy, hydroxy, and trifluoromethoxy; or $R^{10}$ is adamantyl;

$R^{11'}$ is hydrogen or a nitrogen protecting group;

$R^{12}$ is hydrogen or an oxygen protecting group; or an acid addition salt thereof.

The present invention also provides intermediates of Formula IV:

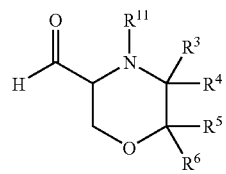

IV where:

$R^3$ is hydrogen or $C_1$-$C_6$ alkyl optionally substituted with $C_3$-$C_8$ cycloalkyl or up to three times with fluoro and $R^4$ is hydrogen or $C_1$-$C_6$ alkyl; or $R^3$ and $R^4$ taken together with the carbon atom to which they are attached form a $C_3$-$C_6$ cycloalkyl ring;

$R^5$ is $R^9$; or —$(CH_2)_{0-2}$—$OR^9$;

$R^6$ is hydrogen or phenyl;

$R^9$ is hydrogen; $C_1$-$C_{10}$ alkyl optionally substituted with 1-6 fluorine atoms or tri-($C_1$-$C_6$ alkyl)silyl; $C_1$-$C_{10}$ acyl; $C_2$-$C_6$ alkenyl; or —$(CH_2)_{0-4}$—$R^{11}$;

$R^{10}$ is $C_3$-$C_8$ cycloalkyl; $C_3$-$C_8$ cycloalkanonyl; tetrahydrofuryl; tetrahydropyranyl; or phenyl each optionally substituted with one substitutent selected from the group consisting of $C_3$-$C_8$ cycloalkyl, phenyl, and benzyl, up to four times with fluoro, or one or two substitutents independently selected from the group consisting of halo, $C_1$-$C_6$ alkyl optionally substituted up to three times with fluoro, $C_2$-$C_6$ acyl, $C_1$-$C_6$ alkoxy, hydroxy, and trifluoromethoxy; or $R^{10}$ is adamantyl;

$R^{11}$ is a nitrogen protecting group; provided that at least one of $R^3$, $R^4$, $R^5$, and $R^6$ are other than hydrogen.

Additionally, the present invention provides intermediates of Formula V:

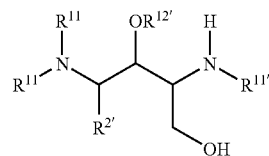

V where:

$R^{2'}$ is $C_1$-$C_3$ alkyl optionally substituted with $C_3$-$C_6$ cycloalkyl; benzyl optionally monosubstituted in the phenyl ring with a substituent selected from the group consisting of halo, —$OR^{12}$, thiol, $C_1$-$C_6$ alkyl optionally substituted in the alkyl chain up to three times with fluoro or with $C_3$-$C_6$ cycloalkyl optionally substituted with $C_1$-$C_3$ alkyl, $C_1$-$C_6$ alkoxy optionally substituted in the alkyl chain up to three times with fluoro or with $C_3$-$C_6$ cycloalkyl optionally substituted with $C_1$-$C_3$ alkyl, $C_2$-$C_6$ alkenyloxy, $C_1$-$C_6$ alkylthio optionally substituted in the alkyl chain up to three times with fluoro or with $C_3$-$C_6$ cycloalkyl optionally substituted with $C_1$-$C_3$ alkyl, $C_3$-$C_8$ cycloalkoxy, phenyl optionally substituted with $C_1$-$C_6$ alkyl or $C_1$-$C_6$ alkoxy, and phenylthio; benzyl disubstituted in the phenyl ring with a first substituent selected from the group consisting of halo, trifluoromethoxy, and $C_1$-$C_6$ alkyl optionally substituted in the alkyl chain up to three times with fluoro or with $C_3$-$C_6$ cycloalkyl optionally substituted with $C_1$-$C_3$ alkyl, and a second substituent selected from the group consisting of halo, —$OR^{12}$, thiol, $C_1$-$C_6$ alkyl optionally substituted in the alkyl chain up to three times with fluoro or with $C_3$-$C_6$ cycloalkyl optionally substituted with $C_1$-$C_3$ alkyl, $C_1$-$C_6$ alkoxy optionally substituted in the alkyl chain up to three times with fluoro or with $C_3$-$C_6$ cycloalkyl optionally substituted with $C_1$-$C_3$ alkyl, $C_2$-$C_6$ alkenyloxy, $C_1$-$C_6$ alkylthio optionally substituted in the alkyl chain up to three times with fluoro or with $C_3$-$C_6$ cycloalkyl optionally substituted with $C_1$-$C_3$ alkyl $C_3$-$C_8$ cycloalkoxy, phenyl optionally substituted with $C_1$-$C_6$ alkyl or $C_1$-$C_6$ alkoxy, and phenylthio; or benzyl trisubstituted in the phenyl ring with three substituents independently selected from halo or two substituents independently selected from halo and a third substituent selected from $C_1$-$C_6$ alkyl;

$R^{11}$ is independently at each instance a nitrogen protecting group;

$R^{11'}$ is hydrogen or a nitrogen protecting group;

$R^{12}$ is hydrogen or an oxygen protecting group;

$R^{12'}$ is an oxygen protecting group; or an acid addition salt thereof.

Furthermore, the present invention provides intermediates of Formula VI:

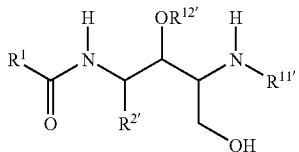

VI where:

$R^1$ is $C_1$-$C_{10}$ allyl optionally substituted with $C_3$-$C_8$ cycloalkyl, phenyl, or furyl; $C_2$-$C_8$ alkenyl optionally substituted with $C_3$-$C_8$ cycloalkyl, phenyl, or furyl; $C_2$-$C_8$ alkynyl optionally substituted with $C_3$-$C_8$ cycloalkyl, phenyl, or furyl; or $C_3$-$C_8$ cycloalkyl; each optionally substituted up to six times with fluoro, or with up to four substituents independently selected from the group consisting of halo, cyano, methyl optionally substituted with up to three fluoro atoms, trifluoromethoxy, $C_1$-$C_6$ alkoxy, $C_3$-$C_7$ cycloalkoxy, oxo, $NR^7R^8$, and $C(O)NR^7R^7$; or $R^1$ is hydrogen; furyl optionally substituted with $C(O)NR^7R^7$ or up to two times with $C_1$-$C_6$ alkyl; thienyl; tetrahydrofuryl; $NR^7R^8$; or $C_1$-$C_6$ alkoxy;

$R^{2'}$ is $C_1$-$C_3$ alkyl optionally substituted with $C_3$-$C_6$ cycloalkyl; benzyl optionally monosubstituted in the phenyl ring with a substituent selected from the group consisting of halo, —$OR^{12}$, thiol, $C_1$-$C_6$ alkyl optionally substituted in the alkyl chain up to three times with fluoro or with $C_3$-$C_6$ cycloalkyl optionally substituted with $C_1$-$C_3$ alkyl, $C_1$-$C_6$ alkoxy optionally substituted in the alkyl chain up to three times with fluoro or with $C_3$-$C_6$ cycloalkyl optionally substituted with $C_1$-$C_3$ alkyl, $C_2$-$C_6$ alkenyloxy, $C_1$-$C_6$ alkylthio optionally substituted in the alkyl chain up to three times with fluoro or with $C_3$-$C_6$ cycloalkyl optionally substituted with $C_1$-$C_3$ alkyl, $C_3$-$C_8$ cycloalkoxy, phenyl optionally substituted with $C_1$-$C_6$ alkyl or $C_1$-$C_6$ alkoxy, and phenylthio; benzyl disubstituted in the phenyl ring with a first substituent selected from the group consisting of halo, trifluoromethoxy, and $C_1$-$C_6$ alkyl optionally substituted in the alkyl chain up to three times with fluoro or with $C_3$-$C_6$ cycloalkyl optionally substituted with $C_1$-$C_3$ alkyl, and a second substituent selected from the group consisting of halo, —$OR^{12}$, thiol, $C_1$-$C_6$ alkyl optionally substituted in the alkyl chain up to three times with fluoro or with $C_3$-$C_6$ cycloalkyl optionally substituted with $C_1$-$C_3$ alkyl, $C_1$-$C_6$ alkoxy optionally substituted in the alkyl chain up to three times with fluoro or with $C_3$-$C_6$ cycloalkyl optionally substituted with $C_1$-$C_3$ alkyl, $C_2$-$C_6$ alkenyloxy, $C_1$-$C_6$ alkylthio optionally substituted in the alkyl chain up to three times with fluoro or with $C_3$-$C_6$ cycloalkyl optionally substituted with $C_1$-$C_3$ alkyl $C_3$-$C_8$ cycloalkoxy, phenyl optionally substituted with $C_1$-$C_6$ alkyl or $C_1$-$C_6$ alkoxy, and phenylthio; or benzyl trisubstituted in the phenyl ring with three substituents independently selected from halo or two substituents independently selected from halo and a third substituent selected from $C_1$-$C_6$ alkyl;

$R^7$ is selected independently at each occurrence from the group consisting of hydrogen; $C_1$-$C_6$ alkyl; and phenyl;

$R^8$ is hydrogen; $C_1$-$C_6$ alkyl; phenyl; —$C(O)(C_1$-$C_6$ alkyl); or —$SO_2(C_1$-$C_6$ alkyl);

$R^{11'}$ is hydrogen or a nitrogen protecting group;

$R^{12}$ is hydrogen or an oxygen protecting group;

$R^{12'}$ is an oxygen protecting group; or an acid addition salt thereof.

Additionally, the present invention provides intermediates of Formula VII:

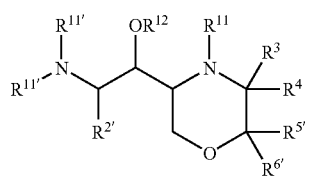

VII where:

$R^{2'}$ is $C_1$-$C_3$ alkyl optionally substituted with $C_3$-$C_6$ cycloalkyl; benzyl optionally monosubstituted in the phenyl ring with a substituent selected from the group consisting of halo, —$OR^{12}$, thiol, $C_1$-$C_6$ alkyl optionally substituted in the alkyl chain up to three times with fluoro or with $C_3$-$C_6$ cycloalkyl optionally substituted with $C_1$-$C_3$ alkyl, $C_1$-$C_6$ alkoxy optionally substituted in the alkyl chain up to three times with fluoro or with $C_3$-$C_6$ cycloalkyl optionally substituted with $C_1$-$C_3$ allyl, $C_2$-$C_6$ alkenyloxy, $C_1$-$C_6$ alkylthio optionally substituted in the alkyl chain up to three times with fluoro or with $C_3$-$C_6$ cycloalkyl optionally substituted with $C_1$-$C_3$ alkyl, $C_3$-$C_8$ cycloalkoxy, phenyl optionally substituted with $C_1$-$C_6$ alkyl or $C_1$-$C_6$ alkoxy, and phenylthio; benzyl disubstituted in the phenyl ring with a first substituent selected from the group consisting of halo, trifluoromethoxy, and $C_1$-$C_6$ alkyl optionally substituted in the alkyl chain up to three times with fluoro or with $C_3$-$C_6$ cycloalkyl optionally substituted with $C_1$-$C_3$ alkyl, and a second substituent selected from the group consisting of halo, —$OR^{12}$, thiol, $C_1$-$C_6$ alkyl optionally substituted in the alkyl chain up to three times with fluoro or with $C_3$-$C_6$ cycloalkyl optionally substituted with $C_1$-$C_3$ alkyl, $C_1$-$C_6$ alkoxy optionally substituted in the alkyl chain up to three times with fluoro or with $C_3$-$C_6$ cycloalkyl optionally substituted with $C_1$-$C_3$ alkyl, $C_2$-$C_6$ alkenyloxy, $C_1$-$C_6$ alkylthio optionally substituted in the alkyl chain up to three times with fluoro or with $C_3$-$C_6$ cycloalkyl optionally substituted with $C_1$-$C_3$ alkyl $C_3$-$C_8$ cycloalkoxy, phenyl optionally substituted with $C_1$-$C_6$ alkyl or $C_1$-$C_6$ alkoxy, and phenylthio; or benzyl trisubstituted in the phenyl ring with three substituents independently selected from halo or two substituents independently selected from halo and a third substituent selected from $C_1$-$C_6$ alkyl;

$R^3$ is hydrogen or $C_1$-$C_6$ alkyl optionally substituted with $C_3$-$C_8$ cycloalkyl or up to three times with fluoro and $R^4$ is hydrogen or $C_1$-$C_6$ alkyl; or $R^3$ and $R^4$ taken together with the carbon atom to which they are attached form a $C_3$-$C_6$ cycloalkyl ring;

$R^{5'}$ is hydroxy and $R^{6'}$ is hydrogen or $R^{5'}$ and $R^{6'}$ together with the carbon to which they are attached form a carbonyl moiety;

$R^{11}$ is a nitrogen protecting group;

$R^{11'}$ is hydrogen or a nitrogen protecting group;

$R^{12}$ is hydrogen or an oxygen protecting group; or an acid addition salt thereof.

The present invention further provides a process for the preparation of a compound of Formula I:

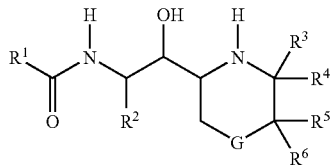

I where:

$R^1$ is hydrogen; $C_1$-$C_{10}$ alkyl optionally substituted with $C_3$-$C_8$ cycloalkyl, phenyl, or furyl; $C_2$-$C_8$ alkenyl optionally substituted with $C_3$-$C_8$ cycloalkyl, phenyl, or furyl; $C_2$-$C_8$ alkynyl optionally substituted with $C_3$-$C_8$ cycloalkyl, phenyl, or furyl; or $C_3$-$C_8$ cycloalkyl; each optionally substituted up to six times with fluoro, or with up to four substituents independently selected from the group consisting of halo, cyano, methyl optionally substituted with up to three fluoro atoms, trifluoromethoxy, $C_1$-$C_6$ alkoxy, $C_3$-$C_7$ cycloalkoxy, oxo, $NR^7R^8$, and $C(O)NR^7R^7$; or $R^1$ is hydrogen; furyl optionally substituted with $C(O)NR^7R^7$ or up to two times with $C_1$-$C_6$ alkyl; thienyl; tetrahydrofuryl; $NR^7R^8$; or $C_1$-$C_6$ alkoxy;

$R^2$ is $C_1$-$C_3$ alkyl optionally substituted with $C_3$-$C_6$ cycloalkyl; benzyl optionally monosubstituted in the phenyl ring with a substituent selected from the group consisting of halo, hydroxy, thiol, benzyloxy, $C_1$-$C_6$ alkyl optionally substituted in the alkyl chain up to three times with fluoro or with $C_3$-$C_6$ cycloalkyl optionally substituted with $C_1$-$C_3$ alkyl, $C_1$-$C_6$ alkoxy optionally substituted in the alkyl chain up to three times with fluoro or with $C_3$-$C_6$ cycloalkyl optionally substituted with $C_1$-$C_3$ alkyl, $C_2$-$C_6$ alkenyloxy, $C_1$-$C_6$ alkylthio optionally substituted in the alkyl chain up to three times with fluoro or with $C_3$-$C_6$ cycloalkyl optionally substituted with $C_1$-$C_3$ alkyl, $C_3$-$C_8$ cycloalkoxy, phenyl optionally substituted with $C_1$-$C_6$ alkyl or $C_1$-$C_6$ alkoxy, and phenylthio; benzyl disubstituted in the phenyl ring with a first substituent selected from the group consisting of halo, trifluoromethoxy, and $C_1$-$C_6$ alkyl optionally substituted in the alkyl chain up to three times with fluoro or with $C_3$-$C_6$ cycloalkyl optionally substituted with $C_1$-$C_3$ alkyl, and a second substituent selected from the group consisting of halo, $C_1$-$C_6$ alkyl optionally substituted in the alkyl chain up to three times with fluoro or with $C_3$-$C_6$ cycloalkyl optionally substituted in the alkyl $C_1$-$C_3$ alkyl, $C_1$-$C_6$ alkoxy optionally substituted in the alkyl chain up to three times with fluoro or with $C_3$-$C_6$ cycloalkyl optionally substituted with $C_1$-$C_3$ alkyl, $C_2$-$C_6$ alkenyloxy, $C_1$-$C_6$ alkylthio optionally substituted in the alkyl chain up to three times with fluoro or with $C_3$-$C_6$ cycloalkyl optionally substituted with $C_1$-$C_3$ alkyl, $C_3$-$C_8$ cycloalkoxy, phenyl optionally substituted with $C_1$-$C_6$ alkyl or $C_1$-$C_6$ alkoxy, and phenylthio; or benzyl trisubstituted in the phenyl ring with three substituents independently selected from halo or two substituents independently selected from halo and a third substituent selected from $C_1$-$C_6$ alkyl;

$R^3$ is hydrogen or $C_1$-$C_6$ alkyl optionally substituted with $C_3$-$C_8$ cycloalkyl or up to three times with fluoro and $R^4$ is hydrogen or $C_1$-$C_6$ alkyl; or $R^3$ and $R^4$ taken together with the carbon atom to which they are attached form a $C_3$-$C_6$ cycloalkyl ring;

$R^5$ is hydrogen; $R^9$; or —$(CH_2)_{0-2}$—$OR^9$;

$R^6$ is hydrogen or phenyl;

G is O;

$R^7$ is selected independently at each occurrence from the group consisting of hydrogen, $C_1$-$C_6$ alkyl, and phenyl;

$R^8$ is hydrogen; $C_1$-$C_6$ alkyl; phenyl; —$C(O)(C_1$-$C_6$ alkyl); or —$SO_2(C_1$-$C_6$ alkyl);

$R^9$ is hydrogen; $C_1$-$C_1$ alkyl optionally substituted with 1-6 fluorine atoms or tri-($C_1$-$C_6$ alkyl)silyl; $C_2$-$C_{10}$ acyl; $C_2$-$C_6$ alkenyl; or —$(CH_2)_{0-4}$—$R^{10}$;

$R^{10}$ is $C_3$-$C_8$ cycloalkyl; $C_3$-$C_8$ cycloalkanonyl; tetrahydrofuryl; tetrahydropyranyl; or phenyl each optionally substituted with one substituent selected from the group consisting of $C_3$-$C_8$ cycloalkyl, phenyl, and benzyl, up to four times with fluoro, or with one or two substitutents independently selected from the group consisting of halo, $C_1$-$C_6$ alkyl optionally substituted up to three times with fluoro, $C_2$-$C_6$ acyl, $C_1$-$C_6$ alkoxy, hydroxy, and trifluoromethoxy; or $R^{10}$ is adamantyl; or a pharmaceutically acceptable salt thereof comprising the steps of:

a) deprotecting a compound of Formula II(a):

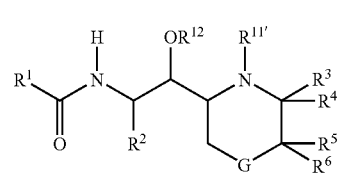

II(a)

where:

$R^1$ is $C_1$-$C_{10}$ alkyl optionally substituted with $C_3$-$C_8$ cycloalkyl, phenyl, or furyl; $C_2$-$C_8$ alkenyl optionally substituted with $C_3$-$C_8$ cycloalkyl, phenyl, or furyl; $C_2$-$C_8$ alkynyl optionally substituted with $C_3$-$C_8$ cycloalkyl, phenyl, or furyl; or $C_3$-$C_8$ cycloalkyl; each optionally substituted up to six times with fluoro, or with up to four substituents independently selected from the group consisting of halo, cyano, methyl optionally substituted with up to three fluoro atoms, trifluoromethoxy, $C_1$-$C_6$ alkoxy, $C_3$-$C_7$ cycloalkoxy, oxo, $NR^7R^8$, and $C(O)NR^7R^7$; or $R^1$ is hydrogen; furyl optionally substituted with $C(O)NR^7R^7$ or up to two times with $C_1$-$C_6$ alkyl; thienyl; tetrahydrofuryl; $NR^7R^8$; or $C_1$-$C_6$ alkoxy;

$R^1$ is $C_1$-$C_3$ alkyl optionally substituted with $C_3$-$C_6$ cycloalkyl; benzyl optionally monosubstituted in the phenyl ring with a substituent selected from the group consisting of halo, hydroxy, thiol, benzyloxy, $C_1$-$C_6$ alkyl optionally substituted in the alkyl chain up to three times with fluoro or with $C_3$-$C_6$ cycloalkyl optionally substituted with $C_1$-$C_3$ alkyl, $C_1$-$C_6$ alkoxy optionally substituted in the alkyl chain up to three times with fluoro or with $C_3$-$C_6$ cycloalkyl optionally substituted with $C_1$-$C_3$ alkyl, $C_2$-$C_6$ alkenyloxy, $C_1$-$C_6$ alkylthio optionally substituted in the alkyl chain up to three times with fluoro or with $C_3$-$C_6$ cycloalkyl optionally substituted with $C_1$-$C_3$ alkyl, $C_3$-$C_8$ cycloalkoxy, phenyl optionally substituted with $C_1$-$C_6$ alkyl or $C_1$-$C_6$ alkoxy, and phenylthio; benzyl disubstituted in the phenyl ring with a first substituent selected from the group consisting of halo, trifluoromethoxy, and $C_1$-$C_6$ alkyl optionally substituted in the alkyl chain up to three times with fluoro or with $C_3$-$C_6$ cycloalkyl optionally substituted with $C_1$-$C_3$ alkyl, and a second substituent selected from the group consisting of halo, $C_1$-$C_6$ alkyl optionally substituted in the alkyl chain up to three times with fluoro or with $C_3$-$C_6$ cycloalkyl optionally substituted with $C_1$-$C_3$ alkyl, $C_1$-$C_6$ alkoxy optionally substituted in the alkyl chain up to three times with fluoro or with $C_3$-$C_6$ cycloalkyl optionally substituted with $C_1$-$C_3$ alkyl, $C_2$-$C_6$ alkenyloxy, $C_1$-$C_6$ alkylthio optionally substituted in the alkyl chain up to three times with fluoro or with $C_3$-$C_6$ cycloalkyl optionally substituted with $C_1$-$C_3$ alkyl, $C_3$-$C_8$ cycloalkoxy, phenyl optionally substituted with $C_1$-$C_6$ alkyl or $C_1$-$C_6$ alkoxy, and phenylthio; or benzyl trisubstituted in the phenyl ring with three substituents independently selected from halo or two substituents independently selected from halo and a third substituent selected from $C_1$-$C_6$ alkyl;

$R^3$ is hydrogen or $C_1$-$C_6$ alkyl optionally substituted with $C_3$-$C_8$ cycloalkyl or up to three times with fluoro and $R^4$ is hydrogen or $C_1$-$C_6$ alkyl; or $R^3$ and $R^4$ taken together with the carbon atom to which they are attached form a $C_3$-$C_6$ cycloalkyl ring;

$R^5$ is $R^9$; or —$(CH_2)_{0-2}$—$OR^9$;

$R^6$ is hydrogen or phenyl;

G is O;

$R^7$ is selected independently at each occurrence from the group consisting of hydrogen, $C_1$-$C_6$ alkyl, and phenyl;

$R^8$ is hydrogen; $C_1$-$C_6$ alkyl; phenyl; —C(O)($C_1$-$C_6$ alkyl); or —$SO_2$($C_1$-$C_6$ alkyl);

$R^9$ is hydrogen; $C_1$-$C_{10}$ alkyl optionally substituted with 1-6 fluorine atoms or tri-($C_1$-$C_6$ alkyl)silyl; $C_2$-$C_{10}$ acyl; $C_2$-$C_6$ alkenyl; or —$(CH_2)_{0-4}$—$R^{10}$;

$R^{10}$ is $C_3$-$C_8$ cycloalkyl; $C_3$-$C_8$ cycloalkanonyl; tetrahydrofuryl; tetrahydropyranyl; or phenyl each optionally substituted with one substituent selected from the group consisting of $C_3$-$C_8$ cycloalkyl, phenyl, and benzyl, up to four times with fluoro, or with one or two substitutents independently selected from the group consisting of halo, $C_1$-$C_6$ alkyl optionally substituted up to three times with fluoro, $C_2$-$C_6$ acyl, $C_1$-$C_6$ alkoxy, hydroxy, and trifluoromethoxy; or $R^{10}$ is adamantyl;

$R^{11'}$ hydrogen or a nitrogen protecting group;

$R^{12}$ is hydrogen or an oxygen protecting group; or an acid addition salt thereof provided that at least one of $R^{11'}$ and $R^{12}$ is other than hydrogen; and b) optionally treating the compound of Formula I with a pharmaceutically acceptable acid to form the corresponding pharmaceutically acceptable salt.

The general chemical terms used in the formulae above have their usual meanings. For example, the term "$C_1$-$C_3$ alkyl" includes methyl, ethyl, propyl, and isopropyl, and the terms "$C_1$-$C_8$ alkyl" and "$C_1$-$C_{10}$ alkyl" include methyl, ethyl, propyl, isopropyl, butyl, isobutyl, sec-butyl, tert-butyl, pentyl, neopentyl, and hexyl moieties, and the like.

The term "$C_3$-$C_5$ cycloalkyl" includes cyclopropyl, cyclobutyl, and cyclopentyl moieties, the term "$C_3$-$C_6$ cycloalkyl" includes cyclopropyl, cyclobutyl, cyclopentyl, cyclohexyl, and bicyclo[2.1.1]hexyl moieties, likewise, the term "$C_3$-$C_8$ cycloalkyl" includes cyclopropyl, cyclobutyl, cyclopentyl, cyclohexyl, bicyclo[2.1.1]hexyl, cycloheptyl, cyclooctyl, and bicyclo[3.1.1]heptyl moieties.

The term "$C_2$-$C_3$ alkenyl" includes ethenyl, prop-1-en-3-yl, prop-1-en-2-yl, and the like. The terms "$C_2$-$C_6$ alkenyl", "$C_2$-$C_8$ alkenyl" and "$C_2$-$C_{10}$ alkenyl" include ethenyl, prop-1-en-3-yl, prop-1-en-2-yl, 2-methylprop-1-en-1-yl, and the like.

The terms "$C_2$-$C_8$ alkynyl" and "$C_2$-$C_{10}$ alkynyl" include ethynyl, prop-1-yn-3-yl, prop-1-yn-1-yl, 4-methylpent-2-yn-1-yl, and the like.

The term "$C_1$-$C_{10}$ acyl" includes formyl, acetyl, propionyl, isobutyryl, and the like.

"Halo" includes fluoro, chloro, bromo, and iodo.

The terms "$C_1$-$C_3$ alkoxy" and "$C_1$-$C_6$ alkoxy" are a $C_1$-$C_3$ alkyl group or a $C_1$-$C_6$ alkyl group, respectively, bonded to an oxygen atom and include methoxy, ethoxy, isopropoxy, tert-butoxy, and the like. Similarly, the terms "$C_3$-$C_5$ cycloalkoxy" and "$C_3$-$C_8$ cycloalkoxy" are a $C_3$-$C_5$ cycloalkyl group or a $C_3$-$C_8$ cycloalkyl group, respectively, bonded through an oxygen atom and include cyclopropoxy, cyclobutoxy, cyclopentoxy, and the like. Similarly the term "$C_1$-$C_6$ alkylthio" is a $C_1$-$C_6$ alkyl group bonded to a sulfur atom and include methylthio, ethylthio, isopropylthio, and the like.

The term "$C_1$-$C_{10}$ alkyl optionally substituted with $C_3$-$C_8$ cycloalkyl, phenyl, or furyl" is taken to mean a $C_1$-$C_{10}$ alkyl moiety optionally substituted with one $C_3$-$C_8$ cycloalkyl, phenyl, or furyl moiety at any available carbon atom in the $C_1$-$C_{10}$ alkyl moiety and includes cyclopropylmethyl, 2-cyclohexyleth-1-yl, benzyl, and the like. Similarly, "$C_2$-$C_8$ alkenyl optionally substituted with $C_3$-$C_8$ cycloalkyl, phenyl, or furyl" and "$C_2$-$C_8$ alkynyl optionally substituted with $C_3$-$C_8$ cycloalkyl, phenyl, or furyl" are taken to mean a $C_2$-$C_8$ alkenyl or $C_2$-$C_8$ alkynyl moiety optionally substituted at any available carbon atom in the $C_2$-$C_8$ alkenyl or $C_2$-$C_8$ alkynyl moiety. Any of the "$C_1$-$C_{10}$ alkyl optionally substituted with $C_3$-$C_8$ cycloalkyl, phenyl, or furyl", "$C_2$-$C_8$ alkenyl optionally substituted with $C_3$-$C_8$ cycloalkyl, phenyl, or furyl" and "$C_2$-$C_8$ alkynyl optionally substituted with $C_3$-$C_8$ cycloalkyl, phenyl, or furyl" moieties may be further substituted up to three times at any available carbon on the alkyl, alkenyl, or alkynyl chains or in the $C_3$-$C_8$ cycloalkyl, phenyl, or furyl rings up to six times with fluoro, or with up to four substituents independently selected from the group consisting of halo, cyano, methyl optionally substituted up to three times with fluoro, trifluoromethoxy, $C_1$-$C_6$ alkoxy, $C_3$-$C_7$ cycloalkoxy, oxo, $NR^7R^8$, and $C(O)NR^7R^7$.

The term "$C_1$-$C_6$ alkoxy optionally substituted in the alkyl chain up to three times with fluoro or with $C_3$-$C_8$ cycloalkyl optionally substituted with $C_1$-$C_3$ alkyl" is taken to mean a $C_1$-$C_6$ alkoxy moiety optionally substituted either up to three times with fluoro groups at any available carbon atoms in the $C_1$-$C_6$ alkoxy moiety or with one $C_3$-$C_8$ cycloalkyl moiety at any available carbon atom in the $C_1$-$C_6$ alkoxy moiety and said $C_3$-$C_8$ cycloalkyl moiety is optionally substituted with a $C_1$-$C_3$ alkyl group. Similarly, the terms "$C_1$-$C_6$ alkyl optionally substituted in the alkyl chain up to three times with fluoro or with $C_3$-$C_6$ cycloalkyl optionally substituted with $C_1$-$C_3$ alkyl" and "$C_1$-$C_6$ alkylthio optionally substituted in the alkyl chain up to three times with fluoro or with $C_3$-$C_6$ cycloalkyl optionally substituted with $C_1$-$C_3$ alkyl" is taken to mean a $C_1$-$C_6$ alkylthio moiety or $C_1$-$C_6$ alkyl moiety optionally substituted either up to three times with fluoro or with one $C_3$-$C_8$ cycloalkyl moiety at any available carbon atoms in the $C_1$-$C_6$ alkylthio or $C_1$-$C_6$ alkyl moiety and said $C_3$-$C_8$ cycloalkyl moiety is optionally substituted with a $C_1$-$C_3$ alkyl group.

The term "$C_1$-$C_4$ alkyl substituted with $C_3$-$C_8$ cycloalkyl" is taken to mean a $C_1$-$C_4$ alkyl moiety substituted at any available carbon with a $C_3$-$C_8$ cycloalkyl group and includes spiro-fusion of the $C_3$-$C_8$ cycloalkyl group to the $C_1$-$C_4$ alkyl moiety.

The term "oxo" is taken to mean an oxygen atom double bonded to a carbon atom to form a carbonyl moiety.

The term "$C_2$-$C_6$ alkenyloxy" is taken to mean a $C_2$-$C_6$ alkenyl moiety bonded through an oxygen atom and include alkyloxy, prop-1-en-3-yloxy, and the like.

The term "$C_3$-$C_8$ cycloalkanonyl" is taken to mean a $C_3$-$C_8$ cycloalkyl moiety substituted with an oxo group and includes cyclohexanone, cyclooctanone and the like.

The term "tri-($C_1$-$C_6$ alkyl)silyl" is taken to mean a silyl group substituted with three substituents independently selected from $C_1$-$C_6$ alkyl and includes trimethylsilyl and ethyldimethylsilyl.

The term "nitrogen protecting group" is taken to mean a moiety that is stable to projected reaction conditions and yet may be selectively removed by reagents and reaction conditions compatible with the regenerated amine. Such groups are well known by the skilled artisan and are described in the literature. (See, for example: Greene and Wuts, *Protective Groups in Organic Synthesis*, Third Edition, Chapter 7, John Wiley and Sons Inc., (1999)). Nitrogen protecting groups contemplated include:

a) suitable carbamates, such as:
  1) $C_1$-$C_7$ alkyl carbamates including methyl, ethyl, tert-butyl, tert-amyl, diisopropylmethyl carbamates, and the like;
  2) substituted ethyl carbamates, such as 2,2,2-trichloroethyl, 2-trimethylsilylethyl, 2-phenylethyl, 1,1-dimethyl-2-haloethyl, 1,1-dimethyl-2,2-dibromoethyl, 1,1-dimethyl-2,2,2-trichloro-ethyl, 2-(pyridin-2-yl) ethyl, 2-(pyridin-4-yl)ethyl, 2-methylthioethyl, 2-methylsulfonylethyl, 2-(p-toluenesulfonyl)ethyl, 2-phosphonioethyl, 1,1-dimethyl-2-cyanoethyl, 2-iodoethyl carbamates, and the like;
  3) 1-adamantyl carbamate;
  4) vinyl carbamate;
  5) allyl carbamate;
  6) 1-isopropylallyl carbamate;
  7) cinnamyl carbamates, such as cinnamyl carbamate, 4-nitrocinnamyl, and the like;
  8) 8-quinolinyl carbamate;
  9) N-hydroxypiperidinyl carbamate;
  10) $C_1$-$C_4$ alkyldithio carbamates;
  11) Benzyl carbamates, such as benzyl, 4-methoxybenzyl, 4-nitrobenzyl, 4-halobenzyl, 4-cyanobenzyl, 4-decyloxybenzyl, 2,4-dichlorobenzyl, 3,5-dimethoxybenzyl, 2-nitrobenzyl, 3,4-dimethoxy-6-nitrobenzyl, phenyl (2-nitrophenyl)methyl, 4-methylsulfinylbenzyl, 9-anthrylmethyl, diphenylmethyl, 3-chloro-4-($C_2$-$C_6$ acyloxy)benzyl, 4-(dihydroxyboryl)benzyl carbamates, and the like;
  12) 2-(1,3-dithianyl)methyl carbamate;
  13) aryl carbamates, such as phenyl, nicotinyl, 4-(methylthio)phenyl, 2,4-di(methylthio)phenyl, 3-nitrophenyl carbamates, and the like;
  14) 2-triphenylphosphonioisopropyl carbamate;
  15) 5-benzisoxazolylmethyl carbamate;
  16) 2-(trifluoromethyl)-6-chromonylmethyl carbamate;
  17) S-benzyl thiocarbamate; and
  18) $C_3$-$C_8$ cycloalkyl carbamates, such as cyclobutyl, cyclopentyl, 1-methylcyclohexyl, cyclopropylmethyl carbamates, and the like;

b) suitable ureas, such as:
  1) phenothiazinyl-(10)-carbonyl;
  2) N'-(p-toluenesulfonylaminocarbonyl); and
  3) N'-phenylaminothiocarbonyl;

c) suitable formyl and acyl groups, such as:
  1) formyl; and
  2) acetyl groups, such as acetyl, chloroacetyl, trichloroacetyl, trifluoroacetyl, 4-chlorobutanoyl, phenylacetyl, 3-phenylpropanoyl, N-benzoylphenylalanyl, 2-nitrophenylacetyl, 2-nitrophenoxyacetyl, acetoacetyl, and the like;

d) suitable aroyl groups, such as:
  1) picolinoyl;
  2) 3-pyridinylcarbonyl;
  3) benzoyl;
  4) 4-phenylbenzoyl;
  5) 2-nitrobenzoyl; and
  6) 2-nitrocinnamoyl, and the like;

e) suitable cyclic imide groups, such as:
  1) N-phthalimide;
  2) N-dithiasuccinimide;
  3) N-2,3-diphenylmaleimide; and
  4) N-2,5-dimethylpyrrole, and the like;

f) allyl;

g) 3-acetoxypropyl;

h) suitable benzylic groups, such as benzyl, 2-methylbenzyl, α-methylbenzyl, and the like;

i) triphenylmethyl; and j) suitable imine moieties, such as:
  1) 1,1-dimethylthiomethyleneimine;
  2) benzylidene imine; and
  3) diphenylmethyleneimine, and the like.

The term "oxygen protecting group" is taken to mean a moiety that is stable to projected reaction conditions and yet may be selectively removed by reagents and reaction conditions compatible with the regenerated alcohol. Such groups are well known by the skilled artisan and are described in the literature. (See, for example: Greene and Wuts, *Protective Groups in Organic Synthesis*, Third Edition, Chapter 7, John Wiley and Sons Inc., (1999)). Oxygen protecting groups contemplated include:

a) methyl and substituted methyl groups such as methoxymethyl, methylthio-methyl, (phenyldimethylsilyl) methoxymethyl, benzyloxymethyl, p-methoxybenzyloxymethyl, p-nitrobenzyloxy-methyl, o-nitrobenzyloxymethyl, (4-methoxyphenoxy)methyl, guiaiacolmethyl, tert-butoxymethyl, 4-pentenyloxymethyl, siloxymethyl, 2-methoxyethoxymethyl, 2,2,2-trichloroeth-oxymethyl, bis(2-chloroethoxy)methyl, 2-(trimethylsilyl)ethoxymethyl, 2-quinolinylmethyl, 1-pyrenylmethyl, diphenylmethyl, triphenylmethyl, and the like;

b) tetrahydropyranyl and substituted tetrahydropyranyl groups such as 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydropyranyl-S,S-dioxide, and the like;

c) tetrahydrofuranyl and substituted tetrahydrofuranyl groups such as tetrahydrothiofuranyl and the like;

d) ethyl and substituted ethyl groups such as 1-ethoxyethyl, 1-(2-chloroethoxy)-ethyl, 1-[(2-trimethylsilyl)ethoxy] ethyl, 1-methyl-1-methoxy-ethyl, 1-methyl-1-benzyloxyethyl, 1-methyl-1-benzyloxy-2-fluoroethyl, 1-methyl-1-phenoxyethyl, 2,2,2-trichloroethyl, 1,1-dianisyl-2,2,2-trichloroethyl, 1,1,1,3,3,3-hexafluoro-2-phenylisopropyl, 2-trimethylsilylethyl, 2-(benzylthio) ethyl, 2-(phenylselenyl)ethyl, tert-butyl, and the like;

e) allyl;
f) propargyl;
g) substituted phenyl groups such as p-chlorophenyl, p-nitrophenyl, 2,4-dinitrophenyl, 2,3,5,6-tetrafluoro-4-(trifluoromethyl)phenyl, and the like;
h) benzyl and substituted benzyl groups such as p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2,6-difluorobenzyl, p-acylaminobenzyl, p-azidobenzyl, 4-azido-3-chlorobenzyl, 2-trifluoromethylbenzyl, p-(methylsulfinyl)benzyl, and the like;
i) silyl groups such as trimethylsilyl, triethylsilyl, triisopropylsilyl, dimethylisopropylsilyl, diethylisopropylsilyl, dimethylthexylsilyl, tert-butyldimethylsilyl, tert-butyldiphenylsilyl, tribenzylsilyl, tri-p-xylylsilyl, triphenylsilyl, diphenylmethylsilyl, di-tert-butylmethylsilyl, tris(trimethylsilyl)silyl, (2-hydroxystyryl)dimethylsilyl, (2-hydroxystyryl)diisopropylsilyl, tert-butylmethoxyphenyl silyl, tert-butoxydiphenylsilyl, and the like;
j) formyl and benzoylformyl groups;
k) acetyl and substituted acetyl groups such as chloroacetyl, dichloroacetyl, trichloroacetyl, trifluoroacetyl, methoxyacetyl, triphenylmethoxyacetyl, phenoxyacetyl, p-chlorophenoxyacetyl, phenylacetyl, chlorodiphenylacetyl and the like;
l) pivaloyl;
m) crotonyl;
n) benzoyl and substituted benzoyl groups such as p-phenylbenzoyl, 2-chlorobenzoyl, 4-bromobenzoyl, 2,4,6-trimethylbenzoyl;
o) methoxycarbonyl and substituted methoxycarbonyl groups such as methoxymethoxycarbonyl, 9-flurenylmethoxycarbonyl, and the like;
p) ethoxycarbonyl and substituted ethoxycarbonyl groups such as 2,2,2-trichloroethoxycarbonyl, 1,1-dimethyl-2,2,2-trichloroethoxycarbonyl, 2-(trimethylsilyl)ethoxycarbonyl, 2-dansylethoxycarbonyl, 2-(4-nitrophenyl)-ethoxycarbonyl, 2-(2,4-dinitrophenyl)ethoxycarbonyl, 2-cyano-1-phenylethoxycarbonyl, and the like;
q) isobutoxycarbonyl;
r) vinyloxycarbonyl;
s) allyloxycarbonyl;
t) substituted phenoxycarbonyl groups such as p-nitrophenoxycarbonyl, 2-iodophenoxycarbonyl, 2-chlorophenoxycarbonyl, 4-bromophenoxycarbonyl, 4-nitrophenoxycarbonyl, o-(dibromomethyl)phenoxycarbonyl, and the like;
u) benzyloxycarbonyl and substituted benzyloxycarbonyl groups such as p-methoxybenzyloxycarbonyl, 3,4-dimethoxybenzyloxycarbonyl, o-nitrobenzyloxycarbonyl, p-nitrobenzyloxycarbonyl, and the like; and
v) sulfonyl groups such as methanesulfonyl, benzylsulfonyl, p-toluenesulfonyl, 2-[(4-nitrophenyl)ethyl]sulfonyl, and the like.

The term "inhibition of production of A-β peptide" is taken to mean decreasing of excessive in vivo levels of A-β peptide in a mammal to normal or sub-normal levels.

The term "effective amount of a compound of Formula I" is taken to mean the dose or doses of a compound of Formula I required to inhibit BACE sufficiently to decrease in vivo levels of A-β peptide in a mammal to normal or sub-normal levels.

The term "treatment" includes treating one or more disease symptoms present in a patient as well as slowing, arresting, or reversing the progression of the disease.

The term "BACE" includes both BACE1 and BACE2.

Mild cognitive impairment has been defined as a potential prodromal phase of dementia associated with Alzheimer's disease based on clinical presentation and on progression of patients exhibiting mild cognitive impairment to Alzheimer's dementia over time. (Morris, et al., *Arch. Neurol.*, 58, 397-405 (2001); Petersen, et al., *Arch. Neurol.*, 56, 303-308 (1999)). The term "prevention of the progression of mild cognitive impairment to Alzheimer's disease" includes slowing, arresting, or reversing the progression of mild cognitive impairment to Alzheimer's disease in a patient.

The skilled artisan will understand that compounds of Formulae I-III and V-VII are comprised of a 1-amino-2-hydroxyethyl core that contains two chiral centers. Although the present invention contemplates all individual enantiomers or diastereomers, as well as mixtures of the enantiomers and diastereomers of said compounds including racemates, the 1(S),2(S) diastereomer is preferred for compounds of Formula I as illustrated in Figure (i):

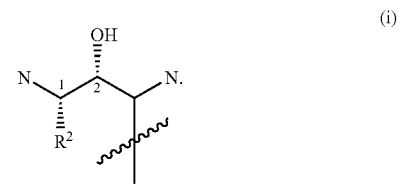

The preferred diastereomers of compounds of Formulae II, III, and V-VII are those that will result in the 1(S),2(S) diastereomer when the intermediate is converted to a compound of Formula I. The skilled artisan will also appreciate that the cyclic amine moiety in these formulae introduces a third contiguous chiral center into the molecules. Although the present invention contemplates all individual enantiomers or diastereomers, as well as mixtures of the enantiomers and diastereomers of said compounds including racemates, it is preferred that compounds of the invention exist as single enantiomers at the chiral center introduced by the cyclic moiety. It is especially preferred that the three contiguous chiral centers in the core structure of compounds of Formulae I-III and V-VII exist with the absolute configurations illustrated in the following Figure (ii):

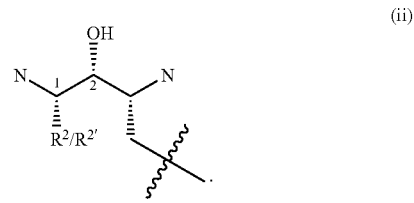

Furthermore, the skilled artisan will appreciate that additional chiral centers are created in compounds of Formulae I-IV and VII when variable $R^3$ differs from variable $R^4$ or when variable $R^5$ differs from variable $R^6$. The present invention contemplates all individual enantiomers or diastereomers, as well as mixtures of the enantiomers and diastereomers of said compounds including racemates. Compounds of Formulae I-IV and VII where $R^4$ and $R^6$ are hydrogen and $R^3$ and $R^5$ are other than hydrogen are preferred. It is also preferred that compounds of Formulae I-IV and VII where $R^4$ and $R^6$ are hydrogen and $R^3$ and $R^5$ are other than hydrogen exist in the following absolute configuration:

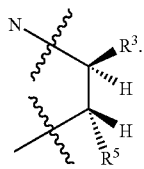

The single enantiomers or diastereomers may be prepared beginning with chiral reagents or by stereoselective or stereospecific synthetic techniques. Alternatively, the single enantiomers or diastereomers may be isolated from mixtures by standard chiral chromatographic or crystallization techniques at any convenient point in the synthesis of compounds of the invention. Single enantiomers and diastereomers of compounds of the invention are a preferred embodiment of the invention.

It will be understood by the skilled reader that many or all of the compounds of Formulae I-III and V-VII are capable of forming salts with any of a number of inorganic and organic acids. In all cases, the pharmaceutically acceptable salts of all of the compounds of Formula I, and acid addition salts of the compounds of Formulae II, III, and V-VII are included in the names of them. Methods for preparation of pharmaceutically acceptable salts of compounds of the present invention are well known to the skilled artisan (See: Stahl, P. Heinrich and Wermuth, Camille G., "Handbook of Pharmaceutical Salts Properties, Selection and Use," VCHA/Wiley-VCH (2002); and Berge, S. M., Bighley, L. D., and Monkhouse, D. C. "Pharmaceutical Salts," *Journal of Pharmaceutical Sciences*, 66(1), (January 1977)). Preferred salts in all cases are those formed with hydrochloric acid or trifluoroacetic acid.

Although all of the compounds of Formula I are useful inhibitors of BACE, certain classes of compounds are preferred. The following paragraphs describe such preferred classes:

aa) $R^1$ is $C_1$-$C_{10}$ alkyl optionally substituted with $C_1$-$C_6$ alkoxy, oxo, or up to three times with fluoro;
ab) $R^1$ is $C_1$-$C_6$ alkyl optionally substituted with $C_1$-$C_6$ alkoxy;
ac) $R^1$ is methyl optionally substituted with methoxy;
ad) $R^1$ is methyl;
ae) $R^1$ is $C_1$-$C_{10}$ alkyl optionally substituted with $C_3$-$C_8$ cycloalkyl, phenyl, or furyl; $C_2$-$C_8$ alkenyl optionally substituted with $C_3$-$C_8$ cycloalkyl, phenyl, or furyl; $C_2$-$C_8$ alkynyl optionally substituted with $C_3$-$C_8$ cycloalkyl, phenyl, or furyl; or $C_3$-$C_8$ cycloalkyl; each optionally substituted up to six times with fluoro, or with up to four substituents independently selected from the group consisting of halo, cyano, methyl optionally substituted with up to three fluoro atoms, trifluoromethoxy, $C_1$-$C_6$ alkoxy, $C_3$-$C_7$ cycloalkoxy, oxo, $NR^7R^8$, and $C(O)NR^7R^7$;
af) $R^1$ is benzyl;
ag) $R^2$ is benzyl optionally mono-or difluorinated in the phenyl ring;
ah) $R^2$ is benzyl;
ai) $R^2$ is 3-fluorobenzyl;
aj) $R^1$ is 3,5-difluorobenzyl;
ak) $R^2$ is benzyl optionally monosubstituted in the 3-position of the phenyl ring with a substituent selected from the group consisting of halo, $C_1$-$C_6$ alkyl optionally substituted in the alkyl chain up to three times with fluoro, $C_1$-$C_6$ alkoxy optionally substituted in the alkyl chain up to three times with fluoro, $C_1$-$C_6$ alkylthio optionally substituted in the alkyl chain up to three times with fluoro, and $C_3$-$C_8$ cycloalkoxy; or disubstituted in the phenyl ring with a first substituent selected from the group consisting of halo and trifluoromethoxy and a second substituent selected from the group consisting of halo, $C_1$-$C_6$ alkyl optionally substituted in the alkyl chain up to three times with fluoro, $C_1$-$C_6$ alkoxy optionally substituted in the alkyl chain up to three times with fluoro, $C_1$-$C_6$ alkylthio optionally substituted in the alkyl chain up to three times with fluoro, and $C_3$-$C_8$ cycloalkoxy;
al) $R^2$ is 3-propoxybenzyl;
am) $R^2$ is 3-(2-fluoroethoxy)benzyl;
an) $R^2$ is 5-fluoro-3-propoxybenzyl;
ao) $R^3$ is hydrogen;
ap) $R^3$ is methyl or ethyl;
aq) $R^4$ is hydrogen;
ar) $R^3$ is methyl or ethyl, and $R^4$ is hydrogen;
as) $R^5$ is $R^9$ or $-(CH_2)_{0-2}-OR^9$;
at) $R^5$ is $-(CH_2)_{0-2}-OR^9$;
au) $R^5$ is $OR^9$;
av) $R^6$ is hydrogen;
aw) $R^5$ is $OR^9$ and $R^6$ is hydrogen;
ax) $R^9$ is $C_1$-$C_{10}$ alkyl optionally substituted with 1-6 fluorine atoms or $C_1$-$C_6$ alkoxy;
ay) $R^9$ is neopentyl;
az) $R^9$ is neopentyl substituted with 1-6 fluorine atoms;
ba) $R^9$ is $-(CH_2)_{0-4}-R^{10}$;
bb) $R^9$ is $-CH_2-R^{10}$;
bc) $R^{10}$ is $C_3$-$C_8$ cycloalkyl optionally substituted with up to 4 fluorine atoms;
bd) $R^{10}$ is cyclohexyl;
be) $R^{10}$ is adamantyl;
bf) The compound of Formula I is a free base;
bg) The compound of Formula I is a pharmaceutically acceptable salt;
bh) The compound of Formula I is the hydrochloride salt.

Preferred embodiments of the invention include all combinations of paragraphs aa)-bh). Especially preferred compounds of Formula I are those where $R^1$ is $C_1$-$C_6$ alkyl optionally substituted with $C_1$-$C_6$ alkoxy and $R^2$ is benzyl; 3-fluorobenzyl; 3,5-difluorobenzyl; or benzyl substituted in the 3-position of the phenyl ring with $C_1$-$C_6$ alkoxy optionally substituted up to three times with fluoro, $C_1$-$C_6$ alkyl optionally substituted up to three times with fluoro, $C_1$-$C_6$ alkylthio optionally substituted up to three times with fluoro, or $C_3$-$C_8$ cycloalkoxy and optionally further substituted in the 5-position with fluoro.

A preferred subgenus of compounds of Formula I are compounds of Formula I(a):

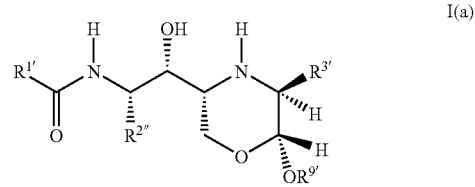

I(a)

where;

$R^{1'}$ is hydrogen; benzyl; or $C_1$-$C_{10}$ alkyl optionally substituted with $C_1$-$C_6$ alkoxy, oxo, or up to six times with fluoro;

$R^{2''}$ is benzyl optionally monosubstituted in the 3-position of the phenyl ring with a substituent selected from the group consisting of halo, $C_1$-$C_6$ alkyl optionally substituted in the alkyl chain up to three times with fluoro, $C_1$-$C_6$ alkoxy optionally substituted in the alkyl chain up to three times with fluoro, $C_1$-$C_6$ alkylthio optionally substituted in the alkyl chain up to three times with fluoro, and $C_3$-$C_8$ cycloalkoxy; or benzyl disubstituted in the phenyl ring with a first substituent selected from the group consisting of halo and trifluoromethoxy and a second substituent selected from the group consisting of halo, $C_1$-$C_6$ alkyl optionally substituted in the alkyl chain up to three times with fluoro, $C_1$-$C_6$ alkoxy optionally substituted in the alkyl chain up to three times with fluoro, $C_1$-$C_6$ alkylthio optionally substituted in the alkyl chain up to three times with fluoro, and $C_3$-$C_8$ alkoxy;

$R^{3'}$ is hydrogen or $C_1$-$C_4$ alkyl;

$R^{9'}$ is $C_1$-$C_{10}$ alkyl optionally substituted with 1-6 fluorine atoms; $C_1$-$C_4$ alkyl substituted with tetrahydrofuryl, tetrahydropyranyl, or $C_3$-$C_8$ cycloalkyl optionally substituted with up to 4 fluoro atoms; or a pharmaceutically acceptable salt thereof. Especially preferred compounds of Formula I(a) are those where $R^{1'}$ is $C_1$-$C_6$ alkyl optionally substituted with $C_1$-$C_6$ alkoxy; $R^{2''}$ is 3,5-difluorobenzyl or benzyl substituted in the 3-position of the phenyl ring with $C_1$-$C_6$ alkyl optionally substituted in the alkyl chain up to three times with fluoro, $C_1$-$C_6$ alkoxy optionally substituted in the alkyl chain up to three times with fluoro, $C_1$-$C_6$ alkylthio optionally substituted in the alkyl chain up to three times with fluoro, or $C_3$-$C_8$ cycloalkoxy, and optionally further substituted in the 5-position with fluoro; and $R^{3'}$ is methyl or ethyl.

Another embodiment of the present invention is compounds of Formula I where:

$R^1$ is $C_1$-$C_6$ alkyl;

$R^2$ is $C_1$-$C_3$ alkyl; benzyl optionally monosubstituted in the phenyl ring with a substituent selected from the group consisting of halo, $C_1$-$C_6$ alkoxy optionally substituted in the alkyl chain with $C_3$-$C_7$ cycloalkyl, and $C_1$-$C_6$ alkylthio optionally substituted in the alkyl chain with $C_3$-$C_7$ cycloalkyl, or benzyl optionally disubstituted in the phenyl ring with a first substituent independently selected from halo and a second substituent independently selected from halo, $C_1$-$C_6$ alkoxy optionally substituted in the alkyl chain with $C_3$-$C_7$ cycloalkyl, and $C_1$-$C_6$ alkylthio optionally substituted in the alkyl chain with $C_3$-$C_7$ cycloalkyl;

$R^3$ is hydrogen or $C_1$-$C_6$ alkyl;

$R^4$ is hydrogen or $C_1$-$C_6$ alkyl;

$R^3$ and $R^4$ taken together with the carbon atom to which they are attached form a $C_3$-$C_6$ cycloalkyl ring;

$R^5$ is hydrogen, $R^9$, or —$(CH_2)_{0\text{-}2}$—$OR^9$;

$R^6$ is hydrogen or phenyl;

G is O or $S(O)_{0\text{-}2}$;

$R^9$ is $C_1$-$C_{10}$ alkyl optionally substituted with 1-6 fluorine atoms, $C_1$-$C_{10\ 1}$, $C_2$-$C_6$ alkenyl, or —$(CH_2)_{0\text{-}3}$—$R^{10}$;

$R^{10}$ is $C_3$-$C_8$ cycloalkyl, tetrahydrofuryl, or phenyl each optionally substituted with one or two substitutents independently selected from the group consisting of halo, $C_1$-$C_6$ alkyl, $C_1$-$C_6$ alkoxy, hydroxy, trifluoromethyl, and trifluoromethoxy, or $R^{10}$ is adamantyl; or a pharmaceutically acceptable salt thereof.

Although all of the compounds of Formula II are useful intermediates for the preparation of BACE inhibitors, certain of the compounds are preferred:

bi) $R^1$ is $C_1$-$C_{10}$ alkyl optionally substituted with $C_1$-$C_6$ alkoxy, oxo, or up to three times with fluoro;

bj) $R^1$ is $C_1$-$C_6$ alkyl optionally substituted with $C_1$-$C_6$ alkoxy;

bk) $R^1$ is methyl optionally substituted with methoxy;

bl) $R^1$ is methyl;

bm) $R^{2'}$ is benzyl optionally mono-or difluorinated in the phenyl ring;

bn) $R^{2'}$ is benzyl;

bo) $R^{2'}$ is 3-fluorobenzyl;

bp) $R^{2'}$ is 3,5-difluorobenzyl;

bq) $R^{2'}$ is benzyl substituted in the phenyl ring with —$OR^{12}$, halo, $C_1$-$C_6$ alkyl optionally substituted in the alkyl chain up to three times with fluoro, $C_1$-$C_6$ alkoxy optionally substituted in the alkyl chain up to three times with fluoro, and $C_1$-$C_6$ alkylthio optionally substituted in the alkyl chain up to three times with fluoro, $C_3$-$C_8$ cycloalkoxy, and optionally further substituted with fluoro;

br) $R^{2'}$ is 3-propoxybenzyl;

bs) $R^{2'}$ is 3-(2-fluoroethoxy)benzyl;

bt) $R^{2'}$ is 5-fluoro-3-propoxybenzyl;

bu) $R^{2'}$ is 3-hydroxybenzyl;

bv) $R^{2'}$ is 5-fluoro-3-hydroxybenzyl;

bw) $R^3$ is hydrogen;

bx) $R^3$ is methyl or ethyl;

by) $R^4$ is hydrogen;

bz) $R^3$ is methyl or ethyl, and $R^4$ is hydrogen;

ca) $R^5$ is $R^9$ or —$(CH_2)_{0\text{-}2}$—$OR^9$;

cb) $R^5$ is —$(CH_2)_{0\text{-}2}$—$OR^9$;

cc) $R^5$ is $OR^9$;

cd) $R^6$ is hydrogen;

ce) $R^5$ is $OR^9$ and $R^6$ is hydrogen;

cf) $R^9$ is $C_1$-$C_{10}$ alkyl optionally substituted with 1-6 fluorine atoms or $C_1$-$C_6$ alkoxy;

cg) $R^9$ is neopentyl;

ch) $R^9$ is neopentyl substituted with 1-6 fluorine atoms;

ci) $R^9$ is —$(CH_2)_{0\text{-}4}$—$R^{10}$;

cj) $R^9$ is —$CH_2$—$R^{10}$;

ck) $R^{10}$ is cyclohexyl;

cl) $R^{10}$ is adamantyl;

cm) $R^{11}$ is a carbamate protecting group;

cn) $R^{11}$ is tert-butoxycarbonyl;

co) $R^{12}$ is hydrogen;

cp) $R^{12}$ is benzyl.

Preferred compounds of Formula II include all combinations of paragraphs bi)-cp). Especially preferred compounds of Formula II are those where $R^1$ is $C_1$-$C_6$ alkyl optionally substituted with $C_1$-$C_6$ alkoxy, $R^{2'}$ is benzyl, 3-fluorobenzyl, 3,5-difluorobenzyl, or benzyl substituted in the 3-position of the phenyl ring with —$OR^{12}$, $C_1$-$C_6$ alkoxy optionally substituted up to three times with fluoro, $C_1$-$C_6$ alkyl optionally substituted up to three times with fluoro, $C_3$-$C_8$ cycloalkoxy, $C_1$-$C_6$ alkylthio optionally substituted up to three times with fluoro and optionally further substituted in the 5-position with fluoro, $R^3$ is hydrogen, methyl, or ethyl, $R^4$ and $R^6$ are both hydrogen, and $R^5$ is $OR^9$.

Although all of the compounds of Formula III are useful intermediates for the preparation of BACE inhibitors, certain of the compounds are preferred:

cq) $R^{2'}$ is benzyl optionally mono-or difluorinated in the phenyl ring;

cr) $R^{2'}$ is benzyl;

cs) $R^{2'}$ is 3-fluorobenzyl;

ct) $R^{2'}$ is 3,5-difluorobenzyl;

cu) $R^{2'}$ is benzyl substituted in the phenyl ring with —$OR^{12}$, halo, $C_1$-$C_6$ alkoxy optionally substituted up to three times with fluoro, $C_1$-$C_6$ alkyl optionally substituted up to three times with fluoro, $C_1$-$C_6$ alkylthio optionally substituted up to three times with fluoro, or $C_3$-$C_8$ cycloalkoxy, and optionally further substituted with fluoro;
cv) $R^{2'}$ is 3-propoxybenzyl;
cw) $R^{2'}$ is 3-(2-fluoroethoxy)benzyl;
cx) $R^{2'}$ is 5-fluoro-3-propoxybenzyl;
cy) $R^{2'}$ is 3-hydroxybenzyl;
cz) Re is 5-fluoro-3-hydroxybenzyl;
da) $R^3$ is hydrogen;
db) $R^3$ is methyl or ethyl;
dc) $R^4$ is hydrogen;
dd) $R^3$ is methyl or ethyl, and $R^4$ is hydrogen;
de) $R^5$ is $R^9$ or —$(CH_2)_{0-2}$—$OR^9$;
df) $R^5$ is —$(CH_2)_{0-2}$—$OR^9$;
dg) $R^5$ is $OR^9$;
dh) $R^6$ is hydrogen;
di) $R^5$ is $OR^9$ and $R^6$ is hydrogen;
dj) $R^9$ is $C_1$-$C_{10}$ alkyl optionally substituted with 1-6 fluorine atoms;
dk) $R^9$ is neopentyl;
dl) $R^9$ is neopentyl substituted up to six times with fluoro;
dm) $R^9$ is —$CH_2$—$R^{10}$;
dn) $R^{10}$ is cyclohexyl;
do) $R^{10}$ is adamantyl;
dp) $R^{11'}$ is hydrogen;
dq) $R^{11'}$ is a carbamate protecting group;
dr) $R^{11'}$ is tert-butoxycarbonyl;
ds) $R^{12}$ is hydrogen;
dt) $R^{12}$ is a silyl group;
du) $R^{12}$ is tert-butyldimethylsilyl;
dv) $R^{12}$ is benzyl.

Preferred compounds of Formula III include all combinations of paragraphs cq)-dv). Especially preferred compounds of Formula III are those where $R^{2'}$ is benzyl, 3-fluorobenzyl, 3,5-difluorobenzyl, or benzyl substituted in the 3-position of the phenyl ring with —$OR^{12}$, halo, $C_1$-$C_6$ alkyl optionally substituted in the alkyl chain up to three times with fluoro, $C_1$-$C_6$ alkoxy optionally substituted in the alkyl chain up to three times with fluoro, $C_1$-$C_6$ alkylthio optionally substituted in the alkyl chain up to three times with fluoro, or $C_3$-$C_8$ cycloalkoxy, and optionally further substituted in the 5-position with fluoro, $R^3$ is hydrogen, methyl, or ethyl, $R^4$ and $R^6$ are both hydrogen, $R^5$ is $OR^9$, and $R^{11'}$ and $R^{12}$ are both hydrogen.

Although all of the compounds of Formula IV are useful intermediates for the preparation of BACE inhibitors, certain of the compounds are preferred:
dw) $R^3$ is hydrogen;
dx) $R^3$ is methyl or ethyl;
dy) $R^4$ is hydrogen;
dz) $R^3$ is methyl or ethyl, and $R^4$ is hydrogen;
ea) $R^5$ is —$OR^9$;
eb) $R^6$ is hydrogen;
ec) $R^9$ is $C_1$-$C_{10}$ alkyl optionally substituted with 1-6 fluorine atoms or $C_1$-$C_6$ alkoxy;
ed) $R^9$ is neopentyl optionally substituted up to six times with fluoro;
ee) $R^9$ is —$(CH_2)_{0-4}$—$R^{10}$;
ef) $R^9$ is —$CH_2$—$R^{10}$;
eg) $R^{10}$ is cyclohexyl;
eh) $R^{10}$ is adamantyl;
ei) $R^{11}$ is a carbamate protecting group;
ej) $R^{11}$ is tert-butoxycarbonyl.

A preferred subgenus of intermediates of Formula IV are compounds of Formula IV(a):

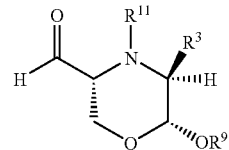

where $R^3$, $R^9$, and $R^{11}$ are as previously defined. Preferred compounds of Formula IV(a) are those where $R^3$ is hydrogen, methyl, or ethyl.

Although all of the compounds of Formula V are useful intermediates for the preparation of BACE inhibitors, certain of the compounds are preferred:
ek) $R^{2'}$ is benzyl optionally mono-or difluorinated in the phenyl ring;
el) $R^{2'}$ is benzyl;
em) $R^{2'}$ is 3-fluorobenzyl;
en) $R^1$ is 3,5-difluorobenzyl;
eo) $R^{2'}$ is benzyl substituted in the phenyl ring with —$OR^{12}$, halo, $C_1$-$C_6$ alkyl optionally substituted in the alkyl chain up to three times with fluoro, $C_1$-$C_6$ alkoxy optionally substituted in the alkyl chain up to three times with fluoro, $C_1$-$C_6$ alkylthio optionally substituted in the alkyl chain up to three times with fluoro, or $C_3$-$C_8$ cycloalkoxy, and optionally further substituted with fluoro;
ep) $R^{2'}$ is 3-propoxybenzyl;
eq) $R^{2'}$ is 3-(2-fluoroethoxy)benzyl;
er) $R^2$ is 5-fluoro-3-propoxybenzyl;
es) $R^{11'}$ is hydrogen or a carbamate protecting group;
et) $R^{11'}$ is hydrogen;
eu) $R^{11'}$ is a carbamate protecting group;
ev) $R^{11'}$ is tert-butoxycarbonyl;
ew) $R^{11}$ is benzyl;
ex) $R^{12'}$ is benzyl;
ey) $R^{11}$ and $R^{12'}$ are all benzyl;

Although all of the compounds of Formula VI are useful intermediates for the preparation of BACE inhibitors, certain of the compounds are preferred:
ez) $R^1$ is $C_1$-$C_{10}$ alkyl optionally substituted with $C_1$-$C_6$ alkoxy, oxo, or up to three times with fluoro;
fa) $R^1$ is $C_1$-$C_6$ alkyl optionally substituted with $C_1$-$C_6$ alkoxy;
fb) $R^1$ is methyl optionally substituted with methoxy;
fc) $R^1$ is methyl
fd) $R^{2'}$ is benzyl optionally mono-or difluorinated in the phenyl ring;
fe) $R^{2'}$ is benzyl;
ff) $R^{2'}$ is 3-fluorobenzyl;
fg) $R^{2'}$ is 3,5-difluorobenzyl;
fh) $R^{2'}$ is benzyl substituted in the phenyl ring with —$OR^{12}$, halo, $C_1$-$C_6$ alkyl optionally substituted in the alkyl chain up to three times with fluoro, $C_1$-$C_6$ alkoxy optionally substituted in the alkyl chain up to three times with fluoro, $C_1$-$C_6$ alkylthio optionally substituted in the alkyl chain up to three times with fluoro, or $C_3$-$C_8$ cycloalkoxy, and optionally further substituted with fluoro;
fi) $R^{2'}$ is 3-propoxybenzyl;
fj) $R^{2'}$ is 3-(2-fluoroethoxy)benzyl;
fk) $R^{2'}$ is 5-fluoro-3-propoxybenzyl;
fl) $R^{2'}$ is 3-hydroxybenzyl;

fm) $R^{2'}$ is 5-fluoro-3-hydroxybenzyl;
fn) $R^{11'}$ is hydrogen or a carbamate protecting group;
fo) $R^{11'}$ is hydrogen;
fp) $R^{11'}$ is a carbamate protecting group;
fq) $R^{11'}$ is tert-butoxycarbonyl;
fr) $R^{12}$ is benzyl.

Although all of the compounds of Formula VII are useful intermediates for the preparation of BACE inhibitors, certain of the compounds are preferred:

fs) $R^{2'}$ is benzyl optionally mono-or difluorinated in the phenyl ring;
ft) $R^{2'}$ is benzyl;
fu) $R^{2'}$ is 3-fluorobenzyl;
fv) $R^{2'}$ is 3,5-difluorobenzyl;
fw) $R^{2'}$ is benzyl substituted in the phenyl ring with $—OR^{12}$, halo, $C_1$-$C_6$ alkyl optionally substituted in the alkyl chain up to three times with fluoro, $C_1$-$C_6$ alkoxy optionally substituted in the alkyl chain up to three times with fluoro, $C_1$-$C_6$ alkylthio optionally substituted in the alkyl chain up to three times with fluoro, or $C_3$-$C_8$ cycloalkoxy, and optionally further substituted with fluoro;
fx) $R^{2'}$ is 3-propoxybenzyl;
fy) $R^{2'}$ is 3-(2-fluoroethoxy)benzyl;
fz) $R^{2'}$ is 5-fluoro-3-propoxybenzyl;
ga) $R^{2'}$ is 3-hydroxybenzyl;
gb) $R^{2'}$ is 5-fluoro-3-hydroxybenzyl;
gc) $R^3$ is hydrogen;
gd) $R^3$ is methyl or ethyl;
ge) $R^4$ is hydrogen;
gf) $R^3$ is methyl or ethyl, and $R^4$ is hydrogen; where $R^{11}$, $R^{11'}$, and $R^{12}$ are as previously defined.

The compounds of Formula I are inhibitors of BACE. It is preferred the compound of Formula I selectively inhibits BACE1 relative to BACE2. Thus, the present invention also provides a method of inhibiting BACE in a mammal that comprises administering to a mammal in need of said treatment a BACE-inhibiting amount of a compound of Formula I. It is preferred that the mammal to be treated by the administration of the compounds of Formula I is human.

As inhibitors of BACE, the compounds of the present invention are useful for suppressing the production of A-β peptide, and therefore for the treatment of disorders resulting from excessive A-β peptide levels due to over-production and/or reduced clearance of A-β peptide. The compounds of Formula I are therefore believed to be useful in treating or preventing Alzheimer's disease, mild cognitive impairment, Down's Syndrome, Hereditary Cerebral Hemorrhage with Amyloidosis of the Dutch-Type, cerebral amyloid angiopathy, other degenerative dementias such as: dementias of mixed vascular and degenerative origin, dementia associated with Parkinson's disease, dementia associated with progressive supranuclear palsy, dementia associated cortical basal degeneration, and diffuse Lewy body type of Alzheimer's disease.

The compounds of the present invention may be prepared by a variety of procedures, some of which are illustrated in the Schemes below. It will be recognized by one of skill in the art that the individual steps in the following schemes may be varied to provide the compounds of Formula I. The particular order of steps required to produce the compounds of Formula I is dependent upon the particular compound being synthesized, the starting compound, and the relative lability of the substituted moieties. Some stereochemical centers have been specified and certain substituents have been eliminated in the following schemes for the sake of clarity and are not intended to limit the teaching of the schemes in any way. Furthermore, individual isomers, enantiomers, or diastereomers may be separated at any convenient point in the synthesis of compounds of Formula I.

The compounds of Formula I may be prepared as described in Scheme I where variables G, $R^1$, $R^2$, $R^{2'}$, $R^3$, $R^4$, $R^5$, $R^6$, $R^{11'}$, and $R^{12}$ are as previously defined:

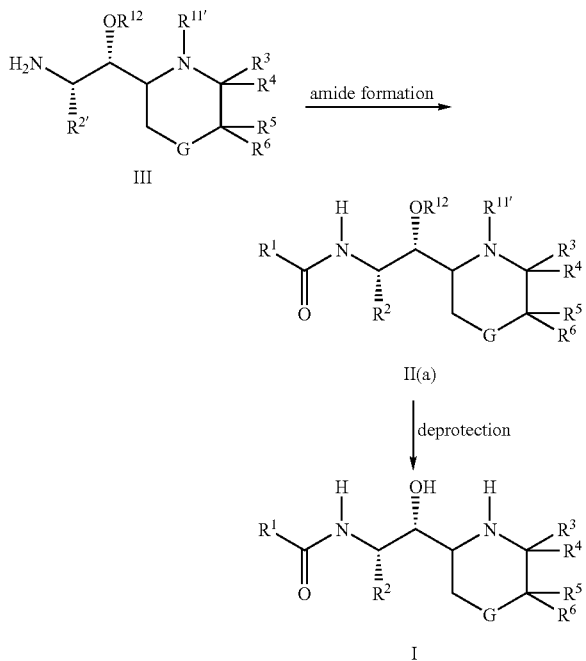

Scheme I

The amine of Formula III is reacted under standard amide forming conditions well known to the skilled artisan to provide compounds of Formula II (for example, see WO 03/040096 and WO 04/024081). An appropriate carboxylic acid of Formula $R^1$—COOH or an equivalent thereof, such as the sodium or, preferably, potassium carboxylate salt is reacted with a peptide coupling agent such as dicyclohexylcarbodiimide (DCC), 1-(3-dimethylaminopropyl)-3-ethylcarbodiimide hydrochloride (EDCl), or n-propylphosphonic anhydride, and an appropriate amine such as N-methylmorpholine or triethylamine, in a suitable solvent such as dichloromethane, dimethylformamide (DMF) or tetrahydrofuran (THF) to provide the compound of Formula II. If necessary or desired, an additive such as 4-(dimethylamino)pyridine and/or 1-hydroxybenzotriazole or equivalents thereof may be added to the reaction mixture to facilitate the reaction. Alternatively, other carboxylic acid equivalents, including acylating agents, such as an appropriate acylimidazole, or a mixed anhydride, such as formic acetic anhydride, or an appropriate acid halide may be reacted directly with the amine of Formula III to provide the desired amide of Formula II. The requisite carboxylic acids, carboxylic acid salts, acylating agents, and mixed anhydrides are either commercially available or may be prepared from commercially available materials by methods well known to the skilled artisan. (For example, See: *Comprehensive Organic Transformations*, Larock, Wiley-VCH Publishers, Inc., New York, (1999); *Advanced Organic Chemistry*, March, Wiley Interscience, New York, Third Edition, (1985)). The skilled artisan will appreciate that any functional group transformations, for example converting an alcohol to an ether, may be performed at any convenient point in the synthesis to provide compounds of Formula I.

The conditions for deprotection of compounds of Formula II to provide compounds of Formula I depend on the nature of variables $R^{11'}$ and $R^{12}$. The deprotection conditions are those well known to the skilled artisan and are described in the literature. (For example, see: Greene and Wuts, *Protective Groups in Organic Synthesis*, Third Edition, Chapters 2 and 7, John Wiley and Sons Inc., (1999)). Depending upon the nature of variables $R^{11}$ and $R^{12}$, they may both be removed in a single reaction, for example by treatment with acid or under hydrogenation conditions, or may be removed sequentially as necessary or desired. Further, if salts of compounds of the invention are desired, an appropriate free base of Formula I is simply reacted with an appropriate pharmaceutically acceptable acid in a suitable solvent under standard conditions to provide a pharmaceutically acceptable salt of a compound of Formula I. The skilled artisan will appreciate that, depending on the nature of variables $R^{11'}$ and $R^{12}$, the deprotection and salt forming steps may occur simultaneously to provide a pharmaceutically acceptable salt of a compound of Formula I in a single step. The skilled artisan will appreciate that in instances where both $R^{11'}$ and $R^{12}$ are hydrogen, no deprotection step is required to provide compounds of Formula I. The process of Scheme I is a further embodiment of the present invention, and the process where $R^{11'}$ and $R^{12}$ are both hydrogen is a preferred embodiment.

Intermediates of Formula III may be prepared as described in the following scheme where G, $R^1$, $R^{2'}$, $R^3$, $R^4$, $R^5$, $R^6$, $R^{11}$, and $R^{12}$ are as previously defined.

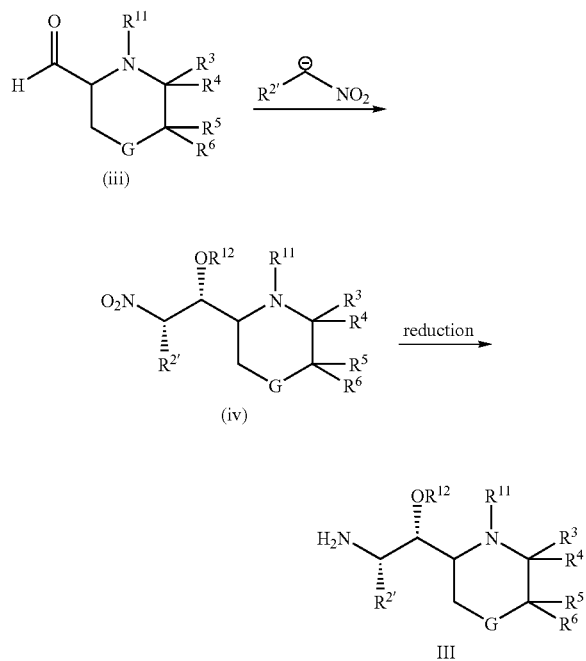

Aldehyde (iii) is reacted with the anion of an appropriately substituted nitroalkane to provide the corresponding nitroethane (iv). The nitroethane is reduced under standard chemical or hydrogenation reducing conditions to provide compounds of Formula III. (See: *Comprehensive Organic Transformations*, Larock, Wiley-VCH Publishers, Inc., New York, (1999); *Advanced Organic Chemistry*, March, Wiley Interscience, New York, Third Edition, (1985)) The skilled artisan will appreciate that the hydroxy moiety generated by the anion addition in the first step of Scheme II may be protected under standard conditions either before or after the reduction step as necessary or desired. (For example, see: Greene and Wuts, *Protective Groups in Organic Synthesis*, Third Edition, Chapter 2, John Wiley and Sons Inc., (1999)). The requisite anions are prepared by treating the appropriately substituted nitroalkane with a suitable base at low temperature. The requisite appropriately substituted nitroalkanes are either commercially available or may be prepared from commercially available starting materials. (For example, see: *Comprehensive Organic Transformations*, Larock, Wiley-VCH Publishers, Inc., New York, (1999); *Advanced Organic Chemistry*, March, Wiley Interscience, New York, Third Edition, (1985)) The aldehydes of Formula (iii) represent a further embodiment of the present invention.

Where $R^2$ is an appropriately substituted benzyl group, the requisite nitroalkanes may be prepared essentially as described in the following scheme where X', X", and X''' are optional substituents for the phenyl group of the benzyl moiety as defined for variables $R^2$ and $R^{2'}$.

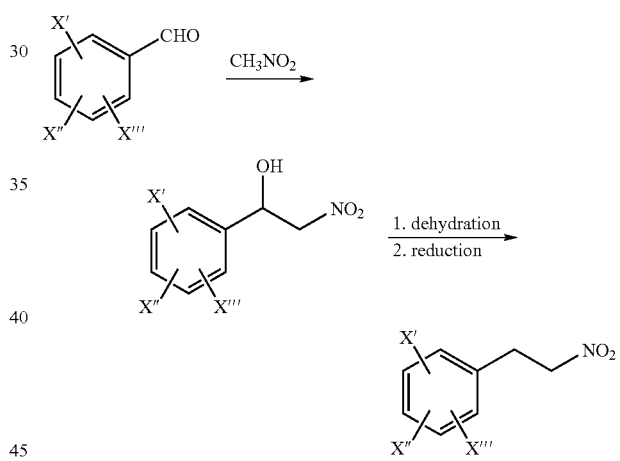

An appropriately substituted benzaldehyde is reacted with nitromethane in the presence of a suitable base to provide the corresponding 1-nitro-2-hydroxy-2-phenylethane. The molecule is dehydrated and the corresponding double bond reduced under standard conditions to provide the desired 1-nitro-2-phenylethane. The skilled artisan will appreciate that the nitromethane addition and dehydration may occur spontaneously in a single step depending upon the reaction conditions employed.

The requisite aldehydes (iii) may be prepared by standard synthetic methodology well known to the skilled artisan. (For example, see: *Comprehensive Organic Transformations*, Larock, Wiley-VCH Publishers, Inc., New York, (1999); *Advanced Organic Chemistry*, March, Wiley Interscience, New York, Third Edition, (1985)) Certain aldehydes may be prepared as described in the following scheme where $R^9$ and $R^{11}$ are as previously defined and $R^{12'}$ is an oxygen protecting group.

Scheme IV

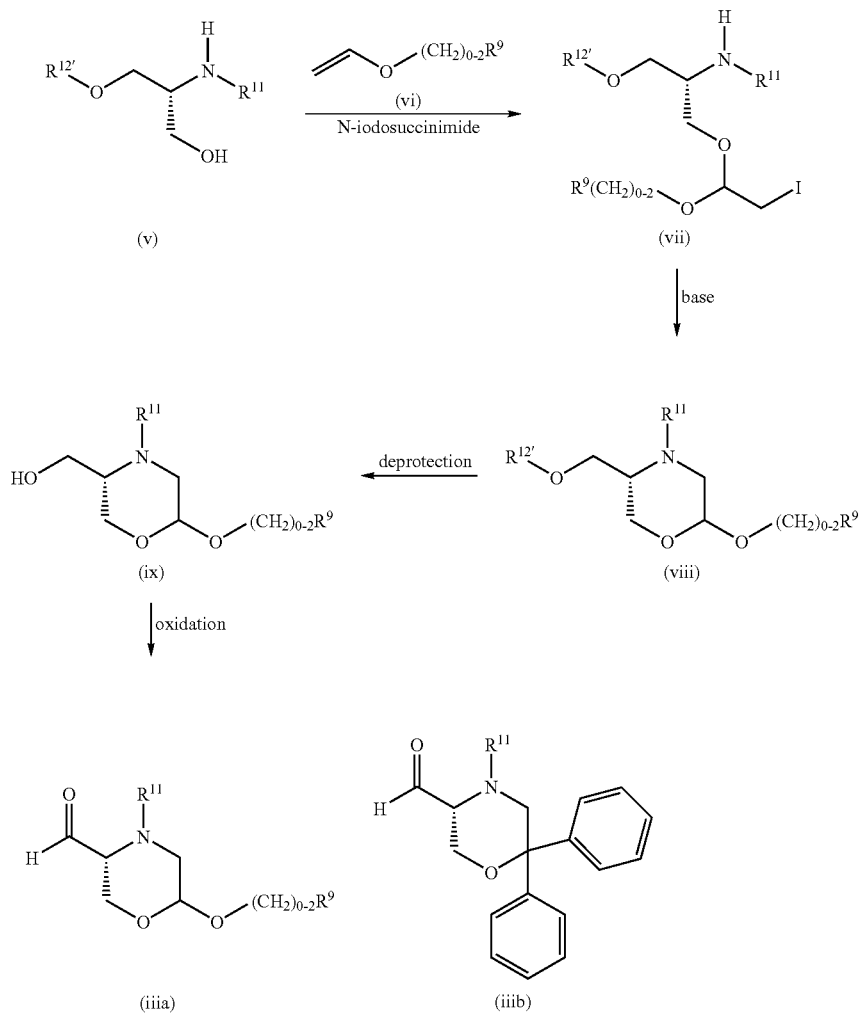

An appropriately protected serinol (v) (Novachek, et al., *Tetrahedron Letters,* 37, 1743-1746 (1996)) is reacted with a vinyl ether (vi) in the presence of a suitable halogenating agent, such as N-iodosuccinimide, to provide the iodo derivative (vii). This iodo derivative is treated with a suitable base, such as sodium hydride, to provide the cyclic compound (viii). The protected alcohol is deprotected to provide alcohol (ix), which is then oxidized under standard conditions to provide the corresponding aldehyde (iiia). Compounds of formula (iiib) may be prepared by substituting 1,1-diphenylethylene for the vinyl ether (v).

Additional aldehydes of formula (iii) may be prepared as described in the following scheme where $R^9$ and $R^{11}$ are as previously defined, $R^4$ is $C_1$-$C_6$ alkyl, and $R^{12'}$ is an oxygen protecting group.

Scheme V

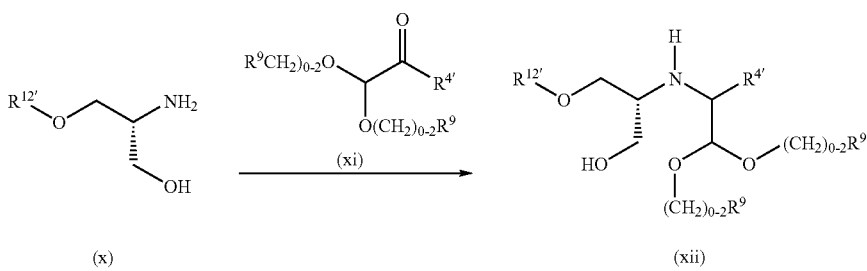

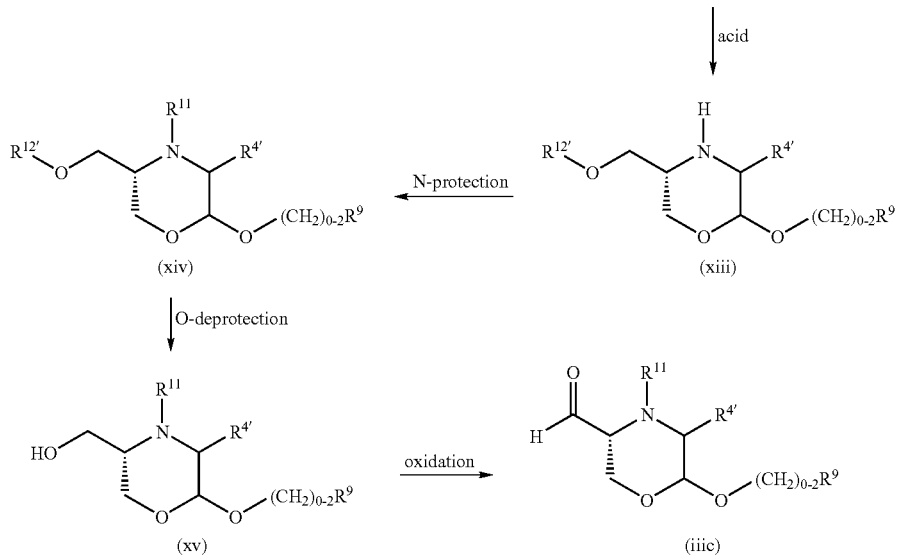

A protected serinol (x) is condensed with an appropriate α,α-disubstituted ketone (xi) in the presence of acid. The resulting imine or enamine is reduced with an appropriate hydride reducing agent, such as sodium cyanoborohydride, to provide the corresponding amine (xii). This amine is then cyclized in the presence of a suitable acid, such as camphorsulfonic acid, to provide the morpholine (xiii). The morpholine nitrogen is protected under standard conditions to provide intermediate (xiv) which is then O-deprotected to provide alcohol (xv), and then oxidized as described in the previous scheme to provide the desired aldehyde (iiic).

Further aldehydes of formula (iii) may be prepared as described in the following scheme where $R^9$ and $R^{11}$ are as previously defined and $R^{12'}$ is an oxygen protecting group.

resulting intermediate (xvii) is reacted with a dehydrating agent, such as 1,1'-azobis(N,N-dimethylformamide) or N,N-tetramethylazodicarboxamide in the presence of tri-n-butylphosphine, to provide the protected morpholine (xviii). This intermediate is then O-deprotected to provide alcohol (xix), which is then oxidized as described in the previous schemes to provide the desired aldehyde (iiid).

Alternatively, the skilled artisan will appreciate that the compounds of Formula I may also be prepared such that the morpholine ring is assembled by applying the synthetic methodology described in Schemes IV, V, and VI to aminoalcohols of Formula V where $R^1$, $R^{2'}$, $R^{11'}$ and $R^{12'}$ are as previously defined and $R^{11}$ is independently at each occurrence a nitro- Scheme VI

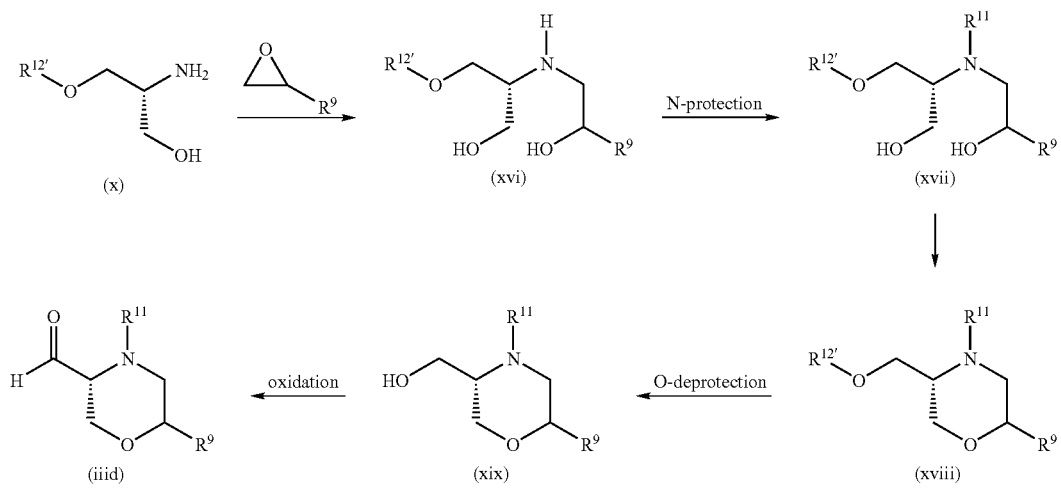

A protected serinol (x) is reacted with an appropriate epoxide or p-toluenesulfonate ester to provide the diol (xvi). The amine moiety is protected under standard conditions and the gen protecting group, and of Formula VI where $R^1$, $R^{2'}$, and $R^{12'}$ are as previously defined and $R^{11'}$ is either hydrogen or a nitrogen protecting group:

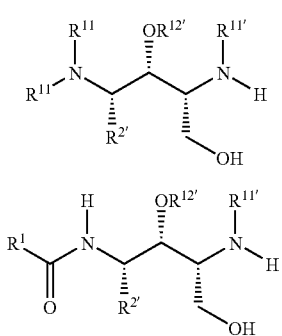

The requisite aminoalcohols V and VI may be prepared as described in the following scheme where variables $R^1$, $R^{2'}$, $R^{11}$, $R^{11'}$, and $R^{12'}$ are as previously defined.

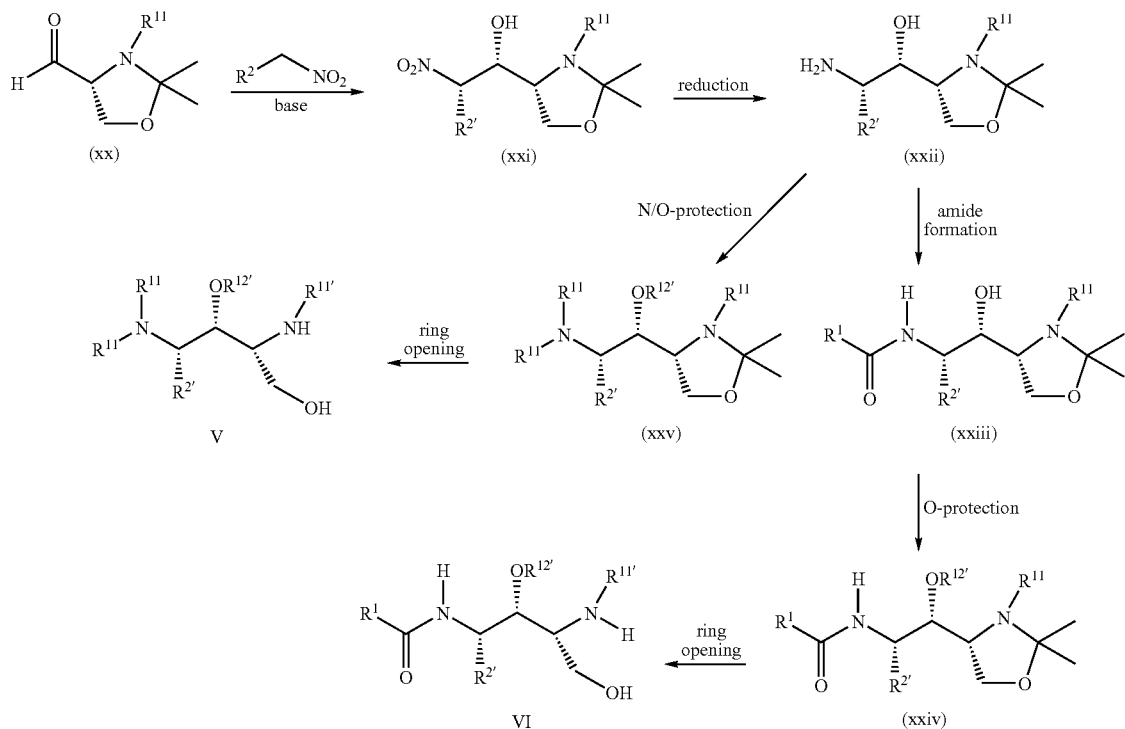

Scheme VII

An appropriately substituted nitromethane is reacted with an N-protected 4-formyl-2,2-dimethyloxazolidine (xx) in the presence of a suitable base, preferably tetrabutylammonium fluoride, in a suitable solvent, preferably tetrahydrofuran, to provide the nitro derivative (xxi). The amount of base employed is not critical and may be in excess or catalytic amounts depending upon the specific circumstances. Preferably 50 mol % is employed. The nitro group is reduced under standard reducing conditions, such as with sodium borohydride in the presence of nickel(II) chloride, to provide the corresponding amine (xxii). The amine-(xxii) is reacted with an appropriate carboxylic acid or carboxylic acid equivalent as previously discussed to provide the desired amide (xxiii). The hydroxy group is protected with an oxygen protecting group under standard conditions to provide the protected alcohol (xxiv). The oxazolidine ring is then hydrolyzed under standard conditions to provide the aminoalcohol VI. Alternatively, the amine intermediate (xxii) may be fully protected sequentially, or conveniently the hydroxyl and amino groups may be fully protected with, for example, an appropriate benzyl protecting group to provide intermediate (xxv). The oxazolidine ring is then hydrolyzed as previously described to provide the aminoalcohol V. The skilled artisan will appreciate that the protecting group on the oxazolidine nitrogen may be removed if necessary or desired in the same step as the ring-opening step or in a separate step to provide aminoalcohols of formula V and VI where $R^{11'}$ is hydrogen. The requisite formyloxazolidines (xx) are either commercially available or may be prepared by standard synthetic techniques.

The requisite vinyl ethers (vi) may be prepared from the appropriate alcohols essentially as described by Okimoto, et al., *Journal of the American Chemical Society*, 124, 1590-1591 (2002), as illustrated in the following scheme where $R^9$ is as previously defined:

Scheme VIII

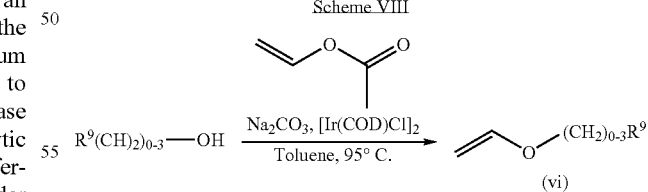

An appropriate alcohol is reacted with vinyl acetate and sodium carbonate in the presence of chloro(1,5-cyclooctadiene)iridium (I) dimer in a suitable solvent, typically toluene at elevated temperature to provide the vinyl ethers (vi). The requisite alcohols are either commercially available or may be prepared by standard synthetic techniques.

The aminoalcohol intermediate V(a) may be converted into additional intermediates useful for preparing certain compounds of Formula I as illustrated in the following scheme where $R^{2'}$, $R^9$, $R^{11}$, and $R^{12'}$ are as previously defined. Where variable $R^{11}$, a nitrogen protecting group, is present in more than one case in a structure in the following scheme, it is understood to be independently selected in each instance.

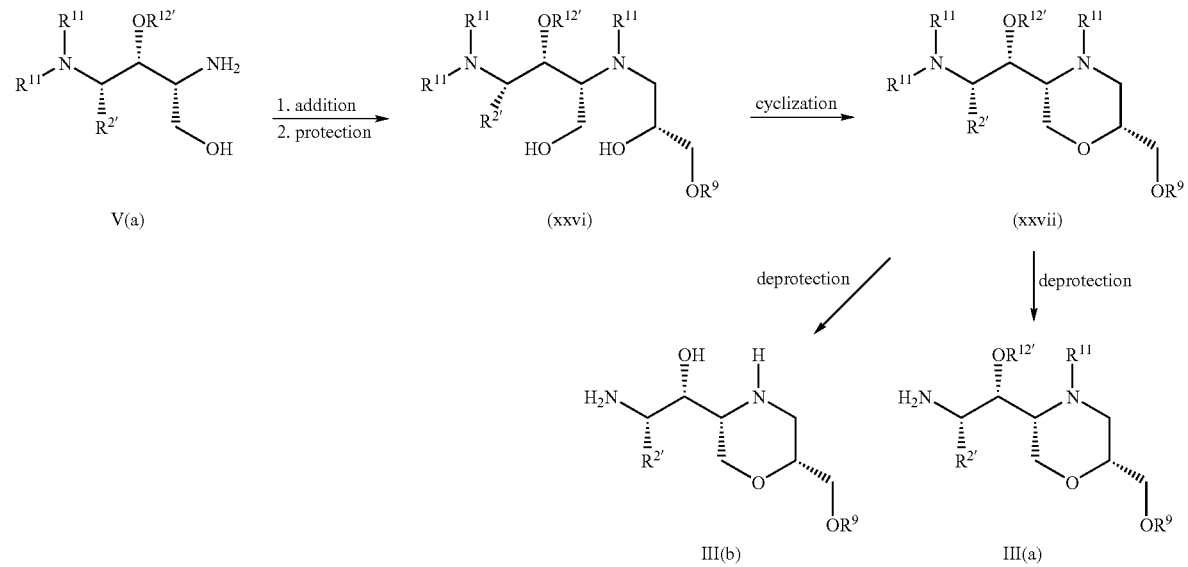

The aminoalcohol V(a) is reacted with an appropriately substituted epoxide and the addition product is then protected with an appropriate nitrogen protecting group, preferably tert-butoxycarbonyl, under standard conditions to provide intermediate (xxvi). This diol intermediate is treated with a dehydrating agent as previously described to provide the protected morpholine (xxvii). This intermediate may be selectively or completely deprotected to provide intermediates III(a) or III(b). These intermediates may then be used to prepare additional compounds of Formula I employing deprotection and amide forming synthetic techniques described in the previous schemes. A useful variation of this scheme is to begin with an appropriately substituted epoxide bearing an oxygen protecting group ($R^{12'}$) instead of the moiety ($R^9$). This protecting group may then be removed at any convenient point in the synthesis of compounds of Formula I to provide a hydroxy moiety that may then be substituted under standard conditions to provide additional compounds of Formula I.

Additional aldehydes of formula (iii) useful for the preparation of compounds of the present invention may be prepared as illustrated in the following scheme where $R^{11}$ and $R^{12}$ are as previously defined and $R^{3''}$ and $R^{4'}$ are independently $C_1$-$C_6$ alkyl.

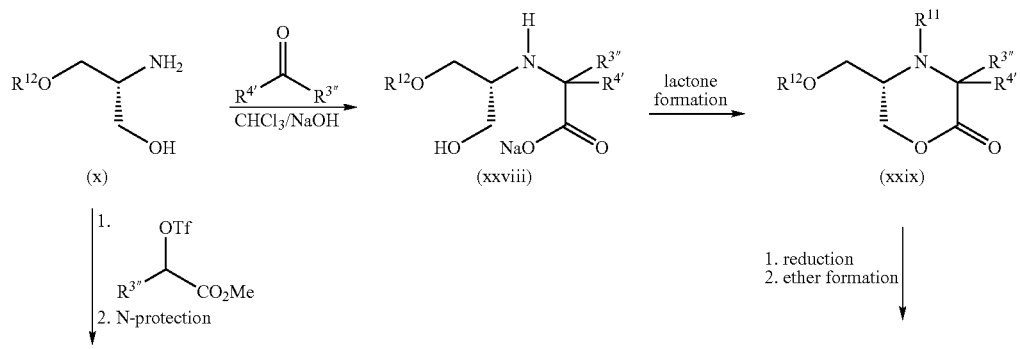

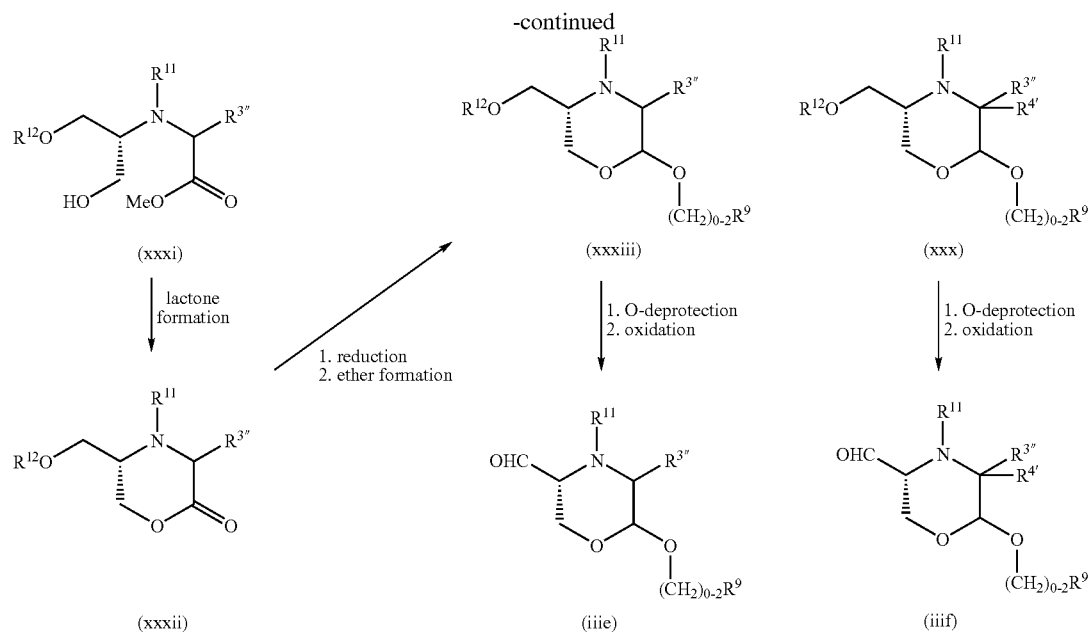

An appropriately substituted serinol (x) (Novachek, et al., Tetrahedron Letters, 37, 1743-1746 (1996)) is reacted with an appropriate ketone and chloroform in the presence of sodium hydroxide essentially as described by Lai (Synthesis, 122-123 (1984)) to provide the hydroxycarboxylate (xxviii). The hydroxycarboxylate is then treated under standard ester forming conditions, for example by reaction with dicyclohexylcarbodiimide (DCC), and then the nitrogen protected under standard conditions to prepare lactone (xxix). The carbonyl is reduced by reaction with a hydride reducing agent, such as diisobutylaluminum hydride (DIBAH) and the corresponding alkoxide alkylated with an appropriate reagent to provide ether (xxx). The primary alcohol is then deprotected, if necessary, and oxidized as previously described to provide aldehyde (iiif). In an analogous manner, the appropriately protected serinol (x) is reacted with an appropriate triflate followed by amine protection to provide the hydroxyester (xxxi). The hydroxy group is deprotonated by reaction with a suitable base, for example sodium hydride, to form the lactone (xxxii). The carbonyl is reduced and alkylated to provide ether (xxxiii) as previously described, and then the protected alcohol is deprotected, if necessary, and oxidized to provide aldehyde (iiie). The skilled artisan will appreciate that the order of these steps may be varied as necessary or desired. The skilled artisan will also appreciate that the synthetic methodology described in the previous scheme may be applied to intermediates V or VI to provide compounds of Formula I.

Additional intermediates useful for the preparation of compounds of Formula I may be prepared as illustrated in the following scheme where $R^{2'}$, $R^5$, $R^3$, $R^{11}$ and $R^{12'}$ are as previously defined. Where variable $R^{11}$, a nitrogen protecting group, is present more than once in a structure in the following scheme, it is understood to be independently selected in each instance.

Scheme XI

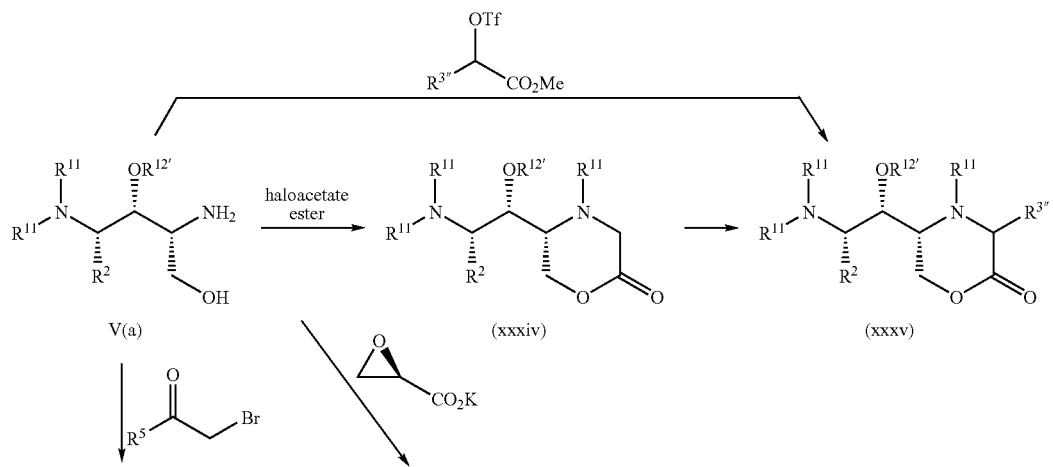

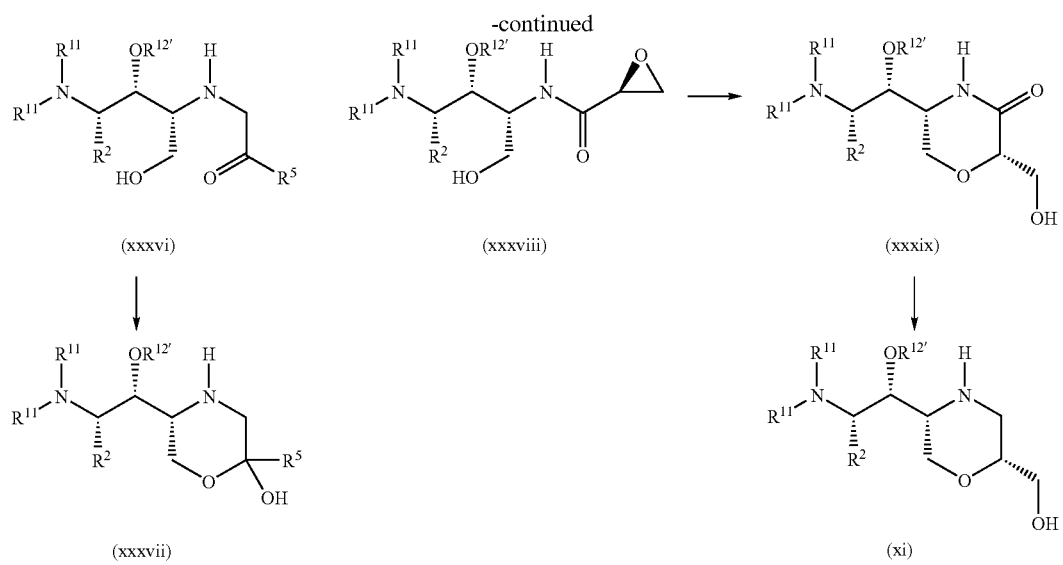

(xxxvi) (xxxviii) (xxxix)

(xxxvii) (xl)

The intermediate aminoalcohol V(a) may be reacted in a number of synthetic pathways to provide more advanced intermediates useful for the preparation of compounds of Formula I. For example, the aminoalcohol V(a) may be treated with an appropriately substituted haloacetate ester, for example methyl or ethyl bromoacetate, to provide the substituted morpholinone (xxxiv). This intermediate may be alkylated under standard conditions to provide the corresponding α-substituted intermediate (xxxv). Alternatively, V(a) may be reacted with an appropriately substituted triflate to provide intermediates of formula (xxxv) directly. Aminoalcohol V(a) may also be treated with an appropriately substituted acetyl compound to provide ketoalcohol (xxxvi). Treatment of this ketoalcohol under standard conditions provides the hemiketal (xxxvii). The aminoalcohol V(a) may also be coupled with oxirane-2-carboxylic acid potassium salt (*Organic Synthesis*, 75, 37-43) to provide the corresponding amidoalcohol (xxxviii). Treatment of this intermediate with an appropriate base, for example, potassium hexamethyldisilazane or potassium hydride, provides the substitituted morpholine (xxxix), which may be subsequently functionalized under standard conditions or the amide carbonyl reduced under standard conditions to provide intermediate (xl). Intermediates (xxxiv), (xxxv), (xxxvii) and (xl), which are further embodiments of the present invention, may be subjected to standard functional group transformation conditions well known to one of ordinary skill in the art, followed by deprotection and coupling reactions described above to provide additional compounds of Formula I. (For example, see: *Comprehensive Organic Transformations*, Larock, Wiley-VCH Publishers, Inc., New York, (1999); *Advanced Organic Chemistry*, March, Wiley Interscience, New York, Third Edition, (1985)).

Compounds of Formula I where $R^2$ is benzyl substituted with a $C_1$-$C_6$ alkoxy moiety optionally further substituted in the alkyl chain with $C_3$-$C_8$ cycloalkyl or up to three times with fluoro may be prepared as described in the following scheme where G, $R^1$, $R^3$, $R^4$, $R^5$, $R^6$, $R^{11}$, and $R^{12}$ are as previously defined, $R^{13}$ is $C_1$-$C_6$ alkyl optionally substituted with $C_3$-$C_8$ cycloalkyl or up to three times with fluoro, and $R^{14}$ is hydrogen or fluoro.

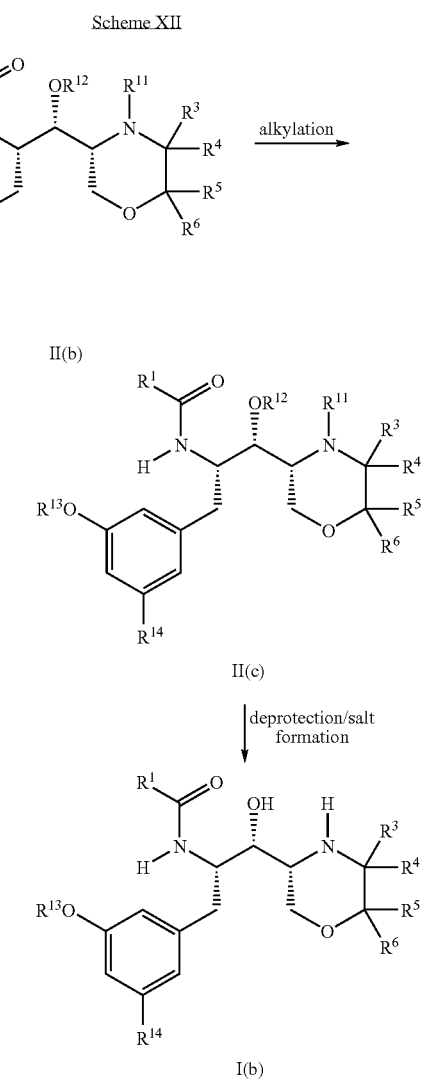

Scheme XII

II(b)

II(c)

deprotection/salt formation

I(b)

The phenol II(b) is reacted with a suitable alkylating reagent, such as an alkyl halide, in the presence of a suitable base, such as cesium carbonate, to provide intermediate II(c). This intermediate is then deprotected under standard conditions as previously described to provide a compound of Formula I(b). If necessary or desired, the deprotected compound may be converted to a pharmaceutically acceptable salt under standard conditions. Compounds of Formula II(b), II(c), and I(b) represent preferred embodiments of the present invention.

Preparation 1

3,5-Difluorophenyl nitroethane 1-(3,5-Difluorophenyl)-2-nitroethanol
Add nitromethane (200 mL) to a suspension of potassium carbonate (30 g) and 3,5-difluorobenzaldehyde (200 g) in tetrahydrofuran (600 mL) at room temperature. Stir at room temperature overnight, filter, wash with ethyl acetate and concentrate to give the desired compound as a crude oil (330 g) which is used in the next step without further purification.

1,3-Difluoro-5-(2-nitrovinyl)-benzene
Add acetic anhydride (160 mL) to a solution of 1-(3,5-difluorophenyl)-2-nitroethanol (330 g) and 4-dimethylaminopyridine (18 g) in dichloromethane (1000 mL), over 30 minutes and stir the reaction mixture overnight. Dilute with dichloromethane (600 mL) and wash with 2% aqueous hydrochloric acid, saturated aqueous sodium chloride, saturated aqueous sodium bicarbonate, dry (magnesium sulfate) and concentrate. Wash the crude with hexanes to give the desired compound (220 g).

3,5-Difluorophenyl nitroethane
Add portionwise sodium borohydride (12 g) over 1.5 hours to a solution of 1,3-difluoro-5-(2-nitrovinyl)-benzene (100 g) in a mixture of dimethylsulfoxide (400 mL) and acetic acid (80 mL) at room temperature using a water bath to keep the temperature below 30° C. Dilute with ethyl acetate (1000 mL) and wash with water (600 mL), saturated aqueous sodium bicarbonate (2×600 mL), saturated aqueous sodium chloride (600 mL), dry (magnesium sulfate) concentrate and purify (silica gel chromatography, eluting with 3:97 ethyl acetate:hexanes) to give the title compound as a pale yellow liquid (63 g, 62%).

Preparation 2

1-Fluoro-2-(2-vinyloxyethyl)-benzene

Combine 2-(2-fluorophenyl)-ethanol (3.08 g, 22.0 mmol), vinyl acetate (4 mL, 43.3 mmol), anhydrous toluene (22 mL), chloro(1,5-cyclooctadiene)iridium(I) dimer (155 mg, 0.231 mmol), and anhydrous sodium carbonate (1.5 g, 14.2 mmol) in a dry round-bottom flask fitted with a reflux condensor under a nitrogen atmosphere. Heat the resulting mixture to 95° C. for 5 hours. Cool the reaction mixture to room temperature. Vacuum filter the resultant slurry to remove inorganic precipitates, washing the collected solid with hexanes. Concentrate and purify (silica gel chromatography, eluting with hexanes) to give the title compound as a yellow oil (2.64 g, 72%).
$^1$H-NMR (400 MHz, CDCl$_3$) δ 7.27-7.18 (m, 2H), 7.10-7.00 (m, 2H), 6.46 (dd, J=6.8, 14.0 Hz, 1H), 4.20 (dd, J=1.6, 14.0 Hz, 1H), 4.01 (dd, J=1.6, 6.4 Hz, 1H), 3.91 (at, J=7.2 Hz, 2H), 3.02 (at, J=7.2 Hz, 2H).

The vinyl ethers of Preparations 3-20 may be prepared essentially as described in Preparation 2.

| Prep | Name |
|------|------|
| 3 | (3-Vinyloxypropyl)cyclopentane |
| 4 | Vinyloxymethylcycloheptane |
| 5 | 1-Vinyloxymethyladamantane |
| 6 | Vinyloxymethylcyclohexane |
| 7 | 1-Trifluoromethyl-2-(2-vinyloxyethyl)-benzene |
| 8 | 1-Methyl-3-(2-vinyloxyethyl)-benzene |
| 9 | Vinyloxyethylcyclohexane |
| 10 | Vinyloxymethylcyclopentane |
| 11 | Vinyloxymethylcyclooctane |
| 12 | 4-Vinyloxymethyltetrahydropyran |
| 13 | Trans-1-Methyl-4-vinyloxymethylcyclohexane |
| 14 | 1-Methylvinyloxymethylcyclohexane |
| 15 | 1-Fluorovinyloxymethylcyclohexane |
| 16 | 4-Fluoro-4-vinyloxymethyltetrahydropyran |
| 17 | Cis-1-tert-butyl-3-vinyloxycyclobutane |
| 18 | (1R,2S,4S)-1-Isopropyl-4-methyl-2-vinyloxycyclohexane |
| 19 | (1S,2R,4R)-1-Isopropyl-4-methyl-2-vinyloxycyclohexane |
| 20 | (1S,2R,5S)-6,6-Dimethyl-2-vinyloxymethylbicyclo[3.1.1]-heptane |

Preparation 21

3,3-Dimethyl-1-vinyloxybutane

Add chloro(1,5-cyclooctadiene)iridium(I) dimer (0.39 g, 0.59 mmol) to 3,3-dimethylbutan-1-ol (3.00 g, 29.35 mmol), vinyl acetate (10.11 g, 117.42 mmol) and sodium carbonate (1.87 g, 17.61 mmol) in benzene (10 mL) at room temperature. Boil under nitrogen 12 hours. Cool to room temperature and filter. Distill the filtrate and collect fraction boiling ~125° C.-130° C. Flush through a silica gel pad with hexanes and concentrate to provide the title compound.

Preparation 22

3-Methyl-1-vinyloxybutane

The title compound may be prepared essentially as described in Preparation 21 and isolated by fractional distillation (collecting the fraction boiling from ~110° C. to 115° C.) followed by flushing through a silica gel pad with hexanes.

Preparation 23

2,2-Dimethyl-1-vinyloxypropane

Boil 2,2-dimethylpropan-1-ol (2.41 g, 27.34 mmol) and mercury (II) trifluoroacetate (1.17 g, 2.73 mmol) in ethyl vinyl ether (19.71 g, 273.40 mmol) under nitrogen for 2 hours. Concentrate to ~10 mL. Dilute with pentane. Wash with 10% aqueous potassium carbonate and saturated aqueous sodium chloride. Dry (magnesium sulfate), filter, concentrate and purify (silica gel chromatography, eluting with pentane) to give the title compound.

The vinyl ethers of Preparations 24-44 may be prepared essentially as described in Preparation 23 starting with the appropriate alcohols.

| Prep | Name |
|---|---|
| 24 | Cis-1-Methoxy-4-vinyloxymethylcyclohexane |
| 25 | Trans-1-Methoxy-4-vinyloxymethylcyclohexane |
| 26 | 1,1-Difluoro-4-vinyloxymethylcyclohexane |
| 27 | 4-Methyl-4-vinyloxymethyltetrahydropyran |
| 28 | 2,2-Dimethyl-1-vinyloxypropane |
| 29 | (R)-2-Vinyloxymethyltetrahydrofuran |
| 30 | 1-Vinyloxy-methylbicyclo[2.2.1]heptane |
| 31 | 1-(1-Cyclohexylcyclopropoxy)-ethenol |
| 32 | (1-Vinyloxymethylcyclohexylmethyl)-benzene |
| 33 | 1-Methyl-1-vinyloxymethylcyclopentane |
| 34 | ((R)-1-Vinyloxyethyl)-cyclohexane |
| 35 | (1-Vinyloxymethylcyclopentylmethyl)-benzene |
| 36 | 4-Vinyloxymethylcyclohexanone |
| 37 | ((1R,2S)-2-Vinyloxycyclohexyl)-benzene |
| 38 | 2,2-Dimethyl-1-vinyloxypentane |
| 39 | 1,1,1,3,3,3-Hexafluoro-2-methyl-2-vinyloxymethylpropane |
| 40 | 2,2-Dimethyl-1-vinyloxybutane |
| 41 | 2,2-Dimethyl-1-vinyloxypentane |
| 42 | (1-Vinyloxymethylcyclopentyl)-benzene |
| 43 | ((S)-1-Vinyloxyethyl)-cyclohexane |
| 44 | 2,2,4-Trimethyl-1-vinyloxypentane |

Preparation 45

[(1R,2S,3S)-3-Acetylamino-2-benzyloxy-4-(3,5-difluorophenyl)-1-hydroxymethylbutyl]-carbamic acid tert-butyl ester

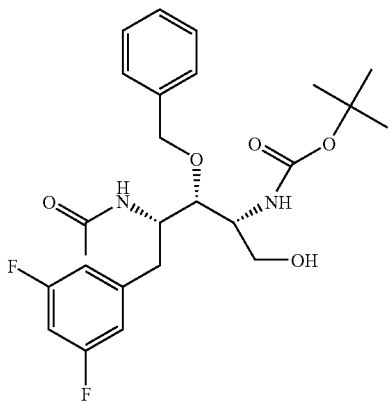

4-[(1R,2S)-3-(3,5-Difluorophenyl)-1-hydroxy-2-nitropropyl]-2,2-dimethyloxazolidine-3-carboxylic acid tert-butyl ester Dissolve (R)-tert-butyl 4-formyl-2,2-dimethyloxazolidine-3-carboxylate (1.60 g, 6.98 mmol) and 1,3-difluoro-5-(2-nitroethyl)-benzene (1.40 g, 7.48 mmol) in dry tetrahydrofuran (14 mL) and add 1 M tetrabutylammonium fluoride (TBAF) in tetrahydrofuran (7.0 ml, 7.0 mmol) in one portion. Stir the resulting mixture for 30 minutes and then dilute with ethyl acetate. Quickly shake the mixture with water and then add a small amount of saturated aqueous sodium chloride. Discard the aqueous phase and wash the organic phase again with water (twice) followed by saturated aqueous sodium chloride. Dry the organic solution over magnesium sulfate (magnesium sulfate), filter, concentrate and purify (silica gel chromatography, eluting with 0:100 to 20:80 ethyl acetate:hexanes) to give the coupling product as an approximately ~80:20 mixture of diastereomers (2.45 g, 84%). Isolate the major isomer by recrystallization of the diastereomeric mixture from dichloromethane (dichloromethane)/hexanes or diethyl ether/hexanes) to give 1.26 g of the desired compound as a white crystalline solid.

MS(ES): 439.3 m/z=[M+Na]

(R)-4-[(1S,2S)-2-Amino-3-(3,5-difluorophenyl)-1-hydroxypropyl]-2,2-dimethyloxazolidine-3-carboxylic acid tert-butyl ester Combine (R)-4-[(1R,2S)-3-(3,5-difluorophenyl)-1-hydroxy-2-nitropropyl]-2,2-dimethyloxazolidine-3-carboxylic acid tert-butyl ester (1.13 g, 2.71 mmol) and nickel (II) chloride (0.58 g, 4.485 mmol) in dry methanol (30 ml) and add sodium borohydride (0.454 g, 12 mmol) over 1 minute. Stir the resulting mixture for 20 minutes and then add water (3 mL). Concentrate and dissolve the residue in ethyl acetate. Filter the black solution through a pad of Celite® and wash the filter cake with ethyl acetate. Wash the filtrate with water (twice), saturated aqueous sodium chloride, dry (magnesium sulfate), filter, and concentrate to give the desired compound as a white solid (920 mg, 95%).

(R)-4-[(1S,2S)-2-Acetylamino-3-(3,5-difluorophenyl)-1-hydroxypropyl]-2,2-dimethyloxazolidine-3-carboxylic acid tert-butyl ester Dissolve (R)-4-[(1S,2S)-2-amino-3-(3,5-difluorophenyl)-1-hydroxypropyl]-2,2-dimethyloxazolidine-3-carboxylic acid tert-butyl ester (920 mg, 2.38 mmol) in dry tetrahydrofuran (20 ml) under an atmosphere of nitrogen. Add to the resulting solution triethylamine (400 µL, 2.87 mmol) and acetic anhydride (235 µL, 2.49 mmol). After 1 hour, dilute with ethyl acetate and wash with water (twice), 0.1 N hydrochloric acid, and saturated aqueous sodium chloride. Dry (magnesium sulfate), filter, concentrate and purify (silica gel chromatography 0:100 to 70:30 ethyl acetate:hexanes) to give the desired compound as a white solid (738 mg, 72% yield).

MS(ES): 451.2 m/z=[M+Na]

(R)-4-[(1S,2S)-2-Acetylamino-1-benzyloxy-3-(3,5-difluoro-phenyl)-propyl]-2,2-dimethyloxazolidine-3-carboxylic acid tert-butyl ester Suspend (R)-4-[(1S,2S)-2-acetylamino-3-(3,5-difluorophenyl)-1-hydroxypropyl]-2,2-dimethyloxazolidine-3-carboxylic acid tert-butyl ester (4.78 g, 11.2 mmol) in dry tetrahydrofuran (115 ml) under a nitrogen atmosphere and add sodium hydride NaH (60% weight dispersion in mineral oil, 1.17 g, 29.3 mmol). Stir the resulting mixture for 30 minutes and then add sequentially sodium iodide (600 mg, 4.0 mmol) and benzyl bromide (2.7 mL, 22.7 mmol). Stir the resulting mixture for 2.5 hours and then quench by the addition of a 1:1 mixture of saturated aqueous ammonium chloride and saturated aqueous sodium chloride. Dilute the resulting mixture with ethyl acetate and discard the aqueous phase. Wash the organic phase with saturated aqueous sodium chloride, dry over magnesium sulfate, filter, concentrate and purify (silica gel chromatography, eluting with 0:100 to 40:60 ethyl acetate:hexanes) to give the desired compound as a white foam (4.96 g, 85%).

MS(ES): 519.2 m/z=[M+H]

Hydrolysis

Dissolve (R)-4-[(1S,2S)-2-acetylamino-1-benzyloxy-3-(3,5-difluorophenyl)-propyl]-2,2-dimethyloxazolidine-3-carboxylic acid tert-butyl ester (4.96 g, 9.56 mmol) in methanol (100 mL). To this solution add p-toluenesulphonic acid monohydrate (200 mg, 1.05 mmol.) and water (150 µL, 8.33 mmol). Heat the resulting mixture to reflux for 5.5 hours and then dilute the reaction mixture with ethyl acetate. Wash the resulting solution with saturated aqueous sodium bicarbonate followed by saturated aqueous sodium chloride. Dry (magnesium sulfate), filter, concentrate and purify (silica gel chromatography, eluting with 0:100 to 90:10 ethyl acetate:hexanes) to give the title compound as a white foam (3.48 g, 76%).

MS(ES): 479.4 m/z=[M+H]

Preparation 46

(a) (2R,5R)-5-[(1S,2S)-2-Acetylamino-1-benzyloxy-3-(3,5-difluorophenyl)-propyl]-2-(3,3-dimethylbutoxy)-morpholine-4-carboxylic acid tert-butyl ester (b) (2S,5R)-5-[(1S,2S)-2-Acetylamino-1-benzyloxy-3-(3,5-difluorophenyl)-propyl]-2-(3,3-dimethylbutoxy)-morpholine-4-carboxylic acid tert-butyl ester

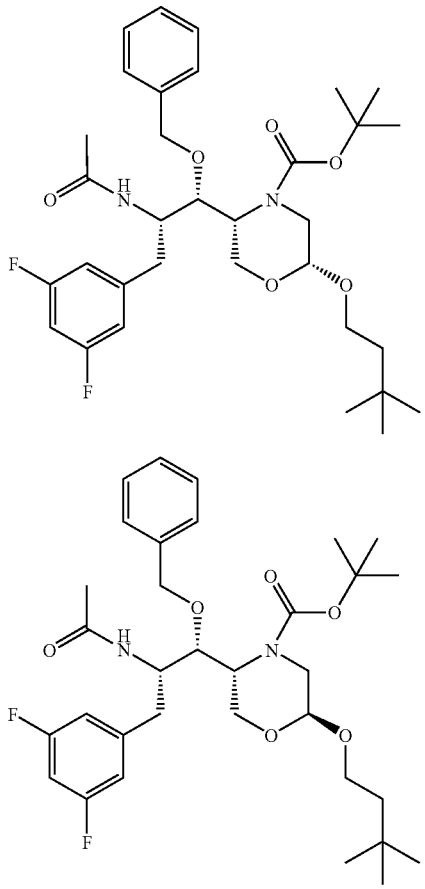

{(1R,2S,3S)-3-Acetylamino-2-benzyloxy-4-(3,5-difluorophenyl)-1-[1-(3,3-dimethylbutoxy)-2-iodo-ethoxymethyl]-butyl}-carbamic acid tert-butyl ester

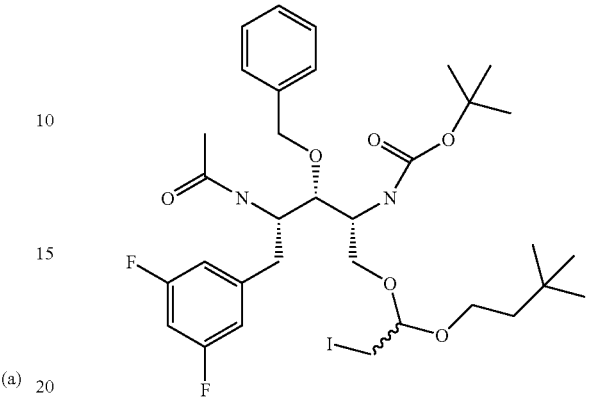

Dissolve [(1R,2S,3S)-3-acetylamino-2-benzyloxy-4-(3,5-difluorophenyl)-1-hydroxymethyl-butyl]-carbamic acid tert-butyl ester (0.52 g, 1.09 mmol) and 3,3-dimethyl-1-vinyloxybutane (0.15 g, 1.20 mmol) in acetonitrile (6 mL) and add N-iodosuccinimide (0.27 g, 1.20 mmol) at room temperature. Heat in oil bath at 80° C. for 2 hours 45 minutes. Cool to room temperature, dilute with ethyl acetate, wash with water or 10% aqueous sodium thiosulfate, saturated aqueous sodium chloride, concentrate and purify (silica gel chromatography, eluting with 10:90 to 30:70 ethyl acetate:hexanes) to give the title compound (0.557 g, 70% yield).

MS(ES): 733.4 m/z=[M+H]

Cyclization

Dissolve {(1R,2S,3S)-3-Acetylamino-2-benzyloxy-4-(3,5-difluorophenyl)-1-[1-(3,3-dimethylbutoxy)-2-iodo-ethoxymethyl]-butyl}-carbamic acid tert-butyl ester (0.53 g, 0.72 mmol) in N,N-dimethylformamide (6.5 mL) and add sodium hydride (0.06 g, 1.58 mmol) at room temperature. Heat in an oil bath at 55° C. for 80 minutes. Cool to room temperature and pour into saturated aqueous ammonium chloride. Extract with ethyl acetate, wash with either 1 N lithium chloride or water and saturated aqueous sodium chloride. Dry (magnesium sulfate), filter, concentrate and purify (silica gel chromatography, eluting with 15:85 to 30:70 ethyl acetate:hexanes) to give:

(a) less polar diastereomer, 0.186 g, 43% yield. MS(ES): m/z=605.5 [M+H]; and (b) more polar diastereomer, 0.182 g, 42% yield. MS(ES): m/z=605.5 [M+H]

The compounds of Preparations 47-107 may be prepared essentially as described in Preparation 46.

| Prep | Compound | MS (ES) [M + H] |
|---|---|---|
| 47 | (a) (2R,5R)-5-[(1S,2S)-2-Acetylamino-1-benzyloxy-3-(3,5-difluorophenyl)-propyl]-2-isobutoxymorpholine-4-carboxylic acid tert-butyl ester | (a) 577.4 |
| | (b) (2S,5R)-5-[(1S,2S)-2-Acetylamino-1-benzyloxy-3-(3,5-difluorophenyl)-propyl]-2-isobutoxymorpholine-4-carboxylic acid tert-butyl ester | (b) 577.4 |

| Prep | Compound | MS (ES) [M + H] |
|---|---|---|
| 48 | (a) (2R,5R)-5-[(1S,2S)-2-Acetylamino-1-benzyloxy-3-(3,5-difluorophenyl)-propyl]-2-(3-methylbutoxy)-morpholine-4-carboxylic acid tert-butyl ester | (a) 591.4 |
|  | (b) (2S,5R)-5-[(1S,2S)-2-Acetylamino-1-benzyloxy-3-(3,5-difluorophenyl)-propyl]-2-(3-methylbutoxy)-morpholine-4-carboxylic acid tert-butyl ester | (b) 591.4 |
| 49 | (a) (2R,5R)-5-[(1S,2S)-2-Acetylamino-1-benzyloxy-3-(3,5-difluorophenyl)-propyl]-2-[2-(2-fluorophenyl)-ethoxy]-morpholine-4-carboxylic acid tert-butyl ester. | (a) 643.4 |
|  | (b) (2S,5R)-5-[(1S,2S)-2-Acetylamino-1-benzyloxy-3-(3,5-difluorophenyl)-propyl]-2-[2-(2-fluorophenyl)-ethoxy]-morpholine-4-carboxylic acid tert-butyl ester | (b) 643.4 |
| 50 | (a) (2R,5R)-5-[(1S,2S)-2-Acetylamino-1-benzyloxy-3-(3,5-difluorophenyl)-propyl]-2-(3-cyclopentylpropoxy)-morpholine-4-carboxylic acid tert-butyl ester | (a) 631.5 |
|  | (b) (2S,5R)-5-[(1S,2S)-2-Acetylamino-1-benzyloxy-3-(3,5-difluorophenyl)-propyl]-2-(3-cyclopentylpropoxy)-morpholine-4-carboxylic acid tert-butyl ester. | (b) 631.4 |
| 51 | (a) (2R,5R)-5-[(1S,2S)-2-Acetylamino-1-benzyloxy-3-(3,5-difluorophenyl)-propyl]-2-cycloheptylmethoxymorpholine-4-carboxylic acid tert-butyl ester | (a) 631.4 |
|  | (b) (2S,5R)-5-[(1S,2S)-2-Acetylamino-1-benzyloxy-3-(3,5-difluorophenyl)-propyl]-2-cycloheptylmethoxymorpholine-4-carboxylic acid tert-butyl ester | (b) 631.5 |
| 52 | (a) (2R,5R)-5-[(1S,2S)-2-Acetylamino-1-benzyloxy-3-(3,5-difluorophenyl)-propyl]-2-(adamantan-1-ylmethoxy)-morpholine-4-carboxylic acid tert-butyl ester | (a) 667.2 [M − H] |
|  | (b) (2S,5R)-5-[(1S,2S)-2-Acetylamino-1-benzyloxy-3-(3,5-difluorophenyl)-propyl]-2-(adamantan-1-ylmethoxy)-morpholine-4-carboxylic acid tert-butyl ester | (b) 667.2 [M − H] |
| 53 | (a) (2R,5R)-5-[(1S,2S)-2-Acetylamino-1-benzyloxy-3-(3,5-difluorophenyl)-propyl]-2-[2-(2-trifluoromethylphenyl)-ethoxy]-morpholine-4-carboxylic acid tert-butyl ester | (a) 691.2 [M − H] |
|  | (b) (2S,5R)-5-[(1S,2S)-2-Acetylamino-1-benzyloxy-3-(3,5-difluorophenyl)-propyl]-2-[2-(2-trifluoromethylphenyl)-ethoxy]-morpholine-4-carboxylic acid tert-butyl ester | (b) 691.2 [M − H] |
| 54 | (a) (2R,5R)-5-[(1S,2S)-2-Acetylamino-1-benzyloxy-3-(3,5-difluorophenyl)-propyl]-2-(2-m-tolylethoxy)-morpholine-4-carboxylic acid tert-butyl ester | (a) 637.3 [M − H] |
|  | (b) (2S,5R)-5-[(1S,2S)-2-Acetylamino-1-benzyloxy-3-(3,5-difluorophenyl)-propyl]-2-(2-m-tolylethoxy)-morpholine-4-carboxylic acid tert-butyl ester | (b) 639.4 [M + H] |
| 55 | (a) (2R,5R)-5-[(1S,2S)-2-Acetylamino-1-benzyloxy-3-(3,5-difluorophenyl)-propyl]-2-(2-cyclohexylethoxy)-morpholine-4-carboxylic acid tert-butyl ester | (a) 629.2 [M − H] |
|  | (b) (2S,5R)-5-[(1S,2S)-2-Acetylamino-1-benzyloxy-3-(3,5-difluorophenyl)-propyl]-2-(2-cyclohexylethoxy)-morpholine-4-carboxylic acid tert-butyl ester | (b) 629.5 [M − H] |
| 56 | (a) (2R,5R)-5-[(1S,2S)-2-Acetylamino-1-benzyloxy-3-(3,5-difluorophenyl)-propyl]-2-cyclopentylmethoxymorpholine-4-carboxylic acid tert-butyl ester | (a) 601.3 [M − H] |
|  | (b) (2S,5R)-5-[(1S,2S)-2-Acetylamino-1-benzyloxy-3-(3,5-difluorophenyl)-propyl]-2-cyclopentylmethoxymorpholine-4-carboxylic acid tert-butyl ester | (b) 601.3 [M − H] |
| 57 | (a) (2R,5R)-5-[(1S,2S)-2-Acetylamino-1-benzyloxy-3-(3,5-difluorophenyl)-propyl]-2-cyclooctylmethoxymorpholine-4-carboxylic acid tert-butyl ester | (a) 643.2 [M − H] |
|  | (b) (2S,5R)-5-[(1S,2S)-2-Acetylamino-1-benzyloxy-3-(3,5-difluorophenyl)-propyl]-2-cyclooctylmethoxymorpholine-4-carboxylic acid tert-butyl ester | (b) 643.2 [M − H] |
| 58 | (a) (2R,5R)-5-[(1S,2S)-2-Acetylamino-1-benzyloxy-3-(3,5-difluorophenyl)-propyl]-2-(tetrahydropyran-4-ylmethoxy)-morpholine-4-carboxylic acid tert-butyl ester | (a) 619.2 [M + H] |
|  | (b) (2S,5R)-5-[(1S,2S)-2-Acetylamino-1-benzyloxy-3-(3,5-difluorophenyl)-propyl]-2-(tetrahydropyran-4-ylmethoxy)-morpholine-4-carboxylic acid tert-butyl ester | (b) 617.3 [M − H] |
| 59 | (a) (2R,5R)-5-[(1S,2S)-2-Acetylamino-1-benzyloxy-3-(3,5-difluorophenyl)-propyl]-2-(4-methylcyclohexylmethoxy)-morpholine-4-carboxylic acid tert-butyl ester | (a) 631.2 [M + H] |
|  | (b) (2S,5R)-5-[(1S,2S)-2-Acetylamino-1-benzyloxy-3-(3,5-difluorophenyl)-propyl]-2-(4-methylcyclohexylmethoxy)-morpholine-4-carboxylic acid tert-butyl ester | (b) 629.2 [M − H] |

-continued

| Prep | Compound | MS (ES) [M + H] |
|---|---|---|
| 60 | (a) (2R,5R)-5-[(1S,2S)-2-Acetylamino-1-benzyloxy-3-(3,5-difluorophenyl)-propyl]-2-(1-methylcyclohexylmethoxy)-morpholine-4-carboxylic acid tert-butyl ester | (a) 631.2 [M + H] |
| | (b) (2S,5R)-5-[(1S,2S)-2-Acetylamino-1-benzyloxy-3-(3,5-difluorophenyl)-propyl]-2-(1-methylcyclohexylmethoxy)-morpholine-4-carboxylic acid tert-butyl ester | (b) 629.2 [M − H] |
| 61 | (a) (2R,5R)-5-[(1S,2S)-2-Acetylamino-1-benzyloxy-3-(3,5-difluorophenyl)-propyl]-2-(1-fluorocyclohexylmethoxy)-morpholine-4-carboxylic acid tert-butyl ester | (a) 633.3 [M − H] |
| | (b) (2S,5R)-5-[(1S,2S)-2-Acetylamino-1-benzyloxy-3-(3,5-difluorophenyl)-propyl]-2-(1-fluoro-cyclohexylmethoxy)-morpholine-4-carboxylic acid tert-butyl ester | (b) 633.3 [M − H] |
| 62 | (a) (2S,5R)-5-[(1S,2S)-2-Acetylamino-1-benzyloxy-3-(3,5-difluorophenyl)-propyl]-2-(4-fluorotetrahydropyran-4-ylmethoxy)-morpholine-4-carboxylic acid tert-butyl ester | (a) 635.2 [M − H] |
| | (b) (2R,5R)-5-[(1S,2S)-2-Acetylamino-1-benzyloxy-3-(3,5-difluorophenyl)-propyl]-2-(4-fluorotetrahydropyran-4-ylmethoxy)-morpholine-4-carboxylic acid tert-butyl ester | (b) 635.2 [M − H] |
| 63 | (a) (2S,5R)-5-[(1S,2S)-2-Acetylamino-1-benzyloxy-3-(3,5-difluorophenyl)-propyl]-2-(3-tert-butylcyclobutoxy)-morpholine-4-carboxylic acid tert-butyl ester | (a) 629.2 [M − H] |
| | (b) (2R,5R)-5-[(1S,2S)-2-Acetylamino-1-benzyloxy-3-(3,5-difluorophenyl)-propyl]-2-(3-tert-butyl-cyclobutoxy)-morpholine-4-carboxylic acid tert-butyl ester | (b) 629.2 [M − H] |
| 64 | (a) (2S,5R)-5-[(1S,2S)-2-Acetylamino-1-benzyloxy-3-(3,5-difluorophenyl)-propyl]-2-((1R,2S,5R)-2-isopropyl-5-methylcyclohexyloxy)-morpholine-4-carboxylic acid tert-butyl ester | (a) 657.3 [M − H] |
| | (b) (2R,5R)-5-[(1S,2S)-2-Acetylamino-1-benzyloxy-3-(3,5-difluorophenyl)-propyl]-2-((1R,2S,5R)-2-isopropyl-5-methylcyclohexyloxy)-morpholine-4-carboxylic acid tert-butyl ester | (b) 657.3 [M − H] |
| 65 | (a) (2S,5R)-5-[(1S,2S)-2-Acetylamino-1-benzyloxy-3-(3,5-difluorophenyl)-propyl]-2-((1S,2R,5S)-2-isopropyl-5-methylcyclohexyloxy)-morpholine-4-carboxylic acid tert-butyl ester | (a) 657.3 [M − H] |
| | (b) (2R,5R)-5-[(1S,2S)-2-Acetylamino-1-benzyloxy-3-(3,5-difluorophenyl)-propyl]-2-((1S,2R,5S)-2-isopropyl-5-methylcyclohexyloxy)-morpholine-4-carboxylic acid tert-butyl ester | (b) 657.3 [M − H] |
| 66 | (a) (2R,5R)-5-[(1S,2S)-2-Acetylamino-1-benzyloxy-3-(3,5-difluorophenyl)-propyl]-2-((1S,2R,5S)-6,6-dimethylbicyclo[3.1.1]hept-2-ylmethoxy)-morpholine-4-carboxylic acid tert-butyl ester | (a) 655.2 [M − H] |
| | (b) (2S,5R)-5-[(1S,2S)-2-Acetylamino-1-benzyloxy-3-(3,5-difluorophenyl)-propyl]-2-((1S,2R,5S)-6,6-dimethylbicyclo[3.1.1]hept-2-ylmethoxy)-morpholine-4-carboxylic acid tert-butyl ester | (b) 655.2 [M − H] |
| 67 | (2R,5R)-5-[(1S,2S)-2-Acetylamino-1-benzyloxy-3-(3,5-difluorophenyl)-propyl]-2-(4-methoxycyclohexylmethoxy)-morpholine-4-carboxylic acid tert-butyl ester-Isomer 1 | 547.6 [M − BOC + H] (APCI) |
| 68 | (2S,5R)-5-[(1S,2S)-2-Acetylamino-1-benzyloxy-3-(3,5-difluorophenyl)-propyl]-2-(4-methoxycyclohexylmethoxy)-morpholine-4-carboxylic acid tert-butyl ester-Isomer 2 | 547.6 [M − BOC + H] (APCI) |
| 69 | (2S,5R)-5-[(1S,2S)-2-Acetylamino-1-benzyloxy-3-(3,5-difluorophenyl)-propyl]-2-(4-methoxycyclohexylmethoxy)-morpholine-4-carboxylic acid tert-butyl ester-Isomer 1 | 647.9 (APCI) |
| 70 | (2R,5R)-5-[(1S,2S)-2-Acetylamino-1-benzyloxy-3-(3,5-difluorophenyl)-propyl]-2-(4-methoxycyclohexylmethoxy)-morpholine-4-carboxylic acid tert-butyl ester-Isomer 2 | 647.9 (APCI) |
| 71 | (2RS,5RS)-5-[(1SR,2SR)-2-Acetylamino-1-benzyloxy-3-(3,5-difluorophenyl)-propyl]-2-(4,4-difluorocyclohexylmethoxy)-morpholine-4-carboxylic acid tert-butyl ester | 653.34 |
| 72 | (2RS,5RS)-5-[(1SR,2SR)-2-Acetylamino-1-benzyloxy-3-(3,5-difluorophenyl)-propyl]-2-(4-methyltetrahydropyran-4-ylmethoxy)-morpholine-4-carboxylic acid tert-butyl ester | 633.56 |
| 73 | (2RS,5RS)-5-[(1SR,2SR)-2-Acetylamino-1-benzyloxy-3-(3,5-difluorophenyl)-propyl]-2-(2,2-dimethylpropoxy)-morpholine-4-carboxylic acid tert-butyl ester | 591.44 |
| 74 | (2S,5R)-5-[(1S,2S)-2-Acetylamino-1-benzyloxy-3-(3,5-difluorophenyl)-propyl]-2-[(R)-1-(tetrahydrofuran-2-yl)methoxy]-morpholine-4-carboxylic acid tert-butyl ester | 605.39 |
| 75 | (2RS,5RS)-5-[(1SR,2SR)-2-Acetylamino-1-benzyloxy-3-(3,5-difluorophenyl)-propyl]-2-(bicyclo[2.2.1]hept-1-ylmethoxy)-morpholine-4-carboxylic acid tert-butyl ester | 629.47 |

-continued

| Prep | Compound | MS (ES) [M + H] |
|---|---|---|
| 76 | (2SR,5RS)-5-[(1SR,2SR)-2-Acetylamino-1-benzyloxy-3-(3,5-difluorophenyl)-propyl]-2-(1-cyclohexylcyclopropoxy)-morpholine-4-carboxylic acid tert-butyl ester | 643.34 |
| 77 | (2R,5R)-5-[(1S,2S)-2-Acetylamino-1-benzyloxy-3-(3,5-difluorophenyl)-propyl]-2-(1-benzylcyclohexylmethoxy)-morpholine-4-carboxylic acid tert-butyl ester | 707.47 |
| 78 | (2RS,5RS)-5-[(1SR,2SR)-2-Acetylamino-1-benzyloxy-3-(3,5-difluorophenyl)-propyl]-2-(1-methylcyclopentylmethoxy)-morpholine-4-carboxylic acid tert-butyl ester | 617.46 |
| 79 | (2S,5R)-5-[(1S,2S)-2-Acetylamino-1-benzyloxy-3-(3,5-difluorophenyl)-propyl]-2-((R)-1-cyclohexylethoxy)-morpholine-4-carboxylic acid tert-butyl ester | 631.49 |
| 80 | (2RS,5RS)-5-[(1SR,2SR)-2-Acetylamino-1-benzyloxy-3-(3,5-difluorophenyl)-propyl]-2-(1-benzylcyclopentylmethoxy)-morpholine-4-carboxylic acid tert-butyl ester | 693.45 |
| 81 | (2RS,5RS)-5-[(1SR,2SR)-2-Acetylamino-1-benzyloxy-3-(3,5-difluorophenyl)-propyl]-2-(4-oxocyclohexylmethoxy)-morpholine-4-carboxylic acid tert-butyl ester | 631.5 |
| 82 | (2S,5R)-5-[(1S,2S)-2-Acetylamino-1-benzyloxy-3-(3,5-difluorophenyl)-propyl]-2-((1S,2R)-2-phenylcyclohexyloxy)-morpholine-4-carboxylic acid tert-butyl ester | 679.5 |
| 83 | (2S,5R)-5-[(1S,2S)-2-Acetylamino-1-benzyloxy-3-(3,5-difluorophenyl)-propyl]-2-(2,2-dimethylpentyloxy)-morpholine-4-carboxylic acid tert-butyl ester | 620.41 |
| 84 | (2R,5R)-5-[(1S,2S)-2-Acetylamino-1-benzyloxy-3-(3,5-difluorophenyl)-propyl]-2-(3,3,3-trifluoro-2-methyl-2-trifluoromethylpropoxy)-morpholine-4-carboxylic acid tert-butyl ester | 699.46 |
| 85 | (2R,5R)-5-[(1S,2S)-2-Acetylamino-1-benzyloxy-3-(3,5-difluorophenyl)-propyl]-2-(2,2-dimethylbutoxy)-morpholine-4-carboxylic acid tert-butyl ester | 605.39 |
| 86 | (2R,5R)-5-[(1S,2S)-2-Acetylamino-1-benzyloxy-3-(3,5-difluorophenyl)-propyl]-2-(2,2-dimethylpentyloxy)-morpholine-4-carboxylic acid tert-butyl ester | 620.41 |
| 87 | (2R,5R)-5-[(1S,2S)-2-Acetylamino-1-benzyloxy-3-(3,5-difluorophenyl)-propyl]-2-(1-phenylcyclopentylmethoxy)-morpholine-4-carboxylic acid tert-butyl ester | 679.48 |
| 88 | (2S,5R)-5-[(1S,2S)-2-Acetylamino-1-benzyloxy-3-(3,5-difluorophenyl)-propyl]-2-((S)-1-cyclohexylethoxy)-morpholine-4-carboxylic acid tert-butyl ester | 631.53 |
| 89 | (2R,5R)-5-[(1S,2S)-2-Acetylamino-1-benzyloxy-3-(3,5-difluorophenyl)-propyl]-2-(2,2,4-trimethylpentyloxy)-morpholine-4-carboxylic acid tert-butyl ester | 633.52 |
| 90 | (2R,5R)-5-[(1S,2S)-2-Acetylamino-1-benzyloxy-3-(3,5-difluorophenyl)-propyl]-2-(2,2-dimethylpropoxy)-morpholine-4-carboxylic acid tert-butyl ester | 591.4 |
| 91 | (2R,5R)-5-[(1S,2S)-2-Acetylamino-1-benzyloxy-3-(3,5-difluorophenyl)-propyl]-2-cyclohexyloxyloxymorpholine-4-carboxylic acid tert-butyl ester | 603.4 |
| 92 | (2S,5R)-5-[(1S,2S)-2-Acetylamino-1-benzyloxy-3-(3,5-difluoro-phenyl)-propyl]-2-cyclohexyloxy-morpholine-4-carboxylic acid tert-butyl ester | 603.4 |
| 93 | (2RS,5RS)-5-[(1SR,2SR)-2-Acetylamino-1-benzyloxy-3-(3,5-difluorophenyl)-propyl]-2-(2,2-dimethylpropoxy)-morpholine-4-carboxylic acid tert-butyl ester | 591.4 |
| 94 | (2SR,5RS)-5-[(1SR,2SR)-2-Acetylamino-1-benzyloxy-3-(3,5-difluorophenyl)-propyl]-2-(3,3-dimethylbutoxy)-morpholine-4-carboxylic acid tert-butyl ester | 605.5 |
| 95 | (2RS,5RS)-5-[(1SR,2SR)-2-Acetylamino-1-benzyloxy-3-(3,5-difluoro-phenyl)-propyl]-2-(3,3-dimethyl-butoxy)-morpholine-4-carboxylic acid tert-butyl ester | 605.5 |
| 96 | (2SR,5RS)-5-[(1SR,2SR)-2-Acetylamino-1-benzyloxy-3-(3,5-difluorophenyl)-propyl]-2-(3-methylbutoxy)-morpholine-4-carboxylic acid tert-butyl ester | 591.4 |
| 97 | (2RS,5RS)-5-[(1SR,2SR)-2-Acetylamino-1-benzyloxy-3-(3,5-difluorophenyl)-propyl]-2-(3-methylbutoxy)-morpholine-4-carboxylic acid tert-butyl ester | 591.4 |

Preparation 98

(2R,5R)-5-[(1S,2S)-2-Acetylamino-3-(3,5-difluorophenyl)-1-hydroxypropyl]-2-(3,3-dimethylbutoxy)-morpholine-4-carboxylic acid tert-butyl ester Stir (2S,5R)-5-[(1S,2S)-2-Acetylamino-1-benzyloxy-3-(3,5-difluorophenyl)-propyl]-2-(3,3-dimethylbutoxy)-morpholine-4-carboxylic acid tert-butyl ester (0.18 g, 0.29 mmol) and 10% palladium on carbon (0.18 g) in ethanol (5 mL) under hydrogen at room temperature for 14 hours. Filter through Celite® and concentrate to give the title compound (0.148 g, 99.4% yield).

MS(ES): m/z=515.4 [M+H]

The compounds of Preparations 99-164 may be prepared essentially as described in Preparation 98.

| Prep | Compound | MS (ES) [M + H] |
|---|---|---|
| 99 | (2S,5R)-5-[(1S,2S)-2-Acetylamino-3-(3,5-difluorophenyl)-1-hydroxypropyl]-2-(3,3-dimethylbutoxy)-morpholine-4-carboxylic acid tert-butyl ester | 515.4 |
| 100 | (2R,5R)-5-[(1S,2S)-2-Acetylamino-3-(3,5-difluorophenyl)-1-hydroxypropyl]-2-isobutoxymorpholine-4-carboxylic acid tert-butyl ester | 487.4 |
| 101 | (2S,5R)-5-[(1S,2S)-2-Acetylamino-3-(3,5-difluorophenyl)-1-hydroxypropyl]-2-isobutoxymorpholine-4-carboxylic acid tert-butyl ester | 487.4 |
| 102 | (2R,5R)-5-[(1S,2S)-2-Acetylamino-3-(3,5-difluorophenyl)-1-hydroxypropyl]-2-(3-methylbutoxy)-morpholine-4-carboxylic acid tert-butyl ester | 501.4 |
| 103 | (2S,5R)-5-[(1S,2S)-2-Acetylamino-3-(3,5-difluorophenyl)-1-hydroxypropyl]-2-(3-methylbutoxy)-morpholine-4-carboxylic acid tert-butyl ester | 501.4 |
| 104 | (2R,5R)-5-[(1S,2S)-2-Acetylamino-3-(3,5-difluorophenyl)-1-hydroxypropyl]-2-[2-(2-fluorophenyl)-ethoxy]-morpholine-4-carboxylic acid tert-butyl ester | 575.2 [M + Na+] |
| 105 | (2S,5R)-5-[(1S,2S)-2-Acetylamino-3-(3,5-difluorophenyl)-1-hydroxypropyl]-2-[2-(2-fluorophenyl)-ethoxy]-morpholine-4-carboxylic acid tert-butyl ester | 575.2 [M + Na+] |
| 106 | (2R,5R)-5-[(1S,2S)-2-Acetylamino-3-(3,5-difluorophenyl)-1-hydroxypropyl]-2-(3-cyclopentylpropoxy)-morpholine-4-carboxylic acid tert-butyl ester | 563.3 [M + Na+] |
| 107 | (2R,5R)-5-[(1S,2S)-2-Acetylamino-3-(3,5-difluorophenyl)-1-hydroxypropyl]-2-cycloheptylmethoxymorpholine-4-carboxylic acid tert-butyl ester | 563.3 [M + Na+] |
| 108 | (2S,5R)-5-[(1S,2S)-2-Acetylamino-3-(3,5-difluorophenyl)-1-hydroxypropyl]-2-cycloheptylmethoxymorpholine-4-carboxylic acid tert-butyl ester | 599.2 [M + $CH_3CO_2^-$] |
| 109 | (2R,5R)-5-[(1S,2S)-2-Acetylamino-3-(3,5-difluorophenyl)-1-hydroxypropyl]-2-(adamantan-1-ylmethoxy)-morpholine-4-carboxylic acid tert-butyl ester | 601.3 [M + Na+] |
| 110 | (2S,5R)-5-[(1S,2S)-2-Acetylamino-3-(3,5-difluorophenyl)-1-hydroxypropyl]-2-(adamantan-1-ylmethoxy)-morpholine-4-carboxylic acid tert-butyl ester | 601.3 [M + Na+] |
| 111 | (2R,5R)-5-[(1S,2S)-2-Acetylamino-3-(3,5-difluorophenyl)-1-hydroxypropyl]-2-cyclohexylmethoxymorpholine-4-carboxylic acid tert-butyl ester | 549.3 [M + Na+] |
| 112 | (2S,5R)-5-[(1S,2S)-2-Acetylamino-3-(3,5-difluorophenyl)-1-hydroxypropyl]-2-cyclohexylmethoxymorpholine-4-carboxylic acid tert-butyl ester | 549.3 [M + Na+] |
| 113 | (2R,5R)-5-[(1S,2S)-2-Acetylamino-3-(3,5-difluorophenyl)-1-hydroxypropyl]-2-[2-(2-trifluoromethylphenyl)-ethoxy]-morpholine-4-carboxylic acid tert-butyl ester | 625.3 [M + Na+] |
| 114 | (2S,5R)-5-[(1S,2S)-2-Acetylamino-3-(3,5-difluorophenyl)-1-hydroxypropyl]-2-(2-m-tolylethoxy)-morpholine-4-carboxylic acid tert-butyl ester | 571.3 [M + Na+] |
| 115 | (2R,5R)-5-[(1S,2S)-2-Acetylamino-3-(3,5-difluorophenyl)-1-hydroxypropyl]-2-(2-m-tolylethoxy)-morpholine-4-carboxylic acid tert-butyl ester | 571.3 [M + Na+] |
| 116 | (2R,5R)-5-[(1S,2S)-2-Acetylamino-3-(3,5-difluorophenyl)-1-hydroxypropyl]-2-(2-cyclohexylethoxy)-morpholine-4-carboxylic acid tert-butyl ester | 539.2 [M − H] |
| 117 | (2R,5R)-5-[(1S,2S)-2-Acetylamino-3-(3,5-difluorophenyl)-1-hydroxypropyl]-2-cyclopentylmethoxymorpholine-4-carboxylic acid tert-butyl ester | 511.2 [M − H] |
| 118 | (2R,5R)-5-[(1S,2S)-2-Acetylamino-3-(3,5-difluorophenyl)-1-hydroxypropyl]-2-cyclooctylmethoxymorpholine-4-carboxylic acid tert-butyl ester | 553.3 [M − H] |
| 119 | (2R,5R)-5-[(1S,2S)-2-Acetylamino-3-(3,5-difluorophenyl)-1-hydroxypropyl]-2-(tetrahydropyran-4-ylmethoxy)-morpholine-4-carboxylic acid tert-butyl ester | 527.2 [M − H] |

-continued

| Prep | Compound | MS (ES) [M + H] |
|---|---|---|
| 120 | (2R,5R)-5-[(1S,2S)-2-Acetylamino-3-(3,5-difluorophenyl)-1-hydroxypropyl]-2-(4-methylcyclohexylmethoxy)-morpholine-4-carboxylic acid tert-butyl ester | 539.2 [M − H] |
| 121 | (2R,5R)-5-[(1S,2S)-2-Acetylamino-3-(3,5-difluorophenyl)-1-hydroxypropyl]-2-(1-methylcyclohexylmethoxy)-morpholine-4-carboxylic acid tert-butyl ester | 539.2 [M − H] |
| 122 | (2S,5R)-5-[(1S,2S)-2-Acetylamino-3-(3,5-difluorophenyl)-1-hydroxypropyl]-2-(1-fluorocyclohexylmethoxy)-morpholine-4-carboxylic acid tert-butyl ester | 543.2 [M − H] |
| 123 | (2S,5R)-5-[(1S,2S)-2-Acetylamino-3-(3,5-difluorophenyl)-1-hydroxypropyl]-2-(4-fluorotetrahydropyran-4-ylmethoxy)-morpholine-4-carboxylic acid tert-butyl ester | 543.2 [M − H] |
| 124 | (2S,5R)-5-[(1S,2S)-2-Acetylamino-3-(3,5-difluorophenyl)-1-hydroxypropyl]-2-(3-tert-butylcyclobutoxy)-morpholine-4-carboxylic acid tert-butyl ester | 539.2 [M − H] |
| 125 | (2S,5R)-5-[(1S,2S)-2-Acetylamino-3-(3,5-difluorophenyl)-1-hydroxypropyl]-2-((1R,2S,5R)-2-isopropyl-5-methylcyclohexyloxy)-morpholine-4-carboxylic acid tert-butyl ester | 567.3 [M − H] |
| 126 | (2R,5R)-5-[(1S,2S)-2-Acetylamino-3-(3,5-difluorophenyl)-1-hydroxypropyl]-2-((1R,2S,5R)-2-isopropyl-5-methylcyclohexyloxy)-morpholine-4-carboxylic acid tert-butyl ester | 567.3 [M − H] |
| 127 | (2S,5R)-5-[(1S,2S)-2-Acetylamino-3-(3,5-difluorophenyl)-1-hydroxypropyl]-2-((1S,2R,5S)-2-isopropyl-5-methylcyclohexyloxy)-morpholine-4-carboxylic acid tert-butyl ester | 567.3 [M − H] |
| 128 | (2R,5R)-5-[(1S,2S)-2-Acetylamino-3-(3,5-difluorophenyl)-1-hydroxypropyl]-2-((1S,2R,5S)-2-isopropyl-5-methylcyclohexyloxy)-morpholine-4-carboxylic acid tert-butyl ester | 567.3 [M − H] |
| 129 | (2R,5R)-5-[(1S,2S)-2-Acetylamino-3-(3,5-difluorophenyl)-1-hydroxypropyl]-2-((1S,2R,5S)-6,6-dimethylbicyclo[3.1.1]hept-2-ylmethoxy)-morpholine-4-carboxylic acid tert-butyl ester | 565.3 [M − H] |
| 130 | (2RS,5RS)-5-[(1SR,2SR)-2-Acetylamino-3-(3,5-difluoro-phenyl)-1-hydroxypropyl]-2-(4-methoxycyclohexyl-methoxy)-morpholine-4-carboxylic acid tert-butyl ester-Isomer 1 | 557.42 |
| 131 | (2SR,5RS)-5-[(1SR,2SR)-2-Acetylamino-3-(3,5-difluoro-phenyl)-1-hydroxypropyl]-2-(4-methoxycyclohexyl-methoxy)-morpholine-4-carboxylic acid tert-butyl ester-Isomer 2 | 557.43 |
| 132 | (2SR,5RS)-5-[(1SR,2SR)-2-Acetylamino-3-(3,5-difluoro-phenyl)-1-hydroxypropyl]-2-(4-methoxycyclohexylmethoxy)-morpholine-4-carboxylic acid tert-butyl ester-Isomer 1 | 557.4 (APCI) |
| 133 | (2RS,5RS)-5-[(1SR,2SR)-2-Acetylamino-3-(3,5-difluoro-phenyl)-1-hydroxy-propyl]-2-(4-methoxycyclohexylmethoxy)-morpholine-4-carboxylic acid tert-butyl ester-Isomer 2 | 557.44 |
| 134 | (2RS,5RS)-5-[(1SR,2SR)-2-Acetylamino-3-(3,5-difluoro-phenyl)-1-hydroxypropyl]-2-(4,4-difluorocyclohexylmethoxy)-morpholine-4-carboxylic acid tert-butyl ester | 563.29 |
| 135 | (2RS,5RS)-5-[(1SR,2SR)-2-Acetylamino-3-(3,5-difluoro-phenyl)-1-hydroxypropyl]-2-(4-methyltetrahydropyran-4-ylmethoxy)-morpholine-4-carboxylic acid tert-butyl ester | 543.7 (APCI) |
| 136 | (2RS,5RS)-5-[(1SR,2SR)-2-Acetylamino-3-(3,5-difluoro-phenyl)-1-hydroxypropyl]-2-(2,2-dimethylpropoxy)-morpholine-4-carboxylic acid tert-butyl ester | 501.37 |
| 137 | (2S,5R)-5-[(1S,2S)-2-Acetylamino-3-(3,5-difluorophenyl)-1-hydroxypropyl]-2-[(R)-1-(tetrahydrofuran-2-yl)-methoxy]-morpholine-4-carboxylic acid tert-butyl ester | 515.29 |
| 138 | (2RS,5RS)-5-[(1SR,2SR)-2-Acetylamino-3-(3,5-difluoro-phenyl)-1-hydroxypropyl]-2-(bicyclo[2.2.1]hept-1-ylmethoxy)-morpholine-4-carboxylic acid tert-butyl ester | 539.4 |
| 139 | (2SR,5RS)-5-[(1SR,2SR)-2-Acetylamino-3-(3,5-difluoro-phenyl)-1-hydroxypropyl]-2-(1-cyclohexylcyclopropoxy)-morpholine-4-carboxylic acid tert-butyl ester | 553.32 |
| 140 | (2R,5R)-5-[(1S,2S)-2-Acetylamino-3-(3,5-difluorophenyl)-1-hydroxypropyl]-2-(1-benzylcyclohexylmethoxy)-morpholine-4-carboxylic acid tert-butyl ester | 617.35 |
| 141 | (2RS,5RS)-5-[(1SR,2SR)-2-Acetylamino-3-(3,5-difluoro-phenyl)-1-hydroxypropyl]-2-(1-methylcyclopentylmethoxy)-morpholine-4-carboxylic acid tert-butyl ester | 527.37 |
| 142 | (2S,5R)-5-[(1S,2S)-2-Acetylamino-3-(3,5-difluorophenyl)-1-hydroxypropyl]-2-((R)-1-cyclohexylethoxy)-morpholine-4-carboxylic acid tert-butyl ester | 541.38 |
| 143 | (2RS,5RS)-5-[(1SR,2SR)-2-Acetylamino-3-(3,5-difluoro-phenyl)-1-hydroxypropyl]-2-(1-benzylcyclopentylmethoxy)-morpholine-4-carboxylic acid tert-butyl ester | 603.34 |
| 144 | (2RS,5RS)-5-[(1SR,2SR)-2-Acetylamino-3-(3,5-difluoro-phenyl)-1-hydroxypropyl]-2-(4-oxo-cyclohexylmethoxy)-morpholine-4-carboxylic acid tert-butyl ester | 541.37 |

| Prep | Compound | MS (ES) [M + H] |
|---|---|---|
| 145 | (2S,5R)-5-[(1S,2S)-2-Acetylamino-3-(3,5-difluorophenyl)-1-hydroxypropyl]-2-((1S,2R)-2-phenylcyclohexyloxy)-morpholine-4-carboxylic acid tert-butyl ester | 589.44 |
| 146 | (2S,5R)-5-[(1S,2S)-2-Acetylamino-3-(3,5-difluorophenyl)-1-hydroxypropyl]-2-(2,2-dimethylpentyloxy)-morpholine-4-carboxylic acid tert-butyl ester | 429.4 [M − BOC + H] (APCI) |
| 147 | (2R,5R)-5-[(1S,2S)-2-Acetylamino-3-(3,5-difluorophenyl)-1-hydroxypropyl]-2-(3,3,3-trifluoro-2-methyl-2-trifluoromethyl-propoxy)-morpholine-4-carboxylic acid tert-butyl ester | 609.41 |
| 148 | (2R,5R)-5-[(1S,2S)-2-Acetylamino-3-(3,5-difluorophenyl)-1-hydroxypropyl]-2-(2,2-dimethylbutoxy)-morpholine-4-carboxylic acid tert-butyl ester | 515.3 |
| 149 | (2R,5R)-5-[(1S,2S)-2-Acetylamino-3-(3,5-difluorophenyl)-1-hydroxypropyl]-2-(2,2-dimethylpentyloxy)-morpholine-4-carboxylic acid tert-butyl ester | 429.4 [M − BOC + H] (APCI) |
| 150 | (2R,5R)-5-[(1S,2S)-2-Acetylamino-3-(3,5-difluorophenyl)-1-hydroxypropyl]-2-(1-phenylcyclopentylmethoxy)-morpholine-4-carboxylic acid tert-butyl ester | 489.7 [M − BOC + H] (APCI) |
| 151 | (2S,5R)-5-[(1S,2S)-2-Acetylamino-3-(3,5-difluorophenyl)-1-hydroxypropyl]-2-((S)-1-cyclohexylethoxy)-morpholine-4-carboxylic acid tert-butyl ester | 541.39 |
| 152 | (2R,5R)-5-[(1S,2S)-2-Acetylamino-3-(3,5-difluorophenyl)-1-hydroxypropyl]-2-(2,2,4-trimethylpentyloxy)-morpholine-4-carboxylic acid tert-butyl ester | 543.42 |
| 153 | (2R,5R)-5-[(1S,2S)-2-Acetylamino-3-(3,5-difluorophenyl)-1-hydroxypropyl]-2-(2,2-dimethylpropoxy)-morpholine-4-carboxylic acid tert-butyl ester | 501.4 |
| 154 | (2R,5R)-5-[(1S,2S)-2-Acetylamino-3-(3,5-difluorophenyl)-1-hydroxypropyl]-2-cyclohexyloxymorpholine-4-carboxylic acid tert-butyl ester | 513.4 |
| 155 | (2S,5R)-5-[(1S,2S)-2-Acetylamino-3-(3,5-difluorophenyl)-1-hydroxypropyl]-2-cyclohexyloxymorpholine-4-carboxylic acid tert-butyl ester | 513.3 |
| 156 | (2RS,5RS)-5-[(1SR,2SR)-2-Acetylamino-3-(3,5-difluorophenyl)-1-hydroxypropyl]-2-(2,2-dimethylpropoxy)-morpholine-4-carboxylic acid tert-butyl ester | 501.4 |
| 157 | (2SR,5RS)-5-[(1SR,2SR)-2-Acetylamino-3-(3,5-difluorophenyl)-1-hydroxypropyl]-2-(3,3-dimethylbutoxy)-morpholine-4-carboxylic acid tert-butyl ester | 515.4 |
| 158 | (2RS,5RS)-5-[(1SR,2SR)-2-Acetylamino-3-(3,5-difluorophenyl)-1-hydroxypropyl]-2-(3,3-dimethylbutoxy)-morpholine-4-carboxylic acid tert-butyl ester | 515.4 |
| 159 | (2SR,5R)-5-[(1SR,2SR)-2-Acetylamino-3-(3,5-difluorophenyl)-1-hydroxypropyl]-2-(3-methylbutoxy)-morpholine-4-carboxylic acid tert-butyl ester | 501.4 |
| 160 | (2RS,5RS)-5-[(1SR,2SR)-2-Acetylamino-3-(3,5-difluoro-phenyl)-1-hydroxypropyl]-2-(3-methylbutoxy)-morpholine-4-carboxylic acid tert-butyl ester | 501.4 |
| 161 | (2RS,5RS)-5-[(1SR,2SR)-2-Acetylamino-3-(3,5-difluoro-phenyl)-1-hydroxypropyl]-2-cyclohexylmethoxymorpholine-4-carboxylic acid tert-butyl ester | 527.5 |
| 162 | (2SR,5RS)-5-[(1SR,2SR)-2-Acetylamino-3-(3,5-difluorophenyl)-1-hydroxypropyl]-2-isobutoxymorpholine-4-carboxylic acid tert-butyl ester | 487.4 |
| 163 | (2RS,5RS)-5-[(1SR,2SR)-2-Acetylamino-3-(3,5-difluorophenyl)-1-hydroxypropyl]-2-isobutoxymorpholine-4-carboxylic acid tert-butyl ester | 487.4 |
| 164 | (R)-5-[(1S,2S)-2-Acetylamino-3-(3,5-difluorophenyl)-1-hydroxypropyl]-2-ethoxymorpholine-4-carboxylic acid tert-butyl ester | 457.2 [M − H] |

Preparation 165

N-[(1S,2S)-2-Benzyloxy-2-[(3R,6S)-6-(3-cyclopentylpropoxy)-morpholin-3-yl]-1-(3,5-difluorobenzyl)-ethyl]-acetamide trifluoroacetate

Dissolve (2S,5R)-5-[(1S,2S)-2-Acetylamino-1-benzyloxy-3-(3,5-difluorophenyl)-propyl]-2-(3-cyclopentylpropoxy)-morpholine-4-carboxylic acid tert-butyl ester (67 mg, 0.106 mmol) in neat trifluoroacetic acid under nitrogen. After 20 min, dilute the reaction mixture with dichloromethane and concentrate it on the rotary evaporator four times, then dilute with benzene and concentrate again. Dry the residue under vacuum to give the title compound.

MS(ES+): 531.2 m/z=[M+H]

Preparation 166

(2S,5R)-5-[(1S,2S)-2-Amino-3-(3,5-difluorophenyl)-1-hydroxypropyl]-2-ethoxymorpholine-4-carboxylic acid tert-butyl ester

[(R)-2-(tert-butyl-dimethylsilanyloxy)-1-(1-ethoxy-2-iodoethoxymethyl)-ethyl]-carbamic acid tert-butyl ester Dissolve [(R)-1-(tert-butyl-dimethylsilanyloxymethyl)-2-hydroxyethyl]-carbamic acid tert-butyl ester (1.0 g, 3.27 mmol) and ethyl vinyl ether (0.20 g, 2.73 mmol) in acetonitrile (20 mL) and add N-iodosuccinimide (0.735 g, 3.27 mmol). Stir at room temperature 72 hours and pour into saturated aqueous sodium chloride. Extract with ethyl acetate, wash with water and saturated aqueous sodium chloride, dry (magnesium sulfate), filter and concentrate. Purify (silica gel chromatography, eluting with 100:0 to 10:90 hexanes:ethyl acetate) to give the desired compound (462 mg, 34%).

MS(ES): m/z=504.4=[M+H]

(2S,5R)-5-(tert-butyldimethylsilanyloxymethyl)-2-ethoxymorpholine-4-carboxylic acid tert-butyl ester Add sodium hydride (0.044 g, 1.10 mmol, 60% dispersion in mineral oil) to [2-(R)-(tert-butyl-dimethylsilanyloxy)-1-(1-ethoxy-2-iodoethoxymethyl)-ethyl]-carbamic acid tert-butyl ester (0.462 g, 0.918 mmol) in N,N-dimethylformamide (9 mL) at room temperature. Heat to 50° C. for 4 hours, cool to room temperature and pour into ethyl acetate. Wash with water, 1 N lithium chloride, and saturated aqueous sodium chloride. Dry (magnesium sulfate), concentrate and purify (silica gel chromatography, eluting with 100:0 to 1:1 hexanes:ethyl acetate) to give a mixture of two diastereomers, the more polar of which is the desired compound.

$^1$H-NMR (400 MHz, CDCl$_3$) δ 4.69 (br s, 1H), 3.98-3.45 (m, 8H), 3.07 (d, J=12.8 Hz, 1H), 1.46 (s, 9H), 1.22 (t, J=7.2 Hz, 3H), 0.89 (s, 9H), 0.07 (s, 6H).

(2S,5S)-2-Ethoxy-5-hydroxymethylmorpholine-4-carboxylic acid tert-butyl ester

Dissolve (2S,5R)-5-(tert-butyldimethylsilanyloxymethyl)-2-ethoxymorpholine-4-carboxylic acid tert-butyl ester (0.39 g, 1.04 mmole) in tetrahydrofuran (3 mL) and add tetrabutylammonium fluoride (2.1 mL, 2.1 mmol, 1.0 M in tetrahydrofuran). Stir 45 minutes at room temperature, concentrate and purify (silica gel chromatography, eluting with 10:90 to 40:60 ethyl acetate:hexanes) to give the desired compound (252 mg, 92%).

$^1$H-NMR (400 MHz, CDCl$_3$) δ 4.69 (br s, 1H), 4.08-4.04 (m, 2H), 3.88-3.66 (m, 4H), 3.56 (d, J=10.8 Hz, 1H), 3.51-3.43 (m, 1H), 3.20 (d, J=14 Hz, 1H), 1.47 (s, 9H), 1.22 (t, J=7.2 Hz, 3H).

(2S,5R)-5-[(1R,2S)-3-(3,5-Difluorophenyl)-1-hydroxy-2-nitropropyl]-2-ethoxymorpholine-4-carboxylic acid tert-butyl ester Add pyridine sulfur trioxide complex (0.283 g, 1.78 mmol) in dimethylsulfoxide (1.5 mL) to a solution of (2S,5S)-2-ethoxy-5-hydroxymethylmorpholine-4-carboxylic acid tert-butyl ester (0.245 g, 0.938 mmol) and triethylamine (0.180 g, 1.78 mmol) in dimethylsulfoxide (3 mL) at room temperature. Stir at room temperature for 4 hours and pour into 50 mL of 10:90 ethyl acetate:hexanes. Wash with water and saturated aqueous sodium chloride, dry (magnesium sulfate), filter and concentrate. Dissolve the residue in tetrahydrofuran (1.5 mL) and add 3,5-difluorophenyl nitroethane (0.134 g, 0.725 mmol). Cool in an ice water bath and add tetrabutyl ammonium fluoride (0.70 mL, 0.70 mmol, 1.0 M in tetrahydrofuran) all at once. Stir 30 minutes and pour into cold water containing saturated aqueous sodium chloride (~20 mL). Extract with ethyl acetate, wash with water and saturated aqueous sodium chloride, dry (magnesium sulfate), concentrate and purify (silica gel chromatography, eluting with 100:0 to 70:30 hexanes:ethyl acetate) to give the desired compound (159 mg, 54%).

MS(ES): m/z=445.2=[M−H]

(2S,5R)-5-[(1S,2S)-2-Amino-3-(3,5-difluoro-phenyl)-1-hydroxypropyl]-2-ethoxymorpholine-4-carboxylic acid tert-butyl ester Add sodium borohydride (0.061 g, 1.62 mmol) portionwise to a solution of (2S,5R)-5-[(1R,2S)-3-(3,5-difluorophenyl)-1-hydroxy-2-nitropropyl]-2-ethoxymorpholine-4-carboxylic acid tert-butyl ester (0.145 g, 0.325 mmol) and nickel (II) chloride (0.063 g, 0.487 mmol) at room temperature in methanol (5 mL) and stir 30 for min. Add water (~3 mL) and concentrate. Dilute with ethyl acetate and filter through a filtering agent. Partition the filtrate between ethyl acetate and water, dry (magnesium sulfate) and concentrate to give the title compound as a white solid (95 mg, 70%).

MS(ES): m/z=417.3=[M+H]

Preparation 167

(2R,5R)-5-[(1S,2S)-2-Acetylamino-3-(3,5-difluorophenyl)-1-hydroxypropyl]-2-butyryloxymethyl-morpholine-4-carboxylic acid tert-butyl ester

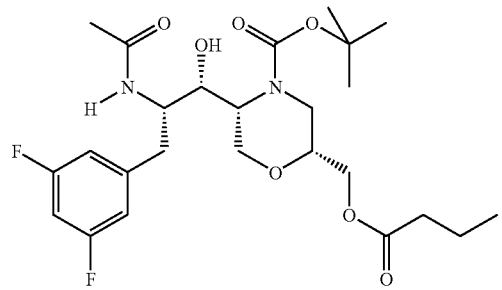

(R)-4-[(1S,2S)-1-benzyloxy-2-dibenzylamino-3-(3,5-difluorophenyl)-propyl]-2,2-dimethyloxazolidine-3-carboxylic acid tert-butyl ester Add sodium hydride (2.26 g, 56.47 mmol) and benzyl bromide (10.53 g, 61.60 mmol) to (R)-4-[(1S,2S)-2-amino-3-(3,5-difluorophenyl)-1-hydroxypropyl]-2,2-dimethyloxazolidine-3-carboxylic acid tert-butyl ester (3.97 g, 10.27 mmol) in N,N-dimethylformamide (100 mL) at room temperature. Heat to 85° C. for 14 hours. Cool to room temperature and pour into ethyl acetate. Wash with water, 1 N lithium chloride and saturated aqueous sodium chloride. Concentrate and purify (silica gel chromatography, eluting with 5:95 to 10:90 diethyl ether:hexanes) to give the desired compound (2.42 g, 36%).

MS(ES): m/z 658=[M+H]$^+$ (2R,3R,4S)-2-Amino-3-benzyloxy-4-dibenzylamino-5-(3,5-difluorophenyl)-pentan-1-ol Dissolve 4-[(1S,2S)-1-benzyloxy-2-dibenzylamino-3-(3,5-difluorophenyl)-propyl]-2,2-dimethyloxazolidine-3-carboxylic acid tert-butyl ester (2.42 g, 3.68 mmol) in dry dioxane (16 mL). To the solution add 4 M hydrogen chloride in 1,4-dioxane (32.2 mL, 129 mmol) and stir for three hours. Concentrate to give the hydrochloride salt of the desired product as a white solid (2.17 g, 100%). Slurry the solid in ethyl acetate (150 mL) and stir vigorously with saturated sodium bicarbonate (100 mL). Separate the layers and dry (magnesium sulfate) to give the desired compound.

MS(ES): m/z=517 [M+H]$^+$

Butyric acid (R)-3-[(1R,2R,3S)-2-benzyloxy-3-dibenzylamino-4-(3,5-difluorophenyl-1-hydroxymethylbutylamino]-2-hydroxypropyl ester Slurry the (2R,3R,4S)-2-amino-3-benzyloxy-4-dibenzylamino-5-(3,5-difluorophenyl)-pentan-1-ol (1.17 g, 2.26 mmol) in ethanol (11.5 mL) in a sealed tube flushed with nitrogen. Add butyric acid (R)-1-oxiranylmethyl ester (0.96 mL, 6.79 mmol), seal the tube and heat at 85° C. for three hours. Concentrate and purify (silica gel chromatography, eluting with 1.25% to 3.75% [2 M ammonia in methanol]/dichloromethane) to give the desired compound as a mixture of isomers as a white foam (1.07 g, 71%).

MS(ES): m/z=662 [M+H]$^+$

Butyric acid (R)-3-{[(1R,2S,3S)-2-benzyloxy-3-dibenzylamino-4-(3,5-difluorophenyl)-1-hydroxymethyl-butyl]-tert-butoxycarbonyl-amino}-2-hydroxypropyl ester Dissolve the butyric acid (R)-3-[(1R,2R,3S)-2-benzyloxy-3-dibenzylamino-4-(3,5-difluorophenyl)-1-hydroxymethyl-butylamino]-2-hydroxypropyl ester mixture (1.06 g, 1.62 mmol) in dry tetrahydrofuran (tetrahydrofuran) (2.5 mL). Add diisopropylethyl amine (0.57 mL, 3.24 mmol) and di-tert-butyl dicarbonate (587 mg, 2.69 mmol) and stir for 3.5 days. Add water (60 mL) and extract the mixture with ethyl acetate (100 mL). Wash the organic layer (60 mL) with water and saturated aqueous sodium chloride (50 mL), dry (magnesium sulfate) and purify (silica gel chromatography, eluting with 25:75 to 45:65 ethyl acetate:hexanes) to give the desired compound as a white foam (479 mg, 39%).

MS(ES): m/z=762 [M+H]$^+$ (2R,5R)-5-[(1S,2S)-1-benzyloxy-2-dibenzylamino-3-(3,5-difluorophenyl)-propyl]-2-butyryloxymethylmorpholine-4-carboxylic acid tert-butyl ester Dissolve in a round bottom flask charged with argon butyric acid (R)-3-{[(1R,2S,3S)-2-benzyloxy-3-dibenzylamino-4-(3,5-difluorophenyl)-1-hydroxymethylbutyl]-tert-butoxycarbonyl-amino}-2-hydroxy-propyl ester (367 mg, 0.483 mmol) in dry benzene (4.5 mL). Add tributylphosphine (0.180 mL, 0.724 mmol) followed by the addition of tetramethylazodicarboxamide (125 mg, 0.724 mmol). Vigorously stir the resulting slurry overnight. Concentrate and purify (silica gel chromatography, eluting with 15:85 to 20:80 diether ether:hexanes) to give the desired compound as a white foam (302 mg, 84%).

MS(ES): m/z=744 [M+H]$^+$ (2R,5R)-5-[(1S,2S)-2-Amino-3-(3,5-difluorophenyl)-1-hydroxypropyl]-2-butyryloxymethyl-morpholine-4-carboxylic acid tert-butyl ester Dissolve (2R,5R)-5-[(1S,2S)-1-benzyloxy-2-dibenzylamino-3-(3,5-difluorophenyl)-propyl]-2-butyryloxymethyl-morpholine-4-carboxylic acid tert-butyl ester (295 mg, 0.397 mmol) in ethanol (29 mL). Add 20% palladium hydroxide on carbon (330 mg) and stir under 1 atmosphere of hydrogen gas for 48 hours. Filter through a filtering agent and wash with ethanol. Concentrate the filtrate to give the desired compound as a white foam (188 mg, 100%).

MS(ESI): m/z=473 [M+H]$^+$

Amide Formation

To (R)-5-[(1S,2S)-2-amino-3-(3,5-difluorophenyl)-1-hydroxypropyl]-2-butyryloxymethyl-morpholine-4-carboxylic acid tert-butyl ester (0.187 g, 0.396 mmol) in tetrahydrofuran (4 mL), add triethylamine (0.037 mL, 0.396 mmol) and acetic anhydride (0.055 mL, 0.396 mmol). Stir the solution for 3 hours. Concentrate and purify (silica gel chromatography, eluting with 50:50 to 60:40 ethyl acetate:hexanes) to give the title compound as a white foam (125 mg, 61%).

MS(ES): m/z=415 [M−100+H]$^+$

Preparation 168

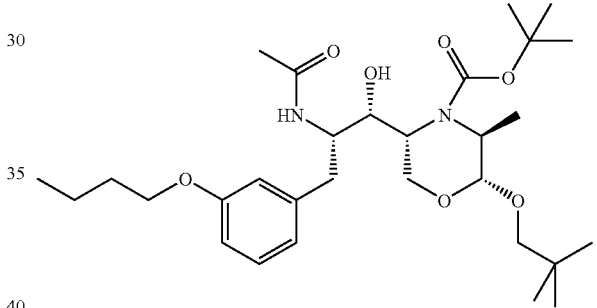

(2R,5R)-5-[(1S,2S)-2-Acetylamino-3-(4-butoxyphenyl)-1-hydroxypropyl]-2-(2,2-dimethylpropoxy)-3-(S)-methylmorpholine 4-carboxylic acid tert-butyl ester 3-(1-Hydroxy-2-nitroethyl)-phenol Dissolve 3-hydroxybenzaldehyde (18.4 g, 15.07 mmol) in tetrahydrofuran (100 mL). Add nitromethane ((42 mL, 780 mmol), cool in an ice bath and add tetrabutylammonium fluoride (151 mL, 151 mmol, 1.0 M in tetrahydrofuran). Stir for 2 hours, dilute with ethyl acetate (200 mL), wash with water (3×500 mL) and saturated aqueous sodium chloride (200 mL). Extract the aqueous washes with diethyl ether (3×), wash with saturated aqueous sodium chloride, dry (magnesium sulfate), filter through a pad of silica gel, and concentrate. Suspend the residue in hot dichloromethane with 5% ethyl acetate, cool and filter solid. Purify filtrate using silica gel chromatography, eluting with 5:95 ethyl acetate:dichloromethane. Combine the solid from the dichloromethane tritutation with the purified filtrate to give the desired compound (24.88 g, 90% total yield).

$^1$H-NMR (400 MHz, CDCl$_3$) δ 3.155 (bs, 2H); 4.50 (m, 2H); 5.340 (dd, 1H); 6.777 (m, 1H); 6.845 (m, 2H); 7.201 (t, 1H)

Acetic acid 3-(2-nitrovinyl)-phenyl ester

Add 3-(1-hydroxy-2-nitroethyl)-phenol (22.3 g, 121.8 mmol), 18-Crown-6 (3.3 g, 12.5 mmol), potassium fluoride (spray-dried) (7.1 g, 141 mmol) to acetic anhydride (115 mL, 1.218 mol). Stir for 1 hour. Cool in an ice bath and pour into ice water (400 mL) and stir for 15 minutes. Decant and extract the aqueous with ethyl acetate (twice). Combine extracts with the solid, wash with water (twice), saturated aqueous sodium chloride (twice), dry (magnesium sulfate), filter, concentrate and purify (silica gel chromatography, eluting with 25:75 hexanes:dichloromethane to 100% dichloromethane) to give the desired compound as an orange oil (25.56 g, 91%).

Acetic acid 3-(2-nitroethyl)-phenyl ester

Dissolve acetic acid 3-(2-nitrovinyl)-phenyl ester (25.56 g, 123.38 mmol) in chloroform (1575 mL). Add silica gel (247 g, 2 g/mmol) and isopropanol (370 mL) with mechanical stirring. Add portionwise sodium borohydride (18.67 g, 493.5 mmol) over 10 minutes. Stir at room temperature for 1 hour. Quench with 1 N hydrochloric acid (130 mL) over 20 minutes and stir at room temperature for 15 minutes. Filter solid and wash with dichloromethane (800 mL). Wash filtrate with saturated aqueous sodium chloride (300 mL), dry (magnesium sulfate), filter and concentrate to give the crude phenol intermediate contaminated with reduced starting material which is used directly in the next step. Dissolve the crude intermediate (23.14 g, ~110 mmol) in pyridine (75 mL), cool in an ice bath and add acetic anhydride (4.1 mL, 44 mmol). Stir for 1 hour. Concentrate at −20° C., dissolve in ethyl acetate (150 mL), wash with cool 1 N hydrochloric acid (4×200 mL), saturated aqueous sodium chloride and dry (magnesium sulfate) and concentrate. Extract the aqueous washes with ethyl acetate, dry (magnesium sulfate) and concentrate. Combine both lots to give the desired compound as an orange oil (25.55 g, 99% total yield).

4-(R)-[3-(3-Acetoxyphenyl)-1-(R)-hydroxy-2-(S)-nitropropyl]-2,2-dimethyloxazolidine-3-carboxylic acid tert-butyl ester Dissolve acetic acid 3-(2-nitroethyl)-phenyl ester (25.53 g, 121.6 mmol) and tert-butyl (R)-(+)-4-formyl-2,2-dimethyl-3-oxazolidinecarboxylate (Gardner's aldehyde) (22.38 g, 97.61 mmol) in dry tetrahydrofuran (200 mL). Cool in ice bath and add tetrabutylammonium fluoride (98 mL, 98 mmol, 1.0 M in tetrahydrofuran) and stir for 15 minutes. Pour into ice water (2.7 L), wash with 1 N hydrochloric acid (200 mL), saturated aqueous sodium chloride, dry (magnesium sulfate), filter through a pad of silica gel and concentrate. Purify using silica gel chromatography, eluting with 5:95 ethyl acetate: dichloromethane, followed by 2 separate crystallizations using hexanes/dichloromethane to give the desired compound (18.372 g, 43% total yield).

MS(ES): m/z=437 [M−H]

4-(R)-[2-(S)-Amino-1-(S)-hydroxy-3-(3-hydroxyphenyl)-propyl]-2,2-dimethyloxazolidine-3-carboxylic acid tert-butyl ester Add nickel (II) chloride (6.0 g, 46.1 mmol) to a solution of 4-(R)-[3-(3-acetoxyphenyl)-1-(R)-hydroxy-2-(S)-nitropropyl]-2,2-dimethyloxazolidine-3-carboxylic acid tert-butyl ester (18.37 g, 41.9 mmol) in dry methanol (900 mL). Cool in an ice bath and portionwise sodium borohydride (6.34 g, 167.6 mmol) over 8 minutes. Stir for 10 minutes. And concentrate. Partition the residue between ethyl acetate (200 mL) and water (200 mL), filter through Celite® and wash with ethyl acetate. Wash the organic layer with saturated aqueous sodium chloride, combine aqueous washes and extract with ethyl acetate. Combine the organic layers, dry (magnesium sulfate), filter and concentrate to give the desired compound as a crude foam. Suspend the Celite® cake in ethyl acetate, filter, wash with saturated aqueous sodium chloride, dry (magnesium sulfate), filter and concentrate to obtain more desired compound.

MS(ES): m/z=367 [M+H]

4-(R)-[1-(S)-benzyloxy-3-(3-benzyloxyphenyl)-2-(S)-dibenzylaminopropyl]-2,2-dimethyloxazolidine-3-carboxylic acid tert-butyl ester Add tricaprylmethylammonium chloride (Aliquat® 336) (4.5 g, 11.2 mmol) and tetrabutylammonium bromide (TBAB) (5.7 g, 15.7 mmol) to a solution of 4-(R)-[2-(S)-amino-1-(S)-hydroxy-3-(3-hydroxyphenyl)-propyl]-2,2-dimethyloxazolidine-3-carboxylic acid tert-butyl ester (16.45 g, crude) in tetrahydrofuran (200 mL). Add portionwise 95% sodium hydride (2.6 g, 90 mmol) and stir for 10 minutes. Add benzyl bromide (13.4 mL, 112.5 mmol) and heat at 60° C. for 40 minutes and concentrate. Add more 95% sodium hydride (5.4 g, 225 mmol) and benzyl bromide (27 mL, 225 mmol) in tetrahydrofuran (~5 mL) and stir overnight at 65° C. Dilute with ethyl acetate, quench with water (300 mL), wash with water, and saturated aqueous sodium chloride. Extract the aqueous washes with ethyl acetate, comvine the organic layers, dry (magnesium sulfate), filter and purify twice (silica gel chromatography, eluting with 5:95 to 10:90 ethyl acetate:hexanes) to give the desired compound as an orange residue (16.01 g, 49%).

MS(ES): m/z=727 [M+H]

2-(R)-Amino-3-(R)-benzyloxy-5-(3-benzyloxyphenyl)-4-(S)-dibenzylaminopentan-1-ol Dissolve 4-(R)-[1-(S)-benzyloxy-3-(3-benzyloxyphenyl)-2-(S)-dibenzylaminopropyl]-2,2-dimethyloxazolidine-3-carboxylic acid tert-butyl ester (16.01 g, 22.0 mmol) in 4 M hydrogen chloride in 1,4-dioxane (130 mL) and stir for 30 minutes. Add water (65 mL) and stir for 18 hours. Slowly add sodium bicarbonate (50 g) and water (~50 mL). Extract with ethyl acetate, wash with saturated aqueous sodium chloride, dry (magnesium sulfate), filter and concentrate to give the crude desired compound.

MS(ES): m/z=587 [M+H]

3-(R)-benzyloxy-5-(3-benzyloxyphenyl)-2-[2,2-bis-(2,2-dimethylpropoxy)-1-(S)-methyl-ethylamino]-4-(S)-dibenzylaminopentan-1-(R)-ol 3-(R)-benzyloxy-5-(3-benzyloxyphenyl)-2-[2,2-bis-(2,2-dimethylpropoxy)-1-(R)-methyl-ethylamino]-4-(S)-dibenzylaminopentan-1-(R)-ol Add 3 Å molecular sieves (3.4 g, 0.155 g/mmol) to a solution of 2-(R)-amino-3-(R)-benzyloxy-5-(3-benzyloxyphenyl)-4-(S)-dibenzylaminopentan-1-ol (12.75 g, 21.73 mmol), 1,1-bis-(2,2-dimethylpropoxy)-propan-2-one (9.3 mL, 34.77 mmol) and pyridinium p-toluenesulfonate (PPTS) (0.545 g, 2.17 mmol) in dry toluene (100 mL) under nitrogen. Reflux in a Dean Stark trap for 18 hours. Cool, filter and dissolve the solid in dry methanol (150 mL). Cool in an ice bath and add sodium cyanoborohydride (5.5 g, 86.92 mmol), followed by the slow addition of glacial acetic acid (2.5 mL, 43.5 mmol) and stir 2.5 hours. Sonicate the reaction to increase solubility. Filter, wash with methanol, and add water (15 mL), 2 N sodium hydroxide (100 mL) and ethyl acetate (100 mL) and stir for 10 minutes. Add saturated aqueous sodium chloride and wash the organic layer with 2 N sodium hydroxide (2×100 mL) and saturated aqueous sodium chloride. Extract the aqueous washes with ethyl acetate, wash with saturated aqueous sodium chloride, combine organic layers, dry (magnesium sulfate), filter and concentrate. Separate the two isomers using silica gel chromatography, eluting with hexanes/dichloromethane to give the two desired compounds 3-(R)-benzyloxy-5-(3-benzyloxyphenyl)-2-[2,2-bis- (2,2-dimethylpropoxy)-1-(S)-methyl-ethylamino]-4-(S)-dibenzylaminopentan-1-(R)-ol (2.911 g, 17%) and 3-(R)-benzyloxy-5-(3-benzyloxyphenyl)-2-[2,2-bis-(2,2-dimethylpropoxy)-1-(R)-methyl-ethylamino]-4-(S)-dibenzylaminopentan-1-(R)-ol (2.167 g, 12%).

(S)-Dibenzyl-{2-0)-benzyloxy-1-(3-benzyloxybenzyl)-2-(R)-[6-(R)-(2,2-dimethylpropoxy)-5-(R)-methylmorpholin-3-yl]-ethyl}-amine Add dropwise boron trifluoride diethyl etherate (1.4 mL, 10.89 mmol) to a solution of 3-(R)-benzyloxy-5-(3-benzyloxyphenyl)-2-[2,2-bis-(2,2-dimethylpropoxy)-1-(S)-methyl-ethylamino]-4-(S)-dibenzylaminopentan-1-(R)-ol (2.91 g, 3.63 mmol) in 1,2-dichloroethane (40 mL) and heat at 100° C. for 10 minutes. Dilute with dichloromethane, wash with saturated aqueous sodium bicarbonate, saturated aqueous sodium chloride, dry (magnesium sulfate), filter, concentrate and purify (silica gel chromatography, eluting with 15:85 ethyl acetate:hexanes) to give the desired compound (1.806 g, 70%).

MS(ES): m/z=713 [M+H]

5-(R)-[1-(S)-benzyloxy-3-(3-benzyloxyphenyl)-2-(R)-dibenzylaminopropyl]-2-(R)-(2,2-dimethylpropoxy)-3-(S)-methylmorpholine-4-carboxylic acid tert-butyl ester Add N,N-diisopropylethylamine (813 μL, 4.67 mmol) to a solution of (S)-dibenzyl-{2-(R)-benzyloxy-1-(3-benzyloxybenzyl)-2-(R)-[6-(R)-(2,2-dimethylpropoxy)-5-(R)-methylmorpholin-3-yl]-ethyl}-amine (1.664 g, 2.335 mmol) and di-tert-butyl dicarbonate (1.53 g, 7.0 mmol) in dry 1,2-dichloroethane (20 mL) and heat to 70° C. for 18 hours. Wash with 1 N hydrochloric acid, dry (magnesium sulfate), filter, concentrate and purify (silica gel chromatography, eluting with 5:95 to 10:90 ethyl acetate:hexanes) to give the desired compound as a white foam (1.38 g, 73%).

MS(ES): m/z=813 [M+H]

5-(R)-[2-(S)-Amino-1-(S)-hydroxy-3-(3-hydroxyphenyl)-propyl]-2-(R)-(2,2-dimethylpropoxy)-3-(S)-methylmorpholine-4-carboxylic acid tert-butyl ester Dissolve 5-(R)-[1-(S)-benzyloxy-3-(3-benzyloxyphenyl)-2-(R)-dibenzylaminopropyl]-2-(R)-(2,2-dimethylpropoxy)-3-(S)-methylmorpholine-4-carboxylic acid tert-butyl ester (1.38 g, 1.70 mmol) in tert-butanol (~50 mL). Add 20% palladium hydroxide on carbon (4 g) and hydrogenate at 50 psi hydrogen gas at 40° C. for 18 hours. Filter and concentrate to give the desired compound (802 mg).

MS(ES): m/z=453 [M+H]

5-[2-(S)-Acetylamino-1-(S)-hydroxy-3-(3-hydroxyphenyl)-propyl]-2-(R)-(2,2-dimethylpropoxy)-3-(S)-methylmorpholine-4-carboxylic acid tert-butyl ester Add acetic anhydride (320 μL, 3.4 mmol) and N,N-diisopropylethylamine (590 μL, 3.4 mmol) to a solution of 5-(R)-[2-(S)-amino-1-(S)-hydroxy-3-(3-hydroxyphenyl)-propyl]-2-(R)-(2,2-dimethylpropoxy)-3-(S)-methylmorpholine-4-carboxylic acid tert-butyl ester (770 mg, 1.70 mmol). Stir for 2.5 hours. Dilute with ethyl acetate, wash with 1 N hydrochloric acid (twice), saturated aqueous sodium bicarbonate, saturated aqueous sodium chloride, dry (magnesium sulfate), filter, concentrate and purify (silica gel chromatography, eluting with 20:80 to 25:75 ethyl acetate:hexanes) to give the desired compound (292 mg).

MS(ES): m/z=495 [M+H]

5-(R)-[2-(S)-Acetylamino-3-(3-butoxyphenyl)-1-(S)-hydroxypropyl]-2-(R)-(2,2-dimethylpropoxy)-3-(S)-methylmorpholine-4-carboxylic acid tert-butyl ester Add 1-bromobutane (6 μL, 55.6 μmol) to a solution of 5-[2-(S)-acetylamino-1-(S)-hydroxy-3-(3-hydroxyphenyl)-propyl]-2-(R)-(2,2-dimethylpropoxy)-3-(S)-methylmorpholine-4-carboxylic acid tert-butyl ester (25 mg, 50.5 μmol) and cesium carbonate (33 mg, 1.01 mmol) in N,N-dimethylformamide (250 μL). Heat to 60° C. for 3 hours. Dilute with ethyl acetate, wash with water, dry (magnesium sulfate), filter, concentrate and purify (silica gel chromatography, eluting with 20:80 to 85:15 ethyl acetate:dichloromethane) to give the title compound (28.5 mg, 80%).

MS(ES): m/z=573 [M+Na]

The compounds of Preparations 169-183 may be prepared essentially as described in Preparation 168 using the appropriate alkyl bromides.

| Prep | Compound | MS (ES) [M + Na] |
|---|---|---|
| 169 | 5-(R)-{2-(S)-Acetylamino-1-(S)-hydroxy-3-[4-(3-methylbutoxy)-phenyl]-propyl}-2-(R)-(2,2-dimethylpropoxy)-3-(S)-methylmorpholine-4-carboxylic acid tert-butyl ester | 587 |
| 170 | 5-(R)-[2-(S)-Acetylamino-1-(S)-hydroxy-3-(3-propoxyphenyl)-propyl]-2-(R)-(2,2-dimethylpropoxy)-3-(S)-methylmorpholine-4-carboxylic acid tert-butyl ester | 559 |
| 171 | 5-(R)-[2-(S)-Acetylamino-1-(S)-hydroxy-3-(3-isobutoxyphenyl)-propyl]-2-(R)-(2,2-dimethylpropoxy)-3-(S)-methylmorpholine-4-carboxylic acid tert-butyl ester | 573 |
| 172 | (2R,3S,5R)-5-{(1S,2S)-2-Acetylamino-3-[3-(2-fluoro-ethoxy)-phenyl]-1-hydroxy-propyl}-2-(2,2-dimethyl-propoxy)-3-methyl-morpholine-4-carboxylic acid tert-butyl ester | 563 |
| 173 | (2R,3S,5R)-5-{(1S,2S)-2-Acetylamino-3-[3-(2,2-difluoro-ethoxy)-phenyl]-1-hydroxy-propyl}-2-(2,2-dimethyl-propoxy)-3-methyl-morpholine-4-carboxylic acid tert-butyl ester | 581 |
| 174 | (2R,3S,5R)-5-{(1S,2S)-2-Acetylamino-1-hydroxy-3-[3-(2-methyl-butoxy)-phenyl]-propyl}-2-(2,2-dimethyl-propoxy)-3-methyl-morpholine-4-carboxylic acid tert-butyl ester | 587 |
| 175 | (2R,3S,5R)-5-[(1S,2S)-2-Acetylamino-1-hydroxy-3-(3-propoxy-phenyl)-propyl]-2-(2,2-dimethyl-propoxy)-3-methyl-morpholine-4-carboxylic acid tert-butyl ester | 439 [M − t-Bu + H] |
| 176 | (2R,3S,5R)-5-[(1S,2S)-2-Acetylamino-1-hydroxy-3-(3-hydroxy-phenyl)-propyl]-2-(2,2-dimethyl-propoxy)-3-methyl-morpholine-4-carboxylic acid tert-butyl ester | 559 |

-continued

| Prep | Compound | MS (ES) [M + Na] |
|---|---|---|
| 177 | (2R,3S,5R)-5-[(1S,2S)-2-Acetylamino-3-(3-cyclopentylmethoxy-phenyl)-1-hydroxy-propyl]-2-(2,2-dimethyl-propoxy)-3-methyl-morpholine-4-carboxylic acid tert-butyl ester | 599 |
| 178 | (2R,3S,5R)-5-{(1S,2S)-2-Acetylamino-1-hydroxy-3-[3-((S)-2-methyl-butoxy)-phenyl]-propyl}-2-(2,2-dimethyl-propoxy)-3-methyl-morpholine-4-carboxylic acid tert-butyl ester | 587 |
| 179 | (2R,3S,5R)-5-[(1S,2S)-2-Acetylamino-3-(3-ethoxy-phenyl)-1-hydroxy-propyl]-2-(2,2-dimethyl-propoxy)-3-methyl-morpholine-4-carboxylic acid tert-butyl ester | 545 |
| 180 | (2R,3S,5R)-5-[(1S,2S)-2-Acetylamino-3-(3-allyloxy-phenyl)-1-hydroxy-propyl]-2-(2,2-dimethyl-propoxy)-3-methyl-morpholine-4-carboxylic acid tert-butyl ester | 557 |
| 181* | (2R,5R)-5-[(1S,2S)-1-Hydroxy-2-acetylamino-3-(3-propoxy-5-fluorophenyl)-propyl]-2-(cyclohexylmethoxy)-morpholine-4-carboxylic acid tert-butyl ester | 567.3 [M+] |
| 182* | (2R,5R)-5-[(1S,2S)-1-Hydroxy-2-acetylamino-3-(3-isobutoxy-5-fluorophenyl)-propyl]-2-(cyclohexylmethoxy)-morpholine-4-carboxylic acid tert-butyl ester | 581.3 [M+] |
| 183* | (2R,5R)-5-[(1S,2S)-1-Hydroxy-2-acetylamino-3-(2,2,2-trifluoroethoxy-5-fluorophenyl)-propyl]-2-(cyclohexylmethoxy)-morpholine-4-carboxylic acid tert-butyl ester | 607.3 [M+] |

*Prepared as described in Preparation 168 beginning with 5-(R)-[1-(S)-benzyloxy-3-(3-benzyloxyphenyl)-2-(R)-dibenzylaminopropyl]-2-(R)-(cyclohexylmethoxy)-lmorpholine-4-carboxylic acid tert-butyl ester Preparation 184

5-(R)-[2-(S)-Acetylamino-3-(3,5-difluorophenyl)-1-(S)-hydroxypropyl]-2-(S)-(3-methylbutyl)-morpholine-4-carboxylic acid tert-butyl ester 5-(S)-[2-(R)-Acetylamino-3-(3,5-difluorophenyl)-1-(R)-hydroxypropyl]-2-(S)-(3-methylbutyl)-morpholine-4-carboxylic acid tert-butyl ester Toluene-4-sulfonic acid 2-(S)-hydroxy-5-methylhexyl ester Add dropwise over 5 minutes isobutylmagnesium bromide (4.4 mL, 8.8 mmol, 2 M in diethyl ether) to a solution of lithium tetrachlorocuprate (4.4 mL, 0.44 mmol, 0.1 M in tetrahydrofuran) cooled to −35-40° C. Dissolve (2S)-(+)-glycidyl tosylate (1.674 g, 7.73 mmol) in tetrahydrofuran (8 mL), cool to −40° C. and cannulate into the stirring Grignard reaction flask. Quench with saturated aqueous ammonium chloride (25 mL), pour supernate into saturated aqueous ammonium chloride (25 mL) and water and shake well. Wash with saturated aqueous sodium chloride, dry (magnesium sulfate), filter, concentrate and purify (silica gel chromatography, eluting with 10:90 to 25:75 ethyl acetate:hexanes) to give the desired compound (1.6711 g, 75%).

1-[2-(R)-benzyloxy-3-(S)-dibenzylamino-4-(3,5-difluorophenyl)-1-(R)-hydroxymethylbutylamino]-5-methylhexan-2-(S)-ol Add potassium carbonate (555 mg, 4.013 mmol) to a solution of 2-amino-3-(R)-benzyloxy-4-(S)-dibenzylamino-5-(3,5-difluorophenyl)-pentan-1-(R)-ol (1.0366 g, 2.06 mmol) and toluene-4-sulfonic acid 2-(S)-hydroxy-5-methylhexyl ester (1.037 g, 2.006 mmol) in dry methanol (4.5 mL). Heat at 80° C. in a sealed vessel for 48 hours. Partition between ethyl acetate and water, wash with saturated aqueous sodium bicarbonate, saturated aqueous sodium chloride, dry (magnesium sulfate), filter, concentrate and purify (silica gel chromatography, eluting with 20:80 to 50:50 ethyl acetate:hexanes) to give the desired compound (672 mg, 53%).

MS(ES): m/z=631 [M+H]

[2-(S)-benzyloxy-3-(S)-dibenzylamino-4-(3,5-difluorophenyl)-1-(R)-hydroxymethylbutyl]-(2-(S)-hydroxy-5-methylhexyl)-carbamic acid tert-butyl ester Dissolve 1-[2-(R)-benzyloxy-3-(S)-dibenzylamino-4-(3,5-difluorophenyl)-1-(R)-hydroxymethylbutylamino]-5-methylhexan-2-(S)-ol (672 mg, 1.06 mmol) in dichloromethane (10 mL). Add 20% aqueous sodium carbonate (10 mL), hydroxylamine (6.5 μL, 0.106 mmol, 50 wt %) and then di-tert-butyl dicarbonate (0.236 g, 1.06 mmol) and stir 72 hours. Separate layers, extract with dichloromethane, dry (magnesium sulfate), filter and concentrate. Dissolve in methanol and add more di-tert-butyl dicarbonate (0.480 g, 2.2 mmol) and stir at room temperature over the weekend. Concentrate and purify on silica gel, eluting with 10:90 to 25:75 ethyl acetate:hexanes to give the desired compound (292 mg).

5-(R)-[1-(S)-benzyloxy-2-(S)-dibenzylamino-3-(3,5-difluorophenyl)-propyl]-2-(S)-(3-methylbutyl)-morpholine-4-carboxylic acid tert-butyl ester Dissolve [2-(S)-benzyloxy-3-(S)-dibenzylamino-4-(3,5-difluorophenyl)-1-(R)-hydroxymethylbutyl]-(2-(S)-hydroxy-5-methylhexyl)-carbamic acid tert-butyl ester (253 mg, 347 mmol) in benzene (3 mL). Deoxygenate the reaction mixture. Add tributyl phosphine (130 μL, 520 mmol), N,N-tetramethyl azodicarboxamide (TMAD) (89.5 mg, 520 mmol) and stir at room temperature 2.5 hours. Add deoxygenated tetrahydrofuran (5 mL), more tributyl phosphate (130 μL), more TMAD (90 mg) and stir 1.5 hours. Filter, rinse with hexanes, concentrate and purify (silica gel chromatography, eluting with 5:95 ethyl acetate:hexanes) to give the desired compound (191.7 mg, 77%).

MS(ES): m/z=713 [M+H]

5-(R)-[2-(S)-Amino-3-(3,5-difluorophenyl)-1-(S)-hydroxypropyl]-2-(S)-(3-methylbutyl)-morpholine-4-carboxylic acid tert-butyl ester Dissolve 5-(R)-[1-(S)-benzyloxy-2-(S)-dibenzylamino-3-(3,5-difluorophenyl)-propyl]-2-(S)-(3-methylbutyl)-morpholine-4-carboxylic acid tert-butyl ester (187.7 mg, 0.263 mmol) in methanol (10 mL). Add 20% palladium hydroxide on carbon 100 mg) and hydrogenate at one atmosphere hydrogen gas for 18 hours. Add more 20% palladium hydroxide on carbon (100 mg) and further hydrogenate at one atmosphere hydrogen gas for 5 hours. Filter and concentrate to give the desired compound (107.8 mg, 93%).

MS(ES): m/z=443 [M+H]

5-(R)-[2-(S)-Acetylamino-3-(3,5-difluorophenyl)-1-(S)-hydroxypropyl]-2-(S)-(3-methylbutyl)-morpholine-4-carboxylic acid tert-butyl ester 5-(S)-[2-(R)-Acetylamino-3-(3,5-difluorophenyl)-1-(R)-hydroxypropyl]-2-(S)-(3-methylbutyl)-morpholine-4-carboxylic acid tert-butyl ester Add acetic anhydride (25 µL, 0.264 mmol) to a solution of 5-(R)-[2-(S)-amino-3-(3,5-difluorophenyl)-1-(S)-hydroxypropyl]-2-(S)-(3-methylbutyl)-morpholine-4-carboxylic acid tert-butyl ester (107 mg, 0.240 mmol) and triethylamine (37 µL, 0.267 mmol) in tetrahydrofuran (5 mL) and stir at room temperature for 18 hours. Concentrate and purify (silica gel chromatography, eluting with 80:20 ethyl acetate:dichloromethane), to separate the two title compounds 5-(R)-[2-(S)-acetylamino-3-(3,5-difluorophenyl)-1-(S)-hydroxypropyl]-2-(S)-(3-methylbutyl)-morpholine-4-carboxylic acid tert-butyl ester (0.141 g, 59%) and 5-(S)-[2-(R)-acetylamino-3-(3,5-difluorophenyl)-1-(R)-hydroxypropyl]-2-(S)-(3-methylbutyl)-morpholine-4-carboxylic acid tert-butyl ester (25.1 mg, 22%).

MS(ES): m/z=507 [M+Na]

The compounds of Preparations 185-186 may be prepared essentially as described in Preparation 184 using neopentylmagnesium bromide and 3,3-dimethylbutanemagnesium bromide (Org Synth, 68, 104, (1989)) respectively.

| Prep | Compound | MS (ES) [M + H] |
|---|---|---|
| 185 | 5-(R)-[2-(S)-Acetylamino-3-(3,5-difluorophenyl)-1-(S)-hydroxypropyl]-2-(S)-(3,3-dimethylbutyl)-morpholine-4-carboxylic acid tert-butyl ester<br>5-(S)-[2-(R)-Acetylamino-3-(3,5-difluorophenyl)-1-(R)-hydroxypropyl]-2-(S)-(3,3-dimethylbutyl)-morpholine-4-carboxylic acid tert-butyl ester | 727 |
| 186 | 5-(R)-[2-(S)-Acetylamino-3-(3,5-difluorophenyl)-1-(S)-hydroxypropyl]-2-(S)-(4,4-dimethylpentyl)-morpholine-4-carboxylic acid tert-butyl ester<br>5-(S)-[2-(R)-Acetylamino-3-(3,5-difluorophenyl)-1-(R)-hydroxypropyl]-2-(S)-(4,4-dimethylpentyl)-morpholine-4-carboxylic acid tert-butyl ester | 741 |

Preparation 187

(S)-Dibenzyl-[2-(4-(R)-benzylmorpholin-3-yl)-2-(S)-benzyloxy-1-(3,5-difluorobenzyl)-ethyl]-amine 3-benzylamino-4-(R)-benzyloxy-5-(S)-dibenzylamino-6-(3,5-difluorophenyl)-hexan-1-(R)-ol Add magnesium sulfate (2.5 g), 4 Å molecular sieves (2.5 g) followed by benzaldehyde (0.95 mL, 9.35 mmol) to a solution of 2-amino-3-(R)-benzyloxy-4-(S)-dibenzylamino-5-(3,5-difluorophenyl)-pentan-1-(R)-ol (4.60 g, 8.90 mmol) in dry tetrahydrofuran (5 mL). Stir at room temperature for 1.5 hours, filter and concentrate. Dissolve the residue in absolute ethanol (5 mL), cool in an ice bath and add sodium borohydride in 3 portions (330 mg, 8.9 mmol). Remove ice bath and stir at room temperature overnight. Add 1 N hydrochloric acid (3 mL) and stir for 5 minutes. Pour into a separatory funnel containing dichloromethane/water and basify to about pH=10 using saturated aqueous potassium carbonate (~20 mL). Extract with dichloromethane (2×150 mL), dry (magnesium sulfate), filter, concentrate and purify (silica gel chromatography, eluting with 30:70 to 40:60 ethyl acetate: hexanes) to give the desired compound as a light yellow oil (3.93 g, 73%).

MS(ES)=607.2 [M+H]

4-benzyl-5-[1-(S)-benzyloxy-2-(S)-dibenzylamino-3-(R)-(3,5-difluorophenyl)-propyl]-morpholin-3-one Dissolve 3-benzylamino-4-(R)-benzyloxy-5-(S)-dibenzylamino-6-(3,5-difluorophenyl)-hexan-1-(R)-ol (0.673 g, 1.11 mmol) in toluene (5 mL), cool to 0° C. and add triethylamine (0.15 mL, 1.11 mmol). Add slowly chloroacetyl chloride (0.09 mL, 1.11 mmol). Stir at 0° C. for 1 hour and at room temperature overnight (JCS Perk Trans 1, 1987, 547). Wash with saturated aqueous sodium chloride (30 mL), dry (sodium sulfate), filter and concentrate. Dissolve in tert-butanol, add potassium tert-butoxide and heat to reflux for 6 hours. Concentrate, dissolve in ethyl acetate, wash with 1 N hydrochloric acid, saturated aqueous sodium chloride, dry (sodium sulfate), filter and purify (silica gel chromatography, eluting with 30:70 ethyl acetate:hexanes to give the desired compound as a white foam (0.375 g, 52%).

MS(ES)=647.2 [M+H]

(S)-Dibenzyl-[2-(4-(R)-benzylmorpholin-3-yl)-2-(S)-benzyloxy-1-(3,5-difluorobenzyl)-ethyl]-amine Dissolve 4-benzyl-5-[1-(S)-benzyloxy-2-(S)-dibenzylamino-3-(R)-(3,5-difluorophenyl)-propyl]-morpholin-3-one (0.308 g, 0.476 mmol) in dry tetrahydrofuran (3 mL) under nitrogen and cool to 0° C. Add borane-methyl sulfide complex (1 mL, 2 mmol, 2 M in tetrahydrofuran) and let stir over the weekend (JCS Perkins Trans., 1, 1987, 547). Add 8 drops of water and concentrate. Dissolve in ethyl acetate and wash with water, 0.1 N sodium hydroxide, dry (sodium sulfate), filter and purify (silica gel chromatography, eluting with 20:80 ethyl acetate:hexanes) to give the title compound as a white foam (0.143 g, 48%).

MS(ES)=633.3 [M+H]

Preparation 188

(2R,5R)-5-[(1S,2S)-2-Acetylamino-3-(3-chloro-5-fluorophenyl)-1-hydroxypropyl]-2-(2,2-dimethylpropoxy)-morpholine-4-carboxylic acid tert-butyl ester (2R,5R)-2-(2,2-Dimethylpropoxy)-5-formylmorpholine-4-carboxylic acid tert-butyl ester Dissolve (2R,5S)-2-(2,2-dimethylpropoxy)-5-hydroxymethylmorpholine-4-carboxylic acid tert-butyl ester (3.67 g, 12.1 mmol) in anyhydrous dimethylsulfoxide (25 mL) and dichloromethane (4 mL) and cool to 0° C. under nitrogen. Add diisopropylethylamine (7.4 mL, 42.3 mmol) then pyridine sulfur trioxide (3.47 g, 21.8 mmol) in 2 portions. Stir at 0° C. for 20 minutes and then remove from the cooling bath to allow all solids to dissolve. Pour into ice cold saturated aqueous sodium chloride, extract with 10% ethyl acetate/hexanes, wash with 0.1 N aqueous citric acid (30 mL), saturated aqueous sodium chloride (30 mL), dry (magnesium sulfate), filter and concentrate to give the desired compound as a colorless oil (3.37 g, 92%).

1-Chloro-3-fluoro-5-((E)-2-nitrovinyl)-benzene

Dissolve 3-chloro-5-fluorobenzaldehyde (4.0 g, 25.2 mmol) in glacial acetic acid (15 mL). Add nitromethane (4.1 mL, 75.7 mmol) and ammonium acetate (1.94 g, 25.2 mmol)

and heat to reflux for 4 hours. Cool and pour over ice. Dilute with 2 N sodium hydroxide and extract with ethyl acetate, dry (magnesium sulfate), concentrate and purify (silica gel chromatography, eluting with 1:1 dichloromethane:hexanes) to give the desired compound as a beige solid (2.97 g, 58%).

1-Chloro-3-fluoro-5-(2-nitroethyl)-benzene

Add sodium borohydride (0.75 g, 19.7 mmol) to a solution of 1,4-dioxane (10 mL) and absolute ethanol (2.5 mL) in a room temperature water bath. Next add 1-chloro-3-fluoro-5-((E)-2-nitrovinyl)-benzene (1.5 g, 8.98 mmol) in 1,4-dioxane (10 mL) dropwise and stir at room temperature for 1 hour (Bhattacharjya, Synthesis, 1985, 886-997). Add ice chips, glacial acetic acid (2 mL), water (2 mL), concentrate and dilute in dichloromethane/water. Wash the dichloromethane layer with water, saturated aqueous sodium chloride, dry (sodium sulfate), filter and purify (silica gel chromatography, eluting with 1:1 dichloromethane:hexanes) to give the desired compound as an oil (1.07 g 70%).

$^1$H NMR (CDCl$_3$) δ 3.30 (t, 2H, J=8 Hz), 4.62 (t, 2H, J=8 Hz), 6.85 (m, 1H), 7.02 (m, 2H)

(2R,5R)-5-[(1R,2S)-3-(3-Chloro-5-fluorophenyl)-1-hydroxy-2-nitropropyl]-2-(2,2-dimethylpropoxy)-morpholine-4-carboxylic acid tert-butyl ester Add 1-chloro-3-fluoro-5-(2-nitroethyl)-benzene (0.343 g, 1.68 mmol) in dry tetrahydrofuran (2 mL) to a solution of (2R,5R)-2-(2,2-dimethylpropoxy)-5-formylmorpholine-4-carboxylic acid tert-butyl ester (0.462 g, 1.53 mmol) in tetrahydrofuran (7 mL). Add tetrabutylammonium fluoride (0.77 mL, 0.765 mmol, 1.0 M in tetrahydrofuran) and stir at room temperature for 1 hour. Dilute with ethyl acetate and wash with saturated aqueous sodium chloride, dry (sodium sulfate), concentrate and purify (silica gel chromatography, eluting with 2:98 ethyl acetate:dichloromethane) to give the desired compound as a white foam (0.455 g, 59%).

MS(ES): m/z=503.3 [M−H]

(2R,5R)-5-[(1S,2S)-2-Amino-3-(3-chloro-5-fluorophenyl)-1-hydroxypropyl]-2-(2,2-dimethylpropoxy)-morpholine-4-carboxylic acid tert-butyl ester Dissolve (2R,5R)-5-[(1R,2S)-3-(3-chloro-5-fluorophenyl)-1-hydroxy-2-nitropropyl]-2-(2,2-dimethylpropoxy)-morpholine-4-carboxylic acid tert-butyl ester (0.455 g, 0.901 mmol) in methanol (8 mL) and stir at room temperature in an oil bath. Add anhydrous nickel (II) chloride (0.175 g, 1.35 mmol) followed by sodium borohydride (0.170 mg, 4.50 mmol) in 3 portions over 5 minutes and stir for 15 minutes. Add water (2 mL), 0.1 N sodium hydroxide (2 mL) and extract with ethyl acetate (2×30 mL). Combine organic extracts, wash with saturated aqueous sodium chloride (30 mL), dry (sodium sulfate), filter through a pad of Celite® and concentrate to give the desired compound as a colorless oil (0.428 g).

MS(ES): m/z=475.2 [M+H]

(2R,5R)-5-[(1S,2S)-2-Acetylamino-3-(3-chloro-5-fluorophenyl)-1-hydroxypropyl]-2-(2,2-dimethylpropoxy)-morpholine-4-carboxylic acid tert-butyl ester Add triethylamine (138 µL, 0.99 mmol) to a solution of (2R,5R)-5-[(1S,2S)-2-amino-3-(3-chloro-5-fluorophenyl)-1-hydroxypropyl]-2-(2,2-dimethylpropoxy)-morpholine-4-carboxylic acid tert-butyl ester (0.428 g, 0.901 mmol) in tetrahydrofuran (5 mL) followed by acetic anhydride (91 µL, 0.991 mmol). Stir at room temperature for 30 minutes, dilute with dichloromethane, wash with 0.1 N hydrochloric acid (30 mL), saturated aqueous sodium chloride (30 mL), dry (sodium sulfate), filter and purify (silica gel chromatography, eluting with 2:98 to 10:90 methanol:dichloromethane) to give the title compound as a white foam (0.212 g, 45%).

MS(ES): m/z=539.2 [M+Na]

The compounds of Preparations 189-202 may be prepared essentially as described in Preparation 188 above using the appropriate benzaldehydes and formylmorpholines.

| Prep | Compound | MS (ES) [M + Na] |
|---|---|---|
| 189 | (2R,5R)-5-[(1S,2S)-2-Acetylamino-1-hydroxy-3-(2,3,5-trifluorophenyl)-propyl]-2-(2,2-dimethylpropoxy)-morpholine-4-carboxylic acid tert-butyl ester | 541.3 |
| 190 | (2R,5R)-5-[(1S,2S)-2-Acetylamino-1-hydroxy-3-(3-trifluoromethoxyphenyl)-propyl]-2-(2,2-dimethylpropoxy)-morpholine-4-carboxylic acid tert-butyl ester | 571.3 |
| 191 | (2R,5R)-5-[(1S,2S)-2-Acetylamino-1-hydroxy-3-(3-trifluoromethylphenyl)-propyl]-2-(2,2-dimethylpropoxy)-morpholine-4-carboxylic acid tert-butyl ester | |
| 192 | (2R,5R)-5-[2-Amino-3-(3-benzyloxyphenyl)-1-hydroxypropyl]-2-(1-methylcyclopentylmethoxy)-morpholine-4-carboxylic acid tert-butyl ester | 555 |
| 193 | (2R,5R)-5-[(1S,2S)-2-Acetylamino-1-hydroxy-3-(3-hydroxyphenyl)-propyl]-2-(2,2-dimethylpropoxy)-morpholine-4-carboxylic acid tert-butyl ester | 503.3 |
| 194 | (2R,5R)-5-[(1S,2S)-2-Acetylamino-3-(3,5-dimethylphenyl)-1-hydroxypropyl]-2-(2,2-dimethylpropoxy)-morpholine-4-carboxylic acid tert-butyl ester | |
| 195 | (2R,3S,5R)-5-[(1S,2S)-2-Acetylamino-1-hydroxy-3-(3-isobutylsulfanylphenyl)-propyl]2-(2,2-dimethylpropoxy)-3-methylmorpholine-4-carboxylic acid tert-butyl ester | |
| 196 | (2R,3S,5R)-5-[(1S,2S)-2-Acetylamino-3-(3-fluoro-5-isobutylsulfanylphenyl)-1-hydroxypropyl]-2-(2,2-dimethylpropoxy)-3-methyl-morpholine-4-carboxylic acid tert-butyl ester | |
| 197 | (2R,3S,5R)-5-[(1S,2S)-2-Acetylamino-3-(3-fluoro-5-propylsulfanylphenyl)-1-hydroxypropyl]-2-(2,2-dimethylpropoxy)-3-methylmorpholine-4-carboxylic acid tert-butyl ester | |

-continued

| Prep | Compound | MS (ES) [M + Na] |
|---|---|---|
| 198 | (2R,3S,5R)-5-[(1S,2S)-2-Acetylamino-1-hydroxy-3-(3-propylsulfanylphenyl)-propyl]-2-(2,2-dimethylpropoxy)-3-methylmorpholine-4-carboxylic acid tert-butyl ester | |
| 199 | (2R,3S,5R)-5-[(1S,2S)-2-Acetylamino-1-hydroxy-3-(3-butyl-5-fluorophenyl)-propyl]-2-(2,2-dimethylpropoxy)-3-methylmorpholine-4-carboxylic acid tert-butyl ester | 553.5 |
| 200 | (2R,3S,5R)-5-[(1S,2S)-2-Acetylamino-1-hydroxy-3-(3-(2,2,2-trifluoroethoxy)-phenyl)-propyl]-2-(2,2-dimethylpropoxy)-3-methylmorpholine-4-carboxylic acid tert-butyl ester | 599.2 |
| 201 | (2R,3S,5R)-5-[(1S,2S)-2-Acetylamino-1-hydroxy-3-(3-trifluoromethoxyphenyl)-propyl]-2-(2,2-dimethylpropoxy)-3-methylmorpholine-4-carboxylic acid tert-butyl ester | |
| 202 | (2R,3S,5R)-5-[(1S,2S)-2-Acetylamino-1-hydroxy-3-(3-methoxyphenyl)-propyl]-2-(2,2-dimethylpropoxy)-3-methylmorpholine-4-carboxylic acid tert-butyl ester | |

Preparation 203

Toluene-4-sulfonic acid (S)-2-hydroxy-4-phenylbutyl ester

Add phenyl methyl magnesium bromide (14 mL, 14 mmol, 1 M in tetrahydrofuran) to a solution of lithium tetrachlorocuprate (5.5 mL, 0.55 mmol, 0.1 M in tetrahydrofuran) in dry tetrahydrofuran (10 mL) and stir at −35° C. (acetonitrile/dry ice bath) for 15 minutes (J. Med. Chem., 41, 2451-2460, (1998); JOC, 54, 1295-1304, (1989)). Cool to −35° C. a solution of (2S)-(+)-glycidyl tosylate (2.51 g, 11.0 mmol) in dry tetrahydrofuran (4 mL) and transfer rapidly via cannula to the Grignard solution. Stir for 1 hour at −35° C., quench with a saturated aqueous ammonium chloride solution and dilute with diethyl ether. Wash the organic layer with saturated aqueous sodium chloride, dry (sodium sulfate), concentrate and purify (silica gel chromatography, eluting with 35:65 ethyl acetate:hexanes) to give the desired compound as a colorless oil (1.77 g, 50%)

MS(ES): m/z=338.3 [M+18]

The compound of Preparation 204 may be prepared essentially as described in Preparation 203 above using cyclohexylmethylmagnesium bromide.

| Prep | Compound | MS (ES) |
|---|---|---|
| 204 | Toluene-4-sulfonic acid (S)-4-cyclohexyl-2-hydroxybutyl ester | 344.3 [M + 18] |

Preparation 205

5-(R)-[2-(S)-Acetylamino-3-(3,5-difluorophenyl)-1-(S)-hydroxypropyl]-2-(S)-(2-cyclohexylethyl)-morpholine-4-carboxylic acid tert-butyl ester 3-(R)-benzyloxy-2-(R)-(4-cyclohexyl-2-(S)-hydro butylamino)-4-(S)-dibenzylamino-5-(3,5-difluorophenyl)-pentan-1-ol Dissolve 2-(R)-amino-3-(R)-benzyloxy-4-(S)-dibenzylamino-5-(3,5-difluorophenyl)-pentan-1-ol (600 mg, 1.16 mmol) and 2-(S)-(2-cyclohexylethyl)-oxirane (179 mg, 1.16 mmol) in absolute ethanol (8 mL) in a sealed glass pressure vessel and heat to 80° C. for 4 days. Concentrate and purify (silica gel chromatography, eluting with 1:99 to 5:95 methanol:dichloromethane) to give the desired compound (510 mg, 65%).

MS(ES): m/z=671.5 [M+H]

[2-(S)-benzyloxy-3-(S)-dibenzylamino-4-(3,5-difluorophenyl)-1-(R)-hydroxymethylbutyl]-(4-cyclohexyl-2-(S)-hydroxy-butyl)-carbamic acid tert-butyl ester Add di-tert-butyl dicarbonate (0.19 mL, 0.82 mmol) to a solution of 3-(R)-benzyloxy-2-(R)-(4-cyclohexyl-2-(S)-hydroxybutylamino)-4-(S)-dibenzylamino-5-(3,5-difluorophenyl)-pentan-1-ol (424 mg, 0.63 mmol) and diisopropylethylamine (0.19 mL, 1.07 mmol) in tetrahydrofuran. Stir overnight at room temperature and add more di-tert-butyl dicarbonate (0.4 mL). Stir another day, concentrate, dilute with ethyl acetate, wash with dilute aqueous sodium bicarbonate, dry (sodium sulfate), filter, concentrate and purify (silica gel chromatography, eluting with 10:90 ethyl acetate:dichloromethane) to give the desired compound (317 mg, 65%).

MS(ES): m/z=771.5 [M+H]

5-(R)-[1-(S)-benzyloxy-2-(S)-dibenzylamino-3-(3,5-difluorophenyl)-propyl]-2-(S)-(2-cyclohexylethyl)-morpholine-4-carboxylic acid tert-butyl ester Add tri-n-butylphosphine (0.20 mL, 0.82 mmol) and 1,1'-azobis(N,N-dimethylformamide) (diamide) (142 mg, 0.82 mmol) to a solution of [2-(S)-benzyloxy-3-(S)-dibenzylamino-4-(3,5-difluorophenyl)-1-(R)-hydroxymethylbutyl]-(4-cyclohexyl-2-(S)-hydroxybutyl)-carbamic acid tert-butyl ester (317 mg, 0.41 mmol) in dry tetrahydrofuran (5 mL) and stir at room temperature for 3 days. Filter, dilute filtrate with ethyl acetate, wash with 0.1 N hydrochloric acid/saturated aqueous sodium chloride (50 mL), dry (sodium sulfate), filter, concentrate and purify (silica gel chromatography, eluting with dichloromethane to give the desired compound as a white foam (232 mg, 75%).

MS(ES): m/z=753.5 [M+H]

5-(R)-[2-(S)-Amino-3-(3,5-difluorophenyl)-1-(S)-hydroxypropyl]-2-(S)-(2-cyclohexylethyl)-morpholine-4-carboxylic acid tert-butyl ester Add 20% palladium hydroxide on carbon (Pearlman's catalyst) (232 mg) to a solution of 5-(R)-[1-(S)-benzyloxy-2-(S)-dibenzylamino-3-(3,5-difluorophenyl)-propyl]-2-(S)-(2-cyclohexylethyl)-morpholine-4-carboxylic acid tert-butyl ester (232 mg, 0.31 mmol) in methanol (5 mL). Stir under 1 atmosphere of hydrogen gas at room temperature overnight, filter through a pad of Celite® and concentrate to give the desired compound as a colorless oil which is used directly without further purification (138 mg, 93%).

MS(ES): m/z=483.3 [M+H]

5-(R)-[2-(S)-Acetylamino-3-(3,5-difluorophenyl)-1-(S)-hydroxypropyl]-2-(S)-(2-cyclohexylethyl)-morpholine-4-carboxylic acid tert-butyl ester Add triethylamine (0.04 mL, 0.32 mmol) followed by acetic anhydride (0.03 mL, 0.32 mmol) to a solution of 5-(R)-[2-(S)-amino-3-(3,5-difluorophenyl)-1-(S)-hydroxypropyl]-2-(S)-(2-cyclohexylethyl)-morpholine-4-carboxylic acid tert-butyl ester (138 mg, 0.29 mmol) in dry tetrahydrofuran (3 mL). Stir at room temperature for 10 min. Dilute with dichloromethane, wash with 0.1 N hydrochloric acid (30 mL), dry (sodium sulfate), filter, concentrate and purify (silica gel chromatography, eluting with 45:55 to 70:30 ethyl acetate:dichloromethane) to give the title compound (57 mg).

MS(ES): m/z=547.2 [M+Na].

The compound of Preparation 206 may be prepared essentially as described in Preparation 228 using toluene-4-sulfonic acid (S)-2-hydroxy-4-phenylbutyl ester.

| Prep | Compound | MS (ES) |
|---|---|---|
| 205 | (2S,5R)-5-[(1S,2S)-2-Acetylamino-3-(3,5-difluorophenyl)-1-hydroxypropyl]-2-phenethylmorpholine-4-carboxylic acid tert-butyl ester | 541.3 [M + Na] |

Preparation 207

5-(R)-(2-(S)-Acetylamino-1-(S)-hydroxy-3-phenylpropyl)-2-(S)-(2-cyclohexylethyl)-morpholine-4-carboxylic acid tert-butyl ester 1-(1-(R)-benzyloxymethyl-2-hydroxyethylamino)-4-cyclohexylbutan-2-(S)-ol Dissolve (R)-(+)-2-amino-3-benzyloxy-1-propanol (317 mg, 1.75 mmol) and 2-(S)-(2-cyclohexylethyl)-oxirane (270 mg, 1.75 mmol) in absolute ethanol (8 mL) and heat at 80° C. in a sealed glass pressure vessel overnight. Concentrate and purify (silica gel chromatography, eluting with 8:92 to 10:90 methanol:dichloromethane) to give the desired compound (336 mg, 57%).

MS(ES): m/z=336.2 [M+H]

(2-(R)-benzyloxy-1-hydroxymethylethyl)-(4-cyclohexyl-2-(S)-hydroxybutyl)-carbamic acid tert-butyl ester Dissolve 1-(1-(R)-benzyloxymethyl-2-hydroxyethylamino)-4-cyclohexylbutan-2-(S)-ol (292 mg, 0.87 mmol) in dry tetrahydrofuran (5 mL) and cool to 0° C. Add diisopropylethylamine (0.26 mL, 1.48 mmol) followed by di-tert-butyl dicarbonate (0.26 mL, 1.13 mmol) and stir at the same temperature for 3 hours. Remove ice bath and stir 30 minutes. Concentrate, dilute with ethyl acetate, wash with cold 0.1 N hydrochloric acid, dry (sodium sulfate), filter and purify (silica gel chromatography, eluting with 2.5:97.5 to 6:94 methanol:dichloromethane) to give the desired compound (325 mg, 86%).

MS(ES): m/z=458.3 [M+Na]

5-(S)-benzyloxymethyl-2-(S)-(2-cyclohexylethyl)-morpholine-4-carboxylic acid tert-butyl ester Add tri-n-butylphosphine (0.37 mL, 1.49 mmol) and 1,1'-azobis(N,N-dimethylformamide) (diamide) (257 mg, 1.49 mmol) to a solution of (2-(R)-benzyloxy-1-hydroxymethylethyl)-(4-cyclohexyl-2-(S)-hydroxybutyl)-carbamic acid tert-butyl ester (325 mg, 0.75 mmol) in dry tetrahydrofuran (4 mL). Stir at room temperature for 3 hours, filter, dilute with ethyl acetate, wash with 0.1 N hydrochloric acid/saturated aqueous sodium chloride (50 mL), dry (sodium sulfate), filter, concentrate and purify (silica gel chromatography, eluting with 0.1% to 3:97 methanol:dichloromethane) to give the desired compound as a colorless oil (215 mg, 69%).

MS(ES): m/z=318.3 (M-BOC)

2-(S)-(2-Cyclohexylethyl)-5-(S)-hydroxymethylmorpholine-4-carboxylic acid tert-butyl ester Add 20% palladium hydroxide on carbon (Pearlman's catalyst) (92 mg) to a solution of 5-(S)-benzyloxymethyl-2-(S)-(2-cyclohexylethyl)-morpholine-4-carboxylic acid tert-butyl ester (211 mg, 0.51 mmol) in absolute ethanol (25 mL) and hydrogenate in a Parr shaker at 40° C. for 18 hours at 60 psi. Filter and concentrate to give the desired compound which is used without further purification.

MS(ES): m/z=350.3 [M+Na]

2-(S)-(2-Cyclohexylethyl)-5-(R)-formylmorpholine-4-carboxylic acid tert-butyl ester Dissolve 2-(S)-(2-cyclohexylethyl)-5-(S)-hydroxymethylmorpholine-4-carboxylic acid tert-butyl ester (165 mg, 0.50 mmol) in dimethylsulfoxide (2 mL), and cool to 10° C. Add triethylamine (0.28 mL, 2.02 mmol) followed by pyridine sulfur trioxide complex and stir for 30 min. Dilute with ethyl acetate and pour into cold water. Wash with 5% citric acid (50 mL), saturated aqueous sodium chloride (50 mL) and dry (sodium sulfate), filter and concentrate give the desired compound as an oil which is used without further purification.

2(S)-(2-Cyclohexylethyl)-5-(R)-(1-(R)-hydroxy-2-(S)-nitro-3-phenylpropyl)-morpholine-4-carboxylic acid tert-butyl ester Add 1-phenyl-2-nitroethane (91 mg, 0.61 mmol) to a solution of 2-(S)-(2-cyclohexylethyl)-5-(R)-formylmorpholine-4-carboxylic acid tert-butyl ester (164 mg, 0.50 mmol) in dry tetrahydrofuran (6 mL). Cool to 0° C. and add tetrabutylammonium fluoride (0.25 mL of a 1 M solution in tetrahydrofuran, 0.25 mmol) and refrigerate the solution overnight. Dilute with ethyl acetate, wash with cold saturated aqueous sodium chloride (50 mL), dry (sodium sulfate), filter, concentrate and purify (silica gel chromatography, eluting with 2.5:97.5 ethyl acetate:dichloromethane) to give the desired compound as a white foam (152 mg, 63%).

MS(ES): m/z=499.2 [M+Na]

5-(R)-(2-(S)-Amino-1-(S)-hydroxy-3-phenylpropyl)-2-(S)-(2-cyclohexylethyl)-morpholine-4-carboxylic acid tert-butyl ester Dissolve 2(S)-(2-cyclohexylethyl)-5-(R)-(1-(R)-hydroxy-2-(S)-nitro-3-phenylpropyl)-morpholine-4-carboxylic acid tert-butyl ester (152 mg, 0.32 mmol) in methanol (5 mL), and place in a room temperature oil bath. Add dry nickel (II) chloride (62 mg, 0.48 mmol) followed by sodium borohydride (30 mg, 0.80 mmol). After 3 minutes add a second portion of sodium borohydride (30 mg, 0.80 mmol). Quench with water (1 mL) then 0.1 N sodium hydroxide (3 mL). Dilute with ethyl acetate and extract (3×30 mL). Wash the combined extracts with saturated aqueous sodium chloride, filter through a pad of Celite®, dry (sodium sulfate) and concentrate to give the desired compound as a white solid which is used without further purification (140 mg, 99%).

MS(ES): m/z=447.5 [M+H]

5-(R)-(2-(S)-Acetylamino-1-(S)-hydroxy-3-phenyl-propyl)-2-(S)-(2-cyclohexyl-ethyl)-morpholine-4-carboxylic acid tert-butyl ester Dissolve 5-(R)-(2-(S)-amino-1-(S)-hydroxy-3-phenylpropyl)-2-(S)-(2-cyclohexylethyl)-morpholine-4-carboxylic acid tert-butyl ester (140 mg, 0.31 mmol) in dry tetrahydrofuran (3 mL). Add triethylamine (0.05 mL, 0.35 mmol) followed by acetic anhydride (0.03 mL, 0.35 mmol) and stir at room temperature for 1 hour. Dilute with dichloromethane, wash with 0.1 N hydrochloric acid/saturated aqueous sodium chloride (30 mL), dry (sodium sulfate), filter, concentrate and purify (silica gel chromatography, eluting with 40:60 to 60:40 ethyl acetate:dichloromethane) acetate/dichloromethane to give the title compound (83 mg, 54%).

MS(ES): m/z 511.2 [M+Na]

Preparation 208

2-(Ethylmethylcarbamoyl)-cyclopropane carboxylic acid trans-Cyclopropane-1,2-dicarboxylic acid monoethyl ester Add a solution of sodium hydroxide pellets (0.501 g, 12.5352 mmol) in methanol (5.22 mL) to a solution of diethyl (E)-cyclopropane-1,2-dicarboxylate (3.00 mL, 16.11 mmol) in acetone (36.9 mL). Stir at room temperature for 24 hours. Acidify the aqueous layer with 5N hydrochloric acid and concentrate. Slurry the residue with ethyl acetate, filter away the sodium chloride and concentrate to give the crude desired compound.

trans-2-(Methylpropylcarbamoyl)-cyclopropane carboxylic acid ethyl ester

Add 1-hydroxybenzotriazole (HOBT) (1.46 g, 10.8118 mmol), 1-(3-dimethylaminopropyl)-3-ethylcarbodiimide hydrochloride (EDCI) (2.07 g, 10.8118 mmol) to a solution of crude trans-cyclopropane-1,2-dicarboxylic acid monoethyl ester (1.71 g, 10.8118 mmol) in N,N-dimethylformamide (11 mL). Stir for 30 minutes. Add triethylamine (2.26 mL, 16.2177 mmol) and methylpropylamine (1.11 mL, 10.8118 mmol) and stir for 16 hours. Quench with 10% aqueous potassium carbonate (10 mL) and extract with ethyl acetate (3×50 mL). Combine the organic extracts, wash with 0.1 N aqueous citric acid (30 mL) and 1 N lithium chloride, dry (magnesium sulfate), concentrate and crystallize with xylenes to give the desired compound (1.02 g, 50%).

trans-2-(Methylpropylcarbamoyl)-cyclo-propane carboxylic acid

Add 1 N lithium hydroxide (25.6 mL, 25.59 mmol) to a solution of trans-2-(methylpropylcarbamoyl)-cyclopropane carboxylic acid ethyl ester (1.02 g, 5.1194 mmol) in tetrahydrofuran (30 mL). Stir vigorously for 2 days at room temperature. Concentrate and treat with water (50 mL) and extract with diethyl ether (50 mL). Acidify the aqueous layer with 1 N hydrochloric acid (26 mL) and extract with diethyl ether (3×125 mL). Combine the organic extracts, dry (magnesium sulfate) and concentrate to give the title compound as a racemic mixture (0.84 g, 89%).

The compounds of Preparations 209-212 may be prepared essentially as described in Preparation 208 using fumaric acid and mesaconic acid.

| Prep | Compound |
|------|----------|
| 209 | (E)-3-Dipropylcarbamoyl-2-methylacrylic acid |
| 210 | (E)-3-Dipropylcarbamoylacrylic acid |
| 211 | (E)-2-Methyl-3-(methylpropylcarbamoyl)-acrylic acid |
| 212 | (E)-3-Dimethylcarbamoyl-2-methylacrylic acid |

Preparation 213

(2R,5R)-5-[(1S,2S)-2-Acetylamino-3-(3,5-difluorophenyl)-1-hydroxypropyl]-2-phenoxymethyl-morpholine-4-carboxylic acid tert-butyl ester (R)-2-phenoxymethyl-oxirane Add phenol (1.089 g, 11.572 mmol) to a slurry of sodium hydride (0.347 g, 14.465 mmol) in N,N-dimethylformamide (77.1 mL) and stir at room temperature for 40 minutes. Add 3-nitrobenzenesulfonic acid (R)-1-oxiranylmethyl ester (3.00 g, 11.572 mmol) and stir at room temperature for 16 hours (J. Org. Chem., 54, 1296-1304 (1989). Quench with saturated aqueous ammonium chloride (75 mL), dilute with water (75 mL) and extract with diethyl ether (3×300 mL). Combine the organic extracts, wash with saturated aqueous sodium bicarbonate (200 mL), saturated aqueous ammonium chloride (200 mL), dry (magnesium sulfate), filter and purify (silica gel chromatography, eluting with 10:90 to 50:50 ethyl acetate:hexanes) to give the desired compound as a clear liquid (1.410 g, 81.1%).

GC-MS=150 [M]

(2R,3R,4S)-3-benzyloxy-4-dibenzylamino-5-(3,5-difluorophenyl)-2-((R)-2-hydroxy-3-phenoxypropylamino)-pentan-1-ol Add (R)-2-phenoxymethyl-oxirane (0.189 g, 1.258 mmol) to a solution of (2R,3R,4S)-2-amino-3-benzyloxy-4-dibenzylamino-5-(3,5-difluorophenyl)-pentan-1-ol (0.205 g, 0.434 mmol) in ethanol (2.1 mL). Heat in a sealed vessel at 80° C. overnight. Concentrate and purify (silica gel chromatography, eluting with 1-1.5% 2 M ammonia in methanol/dichloromethane) to give the desired compound as a clear semi-solid (0.165 g, 56.9%).

MS(ES): m/z=668.0 [M+H]

(1R,2S,3S)-[2-benzyloxy-3-dibenzylamino-4-(3,5-difluorophenyl)-1-hydroxymethylbutyl]-(R)-(2-hydroxy-3-phenoxypropyl)-carbamic acid tert-butyl ester Add di-tert-butyl dicarbonate (0.059 g, 0.271 mmol) and diisopropylethylamine (0.171 mL, 0.984 mmol) to a solution of (2R,3R,4S)-3-benzyloxy-4-dibenzylamino-5-(3,5-difluorophenyl)-2-((R)-2-hydroxy-3-phenoxypropylamino)-pentan-1-ol (0.127 g, 0.246 mmol) in tetrahydrofuran (1.23 mL). Stir at room temperature overnight, add more di-tert-butyl dicarbonate (0.118 g) and stir for 2.5 days. Quench with water (20 mL), extract with ethyl acetate (100 mL), wash with water (30 mL), saturated aqueous sodium chloride (30 mL), dry (magnesium sulfate), filter and purify (silica gel chromatography, eluting with 15:85 to 30:70 ethyl acetate:hexanes) to give the desired compound as a white foam (0.074 g, 39%).

MS(ES): m/z=768.0 [M+H]

(R)-5-[(1R,2S,3S)-1-benzyloxy-2-dibenzylamino-3-(3,5-difluorophenyl)-propyl]-2-phenoxymethylmorpholine-4-carboxylic acid tert-butyl ester Dissolve (1R,2S,3S)-[2-benzyloxy-3-dibenzylamino-4-(3,5-difluorophenyl)-1-hydroxymethylbutyl]-(R)-(2-hydroxy-3-phenoxypropyl)-carbamic acid tert-butyl ester (0.074 g, 0.096 mmol) in dry benzene (0.96 mL). Add tributylphosphine (0.029 g, 0.144 mmol), N,N-tetramethyl azodicarboxamide (0.025 g, 0.144 mmol) and more benzene (2 mL) to facilitate stirring. Stir at room temperature for 2 hours, concentrate and purify (silica gel chromatography, eluting with 10:90 to 15:85 ethyl acetate:hexanes) to give the desired compound as a white foam (0.032 g, 44.7%).

MS(ES): m/z=750.0[M+H]

(2R,5R)-(5-[(1S,2S)-2-Amino-3-(3,5-difluorophenyl)-1-hydroxypropyl]-2-phenoxymethyl-morpholine-4-carboxylic acid tert-butyl ester Add 20% palladium hydroxide on carbon (0.032 g) to a solution of (R)-5-[(1R,2S,3S)-1-benzyloxy-2-dibenzylamino-3-(3,5-difluorophenyl)-propyl]-2-phenoxymethyl-morpholine-4-carboxylic acid tert-butyl ester (0.032 g, 0.043 mmol) in ethanol (0.43 mL). Stir vigorously under one atmosphere of hydrogen gas for 40 hours. Filter through a filtering agent, wash with ethanol and concentrate to give the desired compound.

(2R,5R)-5-[(1S,2S)-2-Acetylamino-3-(3,5-difluorophenyl)-1-hydroxypropyl]-2-phenoxymethylmorpholine-4-carboxylic acid tert-butyl ester Add triethylamine (0.009 mL, 0.066 mmol) and acetic anhydride (0.004 mL, 0.044 mmol) to a solution of (2R,5R)-(5-[(1S,2S)-2-amino-3-(3,5-difluorophenyl)-1-hydroxypropyl]-2-phenoxymethyl-morpholine-4-carboxylic acid tert-butyl ester (0.021 g, 0.044 mmol) in tetrahydrofuran (0.44 mL) and stir at room temperature for 1 hour. Concentrate and purify (silica gel chromatography, eluting with 50:50 to 60:40 ethyl acetate:hexanes) to give the title compound as a white foam (0.010 g, 45.5%).

MS(ES): m/z=519.0 [M−H]

Preparation 214

(R)-5-[2-(S)-Acetylamino-3-(3,5-difluorophenyl)-1-(S)-hydroxypropyl]-2-(R)-hydroxymethylmorpholine-4-carboxylic acid tert-butyl ester (2R,3R,4S)-3-benzyloxy-2-(3-benzyloxy-2-hydroxypropylamino)-4-dibenzylamino-5-(3,5-difluorophenyl)-pentan-1-(R)-ol Dissolve (2R,3R,4S)-2-amino-3-benzyloxy-4-dibenzylamino-5-(3,5-difluorophenyl)-pentan-1-ol (7.440 g, 14.401 mmol) in ethanol (72 mL). Add (R)-2-benzyloxymethyl-oxirane (4.257 g, 25.921 mmol), flush with nitrogen and heat in a sealed vessel at 80° C. for 16 hours. Concentrate and purify (silica gel chromatography, eluting with 1.3% to 1.7% 2 M ammonia in methanol/dichloromethane) to give the desired compound as a clear semi-solid (7.520 g, 76.7%).

MS(ES): m/z=681.5 [M+H]

(2S,3S)-[2-benzyloxy-3-dibenzylamino-4-(3,5-difluorophenyl)-(R)-1-hydroxymethylbutyl]-((R)-3-benzyloxy-2-hydroxypropyl)-carbamic acid tert-butyl ester Add di-tert-butyl dicarbonate (2.649 g, 12.150 mmol) and diisopropylethylamine (3.84 mL, 22.090 mmol) to a solution of (2R,3R,4S)-3-benzyloxy-2-(3-benzyloxy-2-hydroxypropylamino)-4-dibenzylamino-5-(3,5-difluorophenyl)-pentan-1-(R)-ol (7.52 g, 11.04 mmol) in tetrahydrofuran (55 mL) and heat at 50° C. for 2 days and stir at room temperature for 2.5 days. Quench with water (175 mL), extract with ethyl acetate (800 mL), dry (magnesium sulfate), filter and purify (silica gel chromatography, eluting with 20:80 to 40:60 ethyl acetate:hexanes) to give the desired compound as a white foam (5.32 g, 61.7%).

MS(ES): m/z=781.7 [M+H]

(1S,2S)-5-(R)-[1-benzyloxy-2-dibenzylamino-3-(3,5-difluorophenyl)-propyl]-2-(R)-benzyloxymethylmorpholine-4-carboxylic acid tert-butyl ester Add N,N-tetramethyl azodicarboxamide (TMAD) (1.753 g, 10.180 mmol) and tributylphosphine (2.540 mL, 10.180 mmol) to a solution of (2S,3S)-[2-benzyloxy-3-dibenzylamino-4-(3,5-difluorophenyl)-(R)-1-hydroxymethylbutyl]-((R)-3-benzyloxy-2-hydroxypropyl)-carbamic acid tert-butyl ester (5.300 g, 6.787 mmol) in benzene (34 mL) and stir vigorously for 1.5 hours. Filter the slurry, wash with hexanes, concentrate and purify (silica gel chromatography, eluting with 05:95 to 20:80 ethyl acetate:hexanes) to give the desired compound as white foam (4.750 g, 91.7%).

MS(ES): m/z=763.5 [M+H]

(R)-5-[2-(S)-Amino-3-(3,5-difluorophenyl)-1-(S)-hydroxypropyl]-2-(R)-hydroxymethylmorpholine-4-carboxylic acid tert-butyl ester Dissolve (1S,2S)-5-(R)-[1-benzyloxy-2-dibenzylamino-3-(3,5-difluorophenyl)-propyl]-2-(R)-benzyloxymethylmorpholine-4-carboxylic acid tert-butyl ester (4.750 g, 6.226 mmol) in ethanol (63 mL) and add 20% palladium hydroxide on carbon (4.750 g). Stir under one atmosphere of hydrogen gas for 42 hours, flush with nitrogen, dilute slurry with ethanol (175 mL), filter through a filtering agent, wash with ethanol and concentrate to give the desired compound (2.213 g, 88.3%).

MS(ES): m/z=403.3 [M+H]

(R)-5-[2-(S)-Acetylamino-3-(3,5-difluorophenyl)-1-(S)-hydroxypropyl]-2-(R)-hydroxymethylmorpholine-4-carboxylic acid tert-butyl ester Add triethylamine (0.623 mL, 4.473 mmol) and acetic anhydride (0.281 mL, 2.982 mmol) to a solution of (R)-5-[2-(S)-amino-3-(3,5-difluorophenyl)-1-(S)-hydroxypropyl]-2-(R)-hydroxymethylmorpholine-4-carboxylic acid tert-butyl ester (1.20 g, 2.982 mmol) in tetrahydrofuran (30 mL). Stir at room temperature for 45 minutes, concentrate and purify (silica gel chromatography, eluting with 6:94 to 9:91 methanol:dichloromethane) to give the title compound as a white foam (0.906 g, 68.4%).

MS(ES): m/z=445.3 [M+H]

Preparation 215

(R)-5-[2-(S)-Acetylamino-3-(3,5-difluorophenyl)-1-(S)-hydroxypropyl]-2-(R)-2-fluorophenoxymethyl)-morpholine-4-carboxylic acid tert-butyl ester Dissolve (R)-5-[2-(S)-acetylamino-3-(3,5-difluorophenyl)-1-(S)-hydroxypropyl]-2-(R)-hydroxymethylmorpholine-4-carboxylic acid tert-butyl ester (0.040 g, 0.090 mmol) in acetonitrile (1.0 mL). Add diisopropyl azodicarboxylate (DIAD) (0.100 g, 0.495 mmol), then triphenylphosphine (0.130 g, 0.495 mmol) and 2-fluorophenol (0.050 g, 0.450 mmol). Stir at room temperature for 2 days and heat to 50° C. for 2 days, concentrate and purify twice (silica gel chromatography, eluting with 25:75 to 75:25 ethyl acetate:dichloromethane, then 1% to 3% methanol/dichloromethane) to give the title compound (0.005 g, 10.3%).

MS(ES): m/z=537.3 [M−H]

The compound of Preparations 216-217 may be prepared essentially as described in Preparation 215 using 3'-hydroxyacetophenone or 4'-hydroxyacetophenone.

| Prep | Compound | MS (ES) [M + H] |
|---|---|---|
| 216 | (2R,5R)-5-[(1S,2S)-2-Acetylamino-3-(3,5-difluorophenyl)-1-hydroxypropyl]-2-(3-acetylphenoxymethyl)-morpholine-4-carboxylic acid tert-butyl ester | 563.3 |
| 217 | (2R,5R)-5-[(1S,2S)-2-Acetylamino-3-(3,5-difluorophenyl)-1-hydroxypropyl]-2-(4-acetylphenoxymethyl)-morpholine-4-carboxylic acid tert-butyl ester | 563.4 |

Preparation 218

(2R,5R)-5-[(1S,2S)-2-Acetylamino-3-(3,5-difluorophenyl)-1-hydroxypropyl]-2-cyclohexyloxymethylmorpholine-4-carboxylic acid tert-butyl ester (R)-2-Cyclohexyloxymethyl-oxirane In two separate runs, dissolve (R)-2-phenoxymethyl-oxirane (1.410 g, 9.389 mmol) in tetrahydrofuran (50 mL). Add 5% ruthenium on carbon (0.71 g) and hydrogenate at 60 psi of hydrogen gas for 40 minutes. Filter through a filtering agent, wash with tetrahydrofuran, concentrate and purify (silica gel chromatography, eluting with 5:95 to 30:70 ethyl acetate:hexanes) to give the desired compound as a clear liquid (0.850 g, 57.9% combined yield).

(2R,3R,4S)-3-benzyloxy-2-((R)-3-cyclohexyloxy-2-hydroxypropylamino)-4-dibenzylamino-5-(3,5-difluorophenyl)-pentan-1-ol Add (R)-2-cyclohexyloxymethyl-oxirane (0.688 g, 4.402 mmol) to a solution of 2-amino-3-(R)-benzyloxy-4-(S)-dibenzylamino-5-(3,5-difluorophenyl)-pentan-1-(R)-ol (1.300 g, 2.751 mmol) in ethanol (13.76 mL). Flush with nitrogen and heat in a sealed tube at 80° C. overnight. Concentrate and purify (silica gel chromatography, eluting with 1.3% to 1.8% 2 M ammonia in methanol/dichloromethane) to give the desired compound as a yellow semi-solid (1.140 g, 61.6%).

MS(ES): m/z=673.6 [M+H]

[(1R,2S,3S)-2-benzyloxy-3-dibenzylamino-4-(3,5-difluorophenyl)-1-hydroxymethyl-butyl]-((R)-3-cyclohexyloxy-2-hydroxypropyl)-carbamic acid tert-butyl ester Dissolve (2R,3R,4S)-3-benzyloxy-2-((R)-3-cyclohexyloxy-2-hydroxypropylamino)-4-dibenzylamino-5-(3,5-difluorophenyl)-pentan-1-ol (1.140 g, 1.694 mmol) in tetrahydrofuran (8.5 mL) followed by the addition of di-tert-butyl dicarbonate (0.406 g, 1.864 mmol) and diisopropylethylamine (0.589 mL, 3.389 mmol). Heat to 50° C. for 2.5 days, quench with water (60 mL), extract with ethyl acetate, dry (magnesium sulfate) and purify (silica gel chromatography, eluting with 20:80 to 40:60 ethylacetate:hexanes) to give the desired compound (0.948 g, 72.4%).

MS(ES): m/z=773.6 [M+H]

(2R,5R)-5-[(1S,2S)-1-benzyloxy-2-dibenzylamino-3-(3,5-difluorophenyl)-propyl]-2-cyclohexyloxymethyl-morpholine-4-carboxylic acid tert-butyl ester Dissolve [(1R,2S,3S)-2-benzyloxy-3-dibenzylamino-4-(3,5-difluorophenyl)-1-hydroxymethyl-butyl]-((R)-3-cyclohexyloxy-2-hydroxypropyl)-carbamic acid tert-butyl ester (0.940 g, 1.216 mmol) in benzene (6 mL) followed by the addition of tributylphosphine (0.369 g, 1.824 mmol) and N,N-tetramethyl azodicarboxamide (TMAD) (0.314 g, 1.824 mmol). Stir vigorously for 16 hours, filter the slurry, wash with hexanes and purify (silica gel chromatography, eluting with 5:95 to 15:85 ethyl acetate:hexanes) to give the desired compound as a white foam (0.777 g, 84.7%).

MS(ES): m/z=755.6 [M+H]

(2R,5R)-5-[(1S,2S)-2-Amino-3-(3,5-difluorophenyl)-1-hydroxypropyl]-2-cyclohexyloxymethylmorpholine-4-carboxylic acid tert-butyl ester Add 20% palladium hydroxide on carbon (0.772 g) to a solution of (2R,5R)-5-[(1S,2S)-1-benzyloxy-2-dibenzylamino-3-(3,5-difluorophenyl)-propyl]-2-cyclohexyloxymethyl-morpholine-4-carboxylic acid tert-butyl ester (0.772 g, 1.023 mmol) in ethanol (10.2 mL). Stir vigorously under 1 atmosphere of hydrogen gas for 60 hours. Filter through a filtering agent, wash with ethanol and concentrate to give the desired compound (0.481 g, 97.1%).

MS(ES): m/z=485.4 [M+H]

(2R,5R)-5-[(1S,2S)-2-Acetylamino-3-(3,5-difluorophenyl-1-hydroxypropyl]-2-cyclohexyloxymethylmorpholine-4-carboxylic acid tert-butyl ester Dissolve (2R,5R)-5-[(1S,2S)-2-amino-3-(3,5-difluorophenyl)-1-hydroxypropyl]-2-cyclohexyloxymethylmorpholine-4-carboxylic acid tert-butyl ester (0.240 g, 0.495 mmol) in tetrahydrofuran (5 mL) and cool to 0° C. Add triethylamine (0.104 mL, 0.743 mmol) and acetic anhydride (0.047 mL, 0.495 mmol) and stir for 90 minutes. Concentrate and purify (silica gel chromatography, eluting with 2:98 to 3:97 methanol:dichloromethane) to give the title compound as a white foam (0.209 g, 80.1%).

MS(ES): m/z=527.4 [M+H]

Preparation 219

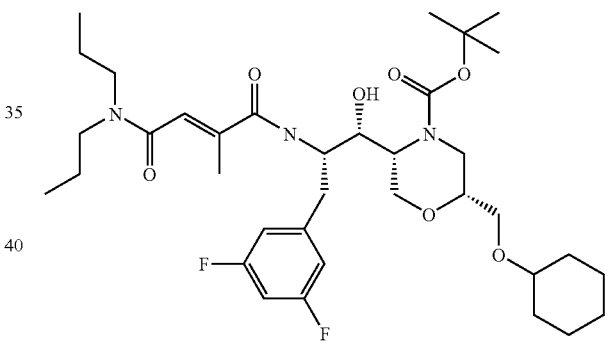

(2R,5R)-2-Cyclohexyloxymethyl-5-[(1S,2S)-3-(3,5-difluorophenyl)-2-((E)-3-dipropylcarbamoyl-2-methylacryloylamino)-1-hydroxypropyl]-morpholine-4-carboxylic acid tert-butyl ester Dissolve (E)-3-dipropylcarbamoyl-2-methylacrylic acid (0.029 g, 0.134 mmol) in dichloromethane (1.3 mL). Add 1-(3-dimethylaminopropyl)-3-ethylcarbodiimide hydrochloride (EDCl) (0.028 g, 0.148 mmol) then 1-hydroxybenzotriazole (HOBT) (0.023 g, 0.148 mmol). Stir at room temperature for 30 minutes. To this stirring solution add (2R,5R)-5-[(1S,2S)-2-amino-3-(3,5-difluorophenyl)-1-hydroxypropyl]-2-cyclohexyloxymethylmorpholine-4-carboxylic acid tert-butyl ester (0.065 g, 0.134 mmol) in dichloromethane (1.5 mL). Stir for 2.5 hours, quench with 10% aqueous potassium carbonate (20 mL), and dilute with dichloromethane (75 mL). Extract the organic layer, wash with 5% aqueous citric acid (25 mL), saturated aqueous sodium chloride (30 mL), dry (magnesium sulfate) and purify (silica gel chromatography, eluting with 30:70 to 70:30 ethyl acetate:hexanes) to give the title compound as a white foam (0.041 g, 45.2%).

MS(ES): m/z=680.6 [M+H]

The compounds of Preparations 220-286 may be prepared essentially as described in Preparation 219.

| Prep | Compound | MS (ES) [M + H] |
|---|---|---|
| 220 | (2R,5R)-2-Cyclohexylmethoxy-5-{(1S,2S)-3-(3,5-difluorophenyl)-2-[(E)-3-(dipropylcarbamoyl)-acryloylamino]-1-hydroxypropyl}-morpholine-4-carboxylic acid tert-butyl ester | 665.5 |
| 221 | (2R,5R)-2-Cyclohexylmethoxy-5-[(1S,2S)-3-(3,5-difluorophenyl)-1-hydroxy-2-(3,3,3-trifluoropropionylamino)-propyl]-morpholine-4-carboxylic acid tert-butyl ester | 593.3 |
| 222 | (2R,5R)-2-Cyclohexylmethoxy-5-[(1S,2S)-3-(3,5-difluorophenyl)-2-((E)-3-dimethylcarbamoyl-2-methylacryloylamino)-1-hydroxypropyl]-morpholine-4-carboxylic acid tert-butyl ester | 624.4 |
| 223 | (2R,5R)-2-Cyclohexylmethoxy-5-{(1S,2S)-3-(3,5-difluorophenyl)-1-hydroxy-2-[(E)-2-methyl-3-(methylpropylcarbamoyl)-acryloylamino]-propyl}-morpholine-4-carboxylic acid tert-butyl ester | 652.5 |
| 224 | (2R,5R)-2-Cyclohexylmethoxy-5-[(1S,2S)-3-(3,5-difluorophenyl)-2-((E)-5,5-dimethyl-4-oxohex-2-enoylamino)-1-hydroxypropyl]-morpholine-4-carboxylic acid tert-butyl ester | 621.3 [M − H] |
| 225 | (2R,5R)-5-[(1S,2S)-3-(3,5-Difluorophenyl)-1-hydroxy-2-((E)-4,4,4-trifluorobut-2-enoylamino)-propyl]-2-(2,2-dimethylpropoxy)-morpholine-4-carboxylic acid tert-butyl ester | 579.2 [M − H] |
| 226 | (2R,5R)-2-Cyclohexylmethoxy-5-((1S,2S)-3-(3,5-difluorophenyl)-1-hydroxy-2-{[trans-2-(methylpropylcarbamoyl)-cyclopropanecarbonyl]-amino}-propyl)-morpholine-4-carboxylic acid tert-butyl ester-Isomers 1 and 2 | 652.5<br>652.5 |
| 227 | (2R,3S,5R)-5-[2-(4,4-difluoro-6-methylheptanoylamino)-3-(3,5-difluorophenyl)-1-hydroxy-propyl]-2-(2,2-dimethylpropoxy)-3-methylmorpholine-4-carboxylic acid tert-butyl ester | 635.5 |
| 228 | (2R,5R)-5-[2-(4,4-difluoro-6-methylheptanoylamino)-3-(3,5-difluorophenyl)-1-hydroxy-propyl]-2-(2,2-dimethylpropoxy)-morpholine-4-carboxylic acid tert-butyl ester | 621.5 |
| 229 | (2R,5R)-5-[2-(trans-(2-fluoromethylcyclopropanecarbonyl)amino)-3-(3,5-difluorophenyl)-1-hydroxy-propyl]-2-(2,2-dimethylpropoxy)-morpholine-4-carboxylic acid tert-butyl ester-Isomers 1 and 2 | 557.3<br>557.3 |
| 230 | (2R,5R)-5-[2-(5,5,5-trifluoropentanoylamino)-3-(3,5-difluorophenyl)-1-hydroxy-propyl]-2-(2,2-dimethylpropoxy)-morpholine-4-carboxylic acid tert-butyl ester | 595.4 [M − H] |
| 231 | (2R,5R)-5-[2-(4,5,5-trifluoropent-4-enoylamino)-3-(3,5-difluorophenyl)-1-hydroxy-propyl]-2-(2,2-dimethylpropoxy)-morpholine-4-carboxylic acid tert-butyl ester | 593.5 [M − H] |
| 232 | (2R,5R)-5-[2-(trans-(2,2-difluoromethylcyclopropanecarbonyl)-amino)-3-(3,5-difluorophenyl)-1-hydroxy-propyl]-2-(2,2-dimethylpropoxy)-morpholine-4-carboxylic acid tert-butyl ester-Isomers 1 and 2 | 575.0 [M − H] |
| 233 | (2R,5R)-5-{2-[cis-2-(methyl-propyl-carbamoyl)cyclopropanecarbonyl]amino-3-(3,5-difluorophenyl)-1-hydroxy-propyl]-2-(2,2-dimethylpropoxy)-morpholine-4-carboxylic acid tert-butyl ester-Isomers 1 and 2 | 624.3 [M − H] |
| 234 | (2R,5R)-5-[2-((2,2-difluoropropionyl)amino)-3-(3,5-difluorophenyl)-1-hydroxy-propyl]-2-(2,2-dimethylpropoxy)-morpholine-4-carboxylic acid tert-butyl ester | 549.3 [M − H] |
| 235 | (2R,5R)-5-[2-((2-fluoropropionyl)amino)-3-(3,5-difluorophenyl)-1-hydroxy-propyl]-2-(2,2-dimethylpropoxy)-morpholine-4-carboxylic acid tert-butyl ester-Isomers 1 and 2 | 531.2 [M − H] |
| 236 | (2R,5R)-5-[2-((4,4,4-trifluorobutyryl)amino)-3-(3,5-difluorophenyl)-1-hydroxy-propyl]-2-(2,2-dimethylpropoxy)-morpholine-4-carboxylic acid tert-butyl ester | 605.3 [M + Na] |
| 237 | (2R,5R)-5-[2-(((E)-4,4,4-trifluoro-2-methyl-but-2-enoyl)amino)-3-(3,5-difluorophenyl)-1-hydroxy-propyl]-2-(2,2-dimethylpropoxy)-morpholine-4-carboxylic acid tert-butyl ester | 593.3 [M − H] |
| 238 | (2R,5R)-5-[(1S,2S)-2-Benzoylamino-3-(3,5-difluorophenyl)-1-hydroxypropyl]-2-cyclohexylmethoxymorpholine-4-carboxylic acid tert-butyl ester | 589.38 |
| 239 | (2R,5R)-2-Cyclohexylmethoxy-5-[(1S,2S)-3-(3,5-difluoro-phenyl)-2-(2,2-dimethylpropionylamino)-1-hydroxypropyl]-morpholine-4-carboxylic acid tert-butyl ester | 569.41 |
| 240 | (2R,5R)-2-Cyclohexylmethoxy-5-[(1S,2S)-3-(3,5-difluoro-phenyl)-1-hydroxy-2-isobutyrylaminopropyl]-morpholine-4-carboxylic acid tert-butyl ester | 555.39 |
| 241 | (2R,5R)-5-[(1S,2S)-2-(Cyclobutanecarbonylamino)-3-(3,5-difluorophenyl)-1-hydroxypropyl]-2-cyclohexylmethoxy-morpholine-4-carboxylic acid tert-butyl ester | 567.51 |
| 242 | (2R,5R)-2-Cyclohexylmethoxy-5-[(1S,2S)-2-(cyclopropane-carbonylamino)-3-(3,5-difluorophenyl)-1-hydroxypropyl]-morpholine-4-carboxylic acid tert-butyl ester | 553.46 |
| 243 | (2R,5R)-2-Cyclohexylmethoxy-5-{(1S,2S)-3-(3,5-difluorophenyl)-1-hydroxy-2-[(thiophene-2-carbonyl)-amino]-propyl}-morpholine-4-carboxylic acid tert-butyl ester | 595.47 |

-continued

| Prep | Compound | MS (ES) [M + H] |
|---|---|---|
| 244 | (2R,5R)-2-Cyclohexylmethoxy-5-[(1S,2S)-3-(3,5-difluorophenyl)-1-hydroxy-2-(2-methoxyacetylamino)-propyl]-morpholine-4-carboxylic acid tert-butyl ester | 557.3 |
| 245 | (2R,5R-2-Cyclohexylmethoxy-5-[(1S,2S)-2-2-cyclopropylacetylamino)-3-(3,5-difluorophenyl)-1-hydroxypropyl]-morpholine-4-carboxylic acid tert-butyl ester | 567.56 |
| 246 | (2R,5R)-2-Cyclohexylmethoxy-5-[(1S,2S)-3-(3,5-difluorophenyl)-2-(3,3-dimethylbutyrylamino)-1-hydroxypropyl]-morpholine-4-carboxylic acid tert-butyl ester | 583.39 |
| 247 | (2R,5R)-2-Cyclohexylmethoxy-5-[(1S,2S)-3-(3,5-difluorophenyl)-1-hydroxy-2-(3-methoxypropionylamino)-propyl]-morpholine-4-carboxylic acid tert-butyl ester | 571.4 |
| 248 | (2R,5R)-2-Cyclohexylmethoxy-5-[(1S,2S)-3-(3,5-difluorophenyl)-2-(3-fluorobenzoylamino)-1-hydroxypropyl]-morpholine-4-carboxylic acid tert-butyl ester | 607.5 |
| 249 | (2R,5R)-2-Cyclohexylmethoxy-5-[(1S,2S)-3-(3,5-difluorophenyl)-1-hydroxy-2-(3-propoxybenzoylamino)-propyl]-morpholine-4-carboxylic acid tert-butyl ester | 647.6 |
| 250 | (2R,5R)-2-Cyclohexylmethoxy-5-{(1S,2S)-3-(3,5-difluoro-phenyl)-1-hydroxy-2-[((R)-tetrahydrofuran-2-carbonyl)-amino]-propyl}-morpholine-4-carboxylic acid tert-butyl ester | 583.5 |
| 251 | (2R,5R)-2-Cyclohexylmethoxy-5-[(1S,2S)-3-(3,5-difluorophenyl)-2-(2-fluorobenzoylamino)-1-hydroxypropyl]-morpholine-4-carboxylic acid tert-butyl ester | 607.5 |
| 252 | (2R,5R)-2-Cyclohexylmethoxy-5-[(1S,2S)-3-(3,5-difluorophenyl)-1-hydroxy-2-(3-methylbenzoylamino)-propyl]-morpholine-4-carboxylic acid tert-butyl ester | 603.5 |
| 253 | (2R,5R)-5-[(1S,2S)-3-(3,5-Difluoro-phenyl)-1-hydroxy-2-octanoylamino-propyl]-2-(2,2-dimethyl-propoxy)-morpholine-4-carboxylic acid tert-butyl ester | 585.4 |
| 254 | (2R,5R)-5-[(1S,2S)-3-(3,5-Difluoro-phenyl)-1-hydroxy-2-(5-methyl-hexanoylamino)-propyl]-2-(2,2-dimethyl-propoxy)-morpholine-4-carboxylic acid tert-butyl ester | 571.56 |
| 255 | (2R,5R)-5-{(1S,2S)-3-(3,5-Difluoro-phenyl)-2-[(2,5-dimethyl-furan-3-carbonyl)-amino]-1-hydroxy-propyl}-2-(2,2-dimethyl-propoxy)-morpholine-4-carboxylic acid tert-butyl ester | 581.45 |
| 256 | (2R,5R)-5-[(1S,2S)-3-(3,5-Difluoro-phenyl)-2-heptanoylamino-1-hydroxy-propyl]-2-(2,2-dimethyl-propoxy)-morpholine-4-carboxylic acid tert-butyl ester | 571.52 |
| 257 | (2R,5R)-5-[(1S,2S)-3-(3,5-Difluoro-phenyl)-1-hydroxy-2-((E)-2-methyl-5-propyl-octa-2,4-dienoylamino)-propyl]-2-(2,2-dimethyl-propoxy)-morpholine-4-carboxylic acid tert-butyl ester | 637.69 |
| 258 | (2R,5R)-5-{(1S,2S)-3-(3,5-Difluoro-phenyl)-1-hydroxy-2-[(E)-3-methyl-3-(methyl-propyl-carbamoyl)-but-2-enoylamino]-propyl}-2-(2,2-dimethyl-propoxy)-morpholine-4-carboxylic acid tert-butyl ester | 626.59 |
| 259 | (2R,5R)-5-{(1S,2S)-3-(3,5-Difluoro-phenyl)-1-hydroxy-2-[3-(methyl-propyl-carbamoyl)-propionylamino]-propyl}-2-(2,2-dimethyl-propoxy)-morpholine-4-carboxylic acid tert-butyl ester | 614.7 |
| 260 | (2R,5R)-5-[(1S,2S)-3-(3,5-Difluoro-phenyl)-1-hydroxy-2-((E)-2-methyl-hex-2-enoylamino)-propyl]-2-(2,2-dimethyl-propoxy)-morpholine-4-carboxylic acid tert-butyl ester | 469.7 [M + 1-BOC] |
| 261 | (2R,5R)-5-[(1S,2S)-3-(3,5-Difluoro-phenyl)-2-(5,5-dimethyl-4-oxo-hexanoylamino)-1-hydroxy-propyl]-2-(2,2-dimethyl-propoxy)-morpholine-4-carboxylic acid tert-butyl ester | 599.49 |
| 262 | (2R,5R)-5-{(1S,2S)-3-(3,5-Difluoro-phenyl)-2-[3-(ethyl-propyl-carbamoyl)-propionylamino]-1-hydroxy-propyl}-2-(2,2-dimethyl-propoxy)-morpholine-4-carboxylic acid tert-butyl ester | 628.75 |
| 263 | (2R,5R)-5-[(1S,2S)-2-Acetylamino-3-(3,5-difluoro-phenyl)-1-hydroxy-propyl]-2-(1-methyl-cyclopentylmethoxy)-morpholine-4-carboxylic acid tert-butyl ester | 527.37 |
| 264 | (2R,5R)-5-((1S,2S)-3-(3,5-Difluoro-phenyl)-1-hydroxy-2-{[5-(methyl-propyl-carbamoyl)-furan-2-carbonyl]-amino}-propyl)-2-(2,2-dimethyl-propoxy)-morpholine-4-carboxylic acid tert-butyl ester | 652.52 |
| 265 | (2R,5R)-5-[(1S,2S)-3-(3,5-Difluoro-phenyl)-1-hydroxy-2-(4-methyl-pentanoylamino)-propyl]-2-(2,2-dimethyl-propoxy)-morpholine-4-carboxylic acid tert-butyl ester | 557.43 |
| 266 | (2R,5R)-5-[(1S,2S)-3-(3,5-Difluoro-phenyl)-1-hydroxy-2-(6-methyl-4-oxo-heptanoylamino)-propyl]-2-(2,2-dimethyl-propoxy)-morpholine-4-carboxylic acid tert-butyl ester | 599.41 |
| 267 | (2R,5R)-5-[(1S,2S)-3-(3,5-Difluoro-phenyl)-1-hydroxy-2-pentyloxycarbonylamino-propyl]-2-(2,2-dimethyl-propoxy)-morpholine-4-carboxylic acid tert-butyl ester | 517.23 [M + 1-t-Bu] |
| 268 | (2R,5R)-5-[(1S,2S)-2-Butoxycarbonylamino-3-(3,5-difluoro-phenyl)-1-hydroxy-propyl]-2-(2,2-dimethyl-propoxy)-morpholine-4-carboxylic acid tert-butyl ester | 503.30 [M + 1-t-Bu] |

-continued

| Prep | Compound | MS (ES) [M + H] |
|---|---|---|
| 269 | (2R,5R)-5-[(1S,2S)-2-[(5-tert-Butyl-2-methyl-furan-3-carbonyl)-amino]-3-(3,5-difluoro-phenyl)-1-hydroxy-propyl]-2-(2,2-dimethyl-propoxy)-morpholine-4-carboxylic acid tert-butyl ester | 623.46 |
| 270 | (2R,5R)-5-[(1S,2S)-3-(3,5-Difluoro-phenyl)-1-hydroxy-2-(4-oxo-hexanoylamino)-propyl]-2-(2,2-dimethyl-propoxy)-morpholine-4-carboxylic acid tert-butyl ester | 571.48 |
| 271 | (2R,5R)-5-[(1S,2S)-3-(3,5-Difluoro-phenyl)-1-hydroxy-2-((E)-3,5,5-trimethyl-4-oxo-hex-2-enoylamino)-propyl]-2-(2,2-dimethyl-propoxy)-morpholine-4-carboxylic acid tert-butyl ester | 644.42 |
| 272 | (2R,5R)-5-[(1S,2S)-3-(3,5-Difluoro-phenyl)-1-hydroxy-2-((E)-2-methyl-oct-2-enoylamino)-propyl]-2-(2,2-dimethyl-propoxy)-morpholine-4-carboxylic acid tert-butyl ester | 597.5 |
| 273 | (2R,5R)-5-[(1S,2S)-3-(3,5-Difluoro-phenyl)-2-(3-dipropylcarbamoyl-propionylamino)-1-hydroxy-propyl]-2-(2,2-dimethyl-propoxy)-morpholine-4-carboxylic acid tert-butyl ester | 642.54 |
| 274 | (2R,5R)-5-[(1S,2S)-3-(3,5-Difluoro-phenyl)-2-hexyloxycarbonylamino-1-hydroxy-propyl]-2-(2,2-dimethyl-propoxy)-morpholine-4-carboxylic acid tert-butyl ester | 487.35 [M + 1-BOC] |
| 275 | (2R,5R)-5-[(1S,2S)-3-(3,5-Difluoro-phenyl)-1-hydroxy-2-((E)-2-methyl-4-oxo-hept-2-enoylamino)-propyl]-2-(2,2-dimethyl-propoxy)-morpholine-4-carboxylic acid tert-butyl ester | 597.52 |
| 276 | (2R,5R)-5-[(1S,2S)-2-(4-Cyclopentyl-4-oxo-butyrylamino)-3-(3,5-difluoro-phenyl)-1-hydroxy-propyl]-2-(2,2-dimethyl-propoxy)-morpholine-4-carboxylic acid tert-butyl ester | |
| 277 | (2R,5R)-5-[(1S,2S)-3-(3,5-Difluoro-phenyl)-2-(5,5-dimethyl-hexanoylamino)-1-hydroxy-propyl]-2-(2,2-dimethyl-propoxy)-morpholine-4-carboxylic acid tert-butyl ester | 585.44 |
| 278 | (2R,5R)-5-[(1S,2S)-3-(3,5-Difluoro-phenyl)-1-hydroxy-2-((E)-2,4,4-trimethyl-hept-2-enoylamino)-propyl]-2-(2,2-dimethyl-propoxy)-morpholine-4-carboxylic acid tert-butyl ester | 611.49 |

The compounds of Preparations 279-286 may be prepared essentially as described in Preparation 98.

| Prep | Compound | MS (ES) [M + H] |
|---|---|---|
| 279 | (2R,5R)-5-[(1S,2S)-2-Acetylamino-3-(3,5-difluoro-phenyl)-1-hydroxy-propyl]-2-(4-methyl-tetrahydro-pyran-4-ylmethoxy)-morpholine-4-carboxylic acid tert-butyl ester | 543.7 |
| 280 | (2R,5R)-5-[(1S,2S)-2-Acetylamino-3-(3,5-difluoro-phenyl)-1-hydroxy-propyl]-2-(bicyclo[2.2.1]hept-1-ylmethoxy)-morpholine-4-carboxylic acid tert-butyl ester | 539.4 |
| 281 | (2R,5R)-5-[(1S,2S)-2-Acetylamino-3-(3,5-difluoro-phenyl)-1-hydroxy-propyl]-2-(1-methyl-cyclopentylmethoxy)-morpholine-4-carboxylic acid tert-butyl ester | 527.37 |
| 282 | (2R,5R)-5-[(1S,2S)-2-Acetylamino-3-(3,5-difluoro-phenyl)-1-hydroxy-propyl]-2-(3,3,3-trifluoro-2-methyl-2-trifluoromethyl-propoxy)-morpholine-4-carboxylic acid tert-butyl ester | 609.41 |
| 283 | (2R,5R)-5-[(1S,2S)-2-Acetylamino-3-(3,5-difluoro-phenyl)-1-hydroxy-propyl]-2-(2,2-dimethyl-butoxy)-morpholine-4-carboxylic acid tert-butyl ester | 515.48 |
| 284 | (2R,5R)-5-[(1S,2S)-2-Acetylamino-3-(3,5-difluoro-phenyl)-1-hydroxy-propyl]-2-(2,2-dimethyl-pentyloxy)-morpholine-4-carboxylic acid tert-butyl ester | |
| 285 | (2R,5R)-5-[(1S,2S)-2-Acetylamino-3-(3,5-difluoro-phenyl)-1-hydroxy-propyl]-2-(1-phenyl-cyclopentylmethoxy)-morpholine-4-carboxylic acid tert-butyl ester | |
| 286 | (2R,5R)-5-[(1S,2S)-2-Acetylamino-3-(3,5-difluoro-phenyl)-1-hydroxy-propyl]-2-(2,2,4-trimethyl-pentyloxy)-morpholine-4-carboxylic acid tert-butyl ester | 543.32 |

Preparation 287

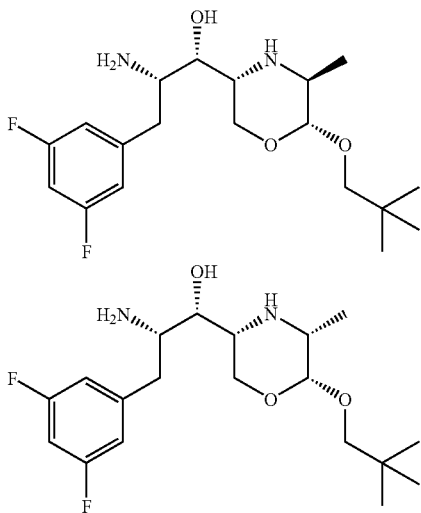

(1S,2S)-2-Amino-3-(3,5-difluorophenyl)-1-[(3R,5R,6R)-6-(2,2-dimethylpropoxy)-5-methylmorpholin-3-yl]-propan-1-ol (1S,2S)-2-Amino-3-(3,5-difluorophenyl)-1-[(3R,5S,6R)-6-(2,2-dimethylpropoxy)-5-methylmorpholin-3-yl]-propan-1-ol 1-bis-(2,2-dimethylpropoxy)-propan-2-one Combine pyruvicaldehyde dimethyl acetal (7 mL, 59 mmol), neopentyl alcohol (12.7 g, 144 mmol), and p-toluenesulfonic acid monohydrate (0.6 g, 3.2 mmol) and heat for 21 hours at 80° C. Cool to room temperature and purify (silica gel chromatography using deactivated silica gel, eluting with 0:100 to 10:90 ethyl acetate:hexanes) to give a yellow liquid (8.0 g).

$^1$H NMR (400 MHz, CDCl$_3$) δ 4.34 (s, 1H), 3.32 (d, J=8.0 Hz, 2H), 3.10 (d, J=8.8 Hz, 2H), 2.19 (s, 3H), 0.93 (s, 18H).

(2R,3R,4S)-3-benzyloxy-2-[(S)-2,2-bis-(2,2-dimethylpropoxy)-1-methylethylamino]-4-dibenzylamino-5-(3,5-difluorophenyl)-pentan-1-ol (2R,3R,4S)-3-benzyloxy-2-[(R)-2,2-bis-(2,2-dimethylpropoxy)-1-methylethylamino]-4-dibenzylamino-5-(3,5-difluorophenyl)-pentan-1-ol Suspend (2R,3R,4S)-2-amino-3-benzyloxy-4-dibenzylamino-5-(3,5-difluorophenyl)-pentan-1-ol (2.7 g, 5.2 mmol), 1-bis-(2,2-dimethylpropoxy)-propan-2-one (3.0 g, 13 mmol), pyridinium p-toluene sulphonate (148 mg, 0.59 mmol), and freshly activated 3 Å molecular sieves (800 mg) in dry toluene (20 mL) under nitrogen and heat to reflux for 17 hours. Filter, concentrate, dissolve the residue in dry methanol (30 mL) and cool to 0° C. Add sodium cyanoborohydride (1.28 g, 20 mmol) followed by the dropwise addition of glacial acetic acid (0.63 mL, 11 mmol). Stir for 15 minutes, then remove the cooling bath and allow to warm to room temperature. After 45 minutes dilute with ethyl acetate and add 2 N sodium hydroxide (25 mL). Stir the mixture for 15 minutes, separate away the aqueous phase, wash the organic solution with saturated aqueous sodium bicarbonate, saturated aqueous sodium chloride solution, dry (sodium sulfate), filter and concentrate. Deactivate the silica gel by thorough washes with 3% 2 M ammonia in methanol/dichloromethane, dichloromethane and then with hexanes. Purify (deactivated silica-gel chromatography using deactivated silica gel, eluting with 0:100 to 20:80 ethyl acetate:hexanes) to give the desired compounds in order of elution: (2R,3R,4S)-3-benzyloxy-2-[(R)-2,2-bis-(2,2-dimethylpropoxy)-1-methylethylamino]-4-dibenzylamino-5-(3,5-difluorophenyl)-pentan-1-ol (1.19 g, 30%, MS(ES) 731.5 m/z [M+H]); followed by (2R,3R,4S)-3-benzyloxy-2-[(S)-2,2-bis-(2,2-dimethylpropoxy)-1-methylethylamino]-4-dibenzylamino-5-(3,5-difluorophenyl)-pentan-1-ol (1.13 g, 30%, MS(ES): m/z=731.5 [M+H]).

Dibenzyl-{(1S,2R)-2-benzyloxy-1-(3,5-difluorobenzyl-2-[(3R,5S,6R)-6-(2,2-dimethylpropoxy)-5-methylmorpholin-3-yl]-ethyl}-amine Dibenzyl-{(1S,2R)-2-benzyloxy-1-(3,5-difluorobenzyl)-2-[(3R,5S,6S)-6-(2,2-dimethylpropoxy)-5-methylmorpholin-3-yl]-ethyl}-amine Add distilled boron trifluoride diethyl etherate (2.8 mL, 22 mmol) dropwise to a solution of (2R,3R,4S)-3-benzyloxy-2-[(S)-2,2-bis-(2,2-dimethylpropoxy)-1-methylethylamino]-4-dibenzylamino-5-(3,5-difluorophenyl)-pentan-1-ol (5.8 g, 7.9 mmol) in dry 1,2-dichloroethane (350 mL) under nitrogen and reflux for 1 hour. Cool to room temperature and dilute with ethyl acetate and saturated aqueous sodium bicarbonate solution. Shake the mixture vigorously, separate away the aqueous, wash the organic solution with saturated aqueous sodium bicarbonate solution (twice) and set aside. Combine the aqueous solutions and extract with ethyl acetate (twice). Combine the organic extracts, wash with saturated aqueous sodium chloride solution, dry (sodium sulfate), filter, concentrate and purify (silica gel chromatography using deactivated silica-gel, eluting with 0:100 to 10:90 ethyl acetate:hexanes) to give in order of elution: dibenzyl-{(1S,2R)-2-benzyloxy-1-(3,5-difluorobenzyl)-2-[(3R,5S,6S)-6-(2,2-dimethylpropoxy)-5-methylmorpholin-3-yl]-ethyl}-amine (0.36 g, 76%, MS(ES): m/z+643 [M+H]); followed by dibenzyl-{(1S,2R)-2-benzyloxy-1-(3,5-difluorobenzyl)-2-[(3R,5S,6R)-6-(2,2-dimethylpropoxy)-5-methylmorpholin-3-yl]-ethyl}-amine (3.78 g, 74%, MS(ES): m/z=643.5 [M+H])

Dibenzyl-{(1S,2R)-2-benzyloxy-1-(3,5-difluorobenzyl)-2-[(3R,5R,6R)-6-(2,2-dimethylpropoxy)-5-methylmorpholin-3-yl]-ethyl}-amine Prepare the desired compound essentially as described above starting from (2R,3R,4S)-3-benzyloxy-2-[(R)-2,2-bis-(2,2-dimethylpropoxy)-1-methylethylamino]-4-dibenzylamino-5-(3,5-difluorophenyl)-pentan-1-ol (57%).

MS(ES): m/z=643.5 [M+H])

(1S,2S)-2-Amino-3-(3,5-difluorophenyl)-1-[(3R,5S,6R)-6-(2,2-dimethylpropoxy)-5-methylmorpholin-3-yl]-propan-1-ol Add 20% palladium hydroxide on carbon (679 mg) to a solution of dibenzyl-{(1S,2R)-2-benzyloxy-1-(3,5-difluorobenzyl)-2-[(3R,5S,6R)-6-(2,2-dimethylpropoxy)-5-methylmorpholin-3-yl]-ethyl}-amine (284 mg, 0.442 mmol) in absolute ethanol (5 mL) and stir under 1 atmosphere of hydrogen gas at room temperature for 18 hours. Filter through a pad of Celite®, wash thoroughly with ethanol and concentrate to give the desired compound as a glass (162 mg, 98%).

MS(ES): m/z=373.3 [M+H]

(1S,2S)-2-Amino-3-(3,5-difluorophenyl)-1-[(3R,5R,6R)-6-(2,2-dimethylpropoxy)-5-methylmorpholin-3-yl]-propan-1-ol Prepare the title compound essentially as described above starting from dibenzyl-{(1S,2R)-2-benzyloxy-1-(3,5-difluorobenzyl)-2-[(3R,5R,6R)-6-(2,2-dimethylpropoxy)-5-methylmorpholin-3-yl]-ethyl}-amine (93%).

MS(ES): m/z=373.3 [M+H]

The compounds of Preparation 288-294 may be prepared essentially as described in Preparation 287. The compound of Preparation 288 may be prepared using camphorsulfonic acid instead of boron trifluoride diethyl etherate. The acetals necessary for the preparation of compounds of Preparations 289-294 may be prepared essentially as described in *J. Am. Chem. Soc.*, 78(16), 4161 (1956).

(4-Fluorotetrahydropyran-4-yl)-hydroxyacetonitrile

Dissolve 1,6-dioxaspiro[2,5]octane-2-carbonitrile (4.14 g, 29.8 mmol) in dry dichloromethane (10 mL) and cool to 0° C. under a nitrogen atmosphere in a polypropylene bottle. Add hydrogen fluoride-pyridine (3 mL) dropwise. Allow the mixture to slowly warm to room temperature over 3 h and then stir an additional 1.5 hours at room temperature. Pour into ethyl acetate and wash with saturated aqueous sodium bicarbonate solution until washes remain basic. Combine the aqueous washes and adjust the pH of the solution to ~pH=8 and extract with ethyl acetate. Combine this organic extract with the ethyl acetate solution of the crude reaction mixture and wash with saturated aqueous sodium chloride solution, dry (magnesium sulfate), filter and concentrate to give the desired compound as a yellow oil which is used directly in the next reaction.

(4-Fluorotetrahydropyran-4-yl)-methanol

Dissolve (4-fluorotetrahydropyran-4-yl)-hydroxyacetonitrile (4.4 g, 29.8 mmol) in 2-propanol (48 mL) and water (12 mL). Cool to 0° C. under a nitrogen atmosphere. Add sodium

| Prep | Compound |
|---|---|
| 288 | (1S,2S)-2-Amino-3-(3,5-difluorophenyl)-1-[(3R,5S,6R)-6-(2,2-dimethylpropoxy)-5-isobutyl-morpholin-3-yl]-propan-1-ol |
| 289 | (1S,2S)-2-Amino-1-[(3R,6R)-5-cyclopropylmethyl-6-(2,2-dimethylpropoxy)-morpholin-3-yl]-3-(3,5-difluorophenyl)-propan-1-ol |
| 290 | (1S,2S)-2-Amino-3-(3,5-difluorophenyl)-1-[(3R,5S,6R)-5-methyl-6-(1-methylcyclopentylmethoxy)-morpholin-3-yl]-propan-1-ol |
| 291 | (1S,2S)-2-Amino-3-(3,5-difluorophenyl)-1-[(3R,5S,6R)-5-methyl-6-(1-methylcyclopropylmethoxy)-morpholin-3-yl]-propan-1-ol |
| 292 | (1S,2S)-2-Amino-3-(3,5-difluorophenyl)-1-[(3R,5S,6R)-6-(2-ethyl-2-methylbutoxy)-5-methylmorpholin-3-yl]-propan-1-ol |
| 293 | (1S,2S)-2-Amino-1-[(3R,5S,6R)-6-(2,2-dimethylpropoxy)-5-methylmorpholin-3-yl]-3-phenylpropan-1-ol |
| 294 | (1S,2S)-2-Amino-3-(3,5-difluoro-phenyl)-1-[(3R,5S,6R)-6-(2,2-dimethylpropoxy)-5-propyl-morpholin-3-yl]-propan-1-ol |

Preparation 295

(1-Fluorocyclohexyl)-methanol

Prepare the title compound essentially as described in the literature procedure *Synthesis*, 1988, 310-313.

Preparation 296

(4-Fluorotetrahydropyran-4-yl)-methanol 1,6-Dioxa-spiro[2,5]octane-2-carbonitrile Dissolve tetrahydropyran-4-one (5.0 mL, 54.2 mmol) and chloroacetonitrile (3.4 mL, 53.5 mmol) in tert-butanol (1 mL) and add drop-wise a solution of potassium tert-butoxide (54 mL, 54 mmol, 1.0 M in tert-butanol) over 20 minutes. Stir for 16 hours, dilute with water and quench slowly with 1 N hydrochloric acid. Extract with diethyl ether (×3). Combine extracts and wash with saturated aqueous sodium chloride solution, dry (magnesium sulfate), filter, concentrate and purify (silica gel chromatography, eluting with 0:100 to 1:1 ethyl acetate:hexanes) to give the desired compound as a light yellow oil (4.4 g, 59%).

$^1$H NMR (400 MHz, CDCl$_3$) δ 3.89-3.87 m (2H), 3.85-3.82 (m, 2H), 3.33 (s, 1H), 2.13-2.06 (m, 1H), 1.93-1.79 (m, 2H), 1.62-1.54 (m, 1H).

borohydride (1.2 g, 31.7 mmol) and allow the resulting mixture to slowly warm to room temperature over 5.5 hours. Quench with acetone and stir for 1 h. Concentrate the mixture to ⅓ volume and dilute with ethyl acetate. Wash the resulting organic solution with saturated aqueous sodium bicarbonate solution and saturated aqueous ammonium chloride solution (twice). Combine the aqueous washes and dilute with saturated aqueous sodium chloride solution and extract with ethyl acetate (twice). Add these extracts to the crude reaction mixture and wash the resulting solution with saturated aqueous sodium chloride solution, dry (magnesium sulfate), filter, concentrate and purify (silica gel chromatography, eluting with 0:100 to 1:1 ethyl acetate:hexanes) to give the desired compound as a yellow oil (740 mg, 18%).

$^1$H NMR (400 MHz, CDCl$_3$) δ 3.83 (ddd, J=2.8, 5.6, 11.6 Hz, 2H), 3.72 (ddd, J 2.8, 11.2, 11.2 Hz, 2H), 3.68 (s, 1H), 3.58 (s, 1H), 1.88-1.63 (m, 5H)

Preparation 297

Cis-3-tert-butylcyclobutanol 3-tert-butyl-2,2-dichlorocyclobutanone

Suspend 3,3-dimethyl-1-butene (10 mL, 80.8 mmol), ethylene glycol dimethyl ether (11.5 mL, 106 mmol), and freshly activated zinc (13.8 g, 211 mmol) in dry diethyl ether (100 mL) under a nitrogen atmosphere. Add to this suspension a solution of trichloroacetyl chloride (11.5 mL, 103 mmol) in dry diethyl ether (50 mL) dropwise over 20 minutes. Heat to reflux for 24 hours. Cool to room temperature and filter off the residual solid materials. Concentrate the filtrate and triturate the residue with hexanes. Filter the mixture to remove solid materials. Wash the filtrate solution with saturated aqueous sodium bicarbonate solution (3×), saturated aqueous sodium chloride solution, dry (magnesium sulfate), filter, concentrate and purify (silica gel chromatography, eluting with 0:100 to 10:90 ethyl acetate:hexanes) to give the pure fractions and concentrate. Isolate the desired compound by vacuum distillation to give a clear liquid (7.59 g, 48%).

$^1$H NMR (400 MHz, CDCl$_3$) δ 3.29 (app. dd, J=7.2, 10.4 Hz, 2H), 2.83 (dd, J=10.0, 11.2 Hz, 1H), 1.14 (s, 9H)

3-tert-butylcyclobutanone

Saturate dry methanol by stirring with excess ammonium chloride under nitrogen for 1.5 h. Add this saturated solution (150 mL) to 3-tert-butyl-2,2-dichlorocyclobutanone (7.5 g, 38.4 mmol) under nitrogen. To the resulting suspension add freshly activated zinc (15.4 g, 236 mmol). Stir for 5 hours, filter and concentrate. Partition the residue between diethyl ether and water. Discard the aqueous phase and wash the diethyl ether layer with water (twice), saturated aqueous sodium chloride solution, dry (magnesium sulfate), filter, concentrate and purify (silica gel chromatography, eluting with 0:100 to 10:90 ethyl acetate:hexanes) to give the desired compound as a clear liquid (2.71 g, 56%).

$^1$H NMR (400 MHz, CDCl$_3$) δ 2.87 (m, 4H), 2.30 (m, 1H), 0.93 (s, 9H)

Cis-3-tert-butylcyclobutanol

Cool lithium aluminum hydride (16 mL, 16 mmol, 1.0 M solution in tetrahydrofuran) under a nitrogen atmosphere to 0° C. Add tert-butanol (4.6 mL, 48.1 mmol) dropwise, warm to room temperature, and stir the resulting solution for 1 hour. Cool the hydride solution to −78° C. and add a solution of 3-tert-butylcyclobutanone (1 g, 7.9 mmol) in dry tetrahydrofuran (3 mL) dropwise. Stir for 1 hour at −78° C. and then warm to room temperature over 1 hour. Slowly quench the mixture with 0.1 N hydrochloric acid. Dilute the resulting mixture with ethyl acetate and a saturated aqueous solution of sodium potassium tartrate (Rochelle salt) and stir the biphasic mixture overnight. Filter the mixture to remove precipitates and separate the aqueous layer. Saturate the aqueous phase with sodium chloride and extract with ethyl acetate. Add the organic extract to the ethyl acetate solution of the reaction mixture and wash the resultant mixture with saturated aqueous sodium chloride solution, dry (magnesium sulfate), filter, and concentrate to give the title compound as a 9:1 mixture of cis/trans diastereomers.

$^1$H NMR (400 MHz, CDCl$_3$) δ 3.99 (m, 1H), 2.17-2.15 (m, 2H), 1.56-1.51 (m, 3H), 0.78 (s, 9H).

Preparation 298

(R)-5-[(1S,2S)-2-Acetylamino-3-(3,5-difluorophenyl)-1-hydroxypropyl]-2-ethoxymorpholine-4-carboxylic acid tert-butyl ester

[(R)-2-(tert-butyl-dimethylsilanyloxy)-1-(1-ethoxy-2-iodoethoxymethyl)-ethyl]-carbamic acid tert-butyl ester Dissolve [(R)-1-tert-butyl-dimethylsilanyloxymethyl)-2-hydroxyethyl]-carbamic acid tert-butyl ester (1.0 g, 3.27 mmol) and ethyl vinyl ether (0.20 g, 2.73 mmol) in acetonitrile (20 mL) and add N-iodosuccinimide (0.735 g, 3.27 mmol). Stir at room temperature 72 hours and pour into saturated aqueous sodium chloride. Extract with ethyl acetate, wash with water and saturated aqueous sodium chloride, dry (magnesium sulfate), filter and concentrate. Purify on silica gel, eluting with 0:100 to 10:90 ethyl acetate:hexanes to give the desired compound.

MS(ES): m/z +504.4 [M+H]

(R)-5-(tert-butyldimethylsilanyloxymethyl)-2-ethoxymorpholine-4-carboxylic acid tert-butyl ester Add sodium hydride (0.044 g, 1.10 mmol) to [(R)-2-(tert-butyldimethylsilanyloxy)-1-(1-ethoxy-2-iodoethoxymethyl)-ethyl]-carbamic acid tert-butyl ester (0.462 g, 0.918 mmol) in N,N-dimethylformamide (9 mL) at room temperature. Heat to −50° C. for 4 hours, cool to room temperature, and pour into ethyl acetate. Wash with water, 1 N lithium chloride and saturated aqueous sodium chloride. Dry (magnesium sulfate), filter and concentrate. Purify on silica gel, eluting with 0:100 to 50:50 ethyl acetate:hexanes to give the desired compound as a mixture of diastereomers.

$^1$HNMR (400 MHz, CDCl$_3$) (more polar diastereomer) δ 4.69 (bs, 1H), 3.98-3.45 (m, 8H), 3.07 (d, J=12.8 Hz, 1H), 1.46 (s, 9H), 1.22 (t, J=7.2 Hz, 3H), 0.89 (s, 9H), 0.07 (s, 6H).

(S)-2-Ethoxy-5-hydroxymethylmorpholine-4-carboxylic acid tert-butyl ester

Dissolve (R)-5-(tert-butyldimethylsilanyloxymethyl)-2-ethoxymorpholine-4-carboxylic acid tert-butyl ester (0.39 g, 1.04 mmol) in tetrahydrofuran (3 mL) and add tetrabutylammonium fluoride (2.1 mL, 2.1 mmol, 1.0 M in tetrahydrofuran). Stir 45 minutes at room temperature and concentrate. Purify on silica gel, eluting with 10:90 to 40:60 ethyl acetate in hexanes to give the desired compound.

$^1$HNMR (400 MHz, CDCl$_3$) δ 4.69 (bs, 1H), 4.08-4.04 (m, 2H), 3.88-3.66 (m, 4H), 3.56 (d, J=10.8 Hz, 1H), 3.51-3.43 (m, 1H), 3.20 (d, J=14 Hz, 1H), 1.47 (s, 9H), 1.22 (t, J=7.2 Hz, 3H)

(R)-5-[(1R,2S)-3-(3,5-Difluorophenyl-1-hydroxy-2-nitropropyl]-2-ethoxymorpholine-4-carboxylic acid tert-butyl ester To (S)-2-ethoxy-5-hydroxymethylmorpholine-4-carboxylic acid tert-butyl ester (0.245 g, 0.938 mmol) in dimethylsulfoxide (3 mL) at room temperature add triethylamine (0.180 g, 1.78 mmol), then pyridine sulfur trioxide complex (0.283 g, 1.78 mmol) in dimethylsulfoxide (1.5 mL). Stir at room temperature 4 hours and pour into 50 mL of 10:90 ethyl acetate/hexanes. Wash with water and saturated aqueous sodium chloride, dry (magnesium sulfate), filter and concentrate. Dissolve the residue in tetrahydrofuran (1.5 mL) and add 3,5-difluorophenylnitroethane (0.134 g, 0.725 mmol). Cool in an ice/water bath and add tetrabutylammonium fluoride (0.70 mL, 0.70 mmol, 1.0 M in tetrahydrofuran) all at once. Stir 30 minutes and pour into cold half saturated aqueous sodium chloride (~20 mL). Extract with ethyl acetate, wash with water and saturated aqueous sodium chloride, dry (magnesium sulfate), and concentrate. Purify on silica gel, eluting with 0:100 to 30:70 ethyl acetate:hexanes to give the desired compound.

MS(ES): m/z=445.2 [M−H]

(R)-5-[(1S,2S)-2-Amino-3-(3,5-difluorophenyl)-1-hydroxypropyl]-2-ethoxymorpholine-4-carboxylic acid tert-butyl ester To a solution of (R)-5-[(1R,2S)-3-(3,5-difluorophenyl)-1-hydroxy-2-nitropropyl]-2-ethoxymorpholine-4-carboxylic acid tert-butyl ester (0.145 g, 0.325 mmol) in methanol (5 mL) at room temperature add nickel (II) chloride (0.063 g, 0.487 mmol) and then sodium borohydride (0.061 g, 1.62 mmol) portionwise. Stir 30 minutes, add water (~3 mL) and concentrate. Dilute with ethyl acetate and filter through Celite®. Partition the filtrate between ethyl acetate and water. Dry the ethyl acetate layer (magnesium sulfate), filter and concentrate to give the desired compound as a white solid.

MS(ES): m/z=417.3 [M+H]

(R)-5-[(1S,2S)-2-Acetylamino-3-(3,5-difluorophenyl)-1-hydroxypropyl]-2-ethoxymorpholine-4-carboxylic acid tert-butyl ester Add triethylamine (0.030 g, 0.30 mmol) and acetic anhydride (0.024 g, 0.23 mmol) to (R)-5-[(1S,2S)-2-amino-3-(3,5-difluorophenyl)-1-hydroxypropyl]-2-ethoxymorpholine-4-carboxylic acid tert-butyl ester (0.095 g, 0.228 mmol) in tetrahydrofuran (4 mL) at room temperature. Stir 4 hours and dilute with ethyl acetate. Wash with water and saturated aqueous sodium chloride, dry (magnesium sulfate), filter and concentrate. Purify on silica gel, eluting with 20:80 to 100% ethyl acetate:hexanes to give the title compound.

MS(ES): m/z=457.2 [M+H]

Preparation 299

(R)-5-[(1S,2S)-2-Acetylamino-3-(3,5-difluorophenyl)-1-hydroxypropyl]-2,2-diphenylmorpholine-4-carboxylic acid tert-butyl ester

[(S)-2-benzyloxy-1-(2-iodo-1,1-diphenylethoxymethyl)-ethyl]-carbamic acid tert-butyl ester Dissolve ((R)-2-benzyloxy-1-hydroxymethylethyl)-carbamic acid tert-butyl ester (1.0 g, 3.55 mmol) and 1,1-diphenylethylene (0.534 g, 2.96 mmol) in acetonitrile (20 mL). Add N-iodosuccinimide (0.800 g, 3.55 mmol) and stir at room temperature 72 hours. Pour into ethyl acetate and wash with saturated aqueous sodium chloride. Dry (magnesium sulfate), filter and concentrate. Purify on silica gel, eluting with 0:100 to 30:70 ethyl acetate:hexanes to give the desired compound.

¹HNMR (400 MHz, CDCl$_3$) δ 7.37-7.21 (m, 15H), 5.04 (d, J=7.6 Hz, 2H), 4.13 (s, 3H), 4.04 (bs, 1H), 3.76-3.66 (m, 2H), 3.32-3.23 (m, 2H), 1.43 (s, 9H)

(S)-5-benzyloxymethyl-2,2-diphenyl-morpholine-4-carboxylic acid tert-butyl ester To [(S)-1-benzyloxymethyl-2-(2-iodo-1,1-diphenylethoxy)-ethyl]-carbamic acid tert-butyl ester (4.74 g, 8.07 mmol) in N,N-dimethylformamide (70 mL) at room temperature add sodium hydride (0.452 g, 11.3 mmol, 60% dispersion in mineral oil). Heat reaction mixture to 60° C. for 4 hours, cool to room temperature and dilute with ethyl acetate (~400 mL). Wash with water and saturated aqueous sodium chloride, dry (magnesium sulfate), filter and concentrate. Purify on silica gel eluting with 0:100 to 20:80 ethyl acetate:hexanes to give the desired compound as an oil.

MS(ES): m/z=460.4 [M+H]

(R)-5-Formyl-2,2-diphenylmorpholine-4-carboxylic acid tert-butyl ester

To 10% palladium on carbon (2.1 g) in ethanol (50 mL) add (S)-5-benzyloxymethyl-2,2-diphenylmorpholine-4-carboxylic acid tert-butyl ester (3.29 g, 7.16 mmol) in ethanol (75 mL) and stir under 1 atmosphere of hydrogen gas at room temperature for 4 hours. Filter and concentrate to give the desired compound as a white solid. Dissolve the solid in dimethylsulfoxide (20 mL) and add triethylamine (1.30 g, 12.82 mmol), then pyridine sulfur trioxide complex (1.84 g, 11.55 mmol). Stir at room temperature 3 hours and dilute with 10% ethyl acetate/hexanes (~150 mL). Wash with water, 1 N aqueous citric acid and saturated aqueous sodium chloride, dry (magnesium sulfate), filter and concentrate to give the desired compound as a white solid.

MS(ES): m/z=268.2 [M-BOC+H]

(R)-5-[(1R,2S)-3-(3,5-difluorophenyl)-1-hydroxy-2-nitropropyl]-2,2-diphenylmorpholine-4-carboxylic acid tert-butyl ester To (R)-5-formyl-2,2-diphenylmorpholine-4-carboxylic acid tert-butyl ester (1.03 g, 2.80 mmol) and 1,3-difluoro-5-(2-nitroethyl)-benzene (0.577 g, 3.08 mmol) in tetrahydrofuran (5 mL) at −0° C. under nitrogen add tetrabutylammonium fluoride (3 mL, 3.0 mmol, 1.0 M in tetrahydrofuran). Stir 20 minutes and add half saturated aqueous sodium chloride (20 mL) and ethyl acetate (100 mL). Separate the layers and wash the organic layer with water and saturated aqueous sodium chloride. Dry (magnesium sulfate), filter and concentrate. Purify on silica gel, eluting with 0:100 to 50:50 ethyl acetate:hexanes, then re-crystallize from hexanes/dichloromethane to give the desired compound.

MS(ES): m/z=455.3 [M-BOC+H]

(R)-5-[(1S,2S)-2-Amino-3-(3,5-difluorophenyl)-1-hydroxypropyl]-2,2-diphenylmorpholine-4-carboxylic acid tert-butyl ester Dissolve (R)-5-[(1R,2S)-3-(3,5-difluorophenyl)-1-hydroxy-2-nitropropyl]-2,2-diphenylmorpholine-4-carboxylic acid tert-butyl ester (0.172 g, 0.31 mmol) in dry methanol (8 mL), add nickel chloride (0.060 g, 0.46 mmol) then sodium borohydride (0.059 g, 1.55 mmol). Stir 15 minutes, add water (~2 mL) and concentrate. Add ethyl acetate (~70 mL), filter (Celite®), wash with water and saturated aqueous sodium chloride. Dry (magnesium sulfate), filter and concentrate to give the desired compound as a white solid.

MS(ES): m/z=525.3 [M+H]

(R)-5-[(1S,2S)-2-Acetylamino-3-(3,5-difluorophenyl)-1-hydroxypropyl]-2,2-diphenylmorpholine-4-carboxylic acid tert-butyl ester Dissolve (R)-5-[(1S,2S)-2-amino-3-(3,5-difluorophenyl)-1-hydroxypropyl]-2,2-diphenylmorpholine-4-carboxylic acid tert-butyl ester (0.163 g, 0.31 mmol) in tetrahydrofuran (4 mL). Add triethylamine (0.044 g, 0.44 mmol) and acetic anhydride (0.036 g, 0.35 mmol). Stir 90 minutes and dilute with ethyl acetate (50 mL). Wash with 0.1 N aqueous citric acid, water, and saturated aqueous sodium chloride. Dry (magnesium sulfate), filter and concentrate. Purify on silica gel, eluting with 10:90 to 50:50 ethyl acetate:hexanes to give the title compound.

MS(ES): m/z=467.3 [M-BOC+H].

Preparation 300

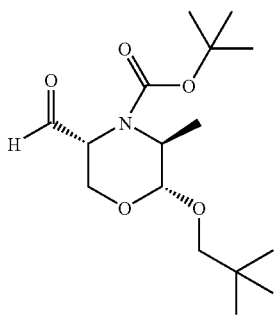

(2R,3S,5R)-2-(2,2-Dimethylpropoxy)-5-formyl-3-methylmorpholine-4-carboxylic acid tert-butyl ester 1,1-bis-(2,2-dimethylpropoxy)-propan-2-one Add p-toluenesulfonic acid hydrate (1.21 g, 10.58 mmol) to 1,1-dimethoxy-propan-2-one (25.00 g, 211.63 mmol) and neopentyl alcohol (46.64 g, 529.08 mmol) at room temperature. Heat in an open flask in an 80° C. oil bath for 8 hours. Allow to cool to room temperature and stir over the weekend. Purify (silica gel chromatography, eluting with 0:100 to 8:92 ethyl acetate:hexanes) to give the desired compound as a colorless oil (32.78 g 67.2%)

(R)-3-benzyloxy-2-[(R)-2,2-bis-(2,2-dimethylpropoxy)-1-methylethylamino]-propan-1-ol (R)-3-benzyloxy-2-[(S)-2,2-bis-(2,2-dimethylpropoxy)-1-methylethylamino]-propan-1-ol Add pyridinium p-toluenesulfonate (PPTS) (0.57 g, 2.25 mmol) and 3 Å molecular sieves (0.73 g) to (R)-2-amino-3-benzyloxypropan-1-ol (4.08 g, 22.51 mmol) and 1,1-bis-(2,2-dimethylpropoxy)-propan-2-one (8.30 g, 36.02 mmol) in dry toluene (90 mL) and reflux under nitrogen for 2 hours. Cool to room temperature, filter and concentrate. Dissolve in dry methanol (90 mL) and add sodium cyanoborohydride (5.66 g, 90.05 mmol) followed by acetic acid (2.5 mL) dropwise. Stir 30 minutes and concentrate. Dilute with ethyl acetate (~200 mL) and add water (~10 ml) followed by 1 N sodium hydroxide (~50 mL). Stir 20 minutes and dilute with saturated aqueous sodium chloride. Dry (sodium sulfate), filter and concentrate. Purify (silica gel chromatography using deactivated silica gel obtained by flushing with 3% (2 M ammonia/methanol) in dichloromethane), and elute with 10:90 to 100:0 ethyl acetate:hexanes) to give the desired compounds: (R)-3-benzyloxy-2-[(R)-2,2-bis-(2,2-dimethylpropoxy)-1-methylethylamino]-propan-1-ol (2.08 g top spot), (R)-3-benzyloxy-2-[(S)-2,2-bis-(2,2-dimethylpropoxy)-1-methylethylamino]-propan-1-ol (1.79 g bottom spot) and 3.4 g of mixed fractions.

MS(ES): m/z=396.5 [+H]

(2S,3S,5S)-5-benzyloxymethyl-2-(2,2-dimethylpropoxy)-3-methylmorpholine 2R,3S,5S)-5-benzyloxymethyl-2-(2,2-dimethylpropoxy)-3-methylmorpholine Add camphorsulfonic acid (1.69 g, 7.28 mmol) to (R)-3-benzyloxy-2-[(S)-2,2-bis-(2,2-dimethylpropoxy)-1-methylethylamino]-propan-1-ol (1.60 g, 4.04 mmol) in toluene (65 mL) and heat to 100° C. for 1 hour. Cool to room temperature, dilute with ethyl acetate, wash with 2 N sodium hydroxide and saturated aqueous sodium chloride. Dry (magnesium sulfate), filter and concentrate. Purify (silica gel chromatography using deactivated silica gel prepared as previously described, eluting with 10:90 to 70:30 ethyl acetate:hexanes) to give the desired compounds (2S,3S,5S)-5-benzyloxymethyl-2-(2,2-dimethylpropoxy)-3-methylmorpholine (490 mg, 39% top spot,) and (2R,3S,5S)-5-benzyloxymethyl-2-(2,2-dimethylpropoxy)-3-methylmorpholine (495 mg, 40% bottom spot).

MS(ES): m/z=308.3 [M+H]

(2R,3S,5S)-5-benzyloxymethyl-2-(2,2-dimethylpropoxy)-3-methyl-morpholine-4-carboxylic acid tert-butyl ester Add N,N-diisopropylethylamine (0.41 g, 3.19 mmol) to (2R,3S,5S)-5-benzyloxymethyl-2-(2,2-dimethylpropoxy)-3-methylmorpholine (0.49 g, 1.59 mmol) and di-tert-butyl dicarbonate (1.04 g, 4.78 mmol) in dichloroethane (16 mL) at room temperature and heat to 70° C. for 12 hours. Cool to room temperature and concentrate. Dilute with ethyl acetate and wash with 1 N aqueous citric acid and saturated aqueous sodium chloride. Dry (magnesium sulfate), filter, concentrate and purify (silica gel chromatography, eluting with 0:100 to 20:80 ethyl acetate:hexanes) to give the desired compound as an oil.

MS(ES): m/z=352.3 [M-tert-butyl]

(2R,3S,5S)-2-(2,2-Dimethylpropoxy)-5-hydroxymethyl-3-methylmorpholine-4-carboxylic acid tert-butyl ester Stir (2R,3S,5S)-5-benzyloxymethyl-2-(2,2-dimethylpropoxy)-3-methylmorpholine-4-carboxylic acid tert-butyl ester (0.65 g, 1.59 mmol) and 20% palladium hydroxide on carbon (0.65 g) in methanol (25 mL) under a hydrogen atmosphere at room temperature for 2 hours. Filter through Celite®, concentrate and purify (silica gel chromatography, eluting with 0:100 to 20:80 ethyl acetate:hexanes) to give the desired compound as an oil (471 mg 93.0%).

MS(ES): m/z=340.3 [M+Na]

(2R,3S,5R)-2-(2,2-Dimethylpropoxy)-5-formyl-3-methylmorpholine-4-carboxylic acid tert-butyl ester Add pyridine sulfur trioxide complex (0.42 g) to (2R,3S,5S)-2-(2,2-dimethylpropoxy)-5-hydroxymethyl-3-methyl-morpholine-4-carboxylic acid tert-butyl ester (0.46 g, 1.45 mmol) and N,N-diisopropylethylamine (0.66 g, 5.07 mmol) in dichloromethane (1 mL) and dimethylsulfoxide (4 mL) at −2° C. and stir 30 minutes. TLC shows some alcohol remaining. Add more pyridine sulfur trioxide (100 mg) and stir 30 minutes. Pour into ice-cold saturated aqueous sodium chloride and extract with ethyl acetate. Wash the ethyl acetate layer with 1 N aqueous citric acid, saturated aqueous sodium chloride), dry (magnesium sulfate), filter and concentrate to give the title compound as an oil (456 mg).

Preparation 301

(R)-3-Benzyloxy-2-[(R)-2,2-bis-(2,2-dimethylpropoxy)-1-methylethylamino]-propan-1-ol (R)-3-Benzyloxy-2-[(S)-2,2-bis-(2,2-dimethylpropoxy)-1-methylethylamino]-propan-1-ol Add magnesium sulfate (30.23 g, 251.10 mmol) to (R)-2-amino-3-benzyloxypropan-1-ol (12.30 g, 67.87 mmol) and 1,1-bis-(2,2-dimethylpropoxy)-propan-2-one (23.45 g, 101.80 mmol) in tetrahydrofuran (100 mL) at room temperature and stir for 2 hours. Filter and concentrate. Dissolve in methanol (200 mL) and cool in an ice water bath. Add sodium cyanoborohydride (8.53 g, 135.73 mmol) and then acetic acid (4.08 g, 67.87 mmol) dropwise. Warm to room temperature, stir 2 hours and concentrate to ~50 mL. Dilute with ethyl acetate (~200 mL) and add water (~50 ml) followed by 1 N sodium hydroxide (~200 mL). Stir 20 minutes and dilute with saturated aqueous sodium chloride. Dry (sodium sulfate), filter and concentrate to give the title compounds.

MS(ES): m/z=396.5 [M+H]

Preparation 302

(2R,5R)-5-[(1S,2S)-2-Amino-3-(3,5-difluorophenyl)-1-hydroxypropyl]-2-(2,2-dimethylpropoxy)-morpholine-4-carboxylic acid tert-butyl ester {(S)-2-benzyloxy-1-[1-(2,2-dimethylpropoxy)-2-iodoethoxymethyl]-ethyl}-carbamic acid tert-butyl ester Add N-iodosuccinimide (14.19 g, 74.63 mmol) to ((R)-2-benzyloxy-1-hydroxymethylethyl)-carbamic acid tert-butyl ester (15.00 g, 53.30 mmol) and 2,2-dimethyl-1-vinyloxypropane (9.13 g, 79.96 mmol) in acetonitrile (267 mL) at room temperature. Heat to 60° C. under nitrogen for 2 hours. Cool to room temperature and dilute with ethyl acetate. Wash with water and saturated aqueous sodium chloride. Dry (magnesium sulfate), filter, concentrate and purify (silica gel chromatography, eluting with 0:100 to 10:90 ethyl acetate:hexanes) to give the desired compound as an oil (23.4 g 84.2%).

MS(ES)=544.2 [M+Na]

(2R,5S)-5-benzyloxymethyl-2-(2,2-dimethylpropoxy-morpholine-4-carboxylic acid tert-butyl ester Add sodium hydride (2.81 g, 70.27 mmol) to {(S)-2-benzyloxy-1-[1-(2,2-dimethylpropoxy)-2-iodoethoxymethyl]-ethyl}-carbamic acid tert-butyl ester (22.90 g, 43.92 mmol) in N,N-dimethylformamide (200 mL) at room temperature and heat to 55° C. for 1 hour. Cool to room temperature and pour into ethyl acetate and saturated aqueous ammonium chloride. Wash the organic layer with water, 10% aqueous potassium carbonate, 1 N citric acid, 1 N lithium chloride and saturated aqueous sodium chloride. Dry (magnesium sulfate), filter, concentrate to 20 g of an orange oil and purify (silica gel chromatography, eluting with 0:100 to 20:80 ethyl acetate:hexanes to give the desired compound as an oil (7.3 g, 84.5%).

MS(ES) =294.2 [M-BOC]

(2R,5S)-2-(2,2-Dimethylpropoxy)-5-hydroxymethyl-morpholine-4-carboxylic acid tert-butyl ester Stir (2R,5S)-5-benzyloxymethyl-2-(2,2-dimethylpropoxy)-morpholine-4-carboxylic acid tert-butyl ester (7.05 g, 17.92 mmol) and 20% palladium hydroxide on carbon in methanol (150 mL) under 1 atmosphere of hydrogen gas at room temperature for 12 hours. Filter and concentrate to give the desired compound as a thick oil which is used directly in the next step without further purification (5.10 g).

MS(ES)=326.3 [M+Na]

(2R,5R)-2-(2,2-Dimethylpropoxy)-5-formylmorpholine-4-carboxylic acid tert-butyl ester Add pyridine sulfur trioxide complex (4.82 g, 30.26 mmol) to (2R,5S)-2-(2,2-dimethylpropoxy)-5-hydroxymethylmorpholine-4-carboxylic acid tert-butyl ester (5.10 g, 16.81 mmol) and N,N-diisopropylethylamine (7.61 g, 58.83 mmol) in dimethylsulfoxide (42 mL) and dichloromethane (8 mL) at −4° C. Stir 20 minutes, pour into ice cold saturated aqueous sodium chloride. Extract with 10% ethyl acetate/hexanes. Wash with 0.1 N aqueous citric-acid and saturated aqueous sodium chloride. Dry (magnesium sulfate), filter and concentrate to give the desired compound of a colorless oil, which is used directly in the next step without further purification (5.02 g).

(2R,5R)-5-[(1R,2S)-3-(3,5-Difluorophenyl)-1-hydroxy-2-nitropropyl]-2-(2,2-dimethylpropoxy)-morpholine-4-carboxylic acid tert-butyl ester Add tetrabutylammonium fluoride (18.32 mL, 18.32 mmol, 1.0 M in tetrahydrofuran) to (2R,5R)-2-(2,2-dimethylpropoxy)-5-formylmorpholine-4-carboxylic acid tert-butyl ester (5.02 g, 16.66 mmol) and 1,3-difluoro-5-(2-nitroethyl)-benzene (3.43 g, 18.32 mmol) in tetrahydrofuran (28 mL) at −10° C. and stir 20 minutes. Pour into ice cold saturated aqueous sodium chloride and extract with ethyl acetate. Wash with 0.1 N aqueous citric acid and saturated aqueous sodium chloride, dry (magnesium sulfate), filter, concentrate and purify (silica gel chromatography, eluting with 20:80 to 30%:70 diethyl ether:hexanes) to give a mixture of 2 diastereomers (3.66 g, 75:25 mixture) which are separated using chiral chromatography to give the desired compound (~2.45 g, 34.0%).

MS(ES): m/z=487.3 [M−H]

(2R,5R)-5-[(1S,2S)-2-Amino-3-(3,5-difluorophenyl)-1-hydroxypropyl]-2-(2,2-dimethylpropoxy)-morpholine-4-carboxylic acid tert-butyl ester Add sodium borohydride (0.86 g, 22.60 mmol) to (2R,5R)-5-[(1R,2S)-3-(3,5-difluorophenyl)-1-hydroxy-2-nitropropyl]-2-(2,2-dimethylpropoxy)-morpholine-4-carboxylic acid tert-butyl ester (2.30 g, 4.71 mmol) and nickel (II) chloride (1.34 g, 10.36 mmol) in methanol (47 mL) at room temperature over 2 minutes. Stir for 20 minutes, add water (~3 mL) and concentrate. Dilute with ethyl acetate (~75 mL), filter through Celite®, wash with 10% aqueous potassium carbonate, saturated aqueous sodium chloride, Dry (magnesium sulfate), filter and concentrate to give the title compound as an off-white solid (1.7 g, 78.7%).

MS(ES): m/z=459.2 [M+H]

The compound of Preparation 303-305 may be prepared as a mixture of diastereomers essentially as described in Preparation 302 using 1-methyl-1-vinyloxymethylcyclopentane and 3-benzyloxyphenyl nitroethane.

| Prep | Compound | MS (ES) [M + H] |
|---|---|---|
| 303 | (2R,5R)-5-[2-Amino-3-(3-benzyloxy-phenyl)-1-hydroxy-propyl]-2-(1-methyl-cyclopentylmethoxy)-morpholine-4-carboxylic acid tert-butyl ester | 555 |
| 304 | (2R,5R)-5-[2-Amino-3-(3,5-difluorophenyl)-1-hydroxy-propyl]-2-(cyclohexylmethoxy)-morpholine-4-carboxylic acid tert-butyl ester | 485.3 |
| 305 | (2R,5R)-5-[2-Amino-3-(3,5-difluorophenyl)-1-hydroxy-propyl]-2-(2,2-dimethylpropoxy)-morpholine-4-carboxylic acid tert-butyl ester | 459.3 |

Preparation 306

(2R,5R)-5-[(1S,2S)-2-Amino-3-(3,5-difluorophenyl)-1-hydroxypropyl]-2-(2,2-dimethylpropoxy)-morpholine-4-carboxylic acid tert-butyl ester (R)-5-[(1S,2S)-1-benzyloxy-2-dibenzylamino-3-(3,5-difluorophenyl)-propyl]-2-oxomorpholine-4-carboxylic acid tert-butyl ester Add diisopropylethylamine (1 mL, 6.05 mmol) to a solution of (2R,3R,4S)-2-amino-3-benzyloxy-4-dibenzylamine-5-(3,5-difluorophenyl)-pentan-1-ol (1.02 g, 1.976 mmol) and phenyl bromoacetate (750 mg, 3.48 mmol) in N,N-dimethylformamide (30 mL) at room temperature. Stir the reaction mixture at room temperature overnight (~14 h). Add di-tert-butyl dicarbonate (1 g, 4.58 mmol) and stir at room temperature for 20 h. Dilute with ethyl acetate, wash with 5% aqueous citric acid, dry (magnesium sulfate), filter, concentrate and purify (silica gel chromatography, eluting with 2:98 ethyl acetate:hexanes), to give the desired compound as a white solid (1.05 g, 81%).
MS(ES): m/z=657 [M+H]+

(R)-5-[(1S,2S)-1-benzyloxy-2-dibenzylamino-3-(3,5-difluorophenyl)-propyl]-2-hydroxymorpholine-4-carboxylic acid tert-butyl ester Add diisobutylaluminum hydride (1.4 mL, 1.37 mmol, 1.0 M in toluene) to a solution of (R)-5-[(1S,2S)-1-benzyloxy-2-dibenzylamino-3-(3,5-difluorophenyl)-propyl]-2-oxomorpholine-4-carboxylic acid tert-butyl ester (0.75 g, 1.1 mmol) in of dry toluene (15 mL) at −78° C. under nitrogen and stir at this temperature for 2 hours (Monitor by TLC). Add methanol to quench the reaction (1.0 mL), then saturated aqueous potassium sodium tartrate (Rochelle salt) and ethyl acetate. Warm to room temperature and stir vigorously for 30 minutes. Separate the organic layer and extract the aqueous with ethyl acetate. Combine the organic layers and dry (magnesium sulfate), filter and concentrate to give the desired compound as a mixture of the two possible isomers as a white solid and used in the next step without further purification (0.75 g).
MS(ES): m/z=659 [M+H]+

Trifluoromethanesulfonic acid 2,2-dimethylpropyl ester

Add trifluoromethanesulphonic anhydride (1.12 mL, 6.8 mmol) to a solution of neopentylalcohol (0.5 g, 5.7 mmol) and 2,6-lutidine (0.7 mL, 6.8 mmol) in dichloromethane (10 mL) at −78° C. and stir for 1 hour. Add water to quench the reaction, separate the organic layer and extract the aqueous layer with dichloromethane. Combine the organic layers, dry (magnesium sulfate), filter, concentrate and purify (silica gel chromatography, eluting with 1:4 hexane:dichloromethane) to give the desired compound as an oil (0.9 g, 72% yield).
1H-NMR (300 MHz, CDCl3,) δ 1.03 (s, 9H), 1.18 (s, 2H)

(2R,5R)-5-[(1S,2S)-1-benzyloxy-2-dibenzylamino-3-(3,5-difluorophenylpropyl]-2-(2,2-dimethylpropoxy)-morpholine-4-carboxylic acid tert-butyl ester Add sodium hydride (16 mg, 0.4 mmol, 60% dispersion in mineral oil) to (R)-5-[(1S,2S)-1-benzyloxy-2-dibenzylamino-3-(3,5-difluorophenyl)-propyl]-2-hydroxymorpholine-4-carboxylic acid tert-butyl ester (175 mg, 0.3 mmol,) in dry dimethylformamide (1.0 mL) at 0° C. and stir for 10 min. Add trifluoromethanesulfonic acid 2,2-dimethylpropyl ester (90 mg, 0.4 mmol) in dry dimethylformamide (0.5 mL), warm slowly to room temperature and stir for 1 hour. Add water to quench the reaction and extract the aqueous layer with diethyl ether. Combine the organic layers, dry (magnesium sulfate), filter, concentrate and purify (silica gel chromatography, eluting with 90:10 hexanes:ethyl acetate) to give the desired compound as white solid (100 mg, 52% yield over two steps).
MS(ES): m/z=729 [M+H]+

(2R,5R)-5-[(1S,2S)-2-Amino-3-(3,5-difluorophenyl)-1-hydroxypropyl]-2-(2,2-dimethylpropoxy)-morpholine-4-carboxylic acid tert-butyl ester Stir (2R,5R)-5-[(1S,2S)-1-benzyloxy-2-dibenzylamino-3-(3,5-difluorophenyl)-propyl]-2-(2,2-dimethylpropoxy)-morpholine-4-carboxylic acid tert-butyl ester (0.1 g, 0.14 mmol) and 20% palladium hydroxide on carbon (0.1 g, 0.06 mmol, 60% moisture) in ethyl acetate (5 mL) under 1 atmosphere of hydrogen gas at room temperature overnight. Filter the suspension through a pad of filtering agent, wash with ethyl acetate and concentrate to give the title compound (0.06 g, 90%).
MS(ES): m/z=459 [M+H]+

Preparation 307

(2R,3S,5R)-5-[(1S,2S)-2-Acetylamino-3-(3,5-difluorophenyl)-1-hydroxypropyl]-2-(2,2-dimethylpropoxy)-3-methylmorpholine-4-carboxylic acid tert-butyl ester (3S,5R)-5-[(1S,2S)-1-benzyloxy-2-dibenzylamino-3-(3,5-difluorophenyl)-propyl]-3-methylmorpholin-2-one Add 2(R)-trifluoromethanesulfonyloxypropionic acid methyl ester (6 g, 25.42 mmol) to a solution of (2R,3S,4S)-2-amino-3-benzyloxy-4-dibenzylamino-5-(3,5-difluorophenyl)-pentan-1-ol bishydrochloride (4.7 g, 7.94 mmol) and triethylamine (5 mL, 35.87 mmol) in dichloromethane (150 mL). Stir the reaction mixture at room temperature for 68-hours. Dilute with dichloromethane and wash with 5% aqueous citric acid, saturated aqueous sodium chloride, dry (magnesium sulfate), filter, concentrate and purify (silica gel chromatography, eluting with 10:90 to 20:80 ethyl acetate: hexanes) to give the desired compound (2.93 g, 65%).

MS(ES): m/z=571

(2RS,3S,5R)-5-[(1S,2S)-1-benzyloxy-2-dibenzylamino-3-(3,5-difluorophenyl)-propyl]-3-methylmorpholin-2-ol Add diisobutylaluminum hydride (2.48 mL, 2.48 mmol, 1.0 M in toluene) to a solution of (3S,5R)-5-[(1S,2S)-1-benzyloxy-2-dibenzylamino-3-(3,5-difluorophenyl)-propyl]-3-methylmorpholin-2-one (1.09 g, 1.91 mmol) in dry toluene (20 mL) at −78° C. under nitrogen and stir at this temperature for 15 minutes. Quench by adding methanol (1.0 mL). Add saturated aqueous potassium sodium tartrate (Rochelle salt) and ethyl acetate, warm to room temperature and stir vigorously for 30 minutes. Separate the organic layer and extract the aqueous with ethyl acetate. Combine the organic layers, dry (magnesium sulfate), filter and concentrate to give the desired compound as a mixture of the two possible epimers as a white solid which is used directly in the next step without further purification (1.08 g, 99% yield).

MS(ES): m/z=573

Dibenzyl-{(1S,2S)-2-benzyloxy-1-(3,5-difluorobenzyl)-2-[(3R,5S,6R)-6-(2,2-dimethylpropoxy)-5-methylmorpholin-3-yl]-ethyl}-amine Mix (3S,5R)-5-[(1S,2S)-1-benzyloxy-2-dibenzylamino-3-(3,5-difluorophenyl)-propyl]-3-methylmorpholin-2-ol (1.06 g, 1.85 mmol) with neopentanol (1.63 g, 18.5 mmol,) in dichloromethane (0.2 mL). Add 4 Å molecular sieves (850 mg), then methanesulphonic acid (2.4 mL, 37 mmol) and heat at 50° C. for 4 hours. Cool to room temperature, dilute with dichloromethane and add slowly to a solution of saturated aqueous sodium bicarbonate. Extract the aqueous layer with dichloromethane, dry (sodium sulfate), filter, concentrate and purify (silica gel chromatography, eluting with 100:0 to 90:10 hexanes:ethyl acetate) to give the desired compound as a white solid (665 mg, 56% yield).

MS(ES): m/z=643

(2R,3S,5R)-5-[(1S,2S)-1-benzyloxy-2-dibenzylamino-3-(3,5-difluorophenyl)-propyl]-2-(2,2-dimethylpropoxy)-3-methylmorpholine-4-carboxylic acid tert-butyl ester Add di-tert-butyl dicarbonate (683 mg, 3.03 mmol) to a solution of dibenzyl-{(1S,2S)-2-benzyloxy-1-(3,5-difluorobenzyl)-2-[(3R,5S,6R)-6-(2,2-dimethylpropoxy)-5-methylmorpholin-3-yl]-ethyl}-amine (650 mg, 1.01 mmol) and diisopropylethylamine (353 mL, 2.02 mmol) in 1,2-dichloroethane (11 mL) and stir at 75° C. for 6 hours. Concentrate and purify (silica gel chromatography, eluting with 80:20 to 0:100 hexanes:dichloromethane) to give the desired compound as a white solid (650 mg, 87% yield).

MS(ES): m/z=743

(2R,3S,5R)-5-[(1S,2S)-2-Amino-3-(3,5-difluorophenyl)-1-hydroxypropyl]-2-(2,2-dimethylpropoxy)-3-methylmorpholine-4-carboxylic acid tert-butyl ester Stir (2R,3S,5R)-5-[(1S,2S)-1-benzyloxy-2-dibenzylamino-3-(3,5-difluorophenyl)-propyl]-2-(2,2-dimethylpropoxy)-3-methylmorpholine-4-carboxylic acid tert-butyl ester (645 mg, 0.87 mmol) and 20% palladium hydroxide on carbon (60% moisture, 645 mg) in ethyl acetate (10 mL) under one-atmosphere of hydrogen gas at room temperature overnight. Filter the suspension through a pad of filtering agent, wash with ethyl acetate and concentrate to give the desired compound (400 mg, 97%).

MS(ES): m/z=473

(2R,3S,5R)-5-[(1S,2S)-2-Acetylamino-3-(3,5-difluorophenyl)-1-hydroxypropyl]-2-(2,2-dimethylpropoxy)-3-methylmorpholine-4-carboxylic acid tert-butyl ester Add acetic anhydride (0.084 ml, 0.89 mmol) to a solution of (2R,3S,5R)-5-[(1R,2S)-2-amino-3-(3,5-difluorophenyl)-1-hydroxypropyl]-2-(2,2-dimethylpropoxy)-3-methylmorpholine-4-carboxylic acid tert-butyl ester (400 mg, 0.85 mmol) in dry dichloromethane (9 mL). Add triethylamine (0.179 mL, 1.27 mmol), stir 1 hour at room temperature, concentrate and purify (silica gel cartridge chromatography, eluting with 1:1 hexanes:ethyl acetate) to give the title compound as a white solid (397 mg, 91%).

MS(ES): m/z=515 [M++H]

The compounds of Preparation 308-332 may be prepared essentially as described in Preparation 307.

| Prep | Compound | MS (ES) [M + H] |
|---|---|---|
| 308 | (2R,3S,5R)-5-[(1S,2S)-2-Acetylamino-3-(3,5-difluorophenyl)-1-hydroxypropyl]-2-(2,2-dimethylbutoxy)-3-methylmorpholine-4-carboxylic acid tert-butyl ester | 529 |
| 309 | (2R,3S,5R)-5-[(1S,2S)-2-Acetylamino-3-(3,5-difluorophenyl)-1-hydroxypropyl]-2-cyclohexylmethoxy)-3-methylmorpholine-4-carboxylic acid tert-butyl ester | 441 [M-BOC + H] |
| 310 | 2R,3S,5R)-5-[(1S,2S)-3-(3,5-Difluorophenyl)-1-hydroxy-2-(2-methoxyacetylamino)-propyl]-2-(2,2-dimethylbutoxy)-3-methylmorpholine-4-carboxylic acid tert-butyl ester | 503 [M-BOC + H] |
| 311 | (2R,3S,5R)-2-Cyclohexylmethoxy-5-[(1S,2S)-3-(3,5-difluorophenyl)-1-hydroxy-2-(3-methoxypropionylamino)-propyl]-3-methylmorpholine-4-carboxylic acid tert-butyl ester | |
| 312 | (2R,3S,5R)-2-Cyclohexylmethoxy-5-[(1S,2S)-3-(3,5-difluorophenyl)-1-hydroxy-2-(2-methoxyacetylamino)-propyl]-3-methylmorpholine-4-carboxylic acid tert-butyl ester | 471 [M-BOC + H] |

-continued

| Prep | Compound | MS (ES) [M + H] |
|---|---|---|
| 313 | (2R,3S,5R)-2-Cyclohexylmethoxy-5-[(1S,2S)-2-(cyclopropane-carbonylamino)-3-(3,5-difluorophenyl)-1-hydroxypropyl]-3-methylmorpholine-4-carboxylic acid tert-butyl ester | 467 [M-BOC + H] |
| 314 | (2R,3S,5R)-5-[(1S,2S)-2-Acetylamino-3-(3,5-difluorophenyl)-1-hydroxypropyl]-2-(bicyclo[2.1.1]hex-5-ylmethoxy)-3-methylmorpholine-4-carboxylic acid tert-butyl ester-Isomer 1 | 439 [M-BOC + H] |
| 315 | (2R,3S,5R)-5-[(1S,2S)-2-Acetylamino-3-(3,5-difluorophenyl)-1-hydroxypropyl]-2-(bicyclo[2.1.1]hex-5-ylmethoxy)-3-methylmorpholine-4-carboxylic acid tert-butyl ester-Isomer 2 | 439 [M-BOC + H] |
| 316* | (2R,3S,5R)-5-[(1S,2S)-2-Acetylamino-3-(3,5-difluorophenyl)-1-hydroxypropyl]-2-(4,4-difluorocyclohexylmethoxy)-3-methylmorpholine-4-carboxylic acid tert-butyl ester | 477 [M-BOC + H] |
| 317 | (2R,3S,5R)-5-[(1S,2S)-2-Acetylamino-3-(3,5-difluorophenyl)-1-hydroxypropyl]-2-(3,3-difluoro-2,2-dimethylbutoxy)-3-methylmorpholine-4-carboxylic acid tert-butyl ester | |
| 318 | (2R,3S,5R)-5-[(1S,2S)-2-Acetylamino-3-(3,5-difluorophenyl)-1-hydroxypropyl]-2-(3-fluoropropoxy)-3-methylmorpholine-4-carboxylic acid tert-butyl ester | 527 [M + Na] |
| 319 | (2R,3S,5R)-5-[(1S,2S)-2-Acetylamino-3-(3,5-difluorophenyl)-1-hydroxypropyl]-3-methyl-2-(3,3,3-trifluoropropoxy)-morpholine-4-carboxylic acid tert-butyl ester | 541 [M + H] |
| 320 | (2R,3S,5R)-5-[(1S,2S)-2-Acetylamino-3-(3,5-difluorophenyl)-1-hydroxypropyl]-2-(2-ethylbutoxy)-3-methylmorpholine-4-carboxylic acid tert-butyl ester | 573 [M + HCO$_2^-$] |
| 321 | (2R,3S,5R)-5-[(1S,2S)-2-Acetylamino-3-(3,5-difluorophenyl)-1-hydroxypropyl]-3-methyl-2-(tetrahydropyran-4-ylmethoxy)-morpholine-4-carboxylic acid tert-butyl ester | 565 [M + Na] |
| 322 | (2R,3S,5R)-5-[(1S,2S)-2-Acetylamino-3-(3,5-difluorophenyl)-1-hydroxypropyl]-3-methyl-2-(4,4,4-trifluorobutoxy)-morpholine-4-carboxylic acid tert-butyl ester | 577 [M + Na] |
| 323** | (2S,3S,5R)-5-[(1S,2S)-2-Acetylamino-3-(3,5-difluorophenyl)-1-hydroxypropyl]-2-(1-fluorocyclohexylmethoxy)-3-methyl-morpholine-4-carboxylic acid tert-butyl ester | 459 |
| 324 | (2R,3S,5R)-5-[(1S,2S)-2-Acetylamino-3-(3,5-difluorophenyl)-1-hydroxypropyl]-3-methyl-2-(4,4,4-trifluoro-2,2-dimethyl-butoxy)-morpholine-4-carboxylic acid tert-butyl ester | 527 [M + H-tBu] |
| 325 | (2R,3S,5R)-5-[(1S,2S)-2-Acetylamino-3-(3,5-difluoro-phenyl)-1-hydroxy-propyl]-3-methyl-2-((S)-2-methyl-butoxy)-morpholine-4-carboxylic acid tert-butyl ester | 515.5 [M$^+$] |
| 326 | (2R,3S,5R)-5-[(1S,2S)-2-acetylamino-3-(3,5-difluorophenyl)-1-hydroxypropyl]-2-(1-fluoromethyl-cyclopentylmethoxy)-3-methyl-morpholine-4-carboxylic acid tert-butyl ester | 581 [M + Na] |
| 327 | (2R,3S,5R)-5-[(1S,2S)-2-acetylamino-3-(3,5-difluorophenyl)-1-hydroxypropyl]-3-methyl-2-(1-trifluoromethylcyclopropyl)-morpholine-4-carboxylic acid tert-butyl ester | 589 [M + Na] |
| 328 | (2R,3S,5R)-5-[(1S,2S)-2-acetylamino-3-(3,5-difluorophenyl)-1-hydroxypropyl]-2-(3,3-difluoro-2,2-dimethyl-propoxy)-3-methyl-morpholine-4-carboxylic acid tert-butyl ester | 573 [M + Na] |
| 329 | (2R,3S,5R)-5-[(1S,2S)-2-Acetylamino-3-(3,5-difluoro-phenyl)-1-hydroxy-propyl]-2-(1-difluoromethyl-cyclopentylmethoxy)-3-methyl-morpholine-4-carboxylic acid tert-butyl ester | 621 [M + HCO$_2^-$] |
| 330 | (2R,3S,5R)-5-[(1S,2S)-2-Acetylamino-3-(3,5-difluoro-phenyl)-1-hydroxy-propyl]-2-(2,2-bis-fluoromethyl-butoxy)-3-methyl-morpholine-4-carboxylic acid tert-butyl ester | 609 [M + HCO$_2^-$] |
| 331 | (2R,3S,5R)-5-[(1S,2S)-[2-Acetylamino-3-(3,5-difluoro-phenyl)-1-hydroxy-propyl]-2-cyclopentylmethoxy-3-methyl-morpholine 4-carboxylic acid tert-butyl ester | 471 [M + H-t-Bu] |

*Glycosidation step may be performed as described in Preparation 306.
**Glycosidation step may be performed as described in Preparation 351.

Preparation 332

(2R,3S,5R)-5-[(1S,2S)-2-Acetylamino-3-(3,5-difluorophenyl)-1-hydroxypropyl]-2-(2,2-dimethylpropoxy)-3-ethylmorpholine-4-carboxylic acid tert-butyl ester

(3S,5R)-5-[(1S,2S)-1-benzyloxy-2-dibenzylamino-3-(3,5-difluoro-phenyl)-propyl]-3-ethyl-2-oxomorpholine-4-carboxylic acid tert-butyl ester Slowly add lithium hexamethyldisilazide (2.28 mL, 2.28 mmol, 1.0 M in tetrahydrofuran) at −78° C. under nitrogen to a solution of (R)-5-[(1S,2S)-1-benzyloxy-2-dibenzylamino-3-(3,5-difluorophenyl)-propyl]-2-oxomorpholine-4-carboxylic acid tert-butyl ester) (1 g, 1.52 mmol) and iodoethane (1.24 mL, 15.2 mmol) in anhydrous tetrahydrofuran (10 mL). Stir at −78° C. for 45 minutes, remove the bath and stir for 1.5 hours. Add water and ethyl acetate. Separate the organic layer and extract the aqueous layer with ethyl acetate. Combine the organic layers, dry (sodium sulfate), filter, concentrate and purify (silica gel chromatography, eluting with 90:10 hexane:ethyl acetate) to give the desired compound as a white solid (848 mg, 82%).

MS(ES): m/z=685

(2R,3S,5R)-5-[(1S,2S)-2-Amino-3-(3,5-difluorophenyl)-1-hydroxypropyl]-2-(2,2-dimethylpropoxy)-3-ethylmorpholine-4-carboxylic acid tert-butyl ester Prepare (2R,3S,5R)-5-[(1S,2S)-2-amino-3-(3,5-difluorophenyl)-1-hydroxypropyl]-2-(2,2-dimethylpropoxy)-3-ethylmorpholine-4-carboxylic acid tert-butyl ester essentially as described for the preparation of (2R,3S,5R)-5-[(1S,2S)-2-amino-3-(3,5-difluorophenyl)-1-hydroxypropyl]-2-(2,2-dimethylpropoxy)-3-methylmorpholine-4-carboxylic acid tert-butyl ester.

MS(ES): m/z=487

(2R,3S,5R)-5-[(1S,2S)-2-Acetylamino-3-(3,5-difluorophenyl)-1-hydroxylpropyl]-2-(2,2-dimethylpropoxy)-3-ethylmorpholine-4-carboxylic acid tert-butyl ester Prepare (2R,3S,5R)-5-[(1S,2S)-2-acetylamino-3-(3,5-difluorophenyl)-1-hydroxypropyl]-2-(2,2-dimethylpropoxy)-3-ethylmorpholine-4-carboxylic acid tert-butyl ester essentially as described for the preparation of (2R,3S,5R)-5-[(1S,2S)-2-acetylamino-3-(3,5-difluorophenyl)-1-hydroxypropyl]-2-(2,2-dimethylpropoxy)-3-methylmorpholine-4-carboxylic acid tert-butyl ester.

MS(ES): m/z=429 [M+-BOC]

The compounds of Preparations 333-334 may be prepared essentially as described in Preparation 332. In Preparation 335 the corresponding triflate may be used as the alkylating agent with potassium hexamethyldisilazane as the base.

| Prep | Compound | MS (ES) [M + H] |
|---|---|---|
| 333 | (2R,3S,5R)-5-[(1S,2S)-2-Acetylamino-3-(3,5-difluorophenyl)-1-hydroxypropyl]-3-butyl-2-(2,2-dimethylpropoxy)-morpholine-4-carboxylic acid tert-butyl ester | 579 [M + Na] |
| 334 | (2R,3S,5R)-5-[(1S,2S)-2-Acetylamino-3-(3,5-difluorophenyl)-1-hydroxydimethylpropoxy)-3-(3-fluoropropyl)-morpholine-4-carboxylic acid tert-butyl ester | 356 [M + HCO$_2$$^-$] |

Preparation 335

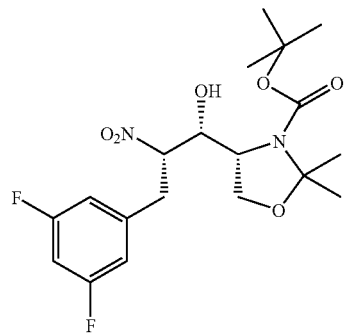

(R)-4-[(1R,2S)-3-(3,5-Difluorophenyl)-1-hydroxy-2-nitropropyl]-2,2-dimethyloxazolidine-3-carboxylic acid tert-butyl ester

(S)-4-Formyl-2,2-dimethyloxazolidine-3-carboxylic acid tert-butyl ester

Add dropwise over 2 hours a solution of pyridine sulfur trioxide (390 g, 2452.83 mmol) in dimethylsulfoxide (1600 mL) to a 6° C. maintained solution of (S)-4-hydroxymethyl-2,2-dimethyloxazolidine-3-carboxylic acid tert-butyl ester (350 g, 1515.15 mmol) in diisopropylethylamine (1225 mL) with a dimethylsulfide trap. Over 30 minutes add water (1050 mL) keeping temperature below 15° C. Stir at 15° C. for 1.5 hours under a stream of nitrogen. Extract with ethyl acetate (5 L), wash with 5%-aqueous citric acid (2×1.5 L), saturated aqueous sodium chloride (2×1.5 L), dry (magnesium sulfate), filter, and concentrate to give the desired compound which is used in the next reaction without further purification (365 g).

MS(ES): m/z=230 [M+H]

(R)-4-[(1R,2S)-3-(3,5-Difluorophenyl)-1-hydroxy-2-nitropropyl]-2,2-dimethyloxazolidine-3-carboxylic acid tert-butyl ester Add tetrabutylammonium fluoride in 5 minutes (50 mL, 50 mmol, 1.0 M solution in tetrahydrofuran) to a solution of (S)-4-formyl-2,2-dimethyloxazolidine-3-carboxylic acid tert-butyl ester (200 g, 873.362 mmol) and 1,3-difluoro-5-(2-nitroethyl)-benzene (164 g, 877.005 mmol) in tetrahydrofuran (1.2 L) at 8° C. Allow to warm to room temperature and stir for 14 hours. Partition between ethyl acetate (4 L) and saturated aqueous sodium chloride (1.5 L). Wash the organic layer with saturated aqueous ammonium chloride, saturated aqueous sodium chloride, water, dry (magnesium sulfate), filter and concentrate to give 379 g of a crude waxy pale

Preparation 336

(R)-4-[(1S,2S)-1-Benzyloxy-2-dibenzylamino-3-(3,5-difluorophenyl)-propyl]-2,2-dimethyloxazolidine-3-carboxylic acid tert-butyl ester (R)-4-[(1S,2S)-2-Dibenzylamino-3-(3,5-difluorophenyl)-1-hydroxypropyl]-2,2-dimethyloxazolidine-3-carboxylic acid tert-butyl ester Add benzyl bromide (75 mL, 630.55 mmol) to a suspension of potassium carbonate (85 g, 615.006 mmol) and (R)-4-[(1S,2S)-2-amino-3-(3,5-difluorophenyl)-1-hydroxypropyl]-2,2-dimethyloxazolidine-3-carboxylic acid tert-butyl ester (80 g, 207.25 mmol) in acetonitrile (900 mL). Heat to reflux for 16 hours, cool to room temperature, and dilute with ethyl acetate (2 L). Wash with ammonium chloride (1.5 L), saturated aqueous sodium chloride (1.5 L), dry (magnesium sulfate), filter, concentrate and purify (silica gel chromatography, eluting with 5:95 to 20:80 ethyl acetate:hexanes) to give the desired compound as a white solid (102.1 g, 87%).

MS(ES): m/z=567 [M+H]

(R)-4-[(1S,2S)-1-benzyloxy-2-dibenzylamino-3-(3,5-difluorophenyl)-propyl]-2,2-dimethyloxazolidine-3-carboxylic acid tert-butyl ester Add sodium hydride (4.4 g, 110 mmol, 60% in mineral oil) portionwise to a room temperature maintained solution of (R)-4-[(1S,2S)-2-dibenzylamino-3-(3,5-difluorophenyl)-1-hydroxypropyl]-2,2-dimethyloxazolidine-3-carboxylic acid tert-butyl ester (50.5 g, 89.222 mmol) and benzyl bromide (22 mL, 184.96 mmol) in N,N-dimethylformamide (400 mL). Stir for 15 minutes and pour into saturated aqueous ammonium chloride. Extract with ethyl acetate, dry (magnesium sulfate), filter, concentrate and purify (silica gel chromatography, eluting with 2:98 to 4:96 ethyl acetate:hexanes) to give the title compound as a viscous oil that solidifies upon standing (48.5 g, 83%).

MS(ES): m/z=657[M+H]

Preparation 337

(2S,5R)-5-[(1S,2S)-2-Acetylamino-3-(3,5-difluorophenyl)-1-hydroxypropyl]-2-(2-fluoro-2-methylpropoxy)-morpholine-4-carboxylic acid tert-butyl ester Trifluoromethanesulfonic acid 2-fluoro-2-methylpropyl ester Add trifluoromethanesulphonic anhydride (4.3 mL, 26.0 mmol) to a solution of 2-fluoro-2-methylpropan-1-ol (2.0 g, 21.7 mmol) and 2,6-lutidine (3.0 mL, 26.0 mmol) in dichloromethane (25 mL) at −78° C. Warm slowly to room temperature and stir at room temperature for 1 hour. Add water to quench the reaction, separate the organic layer and extract the aqueous layer with dichloromethane. Combine the organic layers, dry (magnesium sulfate), filter, concentrate and purify (silica gel chromatography, eluting with dichloromethane), to give the desired compound as an oil (3.4 g, 70% yield).

$^1$H-NMR (300 MHz, CDCl$_3$,) δ 1.46 (d, J=21 Hz, 6H) and 4.41 (d, J=18.6 Hz, 2H)

(2S,5R)-5-[(1S,2S)-1-benzyloxy-2-dibenzylamino-3-(3,5-difluorophenylpropyl]-2-(2-fluoro-2-methylpropoxy)-morpholine-4-carboxylic acid tert-butyl ester Add sodium hydride (0.09 g, 2.28 mmol, 60% dispersion in mineral oil) to (R)-5-[1-benzyloxy-2-dibenzylamino-3-(3,5-difluorophenyl)-propyl]-2-hydroxymorpholine-4-carboxylic acid tert-butyl ester (1.0 g, 1.52 mmol,) in dry N,N-dimethylformamide (12.0 mL) at room temperature and stir for 15 min. Add trifluoromethanesulfonic acid 2-fluoro-2-methylpropyl ester (0.05 g, 2.28 mmol) in dry N,N-dimethylformamide (2 mL), and stir for 1 hour. Add water to quench the reaction and extract the aqueous layer with diethyl ether. Combine the organic layers, dry (magnesium sulfate), filter, concentrate and purify (silica gel chromatography, eluting with 100:0 to 60:40 hexanes:ethyl acetate), to give the desired compound as white solid (0.68 g, 62% yield over two steps).

MS(ES): m/z=733 [M+H]$^+$ (2S,5R)-5-[(1S,2S)-2-Amino-3-(3,5-difluorophenyl)-1-hydroxypropyl]-2-(2-fluoro-2-methylpropoxy)-morpholine-4-carboxylic acid tert-butyl ester Stir (2S,5R)-5-[(1S,2S)-1-benzyloxy-2-dibenzylamino-3-(3,5-difluorophenylpropyl]-2-(2-fluoro-2-methylpropoxy)-morpholine-4-carboxylic acid tert-butyl ester (0.68 g, 0.93 mmol) and 20% palladium hydroxide on carbon (0.68 g, 0.60 mmol, 60% moisture) in ethyl acetate (25 mL) under 1 atmosphere of hydrogen gas at room temperature overnight. Filter the suspension through a pad of filtering agent, wash with ethyl acetate and concentrate to give the desired compound (0.40 g, 93%).

MS(ES): m/z=463 [M+H]$^+$ (2S,5R)-5-[(1S,2S)-2-Acetylamino-3-(3,5-difluorophenyl)-1-hydroxypropyl]-2-(2-fluoro-2-methylpropoxy)-morpholine-4-carboxylic acid tert-butyl ester Add acetic anhydride (0.084 mL, 0.91 mmol) to a solution of (2S,5R)-5-[(1S,2S)-2-amino-3-(3,5-difluorophenyl)-1-hydroxypropyl]-2-(2-fluoro-2-methylpropoxy)-morpholine-4-carboxylic acid tert-butyl ester (400 mg, 0.86 mmol) and triethylamine (0.81 mL, 130 mmol) in dry dichloromethane (10 mL) at room temperature and stir for 4 hours, concentrate and purify (silica gel cartridge chromatography, eluting with 2:1 to 1:2 hexanes:ethyl acetate), to give the desired compound as a white solid (0.37 g, 80%).

MS(ES): m/z=505 [M+H]$^+$

The compounds of Preparations 338-342 may be prepared essentially as described in Preparation 337.

| Prep | Compound | MS (ES) |
|---|---|---|
| 338 | (2R,5R)-5-[(1S,2S)-2-acetylamino-3-(3,5-difluorophenyl)-1-hydroxypropyl]-2-(1-fluoromethyl-cyclopentylmethoxy)-morpholine-4-carboxylic acid tert-butyl ester | 567 [M + Na] |

| Prep | Compound | MS (ES) |
|---|---|---|
| 339 | (2R,5R)-5-[(1S,2S)-2-acetylamino-3-(3,5-difluorophenyl)-1-hydroxypropyl]-2-(1-difluoromethyl-cyclopentylmethoxy)-morpholine-4-carboxylic acid tert-butyl ester | 585 [M + Na] |
| 340 | (2R,5R)-5-[(1S,2S)-2-Acetylamino-3-(3,5-difluoro-phenyl)-1-hydroxy-propyl]-2-(1-fluoro-cyclopentylmethoxy)-morpholine-4-carboxylic acid tert-butyl ester | 575 [M + HCO$_2^-$] |
| 341 | (2R,5R)-5-[(1S,2S)-2-Acetylamino-3-(3,5-difluoro-phenyl)-1-hydroxy-propyl]-2-(2,2-bis-fluoromethyl-butoxy)-morpholine-4-carboxylic acid tert-butyl ester | 595 [M + HCO$_2^-$] |
| 342 | (2R,5R)-5-[(1S,2S)-[2-Acetylamino-3-(3,5-difluoro-phenyl)-1-hydroxy-propyl]-2-(4,4,4-trifluoro-2,2-dimethyl-butoxy)-morpholine-4-carboxylic acid tert-butyl ester | 569 [M + H] |

Preparation 343

3-Propylsulfanylbenzaldehyde

Reflux a suspension of potassium carbonate (22.4 g), 1-iodopropane (10.3 mL) and 3-bromothiophenol (8.4 mL) in acetone (375 mL) for 5 hours. Cool to room temperature, filter through diatomaceous earth, and concentrate. Dissolve the residue in hexanes, filter through a silica gel plug, and concentrate to give 1-bromo-3-propylsulfanylbenzene (18 g, 95%) as an oil (GC-MS: m/z=231). Add this material (12 g) to a solution of n-butyllithium (57 mmol) in THF (50 mL) at −78° C. Stir for 45 min, add 110 N,N-dimethylformamide (8.1 mL) and warm to room temperature. Stir for 15 min, pour into water (175 mL), and extract into diethyl ether (3×200 mL). Dry (magnesium sulfate), filter, concentrate and purify (silica gel chromatography) to give the title compound (7.3 g, 92%).

GC-MS: m/z=180

The compound of Preparation 344 may be prepared essentially as described in Preparation 343.

| Prep | Compound |
|---|---|
| 344 | 3-Isobutylsulfanylbenzaldehyde |

Preparation 345

3-Fluoro-5-propylsulfanylbenzaldehyde

Dissolve sodium propanethiolate (7.5 g) in DMF (250 mL) at ambient temperature, then chill to −30° C. and add 1-bromo-3,5-difluorobenzene (8.35 mL). After 1 hour, warm to −15° C., and stir for an additional 3 hours. Pour into water (2 L) and extract into hexanes (3×500 mL). Wash the resulting organic solution with saturated aqueous sodium chloride (100 mL), dry (magnesium sulfate), filter and concentrate. Filter through a plug of silica gel, wash with 10:90 ethyl acetate: hexanes and concentrate to give 1-bromo-3-fluoro-5-propylsulfanylbenzene (16.2 g, 90%). The title compound is prepared essentially as described in Preparation 343.

The compound of Preparation 346 may be prepared essentially as described in Preparation 345.

| Prep | Compound |
|---|---|
| 346 | 3-Fluoro-5-isobutylsulfanylbenzaldehyde |

Preparation 347

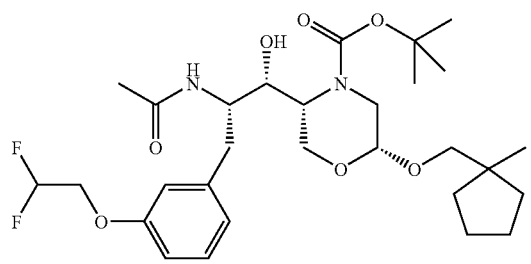

(2R,5R)-5-{(1S,2S)-2-Acetylamino-3-[3-(2,2-difluoroethoxy)-phenyl]-1-hydroxypropyl}-2-(1-methylcyclopentylmethoxy)-morpholine-4-carboxylic acid tert-butyl ester (2R,5R)-5-[(1S,2S)-2-Acetylamino-3-(3-benzyloxyphenyl)-1-hydroxypropyl]-2-(1-methyl-cyclopentylmethoxy)-morpholine-4-carboxylic acid tert-butyl ester Add acetyl chloride (0.13 mL, 1.82 mmol) to an ice cold solution of (2R,5R)-5-[2-amino-3-(3-benzyloxyphenyl)-1-hydroxypropyl]-2-(1-methylcyclopentylmethoxy)-morpholine-4-carboxylic acid tert-butyl ester (0.91 g, 1.652 mmol) and N,N-diisopropyl-ethylamine (0.58 mL, 3.30 mmol) in dichloromethane (20 mL). Stir 15 minutes and dilute with ethyl acetate and wash with 1 N hydrochloric acid, saturated aqueous sodium chloride, dry (magnesium sulfate) and purify (silica gel chromatography, elutin with dichloromethane/ethyl acetate) to give the desired compound (246 mg).

MS(ES): m/z=597 [M+H]

(2R,5R)-5-[(1S,2S)-2-Acetylamino-1-hydroxy-3-(3-hydroxyphenyl)-propyl]-2-(1-methylcyclopentyl-methoxy)-morpholine-4-carboxylic acid tert-butyl ester Hydrogenate (2R,5R)-5-[(1S,2S)-2-Acetylamino-3-(3-benzyloxyphenyl)-1-hydroxypropyl]-2-(1-methylcyclopentylmethoxy)-morpholine-4-carboxylic acid tert-butyl ester (244 mg) in methanol (15 mL) with 20% palladium hydroxide on carbon (26 mg) at 50 psi hydrogen for 18 hours. Filter and concentrate to give the desired compound (204 mg). MS(ES): m/z=507 [M+H]

(2R,5R)-5-{(1S,2S)-2-Acetylamino-3-[3-(2,2-difluoroethoxy)-phenyl]-1-hydroxypropyl}-2-(1-methylcyclopentylmethoxy)-morpholine-4-carboxylic acid tert-butyl ester Dissolve (2R,5R)-5-[(1S,2S)-2-acetylamino-1-hydroxy-3-(3-hydroxyphenyl)-propyl]-2-(1-methylcyclopentylmethoxy)-morpholine-4-carboxylic acid tert-butyl ester (204 mg) and 2,2-difluoro-1-bromoethane (0.065 mL) and cesium carbonate (391 mg) in N,N-dimethylformamide (5 mL) and heat to 60° C. for 18 hours. Dilute with ethyl acetate, wash with saturated aqueous sodium chloride, dry and purify (silica gel chromatography, eluting with 1:1 ethyl acetate:dichloromethane), to give the desired compound (223 mg).

MS(ES): m/z=593 [M+Na]

The compounds of Preparations 348-350 may be prepared essentially as described in Preparation 347.

chromatography, eluting with 0:100 to 20:80 hexanes:ethyl acetate), to give the title compound as a colorless oil (375 mg).

MS(ES): m/z=687 [M+H]

Preparation 352

(2R,3S,5R)-5-[(1S,2S)-2-Acetylamino-3-(2-ethylphenyl)-1-hydroxypropyl]-2-(2,2-dimethylpropoxy)-3-methylmorpholine-4-carboxylic acid tert-butyl ester 1-Ethyl-2-(2-nitroethyl)-benzene Dissolve 2-ethyl benzaldehyde (7 mL, 53.2 mmol), nitromethane (8.5 mL, 158 mmol), and ammonium acetate (1.6 g, 20.8 mmol) in acetic acid (40 mL) and heat to reflux under a nitrogen atmosphere for 17 hours. Cool to room temperature and concentrate. Dissolve in isopropyl alcohol (150 mL) and chloroform (750 mL) and add silica gel (108 g). To the resulting slurry, slowly add sodium borohydride (7.8 g, 206 mmol). Stir the mixture for 17 hours, filter, concentrate and purify (silica gel chromatography, eluting with 0:100 to 10:90 ethyl acetate:hexanes), to give the desired compound as an orange oil.

$^1$HNMR (400 MHz, CDCl$_3$) δ 7.12-7.26 (m, 4H), 4.57 (t, J=8.0 Hz, 2H), 3.67 (t, J=8.0 Hz, 2H), 2.68 (q, J=8.0 Hz, 2H), 1.25 (t, J=7.2 Hz, 3H)

| Prep | Compound | MS (ES) [M + H] |
|---|---|---|
| 348 | (2R,5R)-5-{(1S,2S)-1-Acetoxy-2-acetylamino-3-[3-(2,2-difluoroethoxy)-phenyl]-propyl}-2-(1-methylcyclopentylmethoxy)-morpholine-4-carboxylic acid tert-butyl ester | 635 [M + Na] |
| 349 | (2R,5R)-5-[(1S,2S)-2-Acetylamino-1-hydroxy-3-(3-propoxyphenyl)-propyl]-2-(1-methylcyclopentylmethoxy)-morpholine-4-carboxylic acid tert-butyl ester | 571 [M + Na] |
| 350 | (2R,5R)-5-[(1S,2S)-1-Acetoxy-2-acetylamino-3-(3-propoxyphenyl)-propyl]-2-(1-methylcyclopentylmethoxy)-morpholine-4-carboxylic acid tert-butyl ester | 613 [M + Na] |

Preparation 351

Dibenzyl-{(1S,2R)-2-benzyloxy-1-(3,5-difluorobenzyl)-2-[(3R,5S,6S)-6-(1-fluorocyclohexylmethoxy)-5-methylmorpholin-3-yl]-ethyl}-amine Add triphosgene (246 mg, 0.79 mmol) at room temperature to a solution of (3S,5R)-5-[(1R,2S)-1-benzyloxy-2-dibenzylamino-3-(3,5-difluorophenyl)-propyl]-3-methylmorpholin-2-ol (1 g, 1.75 mmol) and triethylamine (0.99 mL, 7 mmol) in anhydrous dichloromethane (17 mL). Stir for 30 min, cool to 0° C. and add (1-fluorocyclohexyl)-methanol (1.16 g, 8.75 mmol) and trimethylsilyl trifluoromethanesulfonate (TMSOTf) (0.64 mL, 3.5 mmol). Stir at 0° C. for 1 hour and at room temperature for 2 hours. Add more trimethylsilyl trifluoromethanesulfonate (0.16 mL, 0.87 mmol) and stir at room temperature for 30 min. Add 10% aqueous potassium carbonate, separate the organic layer and extract the aqueous layer with dichloromethane. Combine the organic layers, dry (sodium sulfate), filter, concentrate and purify (silica gel (2R,3S,5R)-2-(2,2-Dimethylpropoxy)-5-[(1R,2S)-3-(2-ethylphenyl)-1-hydroxy-2-nitropropyl]-3-methylmorpholine-4-carboxylic acid tert-butyl ester To a 0° C. solution of 1-ethyl-2-(2-nitroethyl)-benzene (430 mg, 2.40 mmol) and (2R,3S,4R)-2-(2,2-dimethylpropoxy)-5-formyl-3-methylmorpholine-4-carboxylic acid tert-butyl ester (565 mg, 1.79 mmol) in dry tetrahydrofuran (10 mL) add tetrabutylammonium fluoride (1.6 mL, 1.6 mmol, 1.0 M in tetrahydrofuran). After 30 minutes, pour into ethyl ether and wash with saturated aqueous sodium chloride followed by water (3×) and saturated aqueous sodium chloride again. Dry (magnesium sulfate), filter, concentrate and purify (silica gel chromatography, eluting with 0:100 to 20:80 ethyl acetate:hexanes), to give an inseparable mixture of aldol product diastereomers containing the desired compound (524 mg, 59% overall).

MS(ES): m/z=493.2 [M−H]

(2R,3S,5R)-5-[(1S,2S)-2-Amino-3-(2-ethylphenyl)-1-hydroxypropyl]-2-(2,2-dimethylpropoxy)-3-methylmorpholine-4-carboxylic acid tert-butyl ester Dissolve the mixture of diastereomers from the previous reaction containing (2R,3S,5R)-2-(2,2-dimethylpropoxy)-5-[(1R,2S)-3-(2-ethylphenyl)-1-hydroxy-2-nitropropyl]-3-methylmorpholine-4-carboxylic acid tert-butyl ester in dry methanol (12 mL) and add nickel (II) chloride (267 mg, 2.06 mmol). To the resulting suspension, add sodium borohydride (284 mg, 7.5 mmol) portion-wise over 1 minute. After 30 minutes, quench with water and reduce the volume on the rotary evaporator. Add more water and saturated aqueous sodium chloride. Extract with ethyl acetate. Combine the extracts, dry (sodium sulfate), filter and concentrate to give a diastereomeric mixture of amines containing the desired compound as a light brown oil (418 mg, 85%).

MS(ES): m/z=465.5 [M+H]

(2R,3S,5R)-5-[(1S,2S)-2-Acetylamino-3-(2-ethylphenyl)-1-hydroxypropyl]-2-(2,2-dimethylpropoxy)-3-methylmorpholine-4-carboxylic acid tert-butyl ester Dissolve the diastereomeric mixture of amines from the previous reaction which contains (2R,3S,5R)-5-[(1S,2S)-2-amino-3-(2-ethylphenyl)-1-hydroxypropyl]-2-(2,2-dimethylpropoxy)-3-methylmorpholine-4-carboxylic acid tert-butyl ester (418 mg, 0.9 mmol) in dry dichloromethane (7 mL) under a nitrogen atmosphere and add acetic anhydride (90 µL, 0.95 mmol) and triethylamine (150 µL, 1.1 mmol). After 4 hours quench with methanol, concentrate and purify (silica gel chromatography) to give a mixture of amide diastereomers containing the title compound (243 mg). Purify the resulting mixture by HPLC, eluting with 65:35 acetonitrile:water with 8 µM hydrochloric acid, to give the title compound as a single diastereomer (47 mg, 10% overall).

MS(ES): m/z=529.3 [M+Na]

Preparation 353

(2R,3S,5R)-5-[(1S,2S)-2-Acetylamino-3-(3-fluoro-5-propoxy-phenyl)-1-hydroxypropyl]-2-(2,2-dimethyl-propoxy)-3-methyl-morpholine-4-carboxylic acid tert-butyl ester

3-bromo-5-fluoro-phenol

Add aluminum chloride (13.51 g, 101.38 mmol) to 1-benzyloxy-3-bromo-5-fluoro-benzene (9.50 g, 33.79 mmol, prepared according to WO 03/101956) and dimethylaniline (40.96 g, 337.92 mmol) in dichloromethane (84 mL) at –0° C. under nitrogen and stir 10 minutes. Remove ice-bath and stir 2 hours. Add 60 mL 2N hydrochloric acid dropwise. Separate layers and wash the organic layer with 2N hydrochloric acid (4×50 mL). Extract the organic layer with 3N potassium hydroxide (4×50 mL). Acidify with 5N hydrochloric acid and extract with dichloromethane (3×50 mL). Dry the dichloromethane layer (sodium sulfate) and concentrate to give 4.3 g (66.6%) of the desired compound as an oil.

1-bromo-3-fluoro-5-propoxy-benzene

Add propyl iodide (5.74 g, 33.77 mmol) to 3-bromo-5-fluoro-phenol (4.30 g, 22.51 mmol) and cesium carbonate (11.00 g, 33.77 mmol) in N,N-dimethylformamide (75 mL) and stir at room temperature 1 hour, then heat at 50° C. for 1 hour. Cool to room temperature and dilute with hexanes. Wash (water, 1N lithium chloride, saturated aqueous sodium chloride), dry (magnesium sulfate), filter and concentrate to give the desired compound as a colorless oil, 4.40 g (83.8%).

$^1$H-NMR (400 MHz, CDCl$_3$) δ 6.85-6.80 (m, 2H), 6.55 (dt, 1H, J=6.4, 3.5 Hz), 3.88 (t, 2H, J=6.6 Hz), 1.84-1.75 (m, 2H), 1.02 (t, 3H, J=7.5 Hz).

3-Fluoro-5-propoxy-benzaldehyde

Add n-butyl lithium (13 mL, 1.6M, 20.76 mmol) to 1-bromo-3-fluoro-5-propoxybenzene (4.40 g, 18.88 mmol) in tetrahydrofuran (100 mL) cooled in a dry ice/acetone bath over 45 minutes, maintaining the internal temperature <–70°. Stir 30 minutes and add N,N-dimethylformamide (2.76 g, 37.75 mmol). Stir 30 minutes and remove cold bath. After 1 hour, quench with saturated aqueous ammonium chloride. Wash organic layer with water and saturated aqueous sodium chloride. Dry (sodium sulfate), filter and concentrate to an oil. Purify on 120 g silica gel eluting with 0 to 10% ethyl acetate in hexanes to give 2.26 g (65.7%) of the desired compound as an oil.

$^1$H-NMR (400 MHz, CDCl$_3$) δ 9.93 (d, 1H, J=1.8 Hz), 7.22-7.21 (m, 1H), 7.18-7.15 (m, 1H), 6.88 (dt, 1H, J=6.3, 3.4 Hz), 3.99 (t, 2H, J=6.6 Hz), 1.90-1.81 (m, 2H), 1.07 (t, 3H, J=7.5 Hz).

1-Fluoro-3-((E)-2-nitro-vinyl)-5-propoxy-benzene

Add ammonium acetate (2.63 g, 34.08 mmol) to 3-fluoro-5-propoxy-benzaldehyde (2.25 g, 12.35 mmol) and nitromethane (3.09 g, 50.63 mmol) in acetic acid (41 mL) at room temperature and heat in 140° C. oil bath for 3 hours. Cool to room temperature and pour into water. Extract with ethyl acetate, dry over magnesium sulfate, filter and concentrate to afford 1.94 g (69.8%) of the desired compound as an oil.

$^1$H-NMR (400 MHz, CDCl$_3$) δ 7.9 (d, 1H, J=13.6 Hz), 7.52 (d, 1H, J=13.6 Hz), 6.85-6.81 (m, 2H), 6.73 (dt, 1H, J=6.4, 3.5 Hz), 3.93 (t, 2H, J=6.4 Hz), 1.87-1.78 (m, 2H), 1.05 (t, 3H, J=7.5 Hz).

1-Fluoro-3-(2-nitro-ethyl)-5-propoxy-benzene

Add sodium borohydride (1.30 g, 34.46 mmol) to 1-fluoro-3-((E)-2-nitro-vinyl)-5-propoxy-benzene (1.94 g, 8.61 mmol) and silica gel (17 g) in chloroform (86 mL) and isopropanol (25 mL) at room temperature in portions over 5 minutes. Stir at room temperature 2 hours and filter. Concentrate the filtrate and dissolve in ethyl acetate. Wash with water and saturated aqueous sodium chloride, dry over magnesium sulfate, filter and concentrate. Purify on 40 g silica gel eluting with 100:0 to 70:30 hexanes:ethyl acetate to give 1.1 g (56.2%) of the desired compound as an oil.

$^1$H-NMR (400 MHz, CDCl$_3$) δ 6.53-6.47 (m, 3H), 4.59 (t, 2H, J=7.3 Hz), 3.88 (t, 2H, J=6.6 Hz), 3.26 (t, 2H, J=7.5 Hz), 1.84-1.75 (m, 2H), 1.03 (t, 3H, J=7.5 Hz).

(2R,3S,5R)-2-(2,2-Dimethyl-propoxy)-5-[3-(3-fluoro-5-propoxy-phenyl)-1-hydroxy-2-nitro-propyl]-3-meth 1-morpholine-4-carboxylic acid tert-butyl ester Add tetrabutyl ammonium fluoride (2 mL, 1.0 M in tetrahydrofuran, 2.15 mmol) to (2R,3S,5R)-2-(2,2-dimethyl-propoxy)-5-formyl-3-methyl-morpholine-4-carboxylic acid tert-butyl ester (0.61 g, 1.94 mmol) and 1-fluoro-3-(2-nitro-ethyl)-5-propoxy-benzene (0.48 g, 2.13 mmol) in tetrahydrofuran (4 mL) at –10° C. and stir 30 minutes. Pour into ice-cold saturated aqueous sodium chloride and separate the layers.

Wash the organic layer with saturated aqueous ammonium chloride and saturated aqueous sodium chloride. Dry over magnesium sulfate, filter and concentrate to an oil. Purify on 80 g silica gel eluting with 100:0 to 50:50 hexanes:diethyl ether to give 0.683 g (65%) of the desired compound as a mixture of 2 major and 1 minor diastereomers.

MS(ES⁻): m/z=541.3.

(2R,3S,5R)-5-[2-Amino-3-(3-fluoro-5-propoxy-phenyl)-1-hydroxy-propyl]-2-(2,2-dimethyl-propoxy)-3-meth 1-morpholine-4-carboxylic acid tert-butyl ester Add sodium borohydride (0.11 g, 2.92 mmol) to (2R,3S,5R)-2-(2,2-dimethylpropoxy)-5-[3-(3-fluoro-5-propoxy-phenyl)-1-hydroxy-2-nitro-propyl]-3-methylmorpholine-4-carboxylic acid tert-butyl ester (0.36 g, 0.66 mmol) and nickel chloride (0.14 g, 1.06 mmol) in methanol (7 mL) at room temperature and stir 30 minutes. Add water (0.7 mL) and concentrate. Dilute with ethyl acetate and filter through celite. Wash (10% potassium carbonate and saturated aqueous sodium chloride), dry (magnesium sulfate), filter and concentrate to give 0.340 g (100%) of the desired compound as a white solid.

MS(ES): m/z=513.5.

(2R,3S,5R)-5-[(1S,2S)-2-Acetylamino-3-(3-fluoro-5-propoxy-phenyl)-1-hydroxypropyl]-2-(2,2-dimethyl-propoxy)-3-methyl-morpholine-4-carboxylic acid tert-butyl ester Add acetic anhydride (0.07 g, 0.70 mmol) to (2R,3S,5R)-5-[2-Amino-3-(3-fluoro-5-propoxy-phenyl)-1-hydroxy-propyl]-2-(2,2-dimethyl-propoxy)-3-methyl-morpholine-4-carboxylic acid tert-butyl ester (0.34 g, 0.66 mmol) and triethylamine (0.10 g, 0.99 mmol) in tetrahydrofuran (6 mL) at room temperature and stir 1 hour. Dilute with ethyl acetate and wash with saturated aqueous ammonium chloride and saturated aqueous sodium chloride. Dry over magnesium sulfate, filter and concentrate. Purify on 12 g silica gel eluting with 100:0 to 20:80 hexanes:ethyl acetate to give 0.175 g of the desired compound as an oil.

Preparation 354

(2R,3S,5R)-5-[(1S,2S)-2-Acetylamino-3-(3-fluoro-5-isobutoxy-phenyl)-1-hydroxypropyl]-2-(2,2-dimethyl-propoxy)-3-methyl-morpholine-4-carboxylic acid tert-butyl ester 3-benzyloxy-5-fluoro-benzaldehyde Add n-butyl lithium (35 mL, 1.6M, 55.96 mmol) over 15 minutes to 1-bromo-3-fluoro-5-benzyloxy-benzene (14.30 g, 50.87 mmol) in tetrahydrofuran (300 mL) cooled in a dry ice/acetone bath, maintaining the internal temperature <−70°. Stir 30 minutes and add N,N-dimethylformamide (7.44 g, 101.74 mmol). Stir 30 minutes and remove cold bath. After 1 hour, quench with saturated aqueous ammonium chloride. Wash organic layer with water and saturated aqueous sodium chloride. Dry (sodium sulfate), filter and concentrate to an oil. Purify on 120 g silica gel eluting with 100:0 to 90:10 hexanes: ethyl acetate to give 3.75 g (32%) of the desired compound as an oil.

¹H-NMR (400 MHz, CDCl₃) δ 9.91 (d, 1H, J=0.9 Hz), 7.45-7.33 (m, 5H), 7.29 (s, 1H), 7.18 (d, 1H, J=7.9 Hz), 6.95 (dt, 1H, J=6.2, 3.5 Hz), 5.12 (s, 2H).

1-benzyloxy-3-fluoro-5-((E)-2-nitro-vinyl)-benzene

Heat 3-benzyloxy-5-fluoro-benzaldehyde (3.75 g, 16.29 mmol), nitromethane (4.08 g, 66.79 mmol), and ammonium acetate (3.47 g, 44.96 mmol) in acetic acid (54 mL) in 125° C. oil bath under nitrogen for 4 hours. Cool to room temperature and pour into ice/water. Extract with hexanes/ethyl acetate. Dry (magnesium sulfate), filter and concentrate. Purify on 120 g silica gel eluting with 100:0 to 80:20 hexanes:ethyl acetate to give 3.05 g (68.5%) of the desired compound as a yellow oil.

¹H-NMR (400 MHz, CDCl₃) δ 7.89 (d, 1H, J=14.1 Hz), 7.51 (d, 1H, J=13.6 Hz), 7.43-7.34 (m, 5H), 6.92 (s, 1H), 6.87-6.80 (m, 2H), 5.09 (s, 2H).

1-benzyloxy-3-fluoro-5-(2-nitro-ethyl)-benzene

Add sodium borohydride (1.69 g, 44.64 mmol) to 1-benzyloxy-3-fluoro-5-((E)-2-nitro-vinyl)-benzene (3.05 g, 11.16 mmol) and silica gel (22 g) in chloroform (112 mL) and isopropanol (33 mL) at room temperature in portions over 5 minutes. Stir at room temperature 90 minutes and filter. Concentrate and dissolve in ethyl acetate. Wash (10% potassium carbonate and saturated aqueous sodium chloride), dry over magnesium sulfate, filter and concentrate. Purify on 120 g silica gel eluting with 100:0 to 80:20 hexanes:ethyl acetate to afford 1.33 g (43.3%) of the desired compound as an oil.

¹H-NMR (400 MHz, CDCl₃) δ 7.42-7.32 (m, 5H), 6.62-6.58 (m, 2H), 6.53 (dt, 1H, J=5.3, 3.1 Hz), 5.03 (s, 2H), 4.59 (t, 2H, J=7.3 Hz), 3.27 (t, 2H, J=7.3 Hz).

(2R,3S,5R)-5-[3-(3-benzyloxy-5-fluoro-phenyl)-1-hydroxy-2-nitro-propyl]-2-(2,2-dimethyl-propoxy)-3-meth 1-morpholine-4-carboxylic acid tert-butyl ester Add tetrabutyl ammonium fluoride (14 mL, 11.0M in tetrahydrofuran, 14.30 mmol) to (2R,3S,5R)-2-(2,2-dimethylpropoxy)-5-formyl-3-methyl-morpholine-4-carboxylic acid tert-butyl ester (4.06 g, 12.88 mmol) and 1-Benzyloxy-3-fluoro-5-(2-nitro-ethyl)-benzene (3.90 g, 14.17 mmol) in tetrahydrofuran (26 mL) at −10° C. and stir 30 minutes. Pour into ice-cold saturated aqueous sodium chloride and separate the layers. Wash the organic layer with saturated aqueous ammonium chloride and saturated aqueous sodium chloride. Dry over magnesium sulfate, filter and concentrate to an oil. Purify on 330 g silica gel eluting with 100:0 to 50:50 hexanes: diethyl ether to give 5.89 g (77.4%) of the desired compound as a mixture of 2 major and 1 minor diastereomers.

MS(ES⁻): m/z=589.3.

(2R,3S,5R)-5-[2-Amino-3-(3-benzyloxy-5-fluoro-phenyl)-1-hydroxy-propyl]-2-(2,2-dimethyl-propoxy)-3-methyl-morpholine-4-carboxylic acid tert-butyl ester Add sodium borohydride (1.66 g, 43.87 mmol) to (2R,3S,5R)-5-[(1R,2S)-3-(3-benzyloxy-5-fluoro-phenyl)-1-hydroxy-2-nitro-propyl]-2-(2,2-dimethyl-propoxy)-3-methyl-morpholine-4-carboxylic acid tert-butyl ester (5.89 g, 9.97 mmol) and nickel chloride (2.07 g, 15.95 mmol) in methanol (100 mL) at room temperature and stir 30 minutes. Add water (~10 mL) and concentrate. Dilute with ethyl acetate and filter through celite. Partition between ethyl acetate and saturated aqueous sodium chloride. Wash the organic layer with saturated aqueous sodium chloride, dry (sodium sulfate), filter and concentrate to give 4.32 g (77.3%) of the desired compound as a white solid.

MS(ES): m/z=561.3.

(2R,3S,5R)-5-[(1S,2S)-2-Acetylamino-3-(3-benzyloxy-5-fluoro-phenyl)-1-hydroxypropyl]-2-(2,2-dimethyl-propoxy)-3-meth 1-morpholine-4-carboxylic acid tert-butyl ester Add acetic anhydride (0.83 g, 8.09 mmol) to (2R,3S,5R)-5-[2-amino-3-(3-benzyloxy-5-fluoro-phenyl)-1-hydroxypropyl]-2-(2,2-dimethyl-propoxy)-3-methylmorpholine-4-carboxylic acid tert-butyl ester (4.32 g, 7.70 mmol) and triethylamine (1.17 g, 11.56 mmol) in tetrahydrofuran (73 mL) and stir at room temperature 1 hour. Pour into ethyl acetate and wash with saturated aqueous ammonium chloride and saturated aqueous sodium chloride. Dry (magnesium sulfate), filter and concentrate. Purify on 330 g silica gel eluting with 100:0 to 40:60 hexanes:ethyl acetate to give 0.850 g of the desired compound as an oil.

MS(ES): m/z=603.5.

(2R,3S,5R)-5-[(1S,2S)-2-Acetylamino-3-(3-fluoro-5-hydroxy-phenyl)-1-hydroxypropyl]-2-(2,2-dimethyl-propoxy)-3-methyl-morpholine-4-carboxylic acid tert-butyl ester Stir (2R,3S,5R)-5-[(1S,2S)-2-acetylamino-3-(3-benzyloxy-5-fluoro-phenyl)-1-hydroxy-propyl]-2-(2,2-dimethyl-propoxy)-3-methyl-morpholine-4-carboxylic acid tert-butyl ester (0.81 g, 1.34 mmol) and 10% palladium on carbon (0.50 g, 1.41 mmol) in ethanol (20 mL) under a hydrogen atmosphere for 3 hours. Filter and concentrate to give 0.652 g (94.7%) of the desired compound as a white solid.

MS(ES⁻): m/z=511.2.

(2R,3S,5R)-5-[(1S,2S)-2-Acetylamino-3-(3-fluoro-5-isobutoxy-phenyl)-1-hydroxypropyl]-2-(2,2-dimethyl-propoxy)-3-methyl-morpholine-4-carboxylic acid tert-butyl ester Add 1-bromo-2-methyl-propane (0.05 g, 0.35 mmol) to (2R,3S,5R)-5-[(1S,2S)-2-acetylamino-3-(3-fluoro-5-hydroxy-phenyl)-1-hydroxy-propyl]-2-(2,2-dimethyl-propoxy)-3-methyl-morpholine-4-carboxylic acid tert-butyl ester (0.12 g, 0.23 mmol) and cesium carbonate (0.15 g, 0.46 mmol) in N,N-dimethylformamide (3 mL) under nitrogen and heat in a 60° C. oil bath for 2.5 hours. Cool to room temperature and dilute with ethyl acetate. Wash (0.1N citric acid, 10% potassium carbonate, saturated aqueous sodium chloride), dry (magnesium sulfate), filter and concentrate. Purify on 12 g silica gel column eluting with 100:0 to 40:60 hexanes:ethyl acetate to give 0.072 g (54.5%) of the title compound as a white foam.

The compounds of Preparations 355-360 may be prepared essentially as described in Preparation 354.

| Prep. | Compound | MS (ES+) |
|---|---|---|
| 355 | (2R,3S,5R)-5-{(1S,2S)-2-Acetylamino-3-[3-(2-ethyl-butoxy)-5-fluoro-phenyl]-1-hydroxy-propyl}-2-(2,2-dimethyl-propoxy)-3-methyl-morpholine-4-carboxylic acid tert-butyl ester | 597.5 |
| 356 | (2R,3S,5R)-5-{(1S,2S)-2-Acetylamino-3-[3-fluoro-5-(3-methyl-butoxy)-phenyl]-1-hydroxy-propyl}-2-(2,2-dimethyl-propoxy)-3-methyl-morpholine-4-carboxylic acid tert-butyl ester | 527.2 (loss of t-Bu) |
| 357 | (2R,3S,5R)-5-[(1S,2S)-2-Acetylamino-3-(3-allyloxy-5-fluoro-phenyl)-1-hydroxy-propyl]-2-(2,2-dimethyl-propoxy)-3-methyl-morpholine-4-carboxylic acid tert-butyl ester | 553.5 |
| 358 | (2R,3S,5R)-5-{(1S,2S)-2-Acetylamino-3-[3-fluoro-5-(3-methyl-but-2-enyloxy)-phenyl]-1-hydroxy-propyl}-2-(2,2-dimethyl-propoxy)-3-methyl-morpholine-4-carboxylic acid tert-butyl ester | 581.5 |
| 359 | (2R,3S,5R)-5-{(1S,2S)-2-Acetylamino-3-[3-fluoro-5-(2,2,2-trifluoro-ethoxy)-phenyl]-1-hydroxy-propyl}-2-(2,2-dimethyl-propoxy)-3-methyl-morpholine-4-carboxylic acid tert-butyl ester | 595.5 |
| 360 | (2R,3S,5R)-5-{(1S,2S)-2-Acetylamino-3-[3-fluoro-5-(2-fluoro-ethoxy)-phenyl]-1-hydroxy-propyl}-2-(3-fluoro-2,2-dimethyl-propoxy)-3-methyl-morpholine-4-carboxylic acid tert-butyl ester | 635.3 [M + AcO⁻] |

Preparation 361

4,4-difluoro-6-methylheptanoic acid

Benzyl 6-methyl-4-oxoheptanoate

Add benzyl chloroformate (0.712 g, 4.17 mmol), triethylamine (0.464 g, 4.59 mmol), and 4-dimethylaminopyridine (0.051 g, 0.42 mmol) to a solution of 6-methyl-4-oxo-heptanoic acid (0.66 g, 4.17 mmol) in dichloromethane (13 mL) at 0° C. Stir at 0° C. for 1 hour. Add saturated aqueous ammonium chloride (30 mL). Extract with dichloromethane (1×50 mL). Dry organic phase over magnesium sulfate and concentrate under reduced pressure. Subject residue to silica gel chromatography, eluting with 0-50% ethyl acetate in hexane to provide 0.87 g (84.1%) of the desired compound.

GCMS: m/z=248.0 [M]

Benzyl 4,4-difluoro-6-methylheptanoate

Add bis(2-methoxyethyl)aminosulfur trifluoride (Deoxo-fluor™, 0.606 g, 2.74 mmol), Aldrich) and ethanol (0.019 mL) to a solution of benzyl 6-methyl-4-oxo-heptanoate (0.40 g, 1.61 mmol) in dichloromethane (0.8 mL) in a plastic vessel at 40° C. for 4 days. Add Deoxo-fluor™ (1.7 equivalents) and stir 24 hours at 60° C. Add 25 mL aqueous sodium bicarbonate. Extract with dichloromethane (2×50 mL). Concentrate the organic phase under reduced pressure and subject the residue to silica gel chromatography, eluting with 0-15% ethyl acetate in hexane to provide the desired compound (0.096 g, 22.0%)

GCMS: m/z=270.0 [M]

Deprotection

Add 0.01 g 10% palladium on carbon to a solution of benzyl 4,4-difluoro-6-methyl heptanoate (0.095 g, 0.35 mmol) in 3.5 mL tetrahydrofuran. Hydrogenate under balloon pressure over night. Filter through a pad of celite and wash with pad with ethyl acetate. Concentrate under reduced pressure to provide 0.068 g of the title compound.

MS: m/z=179.1 [M−1]

Preparation 362

2-fluoropropionic acid

Heat a solution of ethyl 2-fluoropropionate (0.30 g, 2.50 mmol) in 5M sulfuric acid (5 mL) at 120° C. for 1 hour. Saturate the solution with sodium chloride and extract with diethyl ether (4×40 mL). Dry the combined organic extracts with magnesium sulfate and concentrate under reduced pressure to provide 0.18 g (78.3%) of the title compound.

GCMS: m/z=92.0 [M]

Preparation 363

4,4,4-trifluoro-2-methylbut-2-enoic acid

Heat a solution of ethyl 4,4,4-trifluoro-2-methylbut-2-enoic acid (0.544 g, 2.99 mmol) in 5M sulfuric acid (5 mL) at 120° C. for 2.5 days. Saturate the solution with sodium chloride and extract with diethyl ether (1×40 mL). Dry the organic phase with magnesium sulfate and concentrate under reduced pressure to provide 0.288 g (62.6%) of the title compound.

MS: m/z=153.2 [M−1]

Preparation 364

N,N-dipropyl 2-methylsuccinamic acid

Add 40% palladium on carbon (0.064 g) to a solution of (E)-3-dipropylcarbamoyl-2-methylacrylic acid (0.20 g, 0.94 mmol) in tetrahydrofuran (20 mL). Hydrogenate at 60 psi for 18 hours. Filter through a filtering agent and concentrate filtrate under reduced pressure. Subject residue to silica gel chromatography, eluting with dichloromethane containing 10-40% of 5% (2:1 methanol:acetic acid) in dichloromethane to provide the title compound (0.134 g, 66.4%).

MS: m/z=216.2 [M+1]

Preparation 365 cis-2-(methyl-propylcarbamoyl)-cyclopropane carboxylic acid

Add diisopropylethylamine (2.68 mL, 15.4 mmol) and cis-cyclopropane-1,2-dicarboxylic acid (0.50 g, 3.84 mmol) to a slurry of 2-chlorotrityl chloro resin (3.00 g, Nova Bio) in 7:1 dichloromethane:dimethylfomamide (10.0 mL). Stir over night and then filter the slurry. Wash the resin with 17:2:1 dichloromethane:methanol:dimethylformamide (3×20 mL) followed by dichloromethane (3×20 mL). Add the filtered resin to a solution of diisopropylethylamine (1.34 mL, 7.69 mmol), methylpropylamine (0.788 mL, 7.69 mmol), O-benzotriazol-1-yl-N,N,N',N'-tetramethyluronium hexafluorophosphate (HBTU) (2.915 g, 7.69 mmol), and HOBT (1.177 g, 7.69 mmol) in dimethylformamide (10 mL) and shake for 2.5 days. Filter and wash the resin with dimethylformamide (3×20 mL) and dichloromethane (5×20 mL). Add trifluoroacetic acid (1 mL) to a slurry of the washed resin in dichloromethane (20 mL). Shake for 45 minutes and filter. Wash the resin with dichloromethane (2×20 mL) and concentrate this filtrate under reduced pressure. Subject the residue to silica gel chromatography, eluting with dichloromethane containing 10-40% of 5% (2:1 methanol:acetic acid) in dichloromethane to provide the title compound (0.247 g, 34.7%).

MS: m/z=186.2 [M+1]

Preparation 366

(+/−)-trans-2-difluoromethyl-cyclopropane carboxylic acid (+/−)-trans-cyclopropane-1,2-dicarboxylic acid monoethyl ester Add a solution of 0.709 g (17.72 mmol) sodium hydroxide in 7.38 mL ethanol to a solution of (+/−)-trans-cyclopropane-1,2-dicarboxylic acid diethyl ester (3.00 g, 16.11 mmol) in 36.9 mL acetone. Stir at room temperature for 24 hours. Pour reaction mixture into 100 mL water and extract with ethyl acetate (1×70 mL). Acidify the aqueous layer with 5N HCl and concentrate under reduced pressure. Add ethyl acetate and filter the resulting slurry. Concentrate the filtrate under reduced pressure to provide the desired compound (2.26 g, 88.7%).

MS: m/z=157.2 [M−1]

(+/−)-trans-2-hydroxymethyl-cyclopropanecarboxylic acid ethyl ester

Add isobutylchloroformate (0.41 mL, 3.16 mmol) and N-methylmorpholine (0.35 mL, 3.16 mmol) to a solution of (+/−)-trans-cyclopropane-1,2-dicarboxylic acid monoethyl ester (0.50 g, 3.161 mmol) in tetrahydrofuran (21 mL) at −50° C. Stir for 5 minutes and then filter into a slurry of sodium borohydride (0.084 g, 2.21 mmol) in tetrahydrofuran (9 mL) and cool to −50° C. Warm to room temperature over night and then add 9 mL of water. Remove tetrahydrofuran under reduced pressure and extract aqueous layer with diethyl ether (3×20 mL). Wash combined organic layers with saturated aqueous sodium chloride and dry over magnesium sulfate. Concentrate under reduced pressure and subject residue to silica gel chromatography eluting with 25-65% ethyl acetate in hexanes to provide the desired compound (0.224 g, 49.1%).

GCMS: m/z=144.0 [M]

(+/−)-trans-2-formyl-cyclopropanecarboxylic acid ethyl ester

Cool a solution of (+/−)-trans-2-hydroxymethyl-cyclopropanecarboxylic acid ethyl ester (0.22 g, 1.53 mmol) in 1.5 mL DMSO to 0° C. Add to the frozen solution triethyl-amine (0.85 mL, 0.62 mmol) followed by sulfur trioxide pyridine (0.49 g, 3.05 mmol). Warm reaction mixture to 12° C. over 3.5 hours, dilute with diethyl ether (80 mL), and wash with 5% aqueous citric acid (3×20 mL) followed by saturated aqueous sodium chloride (1×20 mL). Dry over magnesium sulfate and concentrate under reduced pressure to provide the desired compound.

GCMS: m/z=142 [M]

(+/−)-trans-2-difluoromethyl-cycloprropanecarboxylic acid ethyl ester

Add a solution of Deoxo-fluor™ (0.32 mL, 1.73 mmol) in 0.3 mL dichloromethane to a solution of (+/−)-trans-2-formyl-cyclopropanecarboxylic acid ethyl ester (0.145 g, 1.02 mmol) in 0.5 mL dichloromethane. Stir the reaction mixture for 16 hours, pour into saturated aqueous sodium bicarbonate (15 mL), and extract with dichloromethane (3×20 mL). Dry the combined organic extracts over sodium sulfate, concentrate under reduced pressure, and subject residue to silica gel chromatography, eluting with 25-65% ethyl acetate in hexanes to provide the desired compound (0.087 g, 52.2%).

Ester Hydrolysis

Add 1.32 mL 2M LiOH to a solution of (+/−)-trans-2-difluoromethyl-cyclopropanecarboxylic acid ethyl ester (0.087 g, 0.53 mmol) in tetrahydrofuran (13.3 mL). Stir for 4 hours and then concentrate under reduced pressure to a volume of about 1.5 mL. Dilute with water (10 mL) and extract with diethyl ether (1×25 mL). Acidify the aqueous layer with 1.0 N HCl and extract with diethyl ether (5×25 mL). Dry combined organic layers over magnesium sulfate and concentrate under reduced pressure to provide the title compound as a yellow oil (0.057 g, 79.6%)

MS: m/z=135.2 [M−1]

Preparation 367

(+/−)-trans-2-fluoromethyl-cyclopropane carboxylic acid

The title compound is prepared by reacting (+/−)-trans-2-hydroxymethylcyclopropanecarboxylic acid ethyl ester with Deoxo-fluor™ followed by ester hydrolysis essentially as described in Preparation 366.

GCMS: m/z=118.0 [M]

Preparation 368

3-butyl-5-fluorobenzaldehyde

3-bromo-5-fluorobenzaldehyde

Add dropwise a solution of 1,3-dibromo-5-fluorobenzene (12.39 mL, 98.5 mmol) in tetrahydrofuran (20 mL) to a solution of n-butyllithium (64.61 mL, 103.4 mmol, 1.6 M in hexanes) in tetrahydrofuran (55 mL) at −78° C. Stir at −78° C. for 45 minutes, add dimethylformamide (7.62 mL, 98.5 mmol), stir at −78° C. for 1.5 hours, remove cooling bath and stir 10 minutes. Add saturated aqueous ammonium chloride (150 mL) and extract with diethyl ether (2×700 mL). Wash combined organic layers sequentially with water (1×300 mL) and saturated aqueous sodium chloride (1×300 mL). Dry over magnesium sulfate and concentrate under reduced pressure. Subject residue to silica gel chromatography, eluting with 0-10% ethyl acetate in hexanes to provide the desired compound (11.05 g, 55.3%).

GCMS: m/z=203.0 [M]

3-butyl-5-fluorobenzaldehyde

Add butylzinc bromide (49.3 mL, 24.6 mmol, 0.5 M in THF) followed by Pd(dppf)$_2$Cl$_2$ dichloromethane complex (1.01 g, 1.23 mmol) to a solution of 3-bromo-5-fluorobenzaldehyde (5.00 g, 24.6 mmol) in tetrahydrofuran (123.1 mL). Stir at room temperature in a sealed vessel flushed with nitrogen for 18 hours. Add saturated aqueous ammonium chloride (125 mL). Separate the layers and extract the aqueous layer with ethyl acetate (1×300 mL). Wash combined organic layers with saturated aqueous sodium chloride, dry over magnesium sulfate and concentrate under reduced pressure. Subject residue to silica gel chromatography, eluting with 0-10% ethyl acetate in hexanes to provide the title compound (3.43 g, 77.3%).

GCMS: m/z=180.0 [M]

Beginning with nitromethane and appropriately substituted benzaldehydes and formylmorpholines, the following compounds may be prepared essentially as described in Preparation 188.

| Prep | Compound | MS (ES) [M + Na] |
|---|---|---|
| 369 | (2R,3S,5R)-5-[(1S,2S)-2-Acetylamino-1-hydroxy-3-(4-fluorophenyl)-propyl]-2-(2,2-dimethylpropoxy)-3-methylmorpholine-4-carboxylic acid tert-butyl ester | 519.3 |
| 370 | (2R,3S,5R)-5-[(1S,2S)-2-Acetylamino-1-hydroxy-3-(3-(trifluoromethylthio)phenyl)-propyl]-2-(2,2-dimethylpropoxy)-3-methyl-morpholine-4-carboxylic acid tert-butyl ester | 601.3 |
| 371 | (2R,3S,5R)-5-[(1S,2S)-2-Acetylamino-1-hydroxy-3-(3-fluorophenyl)-propyl]-2-(2,2-dimethylpropoxy)-3-methyl-morpholine-4-carboxylic acid tert-butyl ester | 519.2 |
| 372 | (2R,3S,5R)-5-[(1S,2S)-2-Acetylamino-1-hydroxy-3-(2,4-difluorophenyl)-propyl]-2-(2,2-dimethylpropoxy)-3-methylmorpholine-4-carboxylic acid tert-butyl ester | 537.3 |
| 373 | (2R,3S,5R)-5-[(1S,2S)-2-Acetylamino-1-hydroxy-3-(3-(trifluoromethyl)phenyl)-propyl]-2-(2,2-dimethylpropoxy)-3-methyl-morpholine-4-carboxylic acid tert-butyl ester | 569.3 |

Preparation 374

(1S,2S)-2-Amino-3-(3,5-difluorobenzyl)-1-[(3R,5S,6R)-6-(2,2-di-(fluoromethyl)propoxy)-5-methylmorpholin-3-yl]-propan-1-ol Dibenzyl-{(1S,2S)-2-benzyloxy-1-(3,5-difluorobenzyl)-2-[(3R,5S,6R)-6-(2,2-di-(fluoromethyl)propoxy)-5-methyl-morpholin-3-yl]-ethyl}-amine React 2,2-di-(fluoromethyl)propanol (2.172 g, 17.5 mmol) with (3S,5R)-5-[(1S,2S)-1-benzyloxy-2-dibenzylamino-3-(3,5-difluorophenyl)-propyl]-3-methylmorpholin-2-ol (2.004 g, 3.5 mmol) essentially as described in Preparation 307 to provide 1.0 g of the desired compound.

Deprotection

Charge a deoxygenated solution of dibenzyl-{(1S,2S)-2-benzyloxy-1-(3,5-difluorobenzyl)-2-[(3R,5S,6R)-6-(2,2-di-(fluoromethyl)propoxy)-5-methylmorpholin-3-yl]-ethyl}-amine (0.95 g, 1.399 mmol) in tert-butanol (17.48 mL) with 20% palladium(II) hydroxide on carbon (2.137 g, 3.06 mmol) and hydrogenate at 60 psi for 4 hours. Dilute reaction mixture with ethyl acetate and filter through Celite™. Concentrate filtrate to provide the title compound (0.571 g).

Preparation 378

(1S,2S)-2-Amino-3-(3,5-difluorophenyl)-1-[(3R,6R)-6-(2,2-di-(fluoromethyl)propoxy)-morpholin-3-yl]-propan-1-ol (2R,5R)-5-{(1S,2S)-2-Dibenzylamino-3-[3,5-difluorophenyl]-1-benzyloxy-1-propyl}-2-(2,2-di-(fluoromethyl)-propoxy)-morpholine-4-carboxylic acid tert-butyl ester React (3S,5R)-5-{(1S,2S)-2-Dibenzylamino-3-[3,5-difluorophenyl]-1-benzyloxy-propyl}-2-hydroxymorpholine-4-carboxylic acid tert-butyl ester (1.0 g, 1.52 mmol) with trifluoromethanesulfonic acid 2,2-di-(fluoromethyl)propyl ester (584 mg, 2.27 mmol) essentially as described in Preparation 306 to provide 1.0 g (86%) of the desired compound.

(2R,3S,5R)-5-{(1S,2S)-2-Amino-3-[3,5-difluorophenyl]-1-hydroxy-propyl}-2-(2,2-di-(fluoromethyl)-propoxy)-morpholine-4-carboxylic acid tert-butyl ester Charge a deoxygenated solution of (2R,3S,5R)-5-{(1S,2S)-2-dibenzylamino-3-[3,5-difluorophenyl]-1-benzyloxy-propyl}-2-(2,2-di-(fluoromethyl)-propoxy)-morpholine-4-carboxylic acid tert-butyl ester (1.0 g, 1.3 mmol) in 16.99 mL ethyl acetate with 20% palladium(II) hydroxide (1.0 g, 1.40 mmol) and hydrogenate at atmospheric pressure over night. Filter the reaction mixture through Celite™ and concentrate the filtrate under reduced pressure to provide 0.629 g (98%) of the desired compound in crude form.

N-Deprotection

Add cold (0° C.) trifluoroacetic acid to (2R,3S,5R)-5-{(1S,2S)-2-amino-3-[3,5-difluorophenyl]-1-hydroxy-propyl}-2-(2,2-di-(fluoromethyl)-propoxy)-morpholine-4-carboxylic acid tert-butyl ester (364 mg, 0.73 mmol) and stir the solution at 0° C. for 10 minutes. Allow reaction mixture to warm to room temperature over 20 minutes and concentrate under reduced pressure. Dissolve resultant oil in ethyl acetate and add saturated aqueous sodium bicarbonate. Wash the organic layer with saturated aqueous sodium bicarbonate, dry over sodium sulfate, and concentrate to provide the title compound.

Preparation 378

(1S,2S)-2-Amino-3-(3-isopropylsulfanyl-5-fluorophenyl)-1-[(3R,5S,6R)-6-(2,2-di-(fluoromethyl)propoxy)-5-methylmorpholin-3-yl]-propan-1-ol Heat a mixture of (1S,2S)-2-Amino-3-(3,5-difluorophenyl)-1-[(3R,5S,6R)-6-(2,2-di-(fluoromethyl)propoxy)-5-methylmorpholin-3-yl]-propan-1-ol (91 mg, 0.22 mol) and sodium 2-propanethiolate (328 mg, 3.34 mmol) in N-methylpyrrolidin-2-one (2.0 mL) at 90° C. in a sealed tube for 1 hour. Cool the reaction mixture to room temperature, dilute with methanol, add ammonium chloride (192 mg, 3.34 mmol), and mix well. Load mixture on SCX™ column and elute with 2.0 M ammonia in methanol to provide the desired compound (60 mg, 58%).

MS(ES): m/z=465 [M$^+$+H]

The compounds of Preparations 379-381 may be prepared essentially as described in Preparation 378.

| Prep | Compound | MS (ES) |
|---|---|---|
| 379 | (1S,2S)-2-Amino-3-(3-propylsulfanyl-5-fluorophenyl)-1-(3R,5S,6R)-6-(2,2-di-(fluoromethyl)propoxy)-5-methylmorpholin-3-yl]-propan-1-ol | 451 [M$^+$ + H] |
| 380 | (1S,2S)-2-Amino-3-(3-(2-methylprop-2-yl)sulfanyl-5-fluorophenyl)-1-(3R,5S,6R)-6-(2,2-di-(fluoromethyl)propoxy)-5-methylmorpholin-3-yl]-propan-1-ol | 479 [M$^+$ + H] |
| 381 | (1S,2S)-2-Amino-3-(3-phenylsulfanyl-5-fluorophenyl)-1-(3R,5S,6R)-6-(2,2-di-(fluoromethyl)propoxy)-5-methylmorpholin-3-yl]-propan-1-ol | 499 [M$^+$ + H] |

Preparation 382

(2R,3S,5R)-5-[(1S,2S)-1-Hydroxy-2-amino-3-(3-propoxy-5-fluorophenyl)-propyl]-2-(3-fluoro-2,2-dimethylpropoxy)-3-methylmorpholine-4-carboxylic acid tert-butyl ester (2R,3S,5R)-5-[(1S,2S)-1-benzyloxy-2-dibenzylamino-3-(3,5-difluorophenyl)-propyl]-2-(3-fluoro-2,2-dimethylpropoxy)-3-methylmorpholine-4-carboxylic acid tert-butyl ester Beginning with (3S,5R)-5-[(1S,2S)-1-Benzyloxy-2-dibenzylamino-3-(3,5-difluorophenyl)-propyl]-3-methylmorpholin-2-ol, the desired compound may be prepared essentially as described in Preparation 307.

(2R,3S,5R)-5-[(1S,2S)-1-benzyloxy-2-dibenzylamino-3-(3-propoxy-5-fluorophenyl)-propyl]-2-(3-fluoro-2,2-dimethylpropoxy)-3-methylmorpholine-4-carboxylic acid tert-butyl ester Stir a mixture of sodium hydride (115 mg, 2.89 mmol, 60% in mineral oil) in N-methyl-2-pyrrolidinone (960 μL) and 1-propanol (234 μL) for 10 minutes and then add a solution of (2R,3S,5R)-5-[(1S,2S)-1-benzyloxy-2-dibenzylamino-3-(3,5-difluorophenyl)-propyl]-2-(3-fluoro-2,2-dimethylpropoxy)-3-methylmorpholine-4-carboxylic acid tert-butyl ester (440 mg, 0.57 mmol) in N-methyl-2-pyrrolidinone (1 mL) and stir in a sealed vial at 90° C. for 4 hours. Cool to room temperature and pour reaction mixture into water and extract well with ethyl acetate. Wash the organic phase with water followed by saturated aqueous sodium chloride and concentrate under reduced pressure. Subject the resulting residue to silica gel chromatography, eluting with hexane containing from 0-50% ethyl acetate to provide the desired compound.

Deprotection

Beginning with (2R,3S,5R)-5-[(1S,2S)-1-Benzyloxy-2-dibenzylamino-3-(3-propoxy-5-fluorophenyl)-propyl]-2-(3-fluoro-2,2-dimethylpropoxy)-3-methylmorpholine-4-carboxylic acid tert-butyl ester (350 mg, 0.436 mmol), the title compound may be prepared essentially as described in Preparation 307.

The compounds of Preparations 383-384 may be prepared essentially as described in Preparation 382.

| Prep | Compound | MS (ES) |
|---|---|---|
| 383 | (1S,2S)-2-Amino-3-(3-propoxy-5-fluorophenyl)-1-[(3R,5S,6R)-6-(2,2,2-tri-(fluoromethyl)ethoxy)-5-methylmorpholin-3-yl]-propan-1-ol | 467 [M$^+$ + H] |
| 384 | (1S,2S)-2-Amino-3-(3-propoxy-5-fluorophenyl)-1-[(3R,5S,6R)-6-(trimethylsilylmethoxy)-5-methylmorpholin-3-yl]-propan-1-ol | 429 [M$^+$ + H] |

Employing the appropriate alcohol in place of 1-propanol, the compounds of Preparations 385-393 may be prepared essentially as described in Preparation 382.

| Prep | Compound | MS (ES) |
|---|---|---|
| 385 | (2R,3S,5R)-5-[(1S,2S)-1-Hydroxy-2-amino-3-(3-hydroxy-5-fluorophenyl)-propyl]-2-(3-fluoro-2,2-dimethylpropoxy)-3-methylmorpholine-4-carboxylic acid tert-butyl ester | 489.3 [M$^+$ + H] |
| 386* | (1S,2S)-2-Amino-3-(3-cyclopropylmethoxy-5-fluoro-phenyl)-1-[(3R,5S,6R)-6-(3-fluoro-2-fluoromethyl-2-methyl-propoxy)-5-methyl-morpholin-3-yl]-propan-1-ol | 461 [M$^+$ + H] |
| 387* | (1S,2S)-2-Amino-1-[(3R,5S,6R)-6-(3-fluoro-2-fluoromethyl-2-methyl-propoxy)-5-methyl-morpholin-3-yl]-3-(3-fluoro-5-isobutoxy-phenyl)-propan-1-ol | 463 [M + H]$^+$ |
| 388* | (1S,2S)-2-Amino-1-[(3R,5S,6R)-6-(3-fluoro-2-fluoromethyl-2-methyl-propoxy)-5-methyl-morpholin-3-yl]-3-[3-fluoro-5-(2-methyl-cyclopropylmethoxy)-phenyl]-propan-1-ol | 475 [M + H]$^+$ |
| 389* | (1S,2S)-2-Amino-1-[(3R,5S,6R)-6-(3-fluoro-2-fluoromethyl-2-methyl-propoxy)-5-methyl-morpholin-3-yl]-3-[3-fluoro-5-(1-methyl-cyclopropylmethoxy)-phenyl]-propan-1-ol | 475 [M + H]$^+$ |
| 390* | (1S,2S)-2-Amino-3-[3-(1-cyclopropyl-ethoxy)-5-fluoro-phenyl]-1-[(3R,5S,6R)-6-(3-fluoro-2-fluoromethyl-2-methyl-propoxy)-5-methyl-morpholin-3-yl]-propan-1-ol | 475 [M + H]$^+$ |
| 391 | 5-[2-amino-3-(3-fluoro-5-propoxy-phenyl)-1-hydroxy-propyl]-2-(3-fluoro-2-fluoromethyl-2-methyl-propoxy)-3-methyl-morpholine-4-carboxylic acid tert-butyl ester | |
| 392* | 2-amino-3-[3-(2,2-dimethyl-propoxy)-5-fluoro-phenyl]-1-[6-(3-fluoro-2,2-bis-(fluoromethyl)-ethoxy)-5-methyl-morpholin-3-yl]-propan-1-ol | 495 [M + H$^+$] |
| 393* | 3-{(2S,3S)-2-Amino-3-[(3R,5S,6R)-(6-(3-fluoro-2-fluoromethyl-2-methyl-propoxy)-5-methyl-morpholin-3-yl]-3-hydroxy-propyl}-5-fluoro-phenol | 407 |

*Hydrogenated under conditions of Preparation 374.

Preparation 394

(1S,2S)-2-Amino-3-(3-(2,2-dimethylpropoxy)-5-fluorophenyl)-1-(3R,5S,6R)-6-(2,2-di-(fluoromethyl)propoxy)-5-methylmorpholin-3-yl]-propan-1-ol Beginning with (1S,2S)-2-Amino-3-(3,5-difluorophenyl)-1-(3R,5S,6R)-6-(2,2-di-(fluoromethyl)propoxy)-5-methylmorpholin-3-yl]-propan-1-ol (196 mg, 0.48 mmol) and neopentyl alcohol (465 mg, 5.28 mmol), the title compound may be prepared essentially as described in Preparation 382.

Compounds of Preparations 395-397 may be prepared essentially as described in Preparation 394.

| Prep | Compound | MS (ES) |
|---|---|---|
| 395 | (1S,2S)-2-Amino-3-(3-cyclopropylmethoxy-5-fluorophenyl)-1-(3R,5S,6R)-6-(3-fluoro-2,2-dimethylpropoxy)-5-methylmorpholin-3-yl]-propan-1-ol | |

| Prep | Compound | MS (ES) |
|---|---|---|
| 396 | (1S,2S)-2-Amino-3-(3-cyclobutoxy-5-fluorophenyl)-1-(3R,5S,6R)-6-(2,2-di-(fluoromethyl)propoxy)-5-methylmorpholin-3-yl]-propan-1-ol | |
| 397 | (1S,2S)-2-Amino-3-(3-isobutoxy-5-fluorophenyl)-1-(3R,5S,6R)-6-(3-fluoro-2,2-dimethylpropoxy)-5-methylmorpholin-3-yl]-propan-1-ol | 445.3 [M$^+$ + H] |

Preparation 398

(2R,3S,5R)-5-[(1S,2S)-1-Hydroxy-2-acetylamino-3-(3-propoxy-5-fluorophenyl)-propyl]-2-(3-fluoro-2,2-dimethylpropoxy)-3-methylmorpholine-4-carboxylic acid tert-butyl ester Add acetic anhydride (43 µL, 0.44 mmol) to a solution of (2R,3S,5R)-5-[(1S,2S)-1-Hydroxy-2-amino-3-(3-propoxy-5-fluorophenyl)-propyl]- 2-(3-fluoro-2,2-dimethylpropoxy)-3-methylmorpholine-4-carboxylic acid tert-butyl ester (231 mg, 0.44 mmol) and triethylamine (92 µL, 0.65 mmol) in dichloromethane (4.6 mL) and stir at room temperature for 30 minutes. Concentrate reaction mixture under a stream of nitrogen and subject residue to silica gel chromatography, eluting with 0-100% ethyl acetate in hexane to provide the title compound.

Compounds of Preparations 399-405 may be prepared essentially as described in Preparation 398.

| Prep | Compound | MS (ES) |
|---|---|---|
| 399 | (2R,3S,5R)-5-[(1S,2S)-1-Hydroxy-2-acetylamino-3-(3-hydroxy-5-fluorophenyl)-propyl]-2-(3-fluoro-2,2-dimethylpropoxy)-3-methylmorpholine-4-carboxylic acid tert-butyl ester | |
| 400 | (2R,3S,5R)-5-[(1S,2S)-1-Hydroxy-2-acetylamino-3-(3,5-difluoro-phenyl)-propyl]-2-(2-methoxypropoxy)-3-methylmorpholine-4-carboxylic acid tert-butyl ester | 539.0 [M$^+$ + Na$^+$] |
| 401 | 2R,5R)-5-[(1S,2S)-1-Hydroxy-2-acetylamino-3-(3-propoxy-5-fluorophenyl)-propyl]-2-(cyclopropylmethoxy)-morpholine-4-carboxylic acid tert-butyl ester | 525.3 [M$^+$] |
| *402 | (2R,3S,5R)-5-[(1S,2S)-1-Hydroxy-2-acetylamino-3-(3-bromo-5-fluoro-phenyl)-propyl]-2-(2,2-dimethylpropoxy)-3-methylmorpholine-4-carboxylic acid tert-butyl ester | 577.4 [M$^+$ + H] |
| *403 | (2R,3S,5R)-5-[(1S,2S)-1-Hydroxy-2-acetylamino-3-(3-butyl-5-fluoro-phenyl)-propyl]-2-(2,2-dimethylpropoxy)-3-methylmorpholine-4-carboxylic acid tert-butyl ester | 553.5 [M$^+$ + H] |
| *404 | (2R,3S,5R)-5-[(1S,2S)-1-Hydroxy-2-acetylamino-3-(4-methyl-3,5-difluoro-phenyl)-propyl]-2-(2,2-dimethylpropoxy)-3-methylmorpholine-4-carboxylic acid tert-butyl ester | 529.5 [M$^+$ + H] |
| *405 | (2R,3S,5R)-5-[(1S,2S)-1-Hydroxy-2-acetylamino-3-(4-(3-methylbutyl)-3,5-difluoro-phenyl)-propyl]-2-(2,2-dimethylpropoxy)-3-methyl-morpholine-4-carboxylic acid tert-butyl ester | 607.3 [M$^+$ + H] |

*Replace dichloromethane with tetrahydrofuran as reaction solvent.

Beginning with (2RS,3S,5R)-5-[(1S,2S)-1-benzyloxy-2-dibenzylamino-3-(3,5-difluorophenyl)-propyl]-3-methyl-morpholin-2-ol, the following compounds may be prepared essentially as described in Preparation 307.

| Prep | Compound | MS (ES) |
|---|---|---|
| 406 | (2R,3S,5R)-5-[(1S,2S)-1-Hydroxy-2-amino-3-(3,5-difluorophenyl)-propyl]-2-(2-methoxypropoxy)-3-methylmorpholine-4-carboxylic acid tert-butyl ester | |
| 407 | (2R,3S,5R)-5-[(1S,2S)-1-Hydroxy-2-amino-3-(3,5-difluorophenyl)-propyl]-2-(2,2-dimethylpropoxy)-3-methylmorpholine-4-carboxylic acid tert-butyl ester | 473.4 [M$^+$ + H] |

Preparation 408

(2R,3S,5R)-5-[(1S,2S)-1-Hydroxy-2-amino-3-(3-bromo-5-fluorophenyl)-propyl]-2-(2,2-dimethylpropoxy)-3-methylmorpholine-4-carboxylic acid tert-butyl ester

3-Butyl-5-fluoro-benzaldehyde

Dissolve 1,3-Dibromo-5-fluoro-benzene (12.00 g, 0.05 mmol) in diethyl ether (470 mL) and cool to −78 C. Slowly add 1.6 M n-butyllithium in hexanes (29.5 mL, 49.6 mmol) and stir at −78 for one hour. Add dimethylformamide (3.45 g, 0.05 mmol) dropwise and warm to room temperature overnight. Quench with saturated aqueous ammonium chloride solution. Separate the layers and extract the organic layer (1×300 mL) with diethyl ether. Combine the organic layers and wash (1×150 mL) with water, (1×100 µL) with saturated aqueous sodium chloride and dry over magnesium sulfate. Purify using medium pressure chromatography (silica gel, 0-10% diethyl ether:hexanes) to give the desired product (4.15 g, 43%) as a yellow liquid.

2-(3-bromo-5-fluorophenyl)-1-nitroethane

Beginning with 3-bromo-5-fluorobenzaldehyde, the desired compound may be prepared essentially as described in Preparation 168.

(2R,3S,5R)-5-[(1S,2S)-1-Hydroxy-2-amino-3-(3-bromo-5-fluorophenyl)-propyl]-2-(2,2-dimethylpropoxy)-3-methylmorpholine-4-carboxylic acid tert-butyl ester Beginning with 2-(3-bromo-5-fluorophenyl)-1-nitroethane, the desired compound may be prepared essentially as described in Preparation 188.

Reduction

Add zinc (0.604 g, 9.23 mmol) to a solution of (2R,3S,5R)-5-[(1R,2S)-3-(3-bromo-5-fluoro-phenyl)-1-hydroxy-2-nitro-propyl]-2-(2,2-dimethyl-propoxy)-3-methyl-morpholine-4-carboxylic acid tert-butyl ester (0.520 g, 0.923 mmol) in acetic acid (9.23 mL). Stir the reaction mixture for 22 hours at room temperature. Filter the reaction mixture and wash the filter cake with cold water (100 mL). Add saturated aqueous sodium bicarbonate to the filtrate to neutralize the acid. Extract the neutralized aqueous phase with ethyl acetate (3×250 mL). Dry the combined organic phases with magnesium sulfate and concentrate under reduced pressure to provide the title compound (0.49 g, 99.5%) as a white foam.
MS(ES): m/z=535.3 [M+H]$^+$

Preparation 409

(2R,3S,5R)-5-[(1S,2S)-1-Hydroxy-2-acetylamino-3-(3-propyl-5-fluorophenyl)-propyl]-2-(2,2-dimethyl-propoxy)-3-methylmorpholine-4-carboxylic acid tert-butyl ester Add propyl zinc bromide (2.311 g) in tetrahydrofuran and (1,1'-bis(diphenylphosphino)ferrocene) palladium(II) chloride (0.015 g) to a solution of (2R,3S,5R)-5-[(1S,2S)-1-hydroxy-2-acetylamino-3-(3-bromo-5-fluorophenyl)-propyl]-2-(2,2-dimethylpropoxy)-3-methylmorpholine-4-carboxylic acid tert-butyl ester (0.07 g, 0.122 mmol) in tetrahydrofuran (1.2 mL) in a sealed tube flushed with nitrogen. Heat the tube at 65° C. for 6.5 hours. Add saturated aqueous ammonium chloride (5 mL). Extract the reaction mixture with ethyl acetate (2×30 mL). Combine the organic phases and wash with saturated aqueous sodium chloride (1×15 mL), dry over magnesium sulfate and concentrate under reduced pressure. Subject residue to silica gel chromatography, eluting with hexanes containing 15-45% ethyl acetate, to provide 0.039 g (60%) of the title compound as an off-white foam.
MS(ES): m/z=539.5 [M+1]$^+$

Preparation 410

(2R,3S,5R)-5-{(1S,2S)-2-Acetylamino-3-[3-fluoro-5-(3-methyl-butyl)-phenyl]-1-hydroxy-propyl}-2-(2,2-dimethyl-propoxy)-3-methyl-morpholine-4-carboxylic acid tert-butyl ester Beginning with 3-methylbutyl zinc bromide and (2R,3S,5R)-5-[(1S,2S)-1-hydroxy-2-acetylamino-3-(3-bromo-5-fluorophenyl)-propyl]-2-(2,2-dimethylpropoxy)-3-methyl-morpholine-4-carboxylic acid tert-butyl ester (0.165 g, 0.287 mmol), the title compound (0.127 g, 78%) may be prepared essentially as described in Preparation 409.
MS(ES): m/z=565.3 [M−1]$^-$

Preparation 411

(2R,3S,5R)-5-[(1S,2S)-1-Hydroxy-2-acetylamino-3-(3-(2-ethoxyphenyl)-5-fluorophenyl)-propyl]-2-(2,2-dimethylpropoxy)-3-methylmorpholine-4-carboxylic acid tert-butyl ester Add 2-ethoxyphenylboronic acid (0.065 g, 0.394 mmol) and (1,1'-bis(diphenylphosphino)ferrocene) palladium(II) chloride (0.021 g) to a mixture of 2M sodium carbonate solution (0.262 g, 0.525 mmol) and (2R,3S,5R)-5-[(1S,2S)-1-hydroxy-2-acetylamino-3-(3-bromo-5-fluorophenyl)-propyl]-2-(2,2-dimethylpropoxy)-3-methylmorpholine-4-carboxylic acid tert-butyl ester (0.151 g, 0.262 mmol) in tetrahydrofuran (2.62 mL) in a sealed tube flushed with nitrogen. Heat the tube at 80° C. for 3 days. Add saturated aqueous sodium chloride and extract with ethyl acetate (2×50 mL). Dry over magnesium sulfate and concentrate under reduced pressure. Subject the residue to silica gel chromatography, eluting with hexanes containing 25-50% ethyl acetate to provide the title compound (0.075 g, 46%) as a white foam.
MS(ES): m/z=639.3 [M+23]$^+$

Preparation 412

(2R,3S,5R)-5-[(1S,2S)-1-Hydroxy-2-amino-3-(4-methyl-3,5-difluorophenyl)-propyl]-2-(2,2-dimethylpropoxy)-3-methylmorpholine-4-carboxylic acid tert-butyl ester

(2R,3S,5R)-5-[(1S,2S)-1-benzyloxy-2-dibenzylamino-3-(4-methyl-3,5-difluorophenyl)-propyl]-2-(2,2-dimethylpropoxy)-3-methylmorpholine-4-carboxylic acid tert-butyl ester Add n-butyllithium (252 µL, 0.404 mmol, 1.6 M in hexanes) dropwise over 5 minutes to a solution of (2R,3S,5R)-5-[(1S,2S)-1-benzyloxy-2-dibenzylamino-3-(3,5-difluorophenyl)-propyl]-2-(2,2-dimethylpropoxy)-3-methylmorpholine-4-carboxylic acid tert-butyl ester (0.30 g, 0.404 mmol) in tetrahydrofuran (0.6 mL) at −78° C. Add potassium tert-butoxide (0.404 mL, 1 M in tetrahydrofuran) dropwise over 10 minutes and stir the reaction mixture for an additional 10 minutes. Add iodomethane (25.1 µL, 0.404 mmol) followed by a solution of hexamethylphosphorus triamide (53.7 µL, 0.294 mmol) in tetrahydrofuran (40.4 µL). Stir reaction mixture at −78° C. for 1 hour. Remove cooling bath and stir for 20 minutes. Add water (20 mL) and extract with ethyl acetate (2×50 mL). Wash combined organic layers with water (3×20 mL), dry over magnesium sulfate, and concentrate under reduced pressure. Subject residue to silica gel chromatography, eluting with hexanes containing 0-10% diethyl ether, to provide the desired compound 0.169 g (55.3%) as a white foam.

MS(ES): m/z=757.3 [M+1]$^+$.

Hydrogenation

Add 20% palladium on carbon (0.085 g) to a solution of (2R,3S,5R)-5-[(1S,2S)-1-benzyloxy-2-dibenzylamino-3-(4-methyl-3,5-difluorophenyl)-propyl]-2-(2,2-dimethylpropoxy)-3-methylmorpholine-4-carboxylic acid tert-butyl ester (0.169 g, 0.223 mmol) in ethyl acetate (3.00 mL) and hydrogenate at balloon pressure for 16 hours. Add additional 20% palladium on carbon (170 mg) and continue hydrogenation for 8 hours. Filter reaction mixture over a pad of filtering agent and wash pad with ethyl acetate. Concentrate filtrate to provide the title compound (0.109 g) as an off-white foam.

MS(ES): m/z=487.3 [M+1]$^+$

Preparation 413

(2R,3S,5R)-5-[(1S,2S)-1-Hydroxy-2-amino-3-(4-(3-methylbutyl)-3,5-difluorophenyl)-propyl]-2-(2,2-dimethylpropoxy)-3-methylmorpholine-4-carboxylic acid tert-butyl ester Using 3-methylbutyl iodide, the title compound may be prepared essentially as described in Preparation 412.

MS(ES): m/z=543.3 [M+1]$^+$

Replacing dichloromethane with tetrahydrofuran, the compounds of Preparations 414-416 may be prepared essentially as described in Preparation 219.

Preparation 418

(2R,3S,5R)-5-[(1S,2S)-1-Hydroxy-2-amino-3-(3-trifluoromethoxyphenyl)-propyl]-2-(2,2-di(fluoromethyl)propoxy)-3-methylmorpholine (R)-4-[(1R,2S)-1-Hydroxy-2-nitro-3-(3-trifluoromethoxy-phenyl)-propyl]-2,2-dimethyl-oxazolidine-3-carboxylic acid tert-butyl ester Beginning with 2-(3-trifluoromethoxyphenyl)-1-nitroethane the desired compound may be prepared essentially as described in Preparation 168.

MS(ES): m/z=463.3 [M$^+$]

(R)-4-[(1S,2S)-2-Amino-1-hydroxy-3-(3-trifluoromethoxy-phenyl)-propyl]-2,2-dimethyloxazolidine-3-carboxylic acid tert-butyl ester Add zinc (8.46 g, 129.4 mmoles) to (R)-4-[(1R,2S)-1-Hydroxy-2-nitro-3-(3-trifluoromethoxy-phenyl)-propyl]-2,2-dimethyl-oxazolidine-3-carboxylic acid tert-butyl ester (6.01 g, 12.9 mmoles) in acetic acid (75 mL) and stir at room temperature for 10 minutes. Filter and wash the solids with water. Extract with ethyl acetate. Wash organic layer with 0.1 N sodium hydroxide and saturated aqueous sodium chloride. Dry over sodium sulfate, filter and concentrate to give 5.18 g (92% yield) of the title compound as a white solid.

MS(ES+): m/z=435.0 [M$^+$]

(2R,3R,4S)-2-Amino-3-benzyloxy-4-dibenzylamino-5-(3-trifluoromethoxy-phenyl)-pentan-1-ol Beginning with (R)-4-[(1S,2S)-2-Amino-1-hydroxy-3-(3-trifluoromethoxyphenyl)-propyl]-2,2-dimethyl-oxazolidine-

| Prep | Compound | MS (ES) |
|---|---|---|
| 414 | (2R,3S,5R)-5-[(1S,2S)-1-Hydroxy-2-(6-methylheptanoylamino)-3-(3,5-difluorophenyl)-propyl]-2-(2,2-dimethylpropoxy)-3-methylmorpholine-4-carboxylic acid tert-butyl ester | 585.5 [M$^+$ + H] |
| 415 | (2R,3S,5R)-5-[(1S,2S)-1-Hydroxy-2-(6-methyl-4,4-difluoroheptanoyl-amino)-3-(3,5-difluorophenyl)-propyl]-2-(2,2-dimethylpropoxy)-3-methylmorpholine-4-carboxylic acid tert-butyl ester | 635.5 [M$^+$ + H] |
| 416 | (2R,3S,5R)-5-[(1S,2S)-1-Hydroxy-2-(6-methyl-4,4-difluoroheptanoyl-amino)-3-(3-butyl-5-fluorophenyl)-propyl]-2-(2,2-dimethylpropoxy)-3-methylmorpholine-4-carboxylic acid tert-butyl ester | 673.6 [M$^+$ + H] |

Preparation 417

(2R,5R)-5-[(1S,2S)-1-Hydroxy-2-amino-3-(3-propoxy-5-fluorophenyl)-propyl]-2-(cyclopropyl-methoxy)-morpholine-4-carboxylic acid tert-butyl ester Beginning with (3S,5R)-5-[(1S,2S)-1-Benzyloxy-2-dibenzylamino-3-(3-benzyloxy-5-fluorophenyl)-propyl]-3-methylmorpholin-2-one, the desired compound may be prepared essentially as described in Preparation 306.

MS(ES): m/z=483.3 [M$^+$]

3-carboxylic acid tert-butyl ester, the desired compound may be prepared essentially as described in Preparation 167.

MS(ES+): m/z=565.3 [M$^+$]

Beginning with (2R,3R,4S)-2-Amino-3-benzyloxy-4-dibenzylamino-5-(3-trifluoromethoxy-phenyl)-pentan-1-ol, the title compound may be prepared essentially as described in Preparation 307 with the exception of protecting the morpholine nitrogen with tert-butoxycarbonyl and replacing 20% palladium hydroxide with 10% palladium hydroxide in the hydrogenolysis step.

MS(ES+): m/z=457.3 [M$^+$]

Preparation 419

(3S,5R)-5-[(1S,2S)-1-benzyloxy-2-dibenzylamino-3-(3-benzyloxy-5-fluorophenyl)-propyl]-morpholin-2-one-4-carboxylic acid tert-butyl ester (R)-4-[(1R,2S)-3-(3-benzyloxy-5-fluorophenyl)-1-benzyloxy-2-dibenzylaminopropyl]-2,2-dimethyloxazolidine-3-carboxylic acid tert-butyl ester Add NaH (12.5 g, 60% mineral oil suspension, 312.5 mmol) in portions to a solution of benzyl alcohol (32 mL, 309.2 mmol) in N-methylpyrrolidinone (1 L). Stir the reaction mixture at r.t. until no gas evolution is detected. Add (R)-4-[(1R,2S)-3-(3,5-difluorophenyl)-1-benzyloxy-2-dibenzylaminopropyl]-2,2-dimethyloxazolidine-3-carboxylic acid tert-butyl ester (130 g) to the mixture and warm it up to 90° C. After 45 min, allow to cool to room temperature and add saturated aqueous ammonium chloride. Dilute with ethyl acetate (2 L) and wash with saturated aqueous sodium chloride (2×1.5 L). Dry the organic layer on MgSO4, filter and concentrate. Subject residue to silical gel chromatography, eluting with 2-4% ethyl acetate in hexanes, to provide 139.45 g (94%) of the desired compound as a white solid.

LCMS: m/z=745 (M+1)

(2R,3S,4S)-2-amino-3-benzyloxy-4-dibenzylamino-5-(3-benzyloxy-2-fluorophenyl)-pentan-1-ol Add concentrated hydrochloric acid (22.7 mL) to a solution of (R)-4-[(1R,2S)-3-(3-benzyloxy-5-fluorophenyl)-1-benzyloxy-2-dibenzylaminopropyl]-2,2-dimethyloxazolidine-3-carboxylic acid tert-butyl ester (25.89 mmol, 19.3 g) in 88 mL methyl tert-butyl ether. Stir at room temperature for 3 hours. Add additional concentrated hydrochloric acid (10 mL) and stir for 1 hour. Add dichloromethane (300 mL) and adjust to pH 12 with NaOH. Separate the two phases and dry the organic phase over magnesium sulfate. Concentrate under reduced pressure and subject the residue to silica gel chromatography, eluting with dichloromethane containing 0-5% 3 M ammonia in methanol, to provide 15 g (96%) of the desired compound.

(3S)-5-[(1S,2S)-1-benzyloxy-2-dibenzylamino-3-(3-benzyloxy-5-fluorophenyl)-propyl]-morpholin-2-one Add phenyl bromoacetate (4.94 g, 23 mmol) to a solution of (2R,3S,4S)-2-amino-3-benzyloxy-4-dibenzylamino-5-(3-benzyloxy-2-fluorophenyl)-pentan-1-ol (12.7 g, 21 mmol) and diisopropylethylamine (11 mL, 63 mmol) in dimethylformamide (210 mL). Stir at room temperature for 20 hours. Dilute the reaction mixture with ethyl acetate and saturated aqueous sodium chloride. Extract the aqueous phase well with ethyl acetate. Wash the combined organic phases well with saturated aqueous sodium chloride, dry over magnesium sulfate, and concentrate under reduced pressure. Subject the residue to silica gel chromatography, eluting with hexane containing 0-40% ethyl acetate to provide 12 g (89%) of the desired compound.

Morpholine Nitrogen Protection

Add BOC$_2$O (6.9 g, 31.64 mmol) to a solution of the morpholin-2-one (12 g, 18.6 mmol) in dichloromethane (180 mL) and diisopropylethylamine (8.1 mL, 46.5 mmol). Stir at room temperature for 6 hours. Add dichloromethane and wash with 5% citric acid solution. Wash the organic phase with saturated aqueous sodium bicarbonate, water, and saturated aqueous sodium chloride. Dry over magnesium sulfate and concentrate under reduced pressure. Subject residue to silica gel chromatography, eluting with 9:1 hexane:methyl tert-butyl ether to provide 10.4 g (75%) of the title compound.

Preparation 420

(1S,2S)-2-Amino-3-(3-cyclopropylmethoxy-phenyl)-1-[(3R,5S,6R)-6-(2,2-dimethylpropoxy)-5-methyl-morpholin-3-yl]-propan-1-ol trifluoroacetate (2R,3S,5R)-5-[(1S,2S)-2-Acetylamino-1-hydroxy-3-(3-hydroxy-phenyl)-propyl]-2-(2,2-dimethyl-propoxy)-3-meth 1-morpholine-4-carboxylic acid benzyl ester trifluoroacetate Add trifluoroacetic acid (3 mL) to (2R,3S,5R)-5-[(1S,2S)-2-acetylamino-1-hydroxy-3-(3-hydroxy-phenyl)-propyl]-2-(2,2-dimethyl-propoxy)-3-methyl-morpholine-4-carboxylic acid tert-butyl ester (84 mg, 0.17 mmol). Stir 40 minutes and evaporate to give N-[(1S,2S)-2-[(3R,5S,6R)-6-(2,2-dimethyl-propoxy)-5-methyl-morpholin-3-yl]-2-hydroxy-1-(3-hydroxy-benzyl)-ethyl]-acetamide trifluoroacetate (115 mg). Add diisopropylethyl-amine (0.074 mL, 0.425 mmol) dropwise to an ice cold solution of N-[(1S,2S)-2-[(3R,5S,6R)-6-(2,2-dimethyl-propoxy)-5-methyl-morpholin-3-yl]-2-hydroxy-1-(3-hydroxy-benzyl)-ethyl]-acetamide (115 mg) and benzyl chloroformate (0.029 mL, 0.20 mmol) in tetrahydrofuran (4 mL). Stir 30 minutes and add an additional portion of diisopropylethylamine (0.074 mL) and benzyl chloroformate (0.025 mL). Stir 50 minutes and warm to ambient temperature, stir 10 minutes and dilute with saturated aqueous sodium chloride followed by ethyl acetate and 1N aqueous hydrochloric acid. Separate layers and wash organic phase with saturated aqueous sodium chloride, dry with magnesium sulfate. Purify on silica gel with dichloromethane/ethyl acetate mixtures to give the desired compound (69 mg) as a white foam. MS(ESI): m/z=529 [M+H]$^+$.

N-{(S)-2-(3-Cyclopropylmethoxy-phenyl)-1-[(1S,5S,6R,8aR)-6-(2,2-dimethyl-propoxy)-5-methyl-3-oxo-tetrahydro-oxazolo[4,3-c][1,4]oxazin-1-yl]-ethyl}-acetamide Heat a mixture of (2R,3S,5R)-5-[(1S,2S)-2-Acetylamino-1-hydroxy-3-(3-hydroxy-phenyl)-propyl]-2-(2,2-dimethyl-propoxy)-3-methyl-morpholine-4-carboxylic acid benzyl ester (69 mg, 0.13 mmol), cyclopropylmethyl bromide (0.019 ml, 0.195 mmol), cesium carbonate (127 mg, 0.39 mmol) and N,N-dimethylformamide (2 mL) to 60° C. for 18 hours. Cool and dilute with ethyl acetate and wash with saturated sodium chloride, dry with magnesium sulfate and purify on silica gel with dichloromethane/ethyl acetate mixtures to give the desired compound (53 mg). MS(ESI): m/z=475 [M+H]$^+$.

Deprotection

Heat a solution of N-{(S)-2-(3-cyclopropylmethoxy-phenyl)-1-[(1S,5S,6R,8aR)-6-(2,2-dimethyl-propoxy)-5-methyl-3-oxo-tetrahydro-oxazolo[4,3-c][1,4]oxazin-1-yl]-ethyl}-acetamide (50 mg, 0.107 mmol) in 1:4:4 tetrahydrofuran/methanol/4N sodium hydroxide (2 mL) to 100° C. for 18 hours, then cool to ambient temperature. Partition with water and ethyl acetate, wash organic layer with saturated sodium bicarbonate, saturated sodium chloride, dry with magnesium chloride and purify on C-18 reversed phase silica gel to provide the title compound (9 mg). MS(ESI): m/z=407 [M+H]$^+$.

Preparation 421

(2S,3S,5R)-5-[(1S,2S)-2-Acetylamino-3-(3-fluoro-5-propoxy-phenyl)-1-hydroxy-propyl]-3-methyl-2-(2,2,2-trifluoro-ethoxy)-morpholine-4-carboxylic acid tert-butyl ester (2S,3S,5R)-5-[(1S,2S)-1-Benzyloxy-3-(3-benzyloxy-5-fluoro-phenyl)-2-dibenzylaminopropyl]-3-methyl-2-(2,2,2-trifluoro-ethoxy)-morpholine-4-carboxylic acid tert-butyl ester Add diisopropyl azodicarboxylate (0.675 mL, 3.43 mmol) dropwise to an ice cold solution of (3S,5R)-5-[(1R,2S)-1-benzyloxy-3-(3-benzyloxy-5-fluoro-phenyl)-2-dibenzylamino-propyl]-3-methyl-morpholin-2-ol (1.30 g, 1.71 mmol), 2,2,2-trifluoroethanol (1.0 mL, 13.7 mmol) and triphenylphosphine (900 mg, 3.43 mmol) in deoxygenated toluene (8 mL). Stir in ice bath for 3 hours and evaporate. Purify on silica gel with hexane/ethyl acetate mixtures to give the desired compound (1.21 g) as a white foam. MS(ESI): m/z=843 [M+H]$^+$.

(2S,3S,5R)-5-[(1S,2S)-2-Amino-3-(3-fluoro-5-hydroxy-phenyl)-1-hydroxy-propyl]-3-methyl-2-(2,2,2-trifluoro-ethoxy)-morpholine-4-carboxylic acid tert-butyl ester Add 20% palladium hydroxide on carbon (200 mg) to a solution of (2S,3S,5R)-5-[(1S,2S)-1-benzyloxy-3-(3-benzyloxy-5-fluoro-phenyl)-2-dibenzylamino-propyl]-3-methyl-2-(2,2,2-trifluoro-ethoxy)-morpholine-4-carboxylic acid tert-butyl ester (116 mg, 0.138 mmol) in tert-butanol (10 mL). Heat to 45° C. and hydrogenate at 50 psi hydrogen gas for 18 hours. Filter and evaporate to give the desired compound (77 mg). MS(ESI): m/z=483 [M+H]$^+$.

(2S,3S,5R)-5-[(1S,2S)-2-Acetylamino-3-(3-fluoro-5-hydroxy-phenyl)-1-hydroxypropyl]-3-methyl-2-(2,2,2-trifluoro-ethoxy)-morpholine-4-carboxylic acid tert-butyl ester Add acetic anhydride (0.142 mL, 1.51 mmol) to an ice cold solution of (2S,3S,5R)-5-[(1S,2S)-2-Amino-3-(3-fluoro-5-hydroxy-phenyl)-1-hydroxy-propyl]-3-methyl-2-(2,2,2-trifluoro-ethoxy)-morpholine-4-carboxylic acid tert-butyl ester (823 mg, 1.43 mmol) in dichloromethane (9 mL). Stir for 50 minutes and add diisopropylethylamine (0.125 mL, 0.717 mmol) and stir for 2 hours. Quench with aqueous 1N hydrochloric acid, wash with saturated aqueous sodium bicarbonate, dry with magnesium sulfate and purify on silica gel with dichloromethane/ethyl acetate mixtures to give the desired compound (493 mg). MS(ESI): m/z=525 [M+H]$^+$.

Ether Formation

Heat a mixture of (2S,3S,5R)-5-[(1S,2S)-2-Acetylamino-3-(3-fluoro-5-hydroxyphenyl)-1-hydroxy-propyl]-3-methyl-2-(2,2,2-trifluoro-ethoxy)-morpholine-4-carboxylic acid tert-butyl ester (169 mg, 322 mmol), 1-bromopropane (0.044 mL, 0.48 mmol) and cesium carbonate (315 mg, 0.966 mmol) in N,N-dimethylformamide (2 mL) to 60° C. for 5 hours then cool to ambient temperature. Dilute with ethyl acetate and wash with saturated sodium chloride, dry with magnesium sulfate and purify on silica gel with dichloromethane/ethyl acetate mixtures to give the title compound (153 mg). MS(ESI): m/z=567 [M+H]$^+$.

The compounds of Preparations 422-423 may be prepared essentially as described in Preparation 421.

| Prep | Compound | MS (ES) |
| --- | --- | --- |
| 422 | (2S,3S,5R)-5-[(1S,2S)-2-Acetylamino-3-(3-fluoro-5-isobutoxy-phenyl)-1-hydroxy-propyl]-3-methyl-2-(2,2,2-trifluoro-ethoxy)-morpholine-4-carboxylic acid tert-butyl ester | 581 [M + H]$^+$ |
| 423 | (2S,3S,5R)-5-{(1S,2S)-2-Acetylamino-3-[3-(2,2-difluoro-ethoxy)-5-fluoro-phenyl]-1-hydroxy-propyl}-3-methyl-2-(2,2,2-trifluoro-ethoxy)-morpholine-4-carboxylic acid tert-butyl ester | 589 [M + H]$^+$ |

Preparation 424

(2R,3S,5R)-5-[(1S,2S)-3-(3,5-Difluoro-phenyl)-2-((E)-2,5-dimethyl-hex-2-enoylamino)-1-hydroxy-propyl]-2-(2,2-dimethyl-propoxy)-morpholine-4-carboxylic acid tert-butyl ester Suspend sodium hydride (60% dispersion) (0.78 g, 19.61 mmol) in tetrahydrofuran (22 mL) and add diethyl phosphite (0.80 g, 6.54 mmol). Add 2-bromo-propionic acid (1.00 g, 6.54 mmol) slowly and wait for gas evolution to cease then add 3-methyl-butyraldehyde (0.56 g, 6.54 mmol) and stir at ambient temperature overnight. Quench with ethanol and pour into water. Acidify with 1M HCl and extract with ethyl acetate. Wash with saturated sodium chloride solution, dry over magnesium sulfate and concentrate under reduced pressure. Combine the crude acid (0.01 g, 0.09 mmol) with 1-(3-dimethylaminopropyl)-3-ethylcarbodiimide hydrochloride (EDC) (0.02 g, 0.09 mmol) and 1-hydroxybenzotriazole (HOBt) (0.01 g, 0.09 mmol) in methylene chloride (1 mL) and stir at room temp. under nitrogen for 30 minutes. Add (2R,3S,5R)-5-[(1S,2S)-2-amino-3-(3,5-difluoro-phenyl)-1-hydroxy-propyl]-2-(2,2-dimethyl-propoxy)-morpholine-4-carboxylic acid tert-butyl ester (0.04 g, 0.09 mmol) and N,N,-diisopropylamine (0.02 g, 0.17 mmol) and continue stirring until starting material is consumed. Dilute with ethyl acetate, wash with saturated potassium carbonate solution and sat'd sodium chloride solution, dry over magnesium sulfate and concentrate in vacuo. Purify by silica gel chromatography eluting with 0% to 10% to 30% ethyl acetate/hexanes. 0.044 g, 66.9% yield. MS(ES): m/z=583.3 [M+H]

Preparation 425

(2R,5R)-5-[(1S,2S)-3-(3,5-Difluoro-phenyl)-1-hydroxy-2-((E)-6,6,6-trifluoro-2-methyl-hex-2-enoylamino)-propyl]-2-(2,2-dimethyl-propoxy)-morpholine-4-carboxylic acid tert-butyl ester Using 4,4,4-trifluorobutyraldehyde, the title compound may be prepared essentially as described in Preparation 424.

MS(ES): m/z=621.3 [M−H]

Preparation 426

1,1-Dimethoxy-pentan-2-one

2-Ethyl-4,4-dimethoxy-3-oxo-butyric acid methyl ester

Dissolve methyl dimethoxyacetate (11.56 g, 86.16 mmol) in toluene (783 mL) then add sodium hydride (6.90 g, 172.33 mmol) and warm to 70-80° C. Add methyl butyrate (8.00 g, 78.33 mmol) dropwise and continue heating to 90 degrees. Cool to ambient temperature and dump into 0.5 M HCl. Wash with ethyl acetate (3×) then wash organics with saturated sodium chloride solution, dry over magnesium sulfate and concentrate in vacuo. Purify by distillation. Product boils at 185° C. 11.5 g, 72% yield.

$^1$H NMR (CDCl$_3$) δ 0.90 (3H, t), 1.82-1.86 (2H, m), 3.37 (6H, s), 3.66 (1H, t), 3.68 (3H, s), 4.58 (1H, s).

Decarboxylation

Dissolve 2-Ethyl-4,4-dimethoxy-3-oxo-butyric acid methyl ester (5.00 g, 24.49 mmol) in methanol (8 mL) and add potassium hydroxide solution (31.83 mmol) then heat at reflux for 1 hr. Cool to ambient temperature and pour into 40 mL water. Wash with diethyl ether, separate organics, dry over magnesium sulfate and concentrate under a stream of nitrogen. 2.5 g, 68% yield.

$^1$H NMR (CDCl$_3$) δ 0.91 (3H, t), 1.57-1.63 (2H, m), 2.52 (2H, t), 3.40 (6H, s), 4.44 (1H, s).

Preparation 427

3-Fluoro-2,2-dimethyl-propan-1-ol

Add a solution of 3-fluoro-2,2-dimethyl-propionyl fluoride (7.8 g, 63.9 mmol) in diethyl ether (10 mL) to a slurry of lithium aluminum hydride (2.4 g) in diethyl ether (100 mL) at 0° C. Warm to room temperature and stir for 1 hour. Add water (2.5 mL), 5M NaOH (1.9 mL) and more water (5 mL) with vigorous stirring. Filter and concentrate filtrate to afford a low melting solid. Dissolve in a minimum of pentane, and precipitate by cooling to −78° C. Filter cold, and wash once with cold pentane. (3 g, 44%). $^1$H-NMR (400 MHz, CDCl$_3$) δ 4.22 (d, J$_{H-F}$=48.2 Hz, 2H), 3.46 (d, J=1.0 Hz, 2H), 0.93 (d, J=1.8 Hz, 6H).

The compounds of Preparations 428-429 may be prepared essentially as described in Preparation 427 except that the reductions are performed at −78° C.

Preparation 428

3-Fluoro-2-fluoromethyl-2-methyl-propan-1-ol $^1$HNMR (400 MHz, CDCl$_3$) δ 4.40 (ddd, J=47.3, 1.3, 1.3 Hz, 4H), 3.61 (t, J=1.3 Hz, 2H), 0.98 (t, J=1.9 Hz, 3H).

Preparation 429

3-Fluoro-2,2-bis-fluoromethyl-propan-1-ol $^1$H-NMR (400 MHz, CDCl$_3$) δ 4.54 (ddd, J=47.0, 1.3, 1.3 Hz, 6H), 3.77 (m, 2H).

Preparation 430

(2R,5R)-5-[(1S,2S)-2-acetylamino-3-(3-fluoro-5-propoxy-phenyl)-1-hydroxy-propyl]-2-(1-fluoromethyl-cyclopentylmethoxy)-morpholine-4-carboxylic acid tert-butyl ester

(2R,5R)-5-[(1S,2S)-1-Benzyloxy-2-dibenzylamino-3-(3,5-difluoro-phenyl)-propyl]-2-(1-fluoromethyl-cyclopentylmethoxy)-morpholine-4-carboxylic acid tert-butyl ester Beginning with (R)-5-[1-benzyloxy-2-dibenzylamino-3-(3,5-difluorophenyl)-propyl]-2-hydroxymorpholine-4-carboxylic acid tert-butyl ester and trifluoromethane-sulfonic acid 1-fluoromethyl-cyclopentylmethyl ester, the desired compound may be prepared essentially as described in Preparation 306.

MS: m/z=773 [M+H]$^+$

(2R,5R)-5-[(1S,2S)-1-benzyloxy-2-dibenzylamino-3-(3-fluoro-5-propoxy-phenyl)-propyl]-2-(1-fluoromethyl-cyclopentylmethoxy)-morpholine-4-carboxylic acid tert-butyl ester Beginning with (2R,5R)-5-[(1S,2S)-1-Benzyloxy-2-dibenzylamino-3-(3,5-difluoro-phenyl)-propyl]-2-(1-fluoromethyl-cyclopentylmethoxy)-morpholine-4-carboxylic acid tert-butyl ester, the desired compound may be prepared essentially as described in Preparation 382.

MS: m/z=814 [M+H]$^+$

(2R,5R)-5-[(1S,2S)-2-amino-3-(3-fluoro-5-propoxy-phenyl-1-hydroxy-propyl]-2-(1-fluoromethyl-cyclopentylmethoxy)-morpholine-4-carboxylic acid tert-butyl ester, trifluoromethanesulfonic acid salt Beginning with (2R,5R)-5-[(1S,2S)-1-benzyloxy-2-dibenzylamino-3-(3-fluoro-5-propoxy-phenyl)-propyl]-2-(1-fluoromethyl-cyclopentylmethoxy)-morpholine-4-carboxylic acid tert-butyl ester, the desired compound may be prepared essentially as described in Preparation 306.

MS: m/z=543 [M+H]$^+$

Acylation

Add acetic anhydride (0.13 mmoles; 12 μL) to a solution of (2R,5R)-5-[(1S,2S)-2-amino-3-(3-fluoro-5-propoxy-phenyl)-1-hydroxy-propyl]-2-(1-fluoromethyl-cyclopentylmethoxy)-morpholine-4-carboxylic acid tert-butyl ester, trifluorosulfonic acid salt (0.12 mmoles; 0.08 g) and triethylamine (0.36 mmoles; 50 μL) in 1.5 mL dichloromethane at room temperature and stir for 4 h. Concentrate under reduced pressure and subject residue to silica gel chromatography, eluting with 2:1 to 1:2 hexane/ethyl acetate gradient to provide the title compound as white solid (50 mg, 70%).

MS: m/z=607 [M+Na]$^+$

The compounds of Preparations 431-433 may be prepared essentially as described in Preparation 430.

| Prep | Compound | MS (ES) |
|---|---|---|
| 431 | (2R,5R)-5-[(1S,2S)-2-Acetylamino-3-(3-fluoro-5-propoxy-phenyl)-1-hydroxy-propyl]-2-(1-difluoromethyl-cyclopentylmethoxy)-morpholine-4-carboxylic acid tert-butyl ester | 647 [M + HCO$_2^-$] |
| 432 | (2R,3S,5R)-5-[(1S,2S)-[2-Acetylamino-3-(3-fluoro-5-propoxy-phenyl)-1-hydroxy-propyl]-2-(4,4-difluoro-cyclohexylmethoxy)-3-methyl-morpholine-4-carboxylic acid tert-butyl ester | 617 [M + H] |
| 433 | (2R,5R)-5-[(1S,2S)-[2-Acetylamino-3-(3-fluoro-5-propoxy-phenyl)-1-hydroxy-propyl]-2-(4,4,4-trifluoro-2,2-dimethyl-butoxy)-morpholine-4-carboxylic acid tert-butyl ester | 553 [M + H − t-Bu] |

Preparation 434

(2R,5R)-5-[(1S,2S)-2-acetylamino-3-(3-fluoro-5-isobutoxy-phenyl)-1-hydroxy-propyl]-2-(2-fluoro-1-fluoromethyl-1-methyl-ethoxy)-morpholine-4-carboxylic acid tert-butyl ester (2R,5R)-5-[(1S,2S)-2-amino-3-(3-fluoro-5-hydroxy-phenyl)-1-hydroxy-propyl]-2-(2-fluoro-1-fluoromethyl-1-methyl-ethoxy)-morpholine-4-carboxylic acid tert-butyl ester Beginning with (5R)-5-[(1S,2S)-1-Benzyloxy-3-(3-benzyloxy-5-fluoro-phenyl)-2-dibenzylamino-propyl]-2-hydroxy-morpholine-4-carboxylic acid tert-butyl ester and trifluoromethanesulfonic acid 2-fluoro-1-fluoromethyl-1-methyl-ethyl ester, the desired compound may be prepared essentially as described in Preparation 306.

MS: m/z=493 [M+H]$^+$ (2R,5R)-5-[(1S,2S)-2-acetylamino-3-(3-fluoro-5-hydroxy-phenyl)-1-hydroxy-propyl]-2-(2-fluoro-1-fluoromethyl-1-methyl-ethoxy)-morpholine-4-carboxylic acid tert-butyl ester Add acetic anhydride (2.13 mmoles; 201.52 μL) to a solution of (2R,5R)-5-[(1S,2S)-2-amino-3-(3-fluoro-5-hydroxy-phenyl)-1-hydroxy-propyl]-2-(2-fluoro-1-fluoromethyl-1-methyl-ethoxy)-morpholine-4-carboxylic acid tert-butyl ester (2.03 mmoles; 1.00 g) and triethylamine (2.23 mmoles; 311.29 μL) in 10 mL dichloromethane at 0° C. (ice bath) and stir the mixture at 0° C. for 1 h. Concentrate under reduced pressure and subject residue to silica gel chromatography eluting with 40:60 to 0:100 hexane/ethyl acetate gradient to give the desired compound as white solid (950.00 mg, 87.53%).

MS: m/z=557 [M+H]$^+$

Ether Formation

Beginning with (2R,5R)-5-[(1S,2S)-2-acetylamino-3-(3-fluoro-5-hydroxyphenyl)-1-hydroxy-propyl]-2-(2-fluoro-1-fluoromethyl-1-methyl-ethoxy)-morpholine-4-carboxylic acid tert-butyl ester and isobutyl iodide, the title compound may be prepared essentially as described in Preparation 421.

MS: m/z=613 [M+Na]$^+$

The compounds of Preparations 435-438 may be prepared essentially as described in Preparation 434.

| Prep | Compound | MS (ES) |
|---|---|---|
| 435 | (2R,5R)-5-[(1S,2S)-2-acetylamino-3-(3-fluoro-5-isobutoxy-phenyl)-1-hydroxypropyl]-2-(3-fluoromethyl-2-methylpropoxy)-morpholine-4-carboxylic acid tert-butyl ester | 613 [M + Na] |
| 436 | (2R,5R)-5-[(1S,2S)-2-acetylamino-3-(3-fluoro-5-isopropoxy-phenyl)-1-hydroxypropyl]-2-(3-fluoromethyl-2-methylpropoxy)-morpholine-4-carboxylic acid tert-butyl ester | 599 [M + Na] |
| 437 | (2R,5R)-5-[(1S,2S)-2-acetylamino-3-(3-fluoro-5-propoxy-phenyl)-1-hydroxypropyl]-2-(3-fluoromethyl-2-methylpropoxy)-morpholine-4-carboxylic acid tert-butyl ester | 599 [M + Na] |
| 438 | (2R,5R)-5-[(1S,2S)-2-acetylamino-3-(3-fluoro-5-isobutoxy-phenyl)-1-hydroxypropyl]-2-(3,3-difluoromethyl-2,2-dimethylpropoxy)-morpholine-4-carboxylic acid tert-butyl ester | 613 [M + Na] |

Preparation 439

N-{(1S,2S)-2-[(3R,5S,6R)-6-(3-Fluoro-2-fluoromethyl-2-methyl-propoxy)-5-methyl-morpholin-3-yl]-1-(3-fluoro-5-hydroxy-benzyl)-2-hydroxy-ethyl}-acetamide Beginning with 3-{(2S,3S)-2-Amino-3-[(3R,5S,6R)-(6-(3-fluoro-2-fluoromethyl-2-methyl-propoxy)-5-methyl-morpholin-3-yl]-3-hydroxy-propyl}-5-fluoro-phenol, the title compound may be prepared by reaction with acetic anhydride as described in Preparation 434.

MS(ES): m/z=493 [M+HCO2$^-$]

Preparation 440

(2R,3S,5R)-5-{(1S,2S)-2-Amino-3-[3-(3-methylbutyl)-5-fluorophenyl]-1-hydroxy-propyl}-2-(2,2-di-(fluoromethyl)-propoxy)-3-methylmorpholine (2R,3S,5R)-5-{(1S,2S)-2-Dibenzylamino-3-[3-(3-methylbutyl)-5-fluorophenyl]-1-benzyloxy-propyl}-2-(2,2-di-(fluoromethyl)-propoxy)-3-methylmorpholine Beginning with (2R,3S,5R)-5-{(1S,2S)-2-Dibenzylamino-3-[3-bromo-5-fluorophenyl]-1-benzyloxy-propyl}-2-(2,2-di-(fluoromethyl)-propoxy)-3-methylmorpholine, prepared essentially as described in Preparation 306, the desired compound may be prepared essentially as described in Preparation 409.

MS(ES): m/z=731.3 [M+1]$^+$

Hydrogenolysis

Beginning with (2R,3S,5R)-5-{(1S,2S)-2-Dibenzylamino-3-[3-(3-methylbutyl)-5-fluorophenyl]-1-benzyloxy-propyl}-2-(2,2-di-(fluoromethyl)-propoxy)-3-methylmorpholine, the title compound may be prepared essentially as described in Preparation 421.

MS(ES): m/z=461.2 [M+1]$^+$

Preparation 441

(2R,3S,5R)-5-{(1S,2S)-2-Amino-3-[3-(3-methylbutyl)-phenyl]-1-hydroxy-propyl}-2-(2,2-di-(fluoromethyl)-propoxy)-3-methylmorpholine Beginning with (2R,3S,5R)-5-{(1S,2S)-2-Dibenzylamino-3-[3-bromo-phenyl]-1-benzyloxy-propyl}-2-(2,2-di-(fluoromethyl)-propoxy)-3-methylmorpholine, prepared essentially as described in Preparation 306, the title compound may be prepared essentially as described in Preparation 440.

MS(ES): m/z=443.2 [M+1]$^+$

Beginning with nitromethane and appropriately substituted benzaldehydes and formylmorpholines, the following compounds may be prepared essentially as described in Preparation 188.

| Prep | Compound | MS (ES) [M + Na] |
|---|---|---|
| 442 | (2R,5R)-5-[(1S,2S)-2-Acetylamino-1-hydroxy-3-(4-fluorophenyl)-propyl]-2-(2,2-dimethylpropoxy)-morpholine-4-carboxylic acid tert-butyl ester | |
| 443 | (2R,5R)-5-[(1S,2S)-2-Acetylamino-1-hydroxy-3-(3-(trifluoromethyl-thio)phenyl)-propyl]-2-(2,2-dimethylpropoxy)-morpholine-4-carboxylic acid tert-butyl ester | |
| 444 | (2R,5R)-5-[(1S,2S)-2-Acetylamino-1-hydroxy-3-(3-fluorophenyl)-propyl]-2-(2,2-dimethylpropoxy)-morpholine-4-carboxylic acid tert-butyl ester | |
| 445 | (2R,5R)-5-[(1S,2S)-2-Acetylamino-1-hydroxy-3-(2,4-difluorophenyl)-propyl]-2-(2,2-dimethylpropoxy)-morpholine-4-carboxylic acid tert-butyl ester | |
| 446 | (2R,5R)-5-[(1S,2S)-2-Acetylamino-1-hydroxy-3-(3-(trifluoromethyl)-phenyl)-propyl]-2-(2,2-dimethylpropoxy)-morpholine-4-carboxylic acid tert-butyl ester | |

The following compounds may be prepared essentially as described in Preparation 46.

| Prep | Compound | MS (ES) |
|---|---|---|
| 447 | (2R,5R)-5-[(1S,2S)-2-Acetylamino-1-benzyloxy-3-(3,5-difluoro-phenyl)-propyl]-2-(4-methyl-tetrahydro-pyran-4-ylmethoxy)-morpholine-4-carboxylic acid tert-butyl ester | 633.56 |
| 448 | (2R,5R)-5-[(1S,2S)-2-Acetylamino-1-benzyloxy-3-(3,5-difluoro-phenyl)-propyl]-2-(bicyclo[2.2.1]hept-1-ylmethoxy)-morpholine-4-carboxylic acid tert-butyl ester | 629.47 |
| 449 | (2R,5R)-5-[(1S,2S)-2-Acetylamino-1-benzyloxy-3-(3,5-difluoro-phenyl)-propyl]-2-(1-methyl-cyclopentylmethoxy)-morpholine-4-carboxylic acid tert-butyl ester | 617.46 |
| 450 | (2R,5R)-5-[(1S,2S)-2-Acetylamino-1-benzyloxy-3-(3,5-difluoro-phenyl)-propyl]-2-(3,3,3-trifluoro-2-methyl-2-trifluoromethyl-propoxy)-morpholine-4-carboxylic acid tert-butyl ester | 699.46 |
| 451 | (2R,5R)-5-[(1S,2S)-2-Acetylamino-1-benzyloxy-3-(3,5-difluoro-phenyl)-propyl]-2-(2,2-dimethyl-butoxy)-morpholine-4-carboxylic acid tert-butyl ester | 605.56 |
| 452 | (2R,5R)-5-[(1S,2S)-2-Acetylamino-1-benzyloxy-3-(3,5-difluoro-phenyl)-propyl]-2-(2,2-dimethyl-pentyloxy)-morpholine-4-carboxylic acid tert-butyl ester | 619.61 |
| 453 | (2R,5R)-5-[(1S,2S)-2-Acetylamino-1-benzyloxy-3-(3,5-difluoro-phenyl)-propyl]-2-(1-phenyl-cyclopentylmethoxy)-morpholine-4-carboxylic acid tert-butyl ester | 679.61 |

| Prep | Compound | MS (ES) |
|---|---|---|
| 454 | (2R,5R)-5-[(1S,2S)-2-Acetylamino-1-benzyloxy-3-(3,5-difluoro-phenyl)-propyl]-2-(2,2,4-trimethyl-pentyloxy)-morpholine-4-carboxylic acid tert-butyl ester | 633.52 |
| 455 | (2R,5R)-5-[(1S,2S)-2-Acetylamino-1-benzyloxy-3-(3,5-difluoro-phenyl)-propyl]-2-(1-methyl-cyclopentylmethoxy)-morpholine-4-carboxylic acid tert-butyl ester | 617.43 |

Preparation 456

N-{(1S,2S)-2-[2-(3R,5S,6R)-5-Ethyl-6-(3-fluoro-2-fluoromethyl-2-methyl-propoxy)-morpholin-3-yl]-1-(3-fluoro-5-hydroxy-benzyl)-2-hydroxy-ethyl]-acetamide Beginning with (3S,5R)-5-[(1S,2S)-1-benzyloxy-2-dibenzylamino-3-(3,5-difluorophenyl)-propyl]-3-ethyl-2-oxo-morpholine-4-carboxylic acid tert-butyl ester, the title compound may be prepared essentially as described in Preparation 439.
MS(ES): m/z=463 (M+H)

EXAMPLE 1

N-[(1S,2S)-1-(3,5-Difluorobenzyl)-2-((R)-6-ethoxy-morpholin-3-yl)-2-hydroxyethyl]-acetamide trifluoroacetate (2S,5R)-5-[(1S,2S)-2-Acetylamino-3-(3,5-difluorophenyl)-1-hydroxypropyl]-2-ethoxymorpholine-4-carboxylic acid tert-butyl ester Add triethylamine (0.030 g, 0.30 mmol) and acetic anhydride (0.024 g, 0.23 mmol) to R)-5-[(1S,2S)-2-amino-3-(3,5-difluorophenyl)-1-hydroxypropyl]-2-ethoxymorpholine-4-carboxylic acid tert-butyl ester (0.095 g, 0.228 mmol) in tetrahydrofuran (4 mL) at room temperature. Stir 4 hours and dilute with ethyl acetate. Wash with water and saturated aqueous sodium chloride, dry (magnesium sulfate), concentrate and purify (silica gel chromatography, eluting with 20:80 to 100:0 ethyl acetate:hexanes) to give the desired compound (69 mg, 66%).
MS(ES): m/z=457.2 [M−H]

N-[(1S,2S)-1-(3,5-Difluorobenzyl)-2-((3R,6S)-6-ethoxymorpholin-3-yl)-2-hydroxyethyl]-acetamide trifluoroacetate Dissolve (R)-5-[(1S,2S)-2-acetylamino-3-(3,5-difluorophenyl)-1-hydroxypropyl]-2-ethoxymorpholine-4-carboxylic acid tert-butyl ester (0.060 g, 0.131 mmol) in dichloromethane (5 mL) and add trifluoroacetic acid (0.74 g, 6.5 mmol). Stir at room temperature for 1.5 hours and concentrate to give the title compound (60 mg, 97%).
MS(ES): m/z=359.2 [M+H]

EXAMPLE 2

N-{(1S,2S)-1-(3,5-Difluorobenzyl)-2-[(3R,6R)-6-(3,3-dimethylbutoxy)-morpholin-3-yl]-2-hydroxy-ethyl}-acetamide trifluoroacetate Dissolve (2R,5R)-5-[(1S,2S)-2-acetylamino-3-(3,5-difluorophenyl)-1-hydroxypropyl]-2-(3,3-dimethylbutoxy)-morpholine-4-carboxylic acid tert-butyl ester (0.14 g, 0.27 mmol) in trifluoroacetic acid (2 mL) and stir 10 minutes. Concentrate to give the title compound. (0.14 g, 98.8% yield).
MS(ES): 415.3 m/z=[M+H]

The compounds of EXAMPLES 3-43 may be prepared essentially as described in EXAMPLE 2.

| EX | Compound | MS (ES) [M + H] |
|---|---|---|
| 3 | N-{(1S,2S)-1-(3,5-Difluorobenzyl)-2-[(3R,6S)-6-(3,3-dimethylbutoxy)-morpholin-3-yl]-2-hydroxyethyl}-acetamide trifluoroacetate | 415.4 |
| 4 | N-[(1S,2S)-1-(3,5-Difluorobenzyl)-2-hydroxy-2-((3R,6R)-6-isobutoxymorpholin-3-yl)-ethyl]-acetamide trifluoroacetate | 387.3 |
| 5 | N-[(1S,2S)-1-(3,5-Difluorobenzyl)-2-hydroxy-2-((3R,6S)-6-isobutoxy-morpholin-3-yl)-ethyl]-acetamide trifluoroacetate | 387.3 |
| 6 | N-{(1S,2S)-1-(3,5-Difluorobenzyl)-2-hydroxy-2-[(3R,6R)-6-(3-methylbutoxy)-morpholin-3-yl]-ethyl}-acetamide trifluoroacetate | 401.4 |
| 7 | N-{(1S,2S)-1-(3,5-Difluorobenzyl)-2-hydroxy-2-[(3R,6S)-6-(3-methylbutoxy)-morpholin-3-yl]-ethyl}-acetamide trifluoroacetate | 401.3 |
| 8* | N-[(1S,2S)-2-((3R,6R)-6-Cycloheptylmethoxymorpholin-3-yl)-1-(3,5-Difluorobenzyl)-2-hydroxyethyl]-acetamide trifluoroacetate | 441.2 |
| 9* | N-[(1S,2S)-2-((3R,6S)-6-Cycloheptylmethoxymorpholin-3-yl)-1-(3,5-Difluorobenzyl)-2-hydroxyethyl]-acetamide trifluoroacetate | 441.2 |
| 10* | N-[(1S,2S)-2-[(3R,6R)-6-(Adamantan-1-ylmethoxy)-morpholin-3-yl]-1-(3,5-Difluorobenzyl)-2-hydroxyethyl]-acetamide trifluoroacetate | 479.2 |
| 11* | N-[(1S,2S)-2-[(3R,6S)-6-(Adamantan-1-ylmethoxy)-morpholin-3-yl]-1-(3,5-Difluorobenzyl)-2-hydroxyethyl]-acetamide trifluoroacetate | 479.2 |
| 12* | N-[(1S,2S)-2-((3R,6R)-6-Cyclohexylmethoxymorpholin-3-yl)-1-(3,5-Difluorobenzyl)-2-hydroxyethyl]-acetamide trifluoroacetate | 427.2 |

-continued

| EX | Compound | MS (ES) [M + H] |
|---|---|---|
| 13* | N-[(1S,2S)-2-((3R,6S)-6-Cyclohexylmethoxymorpholin-3-yl)-1-(3,5-Difluorobenzyl)-2-hydroxyethyl]-acetamide trifluoroacetate | 427.2 |
| 14 | 5-(R)-[2-(S)-Acetylamino-3-(4-butoxyphenyl)-1-(S)-hydroxypropyl]-2-(R)-(2,2-dimethylpropoxy)-3-(S)-methylmorpholine trifluoroacetate | 451 |
| 15 | 5-(R)-{2-(S)-Acetylamino-1-(S)-hydroxy-3-[4-(3-methylbutoxy)-phenyl]-propyl}-2-(R)-(2,2-dimethylpropoxy)-3-(S)-methylmorpholine trifluoroacetate | 465 |
| 16 | 5-(R)-[2-(S)-Acetylamino-1-(S)-hydroxy-3-(4-propoxyphenyl)-propyl]-2-(R)-(2,2-dimethylpropoxy)-3-(S)-methylmorpholine trifluoroacetate | 437 |
| 17 | 5-(R)-[2-(S)-Acetylamino-1-(S)-hydroxy-3-(4-isobutoxyphenyl)-propyl]-2-(R)-(2,2-dimethylpropoxy)-3-(S)-methylmorpholine trifluoroacetate | 451 |
| 18 | N-{(1S,2S)-1-(3-Chloro-5-fluorobenzyl)-2-[(3R,6R)-6-(2,2-dimethylpropoxy)-morpholin-3-yl]-2-hydroxyethyl}-acetamide trifluoroacetate | 417.3 |
| 19 | N-[(1S,2S)-2-[(3R,6R)-6-(2,2-Dimethylpropoxy)-morpholin-3-yl]-2-hydroxy-1-(2,3,5-trifluorobenzyl)-ethyl]-acetamide trifluoroacetate | 419.2 |
| 20 | N-[(1S,2S)-2-[(3R,6R)-6-(2,2-Dimethylpropoxy)-morpholin-3-yl]-2-hydroxy-1-(3-trifluoromethoxybenzyl)-ethyl]-acetamide | 449.2 |
| 21 | N-[(1S,2S)-2-[(3R,6R)-6-(2-Cyclohexylethoxy)-morpholin-3-yl]-1-(3,5-difluorobenzyl)-2-hydroxyethyl]-acetamide trifluoroacetate | 441.2 |
| 22 | N-[(1S,2S)-2-((3R,6R)-6-Cyclopentylmethoxymorpholin-3-yl)-1-(3,5-difluorobenzyl)-2-hydroxyethyl]-acetamide trifluoroacetate | 413.3 |
| 23 | N-[(1S,2S)-2-((3R,6R)-6-Cyclooctylmethoxymorpholin-3-yl)-1-(3,5-difluorobenzyl)-2-hydroxyethyl]-acetamide trifluoroacetate | 455.3 |
| 24 | N-{1-(3,5-Difluorobenzyl)-2-hydroxy-2-[6-(tetrahydropyran-4-ylmethoxy)-morpholin-3-yl]-ethyl}-acetamide trifluoroacetate | 429.2 |
| 25 | N-{1-(3,5-Difluorobenzyl)-2-hydroxy-2-[6-(4-methylcyclohexyl-methoxy)-morpholin-3-yl]-ethyl}-acetamide trifluoroacetate | 441.2 |
| 26 | N-{1-(3,5-Difluorobenzyl)-2-hydroxy-2-[(6-(1-methylcyclohexyl-methoxy)-morpholin-3-yl]-ethyl}-acetamide trifluoroacetate | 441.2 |
| 27 | N-{(1S,2S)-1-(3,5-Difluorobenzyl)-2-[(3R,5S,6R)-6-(2,2-dimethylpropoxy)-5-ethylmorpholin-3-yl]-2-hydroxyethyl}-acetamide trifluoroacetate | 429 |
| 28 | N-[(1S,2S)-2-[(3R,6R)-6-(2,2-Dimethylpropoxy)-morpholin-3-yl]-2-hydroxy-1-(3-hydroxybenzyl)-ethyl]-acetamide trifluoroacetate | 381.2 |
| 29 | N-{(1S,2S)-1-(3,5-Dimethylbenzyl)-2-[(3R,6R)-6-(2,2-dimethyl-propoxy)-morpholin-3-yl]-2-hydroxyethyl}-acetamide trifluoroacetate | 393.5 |
| 30 | N-{(1S,2S)-1-(3,5-Difluorobenzyl)-2-[(3R,5S,6R)-6-(2,2-dimethyl-butoxy)-5-methylmorpholin-3-yl]-2-hydroxyethyl}-2-methoxyacetamide trifluoroacetate | 459 |
| 31 | N-[(1S,2S)-2-((3R,5S,6R)-6-Cyclohexylmethoxy-5-methylmorpholin-3-yl)-1-(3,5-difluorobenzyl)-2-hydroxyethyl]-3-methoxy-propionamide trifluoroacetate | 485 |
| 32 | N-[(1S,2S)-2-((3R,5S,6R)-6-Cyclohexylmethoxy-5-methylmorpholin-3-yl)-1-(3,5-difluorobenzyl)-2-hydroxyethyl]-2-methoxyacet-amide trifluoroacetate | 471 |
| 33 | Cyclopropanecarboxylic acid [(1S,2S)-2-((3R,5S,6R)-6-cyclohexyl-methoxy-5-methylmorpholin-3-yl)-1-(3,5-difluorobenzyl)-2-hydroxyethyl]-amide trifluoroacetate | 467 |
| 34 | N-[(1S,2S)-2-[(3R,5S,6R)-6-(Bicyclo[2.1.1]hex-5-ylmethoxy)-5-methylmorpholin-3-yl]-1-(3,5-difluorobenzyl)-2-hydroxyethyl]-acetamide-Isomer 1 trifluoroacetate | 439 |
| 35 | N-[(1S,2S)-2-[(3R,5S,6R)-6-(Bicyclo[2.1.1]hex-5-ylmethoxy)-5-methylmorpholin-3-yl]-1-(3,5-difluorobenzyl)-2-hydroxyethyl]-acetamide-Isomer 2 trifluoroacetate | 439 |
| 36 | N-{(1S,2S)-1-(3,5-Difluorobenzyl)-2-[(3R,5S,6R)-6-(3,3-difluoro-2,2-dimethylbutoxy)-5-methylmorpholin-3-yl]-2-hydroxyethyl}-acetamide trifluoroacetate | 465 |
| 37 | (2R,3S,5R)-5-{(1S,2S)-2-Acetylamino-3-[3-(2-fluoro-ethoxy)-phenyl]-1-hydroxy-propyl}-2-(2,2-dimethyl-propoxy)-3-methylmorpholine trifluoroacetate | 441 |
| 38 | (2R,3S,5R)-5-{(1S,2S)-2-Acetylamino-3-[3-(2,2-difluoro-ethoxy)-phenyl]-1-hydroxy-propyl}-2-(2,2-dimethyl-propoxy)-3-methylmorpholine trifluoroacetate | 459 |
| 39 | (2R,3S,5R)-5-{(1S,2S)-2-Acetylamino-1-hydroxy-3-[3-(2-methylbutoxy)-phenyl]-propyl}-2-(2,2-dimethyl-propoxy)-3-methylmorpholine trifluoroacetate | 465 |
| 40 | N-{(1S,2S)-1-(3,5-Difluorobenzyl)-2-[(3R,5S,6R)-6-(1-fluorocyclohex-1-ylmethoxy)-5-methylmorpholin-3-yl]-2-hydroxyethyl}-acetamide trifluoroacetate | |

-continued

| EX | Compound | MS (ES) [M + H] |
|---|---|---|
| 41 | N-{(1S,2S)-1-(3,5-Difluoro-benzyl)-2-[(3R,6R)-6-(1-fluoro-cyclopentylmethoxy)-morpholin-3-yl]-2-hydroxy-ethyl}-acetamide trifluoroacetate | 431 |
| 42 | N-{(1S,2S)-1-(3-Fluoro-5-propoxy-benzyl)-2-hydroxy-2-[(3R,6R)-6(4,4,4-trifluoro-2,2-dimethyl-butoxy)-morpholin-3-yl]-ethyl}-acetamide trifluoroacetate | 509 |
| 43 | N-[(1S,2S)-2-[(3R,6R)-6-(2,2-Dimethyl-4-propoxy-butoxy)-morpholin-3-yl]-1-(3-fluoro-5-propoxy-benzyl)-2-hydroxy-ethyl]-acetamide trifluoroacetate | 513 |

*78% enantiomeric excess

EXAMPLE 44

Butyric acid (2R,5R)-5-[(1S,2S)-2-acetylamino-3-(3,5-difluorophenyl)-1-hydroxypropyl]-morpholin-2-ylmethyl ester hydrochloride To (R)-5-[(1S,2S)-2-acetylamino-3-(3,5-difluorophenyl)-1-hydroxypropyl]-2-butyryloxymethyl-morpholine-4-carboxylic acid tert-butyl ester (0.022 g, 0.043 mmol) add 4 M hydrogen chloride in 1,4-dioxane (0.500 mL, 2.00 mmol) and stir for 45 minutes. Concentrate under reduced pressure to give the title compound as an off-white solid (20.0 mg, 100%).

MS(ESI): m/z=415 [M+H]

The compounds of EXAMPLES 45-67 may be prepared essentially as described in EXAMPLE 44.

| EX | Compound | MS (ES) [M + H] |
|---|---|---|
| 45 | 5-(R)-[2-(S)-Acetylamino-3-(3,5-difluorophenyl)-1-(S)-hydroxypropyl]-2-(S)-(3-methylbutyl)-morpholine hydrochloride | 421 |
| 46 | 5-(S)-[2-(R)-Acetylamino-3-(3,5-difluorophenyl)-1-(R)-hydroxypropyl]-2-(S)-(3-methylbutyl)-morpholine hydrochloride | 421 |
| 47 | 5-(R)-[2-(S)-Acetylamino-3-(3,5-difluorophenyl)-1-(S)-hydroxypropyl]-2-(S)-(3,3-dimethylbutyl)-morpholine hydrochloride | 435 |
| 48 | 5-(S)-[2-(R)-Acetylamino-3-(3,5-difluorophenyl)-1-(R)-hydroxypropyl]-2-(S)-(3,3-dimethylbutyl)-morpholine hydrochloride | 435 |
| 49 | 5-(R)-[2-(S)-Acetylamino-3-(3,5-difluorophenyl)-1-(S)-hydroxypropyl]-2-(S)-(4,4-dimethylpentyl)-morpholine hydrochloride | 449 |
| 50 | 5-(S)-[2-(R)-Acetylamino-3-(3,5-difluorophenyl)-1-(R)-hydroxypropyl]-2-(S)-(4,4-dimethylpentyl)-morpholine hydrochloride | 449 |
| 51 | N-[(1S,2S)-1-(3,5-Difluorobenzyl)-2-hydroxy-2-((3R,6R)-6-phenoxymethylmorpholin-3-yl)-ethyl]-acetamide hydrochloride | 456.0 [M − H] |
| 52 | N-[(1S,2S)-1-(3,5-Difluorobenzyl)-2-hydroxy-2-((3R,6R)-6-hydroxymethylmorpholin-3-yl)-ethyl]-acetamide hydrochloride | 345.0 |
| 53 | (R)-5-[2-(S)-Acetylamino-3-(3,5-difluorophenyl)-1-(S)-hydroxypropyl]-2-(R)-2-fluorophenoxymethyl)-morpholine hydrochloride | 439.3 [M] |
| 54 | N-[(1S,2S)-2-((3R,6R)-6-Cyclohexyloxymethylmorpholin-3-yl)-1-(3,5-difluorobenzyl)-2-hydroxyethyl]-acetamide hydrochloride | 427.3 [M] |
| 55 | N-[(1S,2S)-2-[(3R,6R)-6-(3-Acetylphenoxymethyl)-morpholin-3-yl]-1-(3,5-difluorobenzyl)-2-hydroxyethyl]-acetamide hydrochloride | 463.0 |
| 56 | (E)-2-Methylbut-2-enedioic acid 1-{[(1S,2S)-2-((3R,6R)-6-cyclohexyloxymethylmorpholin-3-yl)-1-(3,5-difluorobenzyl)-2-hydroxyethyl]-amide} 4-dipropylamide hydrochloride | 580.5 |
| 57 | N-[(1S,2S)-2-[(3R,6R)-6-(4-Acetylphenoxymethyl)-morpholin-3-yl]-1-(3,5-difluorobenzyl)-2-hydroxyethyl]-acetamide hydrochloride | 463.0 |
| 58 | N-[2-[6-(S)-(2-Cyclohexylethyl)-morpholin-3-(R)-yl]-1-(S)-(3,5-difluorobenzyl)-2-(S)-hydroxyethyl]-acetamide hydrochloride | 425.2 |
| 59 | N-[1(S)-(3,5-Difluorobenzyl)-2-(S)-hydroxy-2-(6-(S)-phenethylmorpholin-3-(R)-yl)-ethyl]-acetamide hydrochloride | 419.2 |
| 60 | N-{1-(S)-Benzyl-2-[6-(S)-(2-cyclohexylethyl)-morpholin-3-(R)-yl]-2-(S)-hydroxyethyl}-acetamide hydrochloride | 389.5 |
| 61 | N-[(1S,2S)-1-(3,5-Difluorobenzyl)-2-((R)-6,6-diphenylmorpholin-3-yl)-2-hydroxyethyl]-acetamide hydrochloride | 467.3 |
| 62 | N-[(1S,2S)-2-[(3R,6R)-6-(2,2-Dimethylpropoxy)-morpholin-3-yl]-2-hydroxy-1-(3-trifluoromethylbenzyl)-ethyl]-acetamide hydrochloride | 433 |
| 63 | N-[(1S,2S)-2-[(3R,5S,6R)-6-(2,2-Dimethylpropoxy)-5-methylmorpholin-3-yl]-2-hydroxy-1-(3-isobutylsulfanylbenzyl)-ethyl]-acetamide hydrochloride | 467 |
| 64 | N-[(1S,2S)-2-[(3R,5S,6R)-6-(2,2-Dimethylpropoxy)-5-methyl-morpholin-3-yl]-1-(3-fluoro-5-isobutylsulfanylbenzyl)-2-hydroxyethyl]-acetamide hydrochloride | 485 |

-continued

| EX | Compound | MS (ES) [M + H] |
|---|---|---|
| 65 | N-[(1S,2S)-2-[(3R,5S,6R)-6-(2,2-Dimethylpropoxy)-5-methylmorpholin-3-yl]-1-(3-fluoro-5-propylsulfanylbenzyl)-2-hydroxyethyl]-acetamide hydrochloride | 471 |
| 66 | N-[(1S,2S)-2-[(3R,5S,6R)-6-(2,2-Dimethylpropoxy)-5-methylmorpholin-3-yl]-2-hydroxy-1-(3-propylsulfanylbenzyl)-ethyl]-acetamide hydrochloride | 453 |

EXAMPLE 67

(2R,5R)-2-Cyclohexylmethoxy-5-[(1S,2S)-3-(3,5-difluorophenyl)-2-((E)-3-dipropylcarbamoyl-2-methylacryloylamino)-1-hydroxypropyl]-morpholine-4-carboxylic acid hydrochloride Dissolve (2R,5R)-2-cyclohexylmethoxy-5-[(1S,2S)-3-(3,5-difluorophenyl)-2-((E)-3-dipropylcarbamoyl-2-methylacryloylamino)-1-hydroxypropyl]-morpholine-4-carboxylic acid tert-butyl ester (0.051 g, 0.075 mmol) in trifluoroacetic acid (1.5 mL) and stir at room temperature for 15 minutes. Dilute with dichloromethane (15 mL), concentrate, dissolve in ethyl acetate (30 mL), wash with 1:1 saturated aqueous sodium chloride:saturated aqueous sodium bicarbonate (30 mL), dry (sodium sulfate) and concentrate. Dissolve the residue in ethyl acetate and add 1 M hydrogen chloride in diethyl ether (0.20 mL, 0.20 mmol) and concentrate to give the title compound (0.045 g, 97.3%).

MS(ES): m/z=580.5 [M+H]

The compounds of EXAMPLES 68-134 may be prepared essentially as described in EXAMPLE 67.

| EX | Compound | MS (ES) [M + H] |
|---|---|---|
| 68 | N-[(1S,2S)-2-((3R,6R)-6-Cyclohexylmethoxymorpholin-3-yl)-1-(3,5-difluorobenzyl)-2-hydroxyethyl]-3,3,3-trifluoropropionamide hydrochloride | 495.0 [M] |
| 69 | (E)-5,5-Dimethyl-4-oxohex-2-enoic acid [(1S,2S)-2-((3R,6R)-6-cyclohexylmethoxymorpholin-3-yl)-1-(3,5-difluorobenzyl)-2-hydroxyethyl]-amide | 523.2 [M] |
| 70 | Trans-Cyclopropane-1,2-dicarboxylic acid 1-{[(1S,2S)-2-((3R,6R)-6-cyclohexylmethoxymorpholin-3-yl)-1-(3,5-difluorobenzyl)-2-hydroxyethyl]-amide} 2-(methylpropylamide) hydrochloride-Isomer 1 | 552.2 [M] |
| 71 | Trans-Cyclopropane-1,2-dicarboxylic acid 1-{[(1S,2S)-2-((3R,6R)-6-cyclohexylmethoxymorpholin-3-yl)-1-(3,5-difluorobenzyl)-2-hydroxyethyl]-amide} 2-(methylpropylamide) hydrochloride-Isomer 2 | 552.2 [M] |
| 72 | (E)-2-Methylbut-2-enedioic acid 1-{[(1S,2S)-2-((3R,6R)-6-cyclohexylmethoxymorpholin-3-yl)-1-(3,5-difluorobenzyl)-2-hydroxyethyl]-amide} 4-dimethylamide hydrochloride | 524.0 [M] |
| 73 | (E)-2-Methylbut-2-enedioic acid 1-{[(1S,2S)-2-((3R,6R)-6-cyclohexylmethoxymorpholin-3-yl)-1-(3,5-difluorobenzyl)-2-hydroxyethyl]-amide} 4-(methylpropylamide) hydrochloride | 552.2 [M] |
| 74 | (E)-But-2-enedioic acid [(1S,2S)-2-((3R,6R)-6-cyclohexylmethoxymorpholin-3-yl)-1-(3,5-difluorobenzyl)-2-hydroxyethyl]-amide dipropylamide hydrochloride | 566.5 |
| 75 | (E)-4,4,4-Trifluorobut-2-enoic acid {(1S,2S)-1-(3,5-difluorobenzyl)-2-[(3R,6R)-6-(2,2-dimethylpropoxy)-morpholin-3-yl]-2-hydroxyethyl}-amide hydrochloride | 481.0 |
| 76 | N-{(1S,2S)-1-(3,5-Difluorobenzyl)-2-[(3R,6S)-6-(1-fluorocyclohexylmethoxy)-morpholin-3-yl]-2-hydroxyethyl}-acetamide hydrochloride | 445.2 |
| 77 | N-[(1S,2S)-2-[(3R,6S)-6-(3-tert-butylcyclobutoxy)-morpholin-3-yl]-1-(3,5-difluorobenzyl)-2-hydroxyethyl]-acetamide hydrochloride | 447.3 |
| 78 | N-{(1S,2S)-1-(3,5-Difluorobenzyl)-2-[(3R,6S)-6-(4-fluorotetrahydropyran-4-ylmethoxy)-morpholin-3-yl]-2-hydroxyethyl}-acetamide hydrochloride | 441.2 |
| 79 | N-{(1S,2S)-1-(3,5-Difluorobenzyl)-2-hydroxy-2-[(3R,6R)-6-((1R,2S,5R)-2-isopropyl-5-methylcyclohexyloxy)-morpholin-3-yl]-ethyl}-acetamide hydrochloride | 469.0 |
| 80 | N-{(1S,2S)-1-(3,5-Difluorobenzyl)-2-[(3R,6R)-6-((1S,2R,5S)-6,6-dimethylbicyclo[3.1.1]hept-2-ylmethoxy)-morpholin-3-yl]-2-hydroxyethyl}-acetamide hydrochloride | 467.3 |
| 81 | N-{(1S,2S)-1-(3,5-Difluorobenzyl)-2-hydroxy-2-[(3R,6R)-6-(4-methoxycyclohexylmethoxy)-morpholin-3-yl]-ethyl}-acetamide hydrochloride-Isomer 1 | 457.35 |
| 82 | N-{1-(1SR,2SR)-(3,5-Difluorobenzyl)-2-[(3RS,6RS)-6-(4,4-difluorocyclohexylmethoxy)-morpholin-3-yl]-2-hydroxyethyl}-acetamide hydrochloride | 463.22 |

-continued

| EX | Compound | MS (ES) [M + H] |
|---|---|---|
| 83 | N-{1-(1SR,2SR)-(3,5-Difluorobenzyl)-2-hydroxy-2-[(3RS,6RS)-6-(4-methyltetrahydropyran-4-ylmethoxy)-morpholin-3-yl]-ethyl}-acetamide hydrochloride | 443.80 |
| 84 | N-((1S,2S)-1-(3,5-Difluorobenzyl)-2-hydroxy-2-{(3R,6S)-6-[(R)-1-(tetrahydrofuran-2-yl)methoxy]-morpholin-3-yl}-ethyl)-acetamide hydrochloride | 415.23 |
| 85 | N-[(1SR,2SR)-2-[(3RS,6RS)-6-(Bicyclo[2.2.1]hept-1-ylmethoxy)-morpholin-3-yl]-1-(3,5-difluorobenzyl)-2-hydroxyethyl]-acetamide hydrochloride | 439.25 |
| 86 | N-[(1S,2S)-2-((3R,6R)-6-Cyclohexylmethoxymorpholin-3-yl)-1-(3,5-difluorobenzyl)-2-hydroxyethyl]-2,2-dimethylpropionamide hydrochloride | 469.40 |
| 87 | N-[(1S,2S)-2-((3R,6R)-6-Cyclohexylmethoxy-morpholin-3-yl)-1-(3,5-difluorobenzyl)-2-hydroxy-ethyl]-isobutyramide hydrochloride | 455.35 |
| 88 | N-{(1SR,2SR)-1-(3,5-Difluorobenzyl)-2-hydroxy-2-[(3RS,6RS)-6-(1-methylcyclopentylmethoxy)-morpholin-3-yl]-ethyl}-acetamide hydrochloride | 427.21 |
| 89 | N-[(1S,2S)-2-[(3R,6S)-6-((R)-1-Cyclohexylethoxy)-morpholin-3-yl]-1-(3,5-difluorobenzyl)-2-hydroxyethyl]-acetamide hydrochloride | 441.26 |
| 90 | N-[(1SR,2SR)-2-[(3RS,6RS)-6-(1-Benzylcyclopentylmethoxy)-morpholin-3-yl]-1-(3,5-difluorobenzyl)-2-hydroxyethyl]-acetamide hydrochloride | 503.40 |
| 91 | N-{(1SR,2SR)-1-(3,5-Difluorobenzyl)-2-hydroxy-2-[(3RS,6RS)-6-(4-oxocyclohexylmethoxy)-morpholin-3-yl]-ethyl}-acetamide hydrochloride | 441.30 |
| 92 | Cyclobutanecarboxylic acid [(1S,2S)-2-((3R,6R)-6-cyclohexylmethoxymorpholin-3-yl)-1-(3,5-difluorobenzyl)-2-hydroxyethyl]-amide hydrochloride | 467.31 |
| 93 | Cyclopropanecarboxylic acid [(1S,2S)-2-((3R,6R)-6-cyclohexylmethoxymorpholin-3-yl)-1-(3,5-difluorobenzyl)-2-hydroxyethyl]-amide hydrochloride | 453.20 |
| 94 | Thiophene-2-carboxylic acid [(1S,2S)-2-((3R,6R)-6-cyclohexylmethoxymorpholin-3-yl)-1-(3,5-difluorobenzyl)-2-hydroxyethyl]-amide hydrochloride | 495.40 |
| 95 | N-[(1S,2S)-2-((3R,6R)-6-Cyclohexylmethoxymorpholin-3-yl)-1-(3,5-difluorobenzyl)-2-hydroxyethyl]-2-methoxyacetamide hydrochloride | 457.40 |
| 96 | N-[(1S,2S)-2-((3R,6R)-6-Cyclohexylmethoxymorpholin-3-yl)-1-(3,5-difluorobenzyl)-2-hydroxyethyl]-2-cyclopropylacetamide hydrochloride | 467.45 |
| 97 | N-[(1S,2S)-2-((3R,6R)-6-Cyclohexylmethoxymorpholin-3-yl)-1-(3,5-difluorobenzyl)-2-hydroxyethyl]-3,3-dimethylbutyramide hydrochloride | 483.42 |
| 98 | N-{(1S,2S)-1-(3,5-Difluorobenzyl)-2-hydroxy-2-[(3R,6R)-6-(3,3,3-trifluoro-2-methyl-2-trifluoromethy-propoxy)-morpholin-3-yl]-ethyl}-acetamide hydrochloride | 509.24 |
| 99 | N-{(1S,2S)-1-(3,5-Difluorobenzyl)-2-[(3R,6R)-6-(2,2-dimethylbutoxy)-morpholin-3-yl]-2-hydroxyethyl}-acetamide hydrochloride | 415.56 |
| 100 | N-{(1S,2S)-1-(3,5-Difluorobenzyl)-2-[(3R,6R)-6-(2,2-dimethylpentyloxy)-morpholin-3-yl]-2-hydroxyethyl}-acetamide hydrochloride | 429.60 |
| 101 | N-{(1S,2S)-1-(3,5-Difluorobenzyl)-2-hydroxy-2-[(3R,6R)-6-(1-phenylcyclopentylmethoxy)-morpholin-3-yl]-ethyl}-acetamide hydrochloride | 489.60 |
| 102 | N-[(1S,2S)-2-[(3R,6S)-6-((S)-1-Cyclohexylethoxy)-morpholin-3-yl]-1-(3,5-difluorobenzyl)-2-hydroxyethyl]-acetamide hydrochloride | 441.30 |
| 103 | N-{(1S,2S)-1-(3,5-Difluorobenzyl)-2-hydroxy-2-[(3R,6R)-6-(2,2,4-trimethylpentyloxy)-morpholin-3-yl]-ethyl}-acetamide hydrochloride | 443.31 |
| 104 | N-[(1S,2S)-2-((3R,6R)-6-Cyclohexylmethoxymorpholin-3-yl)-1-(3,5-difluorobenzyl)-2-hydroxyethyl]-3-methoxypropionamide hydrochloride | 471.4 |
| 105 | N-{(1S,2S)-1-(3,5-Difluorobenzyl)-2-[(3R,6R)-6-(2,2-dimethyl-propoxy)-morpholin-3-yl]-2-hydroxyethyl}-acetamide hydrochloride | 401.2 |
| 106 | N-[(1S,2S)-2-((3R,6S)-6-Cyclohexyloxymorpholin-3-yl)-1-(3,5-difluorobenzyl)-2-hydroxyethyl]-acetamide hydrochloride | 413.3 |
| 107 | (R)-Tetrahydrofuran-2-carboxylic acid [(1S,2S)-2-((3R,6R)-6-cyclohexylmethoxymorpholin-3-yl)-1-(3,5-difluorobenzyl)-2-hydroxyethyl]-amide hydrochloride | |
| 108 | N-[(1S,2S)-1-(3,5-Difluorobenzyl)-2-hydroxy-2-((3R,6S)-6-isobutoxymorpholin-3-yl)-ethyl]-acetamide hydrochloride | 387.2 |
| 109 | N-[(1S,2S)-1-(3,5-Difluorobenzyl)-2-hydroxy-2-((3R,6R)-6-isobutoxymorpholin-3-yl)-ethyl]-acetamide hydrochloride | 387.2 |
| 110 | N-[(1S,2S)-2-[(3R,5S,6R)-6-(2,2-Dimethylpropoxy)-5-methyl-morpholin-3-yl]-1-(2-ethylbenzyl)-2-hydroxyethyl]-acetamide hydrochloride | 407.3 |

-continued

| EX | Compound | MS (ES) [M + H] |
|---|---|---|
| 111 | N-[(1S,2S)-2-[(3R,5S,6R)-6-(2,2-Dimethyl-propoxy)-5-methyl-morpholin-3-yl]-1-(3-fluoro-5-propoxy-benzyl)-2-hydroxy-ethyl]-acetamide hydrochloride | 455.3 |
| 112 | N-[(1S,2S)-2-[(3R,5S,6R)-6-(2,2-Dimethyl-propoxy)-5-methyl-morpholin-3-yl]-1-(3-fluoro-5-isobutoxy-benzyl)-2-hydroxy-ethyl]-acetamide hydrochloride | 459.5 |
| 113 | N-[(1S,2S)-2-[(3R,5S,6R)-6-(2,2-Dimethyl-propoxy)-5-methyl-morpholin-3-yl]-1-(3-fluoro-5-propoxy-benzyl)-2-hydroxy-ethyl]-acetamide hydrochloride | 455.3 |
| 114 | N-{(1S,2S)-2-[(3R,5S,6R)-6-(2,2-Dimethyl-propoxy)-5-methyl-morpholin-3-yl]-1-[3-(2-ethyl-butoxy)-5-fluoro-benzyl]-2-hydroxy-ethyl}-acetamide hydrochloride | 497.2 |
| 115 | N-{(1S,2S)-2-[(3R,5S,6R)-6-(2,2-Dimethyl-propoxy)-5-methyl-morpholin-3-yl]-1-[3-fluoro-5-(3-methyl-butoxy)-benzyl]-2-hydroxy-ethyl}-acetamide hydrochloride | 483.3 |
| 116 | N-{(1S,2S)-1-(3-Allyloxy-5-fluoro-benzyl)-2-[(3R,5S,6R)-6-(2,2-dimethyl-propoxy)-5-methyl-morpholin-3-yl]-2-hydroxy-ethyl}-acetamide hydrochloride | 453.0 |
| 117 | N-{(1S,2S)-2-[(3R,5S,6R)-6-(2,2-Dimethyl-propoxy)-5-methyl-morpholin-3-yl]-1-[3-fluoro-5-(2,2,2-trifluoro-ethoxy)-benzyl]-2-hydroxy-ethyl}-acetamide hydrochloride | 495.4 |
| 118 | N-{(1S,2S)-1-(3,5-Difluorobenzyl)-2-[(3R,5S,6R)-6-(2,2-dimethylpropoxy)-5-methylmorpholin-3-yl]-2-hydroxyethyl}-4,4-difluoro-6-methylheptanoic acid amide hydrochloride | 535.2 |
| 119 | N-{(1S,2S)-1-(3-butyl-5-fluorobenzyl)-2-[(3R,5S,6R)-6-(2,2-dimethylpropoxy)-5-methylmorpholin-3-yl]-2-hydroxyethyl}-acetamide hydrochloride-Isomer 2 | 453.3 |
| 120 | N-{(1S,2S)-1-(3-butyl-5-fluorobenzyl)-2-[(3R,5S,6R)-6-(2,2-dimethylpropoxy)-5-methylmorpholin-3-yl]-2-hydroxyethyl}-acetamide hydrochloride-Isomer 4 | 453.3 |
| 121 | N-{(1S,2S)-1-(3,5-Difluorobenzyl)-2-[(3R,6R)-6-(2,2-dimethylpropoxy)-morpholin-3-yl]-2-hydroxyethyl}-4,4-difluoro-6-methylheptanoic acid amide hydrochloride | 521.3 |
| 122 | N-{(1S,2S)-1-(3,5-Difluorobenzyl)-2-[(3R,6R)-6-(2,2-dimethyl-propoxy)-morpholin-3-yl]-2-hydroxyethyl}-trans-2-fluoromethyl-cyclopropanecarboxylic acid amide hydrochloride-Isomer 1 | 459.2 |
| 123 | N-{(1S,2S)-1-(3,5-Difluorobenzyl)-2-[(3R,6R)-6-(2,2-dimethyl-propoxy)-morpholin-3-yl]-2-hydroxyethyl}-trans-2-fluoromethyl-cyclopropanecarboxylic acid amide hydrochloride-Isomer 2 | 459.2 |
| 124 | N-{(1S,2S)-1-(3,5-Difluorobenzyl)-2-[(3R,6R)-6-(2,2-dimethyl-propoxy)-morpholin-3-yl]-2-hydroxyethyl}-5,5,5-trifluoropentanoic acid amide hydrochloride | 497.2 |
| 125 | N-{(1S,2S)-1-(3,5-Difluorobenzyl)-2-[(3R,6R)-6-(2,2-dimethyl-propoxy)-morpholin-3-yl]-2-hydroxyethyl}-4,5,5-trifluoropent-4-enoic acid amide hydrochloride | 495.0 |
| 126 | N-{(1S,2S)-1-(3,5-Difluorobenzyl)-2-[(3R,6R)-6-(2,2-dimethyl-propoxy)-morpholin-3-yl]-2-hydroxyethyl}-trans-2,2-difluoromethyl-cyclopropanecarboxylic acid amide hydrochloride-Isomer 1 | 477.0 |
| 127 | N-{(1S,2S)-1-(3,5-Difluorobenzyl)-2-[(3R,6R)-6-(2,2-dimethyl-propoxy)-morpholin-3-yl]-2-hydroxyethyl}-trans-2,2-difluoromethyl-cyclopropanecarboxylic acid amide hydrochloride-Isomer 2 | 477.0 |
| 128 | N-{(1S,2S)-1-(3,5-Difluorobenzyl)-2-[(3R,6R)-6-(2,2-dimethyl-propoxy)-morpholin-3-yl]-2-hydroxyethyl}-cis-cyclopropane-1,2-dicarboxylic acid amide 2-methylpropylamide hydrochloride | 526.2 |
| 129 | N-{(1S,2S)-1-(3,5-Difluorobenzyl)-2-[(3R,6R)-6-(2,2-dimethyl-propoxy)-morpholin-3-yl]-2-hydroxyethyl}-2,2-difluoropropionamide hydrochloride | 451.0 |
| 130 | N-{(1S,2S)-1-(3,5-Difluorobenzyl)-2-[(3R,6R)-6-(2,2-dimethyl-propoxy)-morpholin-3-yl]-2-hydroxyethyl}-2-fluoropropionamide hydrochloride-Isomer 1 | 433.0 |
| 131 | N-{(1S,2S)-1-(3,5-Difluorobenzyl)-2-[(3R,6R)-6-(2,2-dimethyl-propoxy)-morpholin-3-yl]-2-hydroxyethyl}-2-fluoropropionamide hydrochloride-Isomer 2 | 433.0 |
| 132 | N-{(1S,2S)-1-(3,5-Difluorobenzyl)-2-[(3R,6R)-6-(2,2-dimethyl-propoxy)-morpholin-3-yl]-2-hydroxyethyl}-4,4,4-trifluorobutyramide hydrochloride | 483.3 |
| 133 | N-{(1S,2S)-1-(3,5-Difluorobenzyl)-2-[(3R,6R)-6-(2,2-dimethyl-propoxy)-morpholin-3-yl]-2-hydroxyethyl}-4,4,4-trifluoro-2-methylbut-2-enoic acid amide hydrochloride | 495.2 |
| 134 | N-{(1S,2S)-1-(3,5-Difluorobenzyl)-2-[(3R,6R)-6-(2,2-dimethyl-propoxy)-morpholin-3-yl]-2-hydroxyethyl}-3-(dipropylcarbamoyl)-2-methylpropionamide hydrochloride | 556.3 |

EXAMPLE 135

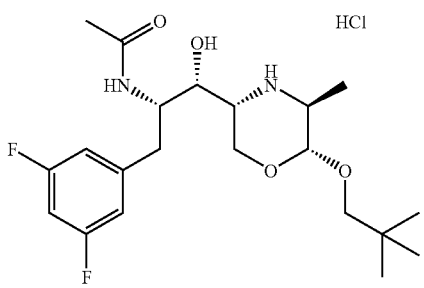

N-{(1S,2S)-1-(3,5-Difluorobenzyl)-2-[(3R,5S,6R)-6-(2,2-dimethylpropoxy)-5-methylmorpholin-3-yl]-2-hydroxyethyl}-acetamide hydrochloride Dissolve (1S,2S)-2-amino-3-(3,5-difluorophenyl)-1-[(3R,5S,6R)-6-(2,2-dimethylpropoxy)-5-methylmorpholin-3-yl]-propan-1-ol (70 mg, 0.188 mmol) in dry dichloromnethane (1.8 mL) under nitrogen. Add dropwise acetic anhydride (22 µL, 0.233 mmol) and stir for 1 hour. Add 1 M hydrogen chloride in diethyl ether (1 mL) and dilute with benzene. Concentrate and purify (HPLC, eluting with 30% to 70% acetonitrile with 0.1% hydrochloric acid in water) to give the title compound as a white solid (38 mg, 45%)

MS(ES): m/z=415.3 [M+H]

The compound of EXAMPLE 136-143 may be prepared essentially as described in EXAMPLE 135.

EXAMPLE 144

N-{(1S,2S)-1-(3,5-Difluorobenzyl)-2-[(3R,5S,6R)-6-(2,2-dimethylpropoxy)-5-methylmorpholin-3-yl]-2-hydroxyethyl}-2-methoxyacetamide hydrochloride Dissolve (1S,2S)-2-amino-3-(3,5-difluorophenyl)-1-[(5S,6R)-6-(2,2-dimethylpropoxy)-5-methylmorpholin-3-yl]-propan-1-ol (31 mg, 0.083 mmol) in dry 1:1 dichloromethane:diethyl ether (1 mL) under nitrogen. Cool to 0° C. and add dropwise methoxyacetyl chloride (7.6 µL, 0.083 mmol). Stir for 1 hour, quench with methanol, concentrate and purify (reverse-phase HPLC, eluting with 10:90 to 50:50 acetonitrile:water with 8 mM hydrochloric acid), to give the title compound (26 mg, 65%).

MS(ES): m/z=445.0 [M+H]

The compounds of EXAMPLES 145-159 may be prepared essentially as described in EXAMPLE 144 using the appropriate acid chloride.

| EX | Compound | MS (ES) [M + H] |
|---|---|---|
| 145 | N-{(1S,2S)-1-(3,5-Difluorobenzyl)-2-[(3R,5S,6R)-6-(2,2-dimethylpropoxy)-5-methylmorpholin-3-yl]-2-hydroxyethyl}-propionamide hydrochloride | 429.0 |
| 146 | N-{(1S,2S)-1-(3,5-Difluorobenzyl)-2-[(3R,5S,6R)-6-(2,2-dimethylpropoxy)-5-methylmorpholin-3-yl]-2-hydroxyethyl}-butyramide hydrochloride | 443.0 |
| 147 | Pentanoic acid {(1S,2S)-1-(3,5-difluorobenzyl)-2-[(3R,5S,6R)-6-(2,2-dimethylpropoxy)-5-methyl-morpholin-3-yl]-2-hydroxyethyl}-amide hydrochloride | 457.2 |

| EX | Compound | MS (ES) [M + H] |
|---|---|---|
| 136 | N-{(1S,2S)-1-(3,5-Difluorobenzyl)-2-[(3R,5R,6R)-6-(2,2-dimethylpropoxy)-5-methylmorpholin-3-yl]-2-hydroxyethyl}-acetamide hydrochloride | 415.3 |
| 137 | N-{(1S,2S)-1-(3,5-Difluorobenzyl)-2-[(3R,5S,6R)-6-(2,2-dimethylpropoxy)-5-isobutyl-morpholin-3-yl]-2-hydroxyethyl}-acetamide hydrochloride | 457 |
| 138 | N-[(1S,2S)-2-[(3R,6R)-5-Cyclopropylmethyl-6-(2,2-dimethylpropoxy)-morpholin-3-yl]-1-(3,5-difluorobenzyl)-2-hydroxyethyl]-acetamide hydrochloride | 455 |
| 139 | N-{(1S,2S)-1-(3,5-Difluorobenzyl)-2-hydroxy-2-[(3R,5S,6R)-5-methyl-6-(1-methylcyclopentylmethoxy)-morpholin-3-yl]-ethyl}-acetamide hydrochloride | 441 |
| 140 | N-{(1S,2S)-1-(3,5-Difluorobenzyl)-2-hydroxy-2-[(3R,5S,6R)-5-methyl-6-(1-methyl-cyclopentylmethoxy)-morpholin-3-yl]-ethyl}-2-methoxy-acetamide hydrochloride | 470 |
| 141 | N-{(1S,2S)-1-(3,5-Difluorobenzyl)-2-hydroxy-2-[(3R,5S,6R)-5-methyl-6-(1-methylcyclopropylmethoxy)-morpholin-3-yl]-ethyl}-acetamide hydrochloride | 413 |
| 142 | N-{(1S,2S)-1-(3,5-Difluorobenzyl)-2-[(3R,5S,6R)-6-(2-ethyl-2-methylbutoxy)-5-methylmorpholin-3-yl]-2-hydroxyethyl}-acetamide hydrochloride | 443 |
| 143 | N-{(1S,2S)-1-Benzyl-2-[(3R,5S,6R)-6-(2,2-dimethylpropoxy)-5-methylmorpholin-3-yl]-2-hydroxyethyl}-acetamide hydrochloride | 379 |

-continued

| EX | Compound | MS (ES) [M + H] |
|---|---|---|
| 148 | {(1S,2S)-1-(3,5-Difluorobenzyl)-2-[(3R,5S,6R)-6-(2,2-dimethylpropoxy)-5-methylmorpholin-3-yl]-2-hydroxyethyl}-carbamic acid methyl ester hydrochloride | 431.0 |
| 149 | {(1S,2S)-1-(3,5-Difluorobenzyl)-2-[(3R,5S,6R)-6-(2,2-dimethylpropoxy)-5-methylmorpholin-3-yl]-2-hydroxyethyl}-carbamic acid ethyl ester hydrochloride | 445.0 |
| 150 | N-{(1S,2S)-1-(3,5-Difluorobenzyl)-2-[(3R,5S,6R)-6-(2,2-dimethylpropoxy)-5-methylmorpholin-3-yl]-2-hydroxyethyl}-4-methoxybutyramide hydrochloride | 473.0 |
| 151 | N-{(1S,2S)-1-(3,5-Difluorobenzyl)-2-[(3R,5S,6R)-6-(2,2-dimethylpropoxy)-5-methylmorpholin-3-yl]-2-hydroxyethyl}-3-methoxypropionamide hydrochloride | 459.0 |
| 152 | N-{(1S,2S)-1-(3,5-Difluorobenzyl)-2-[(3R,5S,6R)-6-(2,2-dimethylpropoxy)-5-methylmorpholin-3-yl]-2-hydroxyethyl}-3-methylbutyramide hydrochloride | 457.2 |
| 153 | N-{(1S,2S)-1-(3,5-Difluorobenzyl)-2-[(3R,5S,6R)-6-(2,2-dimethylpropoxy)-5-methylmorpholin-3-yl]-2-hydroxyethyl}-2-phenylacetamide hydrochloride | 491.0 |
| 154 | Cyclopropanecarboxylic acid {(1S,2S)-1-(3,5-difluorobenzyl)-2-[(3R,5S,6R)-6-(2,2-dimethylpropoxy)-5-methyl-morpholin-3-yl]-2-hydroxyethyl}-amide hydrochloride | 441.0 |
| 155 | 3-Methyl-but-2-enoic acid {(1S,2S)-1-(3,5-difluorobenzyl)-2-[(3R,5S,6R)-6-(2,2-dimethylpropoxy)-5-methyl-morpholin-3-yl]-2-hydroxyethyl}-amide hydrochloride | 445.0 |
| 156 | 2-Butoxy-N-{(1S,2S)-1-(3,5-difluorobenzyl)-2-[(3R,5S,6R)-6-(2,2-dimethylpropoxy)-5-methylmorpholin-3-yl]-2-hydroxyethyl}-acetamide hydrochloride | 487.0 |
| 157 | (S)-N-{(1S,2S)-1-(3,5-Difluorobenzyl)-2-[(3R,5S,6R)-6-(2,2-dimethylpropoxy)-5-methylmorpholin-3-yl]-2-hydroxyethyl}-2-methoxypropionamide hydrochloride | 459.0 |
| 158 | N-{(1S,2S)-1-(3,5-Difluorobenzyl)-2-[(3R,5S,6R)-6-(2,2-dimethylpropoxy)-5-methylmorpholin-3-yl]-2-hydroxyethyl}-4,4,4-trifluorobutyramide hydrochloride | 497.0 |
| 159 | Furan-2-carboxylic acid {(1S,2S)-1-(3,5-difluorobenzyl)-2-[(3R,5S,6R)-6-(2,2-dimethylpropoxy)-5-methylmorpholin-3-yl]-2-hydroxyethyl}-amide hydrochloride | 467.0 |

EXAMPLE 160

(E)-2-Methyl-but-2-enoic acid [(1S,2S)-2-((3R,6R)-6-cyclohexylmethoxymorpholin-3-yl)-1-(3,5-difluorobenzyl)-2-hydroxyethyl]-amide hydrochloride To a suspension of (2R,5R)-5-[(1S,2S)-2-amino-3-(3,5-difluorophenyl)-1-hydroxypropyl]-2-cyclohexylmethoxymorpholine-4-carboxylic acid tert-butyl ester (30 mg, 0.064 mmol) in dichloromethane (1.6 mL), add 1-(3-dimethylaminopropyl)-3-ethylcarbodiimide hydrochloride (EDCl) (13 mg, 0.067 mmol), and tiglic acid (6.2 mg in 300 μL of dichloromethane). Stir at room temperature for 1.5 hours and purify (silica gel chromatography, eluting from 5:95 to 100:0 ethyl acetate:hexanes) to give the acylated BOC intermediate (30 mg). Dissolve the residue in trifluoroacetic acid (1.1 mL), stir for 15 minutes at room temperature, concentrate and dissolve in ethyl acetate. Wash the solution with saturated aqueous sodium chloride, saturated aqueous sodium bicarbonate, dry (sodium sulfate), filter, and concentrate. Dissolve the residue in ethyl acetate (5 mL) add hydrogen chloride (0.14 mL, 1.0 M solution in diethyl ether) and concentrate to give the title compound as a white solid (23 mg).

LC-MS: m/z=467 [M+H]$^+$, 501 [M+35]$^-$

The compound of EXAMPLE 161 may be prepared essentially as described in EXAMPLE 160 using angelic acid.

| EX | Compound | LC-MS [M + H] |
|---|---|---|
| 161 | (Z)-2-Methyl-but-2-enoic acid [(1S,2S)-2-((3R,6R)-6-cyclohexylmethoxymorpholin-3-yl)-1-(3,5-difluorobenzyl)-2-hydroxyethyl]-amide hydrochloride | 467 |

EXAMPLE 162

3-[(1S,2S)-2-((3R,6R)-6-Cyclohexylmethoxymorpholin-3-yl)-1-(3,5-difluorobenzyl)-2-hydroxyethyl]-1-hexyl-1-methylurea hydrochloride Add hexylmethylcarbamic chloride (11 mg, 0.062 mmol) to a solution of (2R,5R)-5-[(1S,2S)-2-amino-3-(3,5-difluorophenyl)-1-hydroxypropyl]-2-cyclohexylmethoxymorpholine-4-carboxylic acid tert-butyl ester (30 mg, 0.062 mmol) and pyridine (10 μL, 0.123 mmol) in dichloromethane at 0° C. Heat to 55° C. for four days. Perform purification, isolation, trifluoroacetic acid deprotection and salt exchange according to the procedure essentially as described for (E)-2-methyl-but-2-enoic acid [(1S,2S)-2-((3R,6R)-6-cyclohexylmethoxymorpholin-3-yl)-1-(3,5-difluorobenzyl)-2-hydroxyethyl]-amide hydrochloride.

LC-MS: l/z=526 [M+H]$^+$, 660 [M+35]$^-$

EXAMPLE 163

Cyclopentanecarboxylic acid {(1S,2S)-1-(3,5-difluorobenzyl)-2-[(3R,6R)-6-(2,2-dimethylpropoxy)morpholin-3-yl]-2-hydroxyethyl}-amide hydrochloride (2R,5R)-5-[(1S,2S)-2-(Cyclopentanecarbonylamino)-3-(3,5-difluorophenyl)-1-hydroxypropyl]-2 (2,2-dimethylpropoxy)-morpholine-4-carboxylic acid tert-butyl ester Stir cyclopentanecarboxylic acid (0.01 mL, 0.12 mmol), 1-(3-dimethylaminopropyl)-3-ethylcarbodiimide hydrochloride (EDCl) (0.02 g, 0.12 mmol) and 1-hydroxybenzotriazole monohydrate (HOBT) (0.02 g, 0.12 mmol) in dichloromethane (1 mL) at room temperature for 30 minutes. Add (2R,5R)-5-[(1S,2S)-2-amino-3-(3,5-difluorophenyl)-1-hydroxypropyl]-2-(2,2-dimethylpropoxy)-morpholine-4-carboxylic acid tert-butyl ester (0.05 g, 0.11 mmol) in dichloromethane (1 mL) and triethylamine (0.06 mL, 0.44 mmol) and stir at room temperature overnight. Wash with saturated aqueous sodium bicarbonate, dry (magnesium sulfate), filter, concentrate and purify (silica gel chromatography, eluting with 80:20 hexane:ethyl acetate), to give the desired compound as white solid (0.06 g, 98%).

MS(ES): m/z=599 [M+HCO2]$^+$

Cyclopentanecarboxylic acid {(1S,2S)-1-(3,5-difluorobenzyl)-2-[(3R,6R)-6-(2,2-dimethylpropoxymorpholin-3-yl]-2-hydroxyethyl}-amide hydrochloride Dissolve (2R,5R)-5-[(1S,2S)-2-(cyclopentanecarbonylamino)-3-(3,5-difluorophenyl)-1-hydroxypropyl]-2(2,2-dimethylpropoxy)-morpholine-4-carboxylic acid tert-butyl ester (0.06 g, 0.11 mmol) in trifluoroacetic acid (1.1 mL, 14.6 mmol) and stir for 15 minutes. Concentrate and add 2 M hydrogen chloride in diethyl ether (0.5 mL, 1 mmol) and concentrate to give the desired compound (0.045 mg, 80%).

MS(ES): m/z=455 [M+H]+

The compounds of EXAMPLES 164-166 may be prepared essentially as described in EXAMPLE 163 using the appropriate acids.

| EX | Compound | MS (ES) [M+H] |
|---|---|---|
| 164 | 2,2-Difluorocyclopropanecarboxylic acid {(1S,2S)-1-(3,5-difluorobenzyl)2-[(3R,6R)-6-(2,2-dimethylpropoxy)-morpholin-3-yl]-2-hydroxyethyl}-amide-Isomer 1 | 463 |
| 165 | 2,2-Difluorocyclopropanecarboxylic acid {(1S,2S)-1-(3,5-difluorobenzyl)2-[(3R,6R)-6-(2,2-dimethylpropoxy)-morpholin-3-yl]-2-hydroxyethyl}-amide-Isomer 2 | 463 |
| 166 | N-{(1S,2S)-1-(3,5-difluorobenzyl)2-[(3R,6R)-6-(2,2-dimethylpropoxy)-morpholin-3-yl]-2-hydroxyethyl}-2,2-difluoroacetamide | 437 |
| 167 | 1-Methyl-hexanoic acid {(1S,2S)-1-(3,5-difluorobenzyl)2-[(3R,6R)-6-(2,2-dimethylpropoxy)-morpholin-3-yl]-2-hydroxyethyl}-amide-Isomer 1 | 471 |

| EX | Compound | MS (ES) [M+H] |
|---|---|---|
| 168 | 1-Methylhexanoic acid {(1S,2S)-1-(3,5-difluorobenzyl)2-[(3R,6R)-6-(2,2-dimethylpropoxy)-morpholin-3-yl]-2-hydroxyethyl}-amide-Isomer 2 | 471 |

EXAMPLE 169

N-{(1S,2S)-1-[3-(2,2-Difluoroethoxy)-benzyl]-2-hydroxy-2-[(3R,6R)-6-(1-methylcyclopentyl-methoxy)-morpholin-3-yl]-ethyl}-acetamide hydrochloride Dissolve (2R,5R)-5-{(1S,2S)-2-acetylamino-3-[3-(2,2-difluoroethoxy)-phenyl]-1-hydroxypropyl}-2-(1-methylcyclopentylmethoxy)-morpholine-4-carboxylic acid tert-butyl ester (223 mg) in trifluoroacetic acid and stir for 45 minutes and concentrate. Coevaporate three times with dichloromethane (2 mL) and 1 M hydrogen chloride in diethyl ether (1 mL) to give the title compound (213 mg).

MS(ES): m/z=471 [M+H]

The compounds of EXAMPLES 170-224 may be prepared essentially as described in EXAMPLE 169.

| EX | Compound | MS (ES) [M+H] |
|---|---|---|
| 170 | Acetic acid (1S,2S)-2-acetylamino-3-[3-(2,2-difluoroethoxy)-phenyl]-1-[(3R,6R)-6-(1-methylcyclopentylmethoxy)-morpholin-3-yl]-propyl ester hydrochloride | 513 |
| 171 | N-[(1S,2S)-2-Hydroxy-2-[(3R,6R)-6-(1-methylcyclopentylmethoxy)-morpholin-3-yl]-1-(3-propoxybenzyl)-ethyl]-acetamide hydrochloride | 449 |
| 172 | Acetic acid (1S,2S)-2-acetylamino-1-[(3R,6R)-6-(1-methylcyclopentylmethoxy)-morpholin-3-yl]-3-(3-propoxyphenyl)-propyl ester hydrochloride | 491 |
| 173 | N-{(1S,2S)-1-(3-Benzyloxybenzyl)-2-hydroxy-2-[(3R,6R)-6-(1-methylcyclopentylmethoxy)-morpholin-3-yl]-ethyl}-acetamide hydrochloride | 497 |
| 174 | N-[(1S,2S)-2-Hydroxy-2-[(3R,5S,6R)-5-methyl-6-(2,2-dimethylpropoxy)-morpholin-3-yl]-1-(3-propoxybenzyl)-ethyl]-acetamide hydrochloride | 437 |
| 175 | N-[(1S,2S)-2-Hydroxy-2-[(3R,5S,6R)-5-methyl-6-(2,2-dimethylpropoxy)-morpholin-3-yl]-1-(3-hydroxybenzyl)-ethyl]-acetamide hydrochloride | 395 |
| 176 | N-[(1S,2S)-2-Hydroxy-2-[(3R,5S,6R)-5-methyl-6-(2,2-dimethylpropoxy)-morpholin-3-yl]-1-(3-cyclopentylmethoxybenzyl)-ethyl]-acetamide hydrochloride | 477 |
| 177 | N-[(1S,2S)-2-Hydroxy-2-[(3R,5S,6R)-5-methyl-6-(2,2-dimethylpropoxy)-morpholin-3-yl]-1-(3-((S)-2-methyl-butoxy)benzyl)-ethyl]-acetamide hydrochloride | 465 |
| 178 | N-[(1S,2S)-2-Hydroxy-2-[(3R,5S,6R)-5-methyl-6-(2,2-dimethylpropoxy)-morpholin-3-yl]-1-(3-ethoxybenzyl)-ethyl]-acetamide hydrochloride | 423 |
| 179 | N-[(1S,2S)-2-Hydroxy-2-[(3R,5S,6R)-5-methyl-6-(2,2-dimethylpropoxy)-morpholin-3-yl]-1-(3-allyloxybenzyl)-ethyl]-acetamide hydrochloride | 435 |
| 180 | N-[(1S,2S)-2-Hydroxy-2-[(3R,5S,6R)-5-methyl-6-(2,2-dimethylpropoxy)-morpholin-3-yl]-1-(3-(2-fluoroethoxy)benzyl)-ethyl]-acetamide hydrochloride | 441 |
| 181 | N-[(1S,2S)-2-Hydroxy-2-[(3R,5S,6R)-5-methyl-6-(2,2-dimethylpropoxy)-morpholin-3-yl]-1-(3-(trifluoromethoxy)benzyl)-ethyl]-acetamide hydrochloride | 463.3 |
| 182 | N-[(1S,2S)-2-Hydroxy-2-[(3R,5S,6R)-5-methyl-6-(2,2-dimethylpropoxy)-morpholin-3-yl]-1-(3-(2,2,2-trifluoroethoxy)benzyl)-ethyl]-acetamide hydrochloride | 477.2 |

-continued

| EX | Compound | MS (ES) [M+H] |
|---|---|---|
| 183 | N-[(1S,2S)-2-Hydroxy-2-[(3R,5S,6R)-5-methyl-6-(2,2-dimethylpropoxy)-morpholin-3-yl]-1-(3-(methoxy)benzyl)-ethyl]-acetamide hydrochloride | 409.5 |
| 184 | N-{(1S,2S)-1-(3,5-Difluorobenzyl)2-[(3R,6S)-6-(2-fluoro-2-methylpropoxy)-morpholin-3-yl]-2-hydroxyethyl}-acetamide hydrochloride | 405 |
| 185 | N-[(1S,2S)-2-[(3R,5S,6R)-5-Butyl-6-(2,2-dimethylpropoxy)-morpholin-3-yl]-1-(3,5-difluorobenzyl)-2-hydroxyethyl]-acetamide hydrochloride | 457 |
| 186 | N-{(1S,2S)-1-(3,5-Difluorobenzyl)-2-[(3R,5S,6R)-6-(2,2-dimethylpropoxy)-5-(3-fluoropropyl)-morpholin-3-yl]-2-hydroxyethyl}-acetamide hydrochloride | 461 |
| 187 | N-{(1S,2S)-1-(3,5-Difluorobenzyl)-2-[(3R,5S,6R)-6-(2,2-dimethylbutoxy)-5-methylmorpholin-3-yl]-2-hydroxy-ethyl}-acetamide hydrochloride | 429 |
| 188 | N-[(1S,2S)-2-((3R,5S,6R)-6-Cyclohexylmethoxy-5-methylmorpholin-3-yl)-1-(3,5-difluorobenzyl)-2-hydroxyethyl]-acetamide hydrochloride | 441 |
| 189 | N-{(1S,2S)-1-(3,5-Difluorobenzyl)-2-[(3R,5S,6R)-6-(4,4-difluorocyclohexylmethoxy)-5-methylmorpholin-3-yl]-2-hydroxyethyl}-acetamide hydrochloride | 477 |
| 190 | N-{(1S,2S)-1-(3,5-Difluorobenzyl)-2-[(3R,5S,6R)-6-(3-fluoropropoxy)-5-methylmorpholin-3-yl]-2-hydroxyethyl}-acetamide hydrochloride | 405 |
| 191 | N-{(1S,2S)-1-(3,5-Difluorobenzyl)-2-hydroxy-2-[(3R,5S,6R)-5-methyl-6-(3,3,3-trifluoropropoxy)-morpholin-3-yl]-ethyl}-acetamide hydrochloride | 441 |
| 192 | N-{(1S,2S)-1-(3,5-Difluorobenzyl)-2-[(3R,5S,6R)-6-(2-ethyl-butoxy)-5-methylmorpholin-3-yl]-2-hydroxyethyl}-acetamide hydrochloride | 429 |
| 193 | N-{(1S,2S)-1-(3,5-Difluorobenzyl)-2-hydroxy-2-[(3R,5S,6R)-5-methyl-6-(tetrahydropyran-4-ylmethoxy)-morpholin-3-yl]-ethyl}-acetamide hydrochloride | 443 |
| 194 | N-{(1S,2S)-1-(3,5-Difluorobenzyl)-2-hydroxy-2-[(3R,5S,6R)-5-methyl-6-(4,4,4-trifluorobutoxy)-morpholin-3-yl]-ethyl}-acetamide hydrochloride | 455 |
| 195 | N-{(1S,2S)-1-(3,5-Difluorobenzyl)-2-hydroxy-2-[(3R,5S,6R)-5-methyl-6-(4,4,4-trifluoro-2,2-dimethyl-butoxy)-morpholin-3-yl]-ethyl}-acetamide hydrochloride | 483 |
| 196 | N-{(1S,2S)-1-(4-Fluorobenzyl)-2-hydroxy-2-[(3R,5S,6R)-5-methyl-6-(2,2-dimethyl-propoxy)-morpholin-3-yl]-ethyl}-acetamide hydrochloride | 397.3 |
| 197 | N-{(1S,2S)-1-(3-(Trifluoromethylthio)benzyl)-2-hydroxy-2-[(3R,5S,6R)-5-methyl-6-(2,2-dimethyl-propoxy)-morpholin-3-yl]-ethyl}-acetamide hydrochloride | 479.2 |
| 198 | N-{(1S,2S)-1-(3-Fluorobenzyl)-2-hydroxy-2-[(3R,5S,6R)-5-methyl-6-(2,2-dimethyl-propoxy)-morpholin-3-yl]-ethyl}-acetamide hydrochloride | 397.2 |
| 199 | N-{(1S,2S)-1-(2,4-Difluorobenzyl)-2-hydroxy-2-[(3R,5S,6R)-5-methyl-6-(2,2-dimethyl-propoxy)-morpholin-3-yl]-ethyl}-acetamide hydrochloride | 415.3 |
| 200 | N-{(1S,2S)-1-(3-Trifluoromethylbenzyl)-2-hydroxy-2-[(3R,5S,6R)-5-methyl-6-(2,2-dimethyl-propoxy)-morpholin-3-yl]-ethyl}-acetamide hydrochloride | 447.3 |
| 201 | N-{(1S,2S)-1-(3-Trifluoromethylbenzyl)-2-hydroxy-2-[(3R,5S,6R)-5-methyl-6-(2,2-dimethyl-propoxy)-morpholin-3-yl]-ethyl}-acetamide hydrochloride | 447.3 |
| 202 | N-{(1S,2S)-1-(3,5-difluorobenzyl)-2-hydroxy-2-[(3R,5S,6R)-5-methyl-6-(2(R)-methoxy-propoxy)-morpholin-3-yl]-ethyl}-acetamide hydrochloride | 417.0 |
| 203 | N-{(1S,2S)-1-(3,5-Difluorobenzyl)-2-[(3R,6R)-6-(1-fluoromethyl-cyclopentylmethoxy)-morpholin-3-yl]-2-hydroxyethyl}-acetamide hydrochloride | 445 |
| 204 | N-{(1S,2S)-1-(3,5-Difluorobenzyl)-2-[(3R,5S,6R)-6-(1-fluoromethyl-cyclopentylmethoxy)-5-methyl-morpholin-3-yl]-2-hydroxyethyl}-acetamide hydrochloride | 459 |
| 205 | N-{(1S,2S)-1-(3,5-Difluorobenzyl)-2-[(3R,6R)-6-(1-difluoromethyl-cyclopentylmethoxy)-morpholin-3-yl]-2-hydroxyethyl}-acetamide hydrochloride | 463 |
| 206 | N-{(1S,2S)-1-(3,5-Difluorobenzyl)-2-hydroxy-2-[(3R,5S,6R)-5-methyl-6-(1-trifluoromethylcyclopropylmethoxy)-morpholin-3-yl]-ethyl}-acetamide hydrochloride | 467 |
| 207 | N-{(1S,2S)-2-[(3R,6R)-6-(1-Fluoromethyl-cyclopentylmethoxy)-morpholin-3-yl]-1-(3-fluoro-5-propoxy-benzyl)-2-hydroxy-ethyl}-acetamide hydrochloride | 485 |

-continued

| EX | Compound | MS (ES) [M+H] |
|---|---|---|
| 208 | N-{(1S,2S)-1-(3,5-Difluorobenzyl)-2-[(3R,5S,6R)-6-(3,3-difluoro-2,2-dimethyl-propoxy)-5-methyl-morpholin-3-yl]-2-hydroxy-ethyl}-acetamide hydrochloride | 451 |
| 209 | N-{(1S,2S)-2-[(3R,6R)-6-(3-fluoro-2-fluoromethyl-2-methyl-propoxy)-morpholin-3-yl]-1-(3-fluoro-5-isobutoxy-benzyl)-2-hydroxy-ethyl}-acetamide hydrochloride | 491 |
| 210 | N-{(1S,2S)-1-(3-cyclopentyloxy-5-fluoro-benzyl)-2-[(3R,6R)-6-(3-fluoro-2-fluoromethyl-2-methyl-propoxy)-morpholin-3-yl]-1-2-hydroxy-ethyl}-acetamide hydrochloride | 503 |
| 211 | N-{(1S,2S)-2-[(3R,6R)-6-(3-fluoro-2-fluoromethyl-2-methyl-propoxy)-morpholin-3-yl]-1-(3-fluoro-5-isopropoxy-benzyl)-2-hydroxy-ethyl}-acetamide hydrochloride | 477 |
| 212 | N-{(1S,2S)-2-[(3R,6R)-6-(3-fluoro-2-fluoromethyl-2-methyl-propoxy)-morpholin-3-yl]-1-(3-fluoro-5-propoxy-benzyl)-2-hydroxy-ethyl}-acetamide hydrochloride | 477 |
| 213 | N-{(1S,2S)-2-[(3R,6R)-6-(3,3-Difluoro-2,2-dimethyl-propoxy)-morpholin-3-yl]-1-(3-fluoro-5-isobutoxy-benzyl)-2-hydroxy-ethyl}-acetamide hydrochloride | 491 |
| 214 | N-{2-[(3R,6R)-6-(2,2-Bis-(fluoromethyl)-butoxy)-morpholin-3-yl]-(1S,2S)-1-(3,5-difluoro-benzyl)-2-hydroxy-ethyl}-acetamide hydrochloride | 451 |
| 215 | N-{(1S,2S)-1-(3,5-Difluoro-benzyl)-2-[(3R,5S,6R)-6-(1-difluoromethyl-cyclopentylmethoxy)-5-methyl-morpholin-3-yl]-2-hydroxy-ethyl}-acetamide hydrochloride | 477 |
| 216 | N-{2-[(3R,5S,6R)-6-(2,2-Bis-(fluoromethyl)-butoxy)-5-methyl-morpholin-3-yl]-(1S,2S)-1-(3,5-difluoro-benzyl)-2-hydroxy-ethyl}-acetamide hydrochloride | 465 |
| 217 | N-{2-[(3R,6R)-6-(1-Difluoromethyl-cyclopentylmethoxy)-morpholin-3-yl]-(1S,2S)-1-(3-fluoro-5-propoxy-benzyl)-2-hydroxy-ethyl}-acetamide hydrochloride | 503 |
| 218 | N-{2-[(3R,6R)-6-(2,2-Bis-(fluoromethyl)-butoxy)-morpholin-3-yl]-(1S,2S)-1-(3-fluoro-5-propoxy-benzyl)-2-hydroxy-ethyl}-acetamide hydrochloride | 491 |
| 219 | N-{(1S,2S)-[2-(3R,5S,6R)(6-Cyclopentylmethoxy-5-methyl-morpholin-3-yl)-1-(3,5-difluoro-benzyl)-2-hydroxy-ethyl]}-acetamide hydrochloride | 427 |
| 220 | N-{(1S,2S)-[2-(3R,5S,6R)-[6-(4,4-Difluoro-cyclohexylmethoxy)-5-methyl-morpholin-3-yl]-1-(3-fluoro-5-propoxy-benzyl)-2-hydroxy-ethyl]-acetamide hydrochloride | 517 |
| 221 | N-{(1S,2S)-1-(3,5-Difluorobenzyl)-2-hydroxy-2-[(3R,6R)-6-(4,4,4-trifluoro-2,2-dimethyl-butoxy)-morpholin-3-yl]-ethyl}-acetamide hydrochloride | 469 |
| 222 | N-{(1S,2S)-1-(3-Fluoro-5-propoxy-benzyl)-2-hydroxy-2-[(3R,5S,6S)-5-methyl-6-(2,2,2-trifluoro-ethoxy)-morpholin-3-yl]-ethyl}-acetamide hydrochloride | 467 |
| 223 | N-{(1S,2S)-1-(3-Fluoro-5-isobutoxy-benzyl)-2-hydroxy-2-[(3R,5S,6S)-5-methyl-6-(2,2,2-trifluoro-ethoxy)-morpholin-3-yl]-ethyl}-acetamide hydrochloride | 481 |
| 224 | N-{(1S,2S)-1-[3-(2,2-Difluoro-ethoxy)-5-fluoro-benzyl]-2-hydroxy-2-[(3R,5S,6S)-5-methyl-6-(2,2,2-trifluoro-ethoxy)-morpholin-3-yl]-ethyl}-acetamide hydrochloride | 489 |

EXAMPLE 225

N-{1-Cyclohexylmethyl-2-[6-(2,2-dimethyl-propoxy)-5-methyl-morpholin-3-yl]-2-hydroxy-ethyl}-acetamide hydrochloride Dissolve N-{1-benzyl-2-[6-(2,2-dimethylpropoxy)-5-methylmorpholin-3-yl]-2-hydroxyethyl}-acetamide (21 mg, 0.051 mmol) in glacial acetic acid (5.0 mL) with 30% platinum (IV) oxide (40 mg) in a high pressure reaction vessel. Stir under an atmosphere of 50 psi hydrogen gas overnight. Filter catalyst, concentrate, and purify (reverse phase chromatography, eluting with acetonitrile/0.01 M hydrochloric acid). Lyophilize overnight to give the title compound as a white powder (15 mg, 69% yield).

LC-MS: m/z=385 [M+H]$^+$, 383 [M−H]

EXAMPLE 226

N-{(1S,2S)-1-(3-Isopropylsulfanyl-5-fluorobenzyl)-2-hydroxy-2-[(3R,5S,6R)-5-methyl-6-(2,2-di-(fluoromethyl)propoxy)-morpholin-3-yl]-ethyl}-acetamide hydrochloride Cool a solution of (1S,2S)-2-Amino-3-(3-isopropylsulfanyl-5-fluorobenzyl)-1-[(3R,5S,6R)-6-(2,2-di-(fluoromethyl)propoxy)-5-methylmorpholin-3-yl]-propan-1-ol (60 mg, 0.13 mmol) in 1:1 dichloromethane:diethyl ether (1.29 mL) to 0° C. Add acetyl chloride (9 μL, 0.13 mmol) and stir at 0° C. for 1 hour. Dilute reaction mixture with methanol and concentrate under a stream of nitrogen. Subject residue to reverse phase HPLC chromatography, eluting with a gradient of 10-100% acetonitrile in 0.01 M HCl. Combine desired fractions, freeze, and remove volatiles by lyophilization to provide the title compound as a white powder (20 mg, 28%).

LC-MS: m/z=507 [M+H]$^+$

The compounds of EXAMPLES 227-257 may be prepared essentially as described in EXAMPLE 226.

| EX | Compound | MS (ES) |
|---|---|---|
| 227 | N-{(1S,2S)-1-(3-Isopropylsulfanyl-5-fluorobenzyl)-2-hydroxy-2-[(3R,6R)-6-(2,2-di-(fluoromethyl)propoxy)-morpholin-3-yl]-ethyl}-acetamide hydrochloride | 492.8 [M$^+$] |
| 228 | N-{(1S,2S)-1-(3-(2-methylprop-2-yl)sulfanyl-5-fluorobenzyl)-2-hydroxy-2-[(3R,5S,6R)-6-(2,2-di-(fluoromethyl)propoxy)-5-methyl-morpholin-3-yl]-ethyl}-acetamide hydrochloride | 520.8 [M$^+$] |
| 229 | N-{(1S,2S)-1-(3-(2,2-dimethylpropoxy)-5-fluorobenzyl)-2-hydroxy-2-[(3R,5S,6R)-6-(2,2-di-(fluoromethyl)propoxy)-5-methyl-morpholin-3-yl]-ethyl}-acetamide hydrochloride | 519.3 [M$^+$ + H] |
| 230 | N-{(1S,2S)-1-(3-isobutoxy-5-fluorobenzyl)-2-hydroxy-2-(3R,5S,6R)-5-methyl-6-(3-fluoro-2,2-dimethylpropoxy)-morpholin-3-yl]-ethyl}-acetamide hydrochloride | 487.3 [M$^+$ + H] |
| 231 | N-{(1S,2S)-1-(3-cyclopropylmethoxy-5-fluorobenzyl)-2-hydroxy-2-(3R,5S,6R)-5-methyl-6-(3-fluoro-2,2-dimethylpropoxy)-morpholin-3-yl]-ethyl}-acetamide hydrochloride | 485.0 [M$^+$ + H] |
| 232 | N-{(1S,2S)-1-(3-cyclobutoxy-5-fluorobenzyl)-2-hydroxy-2-(3R,5S,6R)-5-methyl-6-(2,2-di-(fluoromethyl)propoxy)-morpholin-3-yl]-ethyl}-acetamide hydrochloride | 502.8 [M$^+$ + H] |
| 233 | N-{(1S,2S)-1-(3-propoxy-5-fluorobenzyl)-2-hydroxy-2-(3R,5S,6R)-5-methyl-6-(2,2,2-tri-(fluoromethyl)ethoxy)-morpholin-3-yl]-ethyl}-acetamide hydrochloride | 509.3 [M$^+$ + H] |
| 234 | N-{(1S,2S)-1-(3-propoxy-5-fluorobenzyl)-2-hydroxy-2-(3R,5S,6R)-5-methyl-6-(trimethylsilylmethoxy)-morpholin-3-yl]-ethyl}-acetamide hydrochloride | 471 [M$^+$ + H] |
| 235 | N-{(1S,2S)-1-(3-phenylsulfanyl-5-fluorobenzyl)-2-hydroxy-2-(3R,5S,6R)-5-methyl-6-(2,2-di-(fluoromethyl)propoxy)-morpholin-3-yl]-ethyl}-acetamide hydrochloride | 441.0 [M$^+$ + H] |
| 236 | N-[(1S,2S)-2-[(3R,5S,6R)-6-(3-Fluoro-2-fluoromethyl-2-methyl-propoxy)-5-methyl-morpholin-3-yl]-2-hydroxy-1-(3-trifluoromethoxy-benzyl)-ethyl]-acetamide hydrochloride | 499.3 [M$^+$] |
| 237 | Pentanoic acid {(1S,2S)-1-(3,5-difluoro-benzyl)-2-[(3R,5S,6R)-6-(2,2-dimethyl-propoxy)-5-methyl-morpholin-3-yl]-2-hydroxy-ethyl}-amide hydrochloride | 457.39 [M$^+$] |
| 238 | N-{(1S,2S)-1-(3,5-Difluoro-benzyl)-2-[(3R,5S,6R)-6-(2,2-dimethyl-propoxy)-5-methyl-morpholin-3-yl]-2-hydroxy-ethyl}-3-methoxy-propionamide hydrochloride | 459.29 [M$^+$] |
| 239 | 5-Methyl-hexanoic acid {(1S,2S)-1-(3,5-difluoro-benzyl)-2-[(3R,5S,6R)-6-(2,2-dimethyl-propoxy)-5-methyl-morpholin-3-yl]-2-hydroxy-ethyl}-amide hydrochloride | 485.7 [M$^+$] |
| 240 | Octanoic acid {(1S,2S)-1-(3,5-difluoro-benzyl)-2-[(3R,5S,6R)-6-(2,2-dimethyl-propoxy)-5-methyl-morpholin-3-yl]-2-hydroxy-ethyl}-amide hydrochloride | 499.9 [M$^+$] |
| 241 | Heptanoic acid {(1S,2S)-1-(3,5-difluoro-benzyl)-2-[(3R,5S,6R)-6-(2,2-dimethyl-propoxy)-5-methyl-morpholin-3-yl]-2-hydroxy-ethyl}-amide hydrochloride | 485.56 [M$^+$] |
| 242 | 4-Methyl-pentanoic acid {(1S,2S)-1-(3,5-difluoro-benzyl)-2-[(3R,5S,6R)-6-(2,2-dimethyl-propoxy)-5-methyl-morpholin-3-yl]-2-hydroxy-ethyl}-amide hydrochloride | 471.36 [M$^+$] |
| 243 | Cyclobutanecarboxylic acid {(1S,2S)-1-(3,5-difluoro-benzyl)-2-[(3R,5S,6R)-6-(2,2-dimethyl-propoxy)-5-methyl-morpholin-3-yl]-2-hydroxy-ethyl}-amide hydrochloride | 455.39 [M$^+$] |
| 244 | Cyclohexanecarboxylic acid {(1S,2S)-1-(3,5-difluoro-benzyl)-2-[(3R,5S,6R)-6-(2,2-dimethyl-propoxy)-5-methyl-morpholin-3-yl]-2-hydroxy-ethyl}-amide hydrochloride | 483.34 [M$^+$] |
| 245 | 2-Cyclopentyl-N-{(1S,2S)-1-(3,5-difluoro-benzyl)-2-[(3R,5S,6R)-6-(2,2-dimethyl-propoxy)-5-methyl-morpholin-3-yl]-2-hydroxy-ethyl}-acetamide hydrochloride | 483.35 [M$^+$] |
| 246 | N-{(1S,2S)-1-(3,5-Difluoro-benzyl)-2-[(3R,5S,6R)-6-(2,2-dimethyl-propoxy)-5-methyl-morpholin-3-yl]-2-hydroxy-ethyl}-3,3-dimethyl-butyramide hydrochloride | 471.47 [M$^+$] |
| 247 | Cyclopentanecarboxylic acid {(1S,2S)-1-(3,5-difluoro-benzyl)-2-[(3R,5S,6R)-6-(2,2-dimethyl-propoxy)-5-methyl-morpholin-3-yl]-2-hydroxy-ethyl}-amide hydrochloride | 469.38 [M$^+$] |
| 248 | N-{(1S,2S)-1-(3,5-Difluoro-benzyl)-2-[(3R,5S,6R)-6-(2,2-dimethyl-propoxy)-5-methyl-morpholin-3-yl]-2-hydroxy-ethyl}-isobutyramide hydrochloride | 443.39 [M$^+$] |
| 249 | {(1S,2S)-1-(3,5-Difluoro-benzyl)-2-[(3R,5S,6R)-6-(2,2-dimethyl-propoxy)-5-methyl-morpholin-3-yl]-2-hydroxy-ethyl}-carbamic acid butyl ester hydrochloride | 473.34 [M$^+$] |

| EX | Compound | MS (ES) |
|---|---|---|
| 250 | {(1S,2S)-1-(3,5-Difluoro-benzyl)-2-[(3R,5S,6R)-6-(2,2-dimethyl-propoxy)-5-methyl-morpholin-3-yl]-2-hydroxy-ethyl}-carbamic acid isopropyl ester hydrochloride | 459.31 [M⁺] |
| 251 | {(1S,2S)-1-(3,5-Difluoro-benzyl)-2-[(3R,5S,6R)-6-(2,2-dimethyl-propoxy)-5-methyl-morpholin-3-yl]-2-hydroxy-ethyl}-carbamic acid pentyl ester hydrochloride | 487.34 [M⁺] |
| 252 | {(1S,2S)-1-(3,5-Difluoro-benzyl)-2-[(3R,5S,6R)-6-(2,2-dimethyl-propoxy)-5-methyl-morpholin-3-yl]-2-hydroxy-ethyl}-carbamic acid propyl ester hydrochloride | 459.38 [M⁺] |
| 253 | N-{(1S,2S)-1-(3,5-Difluoro-benzyl)-2-[(3R,5S,6R)-6-(2,2-dimethyl-propoxy)-5-propyl-morpholin-3-yl]-2-hydroxy-ethyl}-acetamide hydrochloride | 443.0 [M + H] |
| 254 | N-{(1S,2S)-1-(3,5-Difluoro-benzyl)-2-[(3R,5S,6R)-6-(2,2-dimethyl-propoxy)-5-propyl-morpholin-3-yl]-2-hydroxy-ethyl}-propionamide hydrochloride | 457.2 [M + H] |
| 255 | N-{(1S,2S)-1-(3,5-Difluoro-benzyl)-2-[(3R,5S,6R)-6-(2,2-dimethyl-propoxy)-5-propyl-morpholin-3-yl]-2-hydroxy-ethyl}-2-methoxy-acetamide hydrochloride | 473.2 [M + H] |
| 256 | N-{1-[3-(2,2-Dimethyl-propoxy)-5-fluoro-benzyl]-2-[6-(3-fluoro-2,2-bis-fluoromethyl-propoxy)-5-methyl-morpholin-3-yl]-2-hydroxy-ethyl}-acetamide hydrochloride | 537 [M + H] |
| 257 | N-{1-[3-(3,5-difluorobenzyl)-2-[6-(1-methylcyclobutylmethoxy)-5-methyl-morpholin-3-yl]-2-hydroxy-ethyl}-acetamide hydrochloride | 427 [M + H] |

EXAMPLE 258

N-{(1S,2S)-1-(3-Propylsulfanyl-5-fluorobenzyl)-2-hydroxy-2-[(3R,5S,6R)-5-methyl-6-(2,2-di-(fluoromethyl)propoxy)-morpholin-3-yl]-ethyl}-acetamide hydrochloride Cool a solution of (1S,2S)-2-Amino-3-(3,5-difluorobenzyl)-1-[(3R,5S,6R)-6-(2,2-di-(fluoromethyl)propoxy)-5-methylmorpholin-3-yl]-propan-1-ol (148 mg, 0.33 mmol) in dichloromethane (3.29 mL) to 0° C. Add N-acetyl imidazole (43 mg, 0.39 mmol) and triethylamine (91 µL, 0.65 mmol). Allow reaction mixture to warm to room temperature and stir over night. Dilute reaction mixture with dichloromethane and add 1N KH₂PO₄. Wash organic phase with 1N KH₂PO₄, dry over sodium sulfate, and concentrate under reduced pressure. Subject residue to reverse phase HPLC chromatography, eluting with a gradient of acetonitrile (10-100%) in 0.01 M HCl to provide 50 mg (29%) of the title compound.

MS(ES): m/z=493.3 [M⁺+H]

The compounds of EXAMPLES 259-260 may be prepared essentially as described in EXAMPLE 258.

| EX | Compound | MS (ES) |
|---|---|---|
| 259 | {(1S,2S)-1-(3-(3-methylbutyl)-benzyl)-2-[(3R,5S,6R)-6-(2,2-di-(fluoromethyl)-propoxy)-5-methyl-morpholin-3-yl]-2-hydroxy-ethyl}-acetamide hydrochloride | 485.3 [M + H] |
| 260 | {(1S,2S)-1-(3-(3-methylbutyl)-5-fluoro-benzyl)-2-[(3R,5S,6R)-6-(2,2-di-(fluoromethyl)-propoxy)-5-methyl-morpholin-3-yl]-2-hydroxy-ethyl}-acetamide hydrochloride | 503.3 [M + H] |

EXAMPLE 261

N-{(1S,2S)-1-(3-Propoxy-5-fluorobenzyl)-2-hydroxy-2-[(3R,5S,6R)-5-methyl-6-(3-fluoro-2,2-dimethylpropoxy)-morpholin-3-yl]-ethyl}-acetamide hydrochloride Stir a solution of (2R,3S,5R)-5-[(1S,2S)-1-Hydroxy-2-acetylamino-3-(3-propoxy-5-fluorophenyl)-propyl]-2-(3-fluoro-2,2-dimethylpropoxy)-3-methylmorpholine-4-carboxylic acid tert-butyl ester (175 mg) in trifluoroacetic acid (5 mL) for 30 minutes at room temperature. Concentrate under a stream of nitrogen and subject the residue to reverse phase HPLC, eluting with 10-100% acetonitrile in 0.01 M HCl, to provide the title compound.

MS(ES): m/z=473 [M⁺+H]

EXAMPLE 262

3-Methoxypropionic acid {(1S,2S)-1-(3-cyclopropylmethoxy-5-fluorobenzyl)-2-[(3R,5S,6R)-5-methyl-6-(3-fluoro-2,2-dimethylpropoxy)-morpholin-3-yl]-2-hydroxyethyl}-amide hydrochloride Add 3-methoxypropionic acid (30 µL, 0.322 mmol), EDCl (93 mg, 0.484 mmol), and HOBT (65 mg, 0.484 mmol) to a solution of (1S,2S)-2-amino-3-(3-cyclopropylmethoxy-5-fluorophenyl)-1-(3R,5S,6R)-6-(3-fluoro-2,2-dimethylpropoxy)-5-methylmorpholin-3-yl]-propan-1-ol (138.2 mg, 0.322 mmol) in tetrahydrofuran 5 mL and stir at room temperature for 3 hours. Dilute the reaction mixture with ethyl acetate, and wash with 1.0 N HCl followed by saturated aqueous sodium chloride. Dry the organic phase with magnesium sulfate and concentrate under reduced pressure. Subject the residue to reverse phase chromatography, eluting with 10-40% acetonitrile in 0.001 N HCl to provide the title compound.

MS(ES): m/e=529.3 (M⁺+H)

The compounds of EXAMPLES 263-273 may be prepared essentially as described in EXAMPLE 262.

| EX | Compound | MS (ES) |
|---|---|---|
| 263 | 5,5-Dimethyl-4-oxo-hexanoic acid {(1S,2S)-1-(3,5-difluoro-benzyl)-2-[(3R,5S,6R)-6-(2,2-dimethyl-propoxy)-5-methyl-morpholin-3-yl]-2-hydroxy-ethyl}-amide hydrochloride | 513.57 [M$^+$] |
| 264 | (E)-2-Methyl-hex-2-enoic acid {(1S,2S)-1-(3,5-difluoro-benzyl)-2-[(3R,5S,6R)-6-(2,2-dimethyl-propoxy)-5-methyl-morpholin-3-yl]-2-hydroxy-ethyl}-amide hydrochloride | 483.37 [M$^+$] |
| 265 | (R)-N-{(1S,2S)-1-(3,5-Difluoro-benzyl)-2-[(3R,5S,6R)-6-(2,2-dimethyl-propoxy)-5-methyl-morpholin-3-yl]-2-hydroxy-ethyl}-2-methoxy-propionamide hydrochloride | 459.33 [M$^+$] |
| 266 | Hex-5-ynoic acid {(1S,2S)-1-(3,5-difluoro-benzyl)-2-[(3R,5S,6R)-6-(2,2-dimethyl-propoxy)-5-methyl-morpholin-3-yl]-2-hydroxy-ethyl}-amide hydrochloride | 467.33 [M$^+$] |
| 267 | N-{(1S,2S)-1-(3,5-Difluoro-benzyl)-2-[(3R,5S,6R)-6-(2,2-dimethyl-propoxy)-5-methyl-morpholin-3-yl]-2-hydroxy-ethyl}-2-ethoxy-acetamide hydrochloride | 459.37 [M$^+$] |
| 268 | Pent-4-ynoic acid {(1S,2S)-1-(3,5-difluoro-benzyl)-2-[(3R,5S,6R)-6-(2,2-dimethyl-propoxy)-5-methyl-morpholin-3-yl]-2-hydroxy-ethyl}-amide hydrochloride | 453.36 [M$^+$] |
| 269 | N-{(1S,2S)-1-(3,5-Difluoro-benzyl)-2-[(3R,5S,6R)-6-(2,2-dimethyl-propoxy)-5-methyl-morpholin-3-yl]-2-hydroxy-ethyl}-3-ethoxy-propionamide hydrochloride | 473.35 [M$^+$] |
| 270 | 6-Methyl-4-oxo-heptanoic acid {(1S,2S)-1-(3,5-difluoro-benzyl)-2-[(3R,5S,6R)-6-(2,2-dimethyl-propoxy)-5-methyl-morpholin-3-yl]-2-hydroxy-ethyl}-amide hydrochloride | 513.36 [M$^+$] |
| 271 | N-{(1S,2S)-1-(3,5-Difluoro-benzyl)-2-[(3R,5S,6R)-6-(2,2-dimethyl-propoxy)-5-methyl-morpholin-3-yl]-2-hydroxy-ethyl}-2-propoxy-acetamide hydrochloride | 473.35 [M$^+$] |
| 272 | 4-Cyclopentyl-N-{(1S,2S)-1-(3,5-difluoro-benzyl)-2-[(3R,5S,6R)-6-(2,2-dimethyl-propoxy)-5-methyl-morpholin-3-yl]-2-hydroxy-ethyl}-4-oxo-butyramide hydrochloride | 525.32 [M$^+$] |
| 273 | 5,5-Dimethyl-hexanoic acid {(1S,2S)-1-(3,5-difluoro-benzyl)-2-[(3R,5S,6R)-6-(2,2-dimethyl-propoxy)-5-methyl-morpholin-3-yl]-2-hydroxy-ethyl}-amide hydrochloride | 499.33 [M$^+$] |

The compounds of EXAMPLES 274-324 may be prepared essentially as described in EXAMPLE 67.

| EX | Compound | MS (ES) |
|---|---|---|
| 274 | N-{(1S,2S)-1-(3-Bromo-5-fluorobenzyl)-2-[(3R,5S,6R)-6-(2,2-dimethyl-propoxy)-5-methyl-morpholin-3-yl]-2-hydroxyethyl}-acetamide hydrochloride | 476.0 [M$^+$ + H] |
| 275 | N-{(1S,2S)-1-(3-Propyl-5-fluorobenzyl)-2-[(3R,5S,6R)-6-(2,2-dimethyl-propoxy)-5-methyl-morpholin-3-yl]-2-hydroxyethyl}-acetamide hydrochloride | 439.3 [M$^+$ + H] |
| 276 | N-{(1S,2S)-1-(3-(3-Methylbutyl-5-fluorobenzyl)-2-[(3R,5S,6R)-6-(2,2-dimethyl-propoxy)-5-methyl-morpholin-3-yl]-2-hydroxyethyl}-acetamide hydrochloride | 467.5 [M$^+$ + H] |
| 277 | N-{(1S,2S)-1-(3-(2-Ethoxyphenyl-5-fluorobenzyl)-2-[(3R,5S,6R)-6-(2,2-dimethyl-propoxy)-5-methyl-morpholin-3-yl]-2-hydroxyethyl}-acetamide hydrochloride | 517.3 [M$^+$ + H] |
| 278 | N-{(1S,2S)-1-(4-Methyl-3,5-difluorobenzyl)-2-[(3R,5S,6R)-6-(2,2-dimethyl-propoxy)-5-methyl-morpholin-3-yl]-2-hydroxyethyl}-acetamide hydrochloride | 429.0 [M$^+$ + H] |
| 279 | N-{(1S,2S)-1-(4-(3-methylbutyl)-3,5-difluorobenzyl)-2-[(3R,5S,6R)-6-(2,2-di-(fluoromethyl)-propoxy)-5-methyl-morpholin-3-yl]-2-hydroxyethyl}-acetamide hydrochloride | 485.3 [M$^+$ + H] |
| 280 | N-{(1S,2S)-1-(3-Butyl-5-fluorobenzyl)-2-[(3R,5S,6R)-6-(2,2-dimethyl-propoxy)-5-methyl-morpholin-3-yl]-2-hydroxyethyl}-acetamide hydrochloride | 453.3 [M$^+$ + H] |
| 281 | N-{(1S,2S)-1-(3,5-Difluorobenzyl)-2-[(3R,5S,6R)-6-(2,2-dimethyl-propoxy)-5-methyl-morpholin-3-yl]-2-hydroxyethyl}-6-methyl-4,4-difluoroheptanoic acid amide hydrochloride | 535.2 [M$^+$ + H] |
| 282 | N-{(1S,2S)-1-(3-Butyl-5-fluorobenzyl)-2-[(3R,5S,6R)-6-(2,2-dimethyl-propoxy)-5-methyl-morpholin-3-yl]-2-hydroxyethyl}-6-methyl-4,4-difluoroheptanoic acid amide hydrochloride | 573.3 [M$^+$ + H] |

-continued

| EX | Compound | MS (ES) |
|---|---|---|
| 283 | N-{1-(3-Bromo-5-fluorobenzyl)-2-[(3R,5S,6R)-6-(2,2-dimethyl-propoxy)-5-methyl-morpholin-3-yl]-2-hydroxyethyl}-acetamide hydrochloride | 475.0 [M+ + H] |
| 284 | N-{(1S,2S)-1-(3,5-Difluorobenzyl)-2-[(3R,6R)-6-(2,2-dimethyl-propoxy)-morpholin-3-yl]-2-hydroxyethyl}-6-methyl-heptanoic acid amide hydrochloride | 485.2 [M+ + H] |
| 285 | N-[(1S,2S)-2-((3R,6R)-6-Cyclohexylmethoxy-morpholin-3-yl)-1-(3-fluoro-5-propoxy-benzyl)-2-hydroxy-ethyl]-acetamide hydrochloride | 467.3 [M+] |
| 286 | N-[(1S,2S)-2-((3R,6R)-6-Cyclohexylmethoxy-morpholin-3-yl)-1-(3-fluoro-5-isobutoxy-benzyl)-2-hydroxy-ethyl]-acetamide hydrochloride | 481.2 [M+] |
| 287 | N-[(1S,2S)-2-((3R,6R)-6-Cyclohexylmethoxy-morpholin-3-yl)-1-(3-fluoro-5-(2,2,2-trifluoroethoxy)-benzyl)-2-hydroxy-ethyl]-acetamide hydrochloride | 507.3 [M+] |
| 288 | N-{(1S,2S)-1-(3,5-Difluoro-benzyl)-2-hydroxy-2-[(3R,5S,6R)-5-methyl-6-((S)-2-methyl-butoxy)-morpholin-3-yl]-ethyl}-acetamide hydrochloride | 415.6 [M+] |
| 289 | N-{(1S,2S)-1-(3,5-Difluoro-benzyl)-2-hydroxy-2-[(3R,6R)-6-(4-methyl-tetrahydro-pyran-4-ylmethoxy)-morpholin-3-yl]-ethyl}-acetamide hydrochloride | 443.8 [M+] |
| 290 | N-[(1S,2S)-2-[(3R,6R)-6-(Bicyclo[2.2.1]hept-1-ylmethoxy)-morpholin-3-yl]-1-(3,5-difluoro-benzyl)-2-hydroxy-ethyl]-acetamide hydrochloride | 439.25 [M+] |
| 291 | N-{(1S,2S)-1-(3,5-Difluoro-benzyl)-2-hydroxy-2-[(3R,6R)-6-(1-methyl-cyclopentylmethoxy)-morpholin-3-yl]-ethyl}-acetamide hydrochloride | 427.21 [M+] |
| 292 | N-{(1S,2S)-1-(3,5-Difluoro-benzyl)-2-hydroxy-2-[(3R,6R)-6-(3,3,3-trifluoro-2-methyl-2-trifluoromethyl-propoxy)-morpholin-3-yl]-ethyl}-acetamide hydrochloride | 509.24 [M+] |
| 293 | N-{(1S,2S)-1-(3,5-Difluoro-benzyl)-2-[(3R,6R)-6-(2,2-dimethyl-butoxy)-morpholin-3-yl]-2-hydroxy-ethyl}-acetamide hydrochloride | 415.56 [M+] |
| 294 | N-{(1S,2S)-1-(3,5-Difluoro-benzyl)-2-[(3R,6R)-6-(2,2-dimethyl-pentyloxy)-morpholin-3-yl]-2-hydroxy-ethyl}-acetamide hydrochloride | 429.6 [M+] |
| 295 | N-{(1S,2S)-1-(3,5-Difluoro-benzyl)-2-hydroxy-2-[(3R,6R)-6-(1-phenyl-cyclopentylmethoxy)-morpholin-3-yl]-ethyl}-acetamide hydrochloride | 489.6 [M+] |
| 296 | N-{(1S,2S)-1-(3,5-Difluoro-benzyl)-2-hydroxy-2-[(3R,6R)-6-(2,2,4-trimethyl-pentyloxy)-morpholin-3-yl]-ethyl}-acetamide hydrochloride | 443.31 [M+] |
| 297 | Octanoic acid {(1S,2S)-1-(3,5-difluoro-benzyl)-2-[(3R,6R)-6-(2,2-dimethyl-propoxy)-morpholin-3-yl]-2-hydroxy-ethyl}-amide hydrochloride | 485.7 [M+] |
| 298 | 5-Methyl-hexanoic acid {(1S,2S)-1-(3,5-difluoro-benzyl)-2-[(3R,6R)-6-(2,2-dimethyl-propoxy)-morpholin-3-yl]-2-hydroxy-ethyl}-amide hydrochloride | 471.9 [M+] |
| 299 | 2,5-Dimethyl-furan-3-carboxylic acid {(1S,2S)-1-(3,5-difluoro-benzyl)-2-[(3R,6R)-6-(2,2-dimethyl-propoxy)-morpholin-3-yl]-2-hydroxy-ethyl}-amide hydrochloride | 481.34 [M+] |
| 300 | Heptanoic acid {(1S,2S)-1-(3,5-difluoro-benzyl)-2-[(3R,6R)-6-(2,2-dimethyl-propoxy)-morpholin-3-yl]-2-hydroxy-ethyl}-amide hydrochloride | 471.39 [M+] |
| 301 | (E)-2-Methyl-but-2-enedioic acid 4-({(1S,2S)-1-(3,5-difluoro-benzyl)-2-[(3R,6R)-6-(2,2-dimethyl-propoxy)-morpholin-3-yl]-2-hydroxy-ethyl}-amide) 1-(methyl-propyl-amide) hydrochloride | 526.9 [M+] |
| 302 | N-{(1S,2S)-1-(3,5-Difluoro-benzyl)-2-[(3R,6R)-6-(2,2-dimethyl-propoxy)-morpholin-3-yl]-2-hydroxy-ethyl}-N'-methyl-N'-propyl-succinamide hydrochloride | 514.9 [M+] |
| 303 | (E)-2-Methyl-hex-2-enoic acid {(1S,2S)-1-(3,5-difluoro-benzyl)-2-[(3R,6R)-6-(2,2-dimethyl-propoxy)-morpholin-3-yl]-2-hydroxy-ethyl}-amide hydrochloride | 469.7 [M+] |

-continued

| EX | Compound | MS (ES) |
|---|---|---|
| 304 | 5,5-Dimethyl-4-oxo-hexanoic acid {(1S,2S)-1-(3,5-difluoro-benzyl)-2-[(3R,6R)-6-(2,2-dimethyl-propoxy)-morpholin-3-yl]-2-hydroxy-ethyl}-amide hydrochloride | 499.68 [M$^+$] |
| 305 | N-{(1S,2S)-1-(3,5-Difluoro-benzyl)-2-[(3R,6R)-6-(2,2-dimethyl-propoxy)-morpholin-3-yl]-2-hydroxy-ethyl}-N'-ethyl-N'-propyl-succinamide hydrochloride | 528.35 [M$^+$] |
| 306 | N-{(1S,2S)-1-(3,5-Difluoro-benzyl)-2-hydroxy-2-[(3R,6R)-6-(1-methyl-cyclopentylmethoxy)-morpholin-3-yl]-ethyl}-acetamide hydrochloride | 427.33 [M$^+$] |
| 307 | Furan-2,5-dicarboxylic acid 2-({(1S,2S)-1-(3,5-difluoro-benzyl)-2-[(3R,6R)-6-(2,2-dimethyl-propoxy)-morpholin-3-yl]-2-hydroxy-ethyl}-amide)-5-(methyl-propyl-amide) hydrochloride | 552.41 [M$^+$] |
| 308 | 4-Methyl-pentanoic acid {(1S,2S)-1-(3,5-difluoro-benzyl)-2-[(3R,6R)-6-(2,2-dimethyl-propoxy)-morpholin-3-yl]-2-hydroxy-ethyl}-amide hydrochloride | 457.4 [M$^+$] |
| 309 | 6-Methyl-4-oxo-heptanoic acid {(1S,2S)-1-(3,5-difluoro-benzyl)-2-[(3R,6R)-6-(2,2-dimethyl-propoxy)-morpholin-3-yl]-2-hydroxy-ethyl}-amide hydrochloride | 499.33 [M$^+$] |
| 310 | {(1S,2S)-1-(3,5-Difluoro-benzyl)-2-[(3R,6R)-6-(2,2-dimethyl-propoxy)-morpholin-3-yl]-2-hydroxy-ethyl}-carbamic acid pentyl ester hydrochloride | 473.33 [M$^+$] |
| 311 | {(1S,2S)-1-(3,5-Difluoro-benzyl)-2-[(3R,6R)-6-(2,2-dimethyl-propoxy)-morpholin-3-yl]-2-hydroxy-ethyl}-carbamic acid butyl ester hydrochloride | 459.32 [M$^+$] |
| 312 | 5-tert-Butyl-2-methyl-furan-3-carboxylic acid {(1S,2S)-1-(3,5-difluoro-benzyl)-2-[(3R,6R)-6-(2,2-dimethyl-propoxy)-morpholin-3-yl]-2-hydroxy-ethyl}-amide hydrochloride | 523.37 [M$^+$] |
| 313 | 4-Oxo-hexanoic acid {(1S,2S)-1-(3,5-difluoro-benzyl)-2-[(3R,6R)-6-(2,2-dimethyl-propoxy)-morpholin-3-yl]-2-hydroxy-ethyl}-amide hydrochloride | 471.35 [M$^+$] |
| 314 | (E)-3,5,5-Trimethyl-4-oxo-hex-2-enoic acid {(1S,2S)-1-(3,5-difluoro-benzyl)-2-[(3R,6R)-6-(2,2-dimethyl-propoxy)-morpholin-3-yl]-2-hydroxy-ethyl}-amide hydrochloride | 511.33 [M$^+$] |
| 315 | (E)-2-Methyl-oct-2-enoic acid {(1S,2S)-1-(3,5-difluoro-benzyl)-2-[(3R,6R)-6-(2,2-dimethyl-propoxy)-morpholin-3-yl]-2-hydroxy-ethyl}-amide hydrochloride | 497.36 [M$^+$] |
| 316 | N-{(1S,2S)-1-(3,5-Difluoro-benzyl)-2-[(3R,6R)-6-(2,2-dimethyl-propoxy)-morpholin-3-yl]-2-hydroxy-ethyl}-N',N'-dipropyl-succinamide hydrochloride | 542.55 [M$^+$] |
| 317 | {(1S,2S)-1-(3,5-Difluoro-benzyl)-2-[(3R,6R)-6-(2,2-dimethyl-propoxy)-morpholin-3-yl]-2-hydroxy-ethyl}-carbamic acid hexyl ester hydrochloride | 487.37 [M$^+$] |
| 318 | (E)-2-Methyl-4-oxo-hept-2-enoic acid {(1S,2S)-1-(3,5-difluoro-benzyl)-2-[(3R,6R)-6-(2,2-dimethyl-propoxy)-morpholin-3-yl]-2-hydroxy-ethyl}-amide hydrochloride | 497.33 [M$^+$] |
| 319 | 4-Cyclopentyl-N-{(1S,2S)-1-(3,5-difluoro-benzyl)-2-[(3R,6R)-6-(2,2-dimethyl-propoxy)-morpholin-3-yl]-2-hydroxy-ethyl}-4-oxo-butyramide hydrochloride | 511.32 [M$^+$] |
| 320 | 5,5-Dimethyl-hexanoic acid {(1S,2S)-1-(3,5-difluoro-benzyl)-2-[(3R,6R)-6-(2,2-dimethyl-propoxy)-morpholin-3-yl]-2-hydroxy-ethyl}-amide hydrochloride | 485.32 [M$^+$] |
| 321 | (E)-2,4,4-Trimethyl-hept-2-enoic acid {(1S,2S)-1-(3,5-difluoro-benzyl)-2-[(3R,6R)-6-(2,2-dimethyl-propoxy)-morpholin-3-yl]-2-hydroxy-ethyl}-amide hydrochloride | 511.4 [M$^+$] |
| 322 | (E)-2,5-Dimethyl-hex-2-enoic acid {(1S,2S)-1-(3,5-difluoro-benzyl)-2-[(3R,6R)-6-(2,2-dimethyl-propoxy)-mrpholin-3-yl]-2-hydroxy-ethyl}-amide hydrochloride | 483.2 [M + H] |
| 323 | (E)-6,6,6-Trifluoro-2-methyl-hex-2-enoic acid {(1S,2S)-1-(3,5-difluoro-benzyl)-2-[(3R,6R)-6-(2,2-dimethyl-propoxy)-morpholin-3-yl]-2-hydroxy-ethyl}-amide hydrochloride | 523.0 [M + H] |

EXAMPLE 324

N-{(1S,2S)-1-(3-Cyclopropylmethoxy-benzyl)-2-[(3R,5S,6R)-6-(2,2-dimethyl-propoxy)-5-methyl-morpholin-3-yl]-2-hydroxy-ethyl}-acetamide hydrochloride Add diisopropylethylamine (0.003 mL) to an ice cold solution of acetic anhydride (0.0018 mL) and (1S,2S)-2-amino-3-(3-cyclopropylmethoxy-phenyl)-1-[(3R,5S,6R)-6-(2,2-dimethyl-propoxy)-5-methyl-morpholin-3-yl]-propan-1-ol trifluoroacetate (9 mg). Stir 2 hours and add saturated aqueous sodium bicarbonate. Wash organic layer with 1N aqueous hydrochloric acid, dry with magnesium sulfate and filter. Add 1N hydrogen chloride in ether (0.05 mL) and evaporate to give the title compound (5.5 mg). MS(ESI): m/z=449 [M+H]$^+$.

EXAMPLE 325

N-{(1S,2S)-1-(3-Cyclopropylmethoxy-5-fluoro-benzyl)-2-[(3R,5S,6R)-6-(3-fluoro-2-fluoromethyl-2-methyl-propoxy)-5-methyl-morpholin-3-yl]-2-hydroxy-ethyl}-acetamide hydrochloride Add acetic anhydride (0.040 mL, 0.428 mmol) to an ice cold solution of (1S,2S)-2-amino-3-(3-cyclopropylmethoxy-5-fluoro-phenyl)-1-[(3R,5S,6R)-6-(3-fluoro-2-fluoromethyl-2-methyl-propoxy)-5-methyl-morpholin-3-yl]-propan-1-ol (187 mg, 0.41 mmol) and stir 45 minutes. Add aqueous 1N hydrochloric acid, back extract with dichloromethane, wash with saturated sodium chloride, dry with magnesium sulfate and purify on C-18 reversed phase silica gel with acetonitrile/water/trifluoroacetic acid mixtures. Combine fractions and remove acetonitrile by evaporation. Lypholize for 18 hours and dissolve in dichloromethane and add 1N hydrogen chloride (0.25 mL) in diethyl ether and evaporate. Coevaporate twice with 1N hydrogen chloride (0.25 mL) in diethyl ether to give the title compound (106 mg). MS(ESI): m/z=503 [M+H]$^+$.

The compounds of EXAMPLES 326-330 may be prepared essentially as described in EXAMPLE 325.

EXAMPLE 331

N-[2-[6-(3-Fluoro-2-fluoromethyl-2-methyl-propoxy)-5-methyl-morpholin-3-yl]-1-(3-fluoro-5-propoxy-benzyl)-2-hydroxy-ethyl]-acetamide hydrochloride Add triethyl amine (0.025 mL) and acetic anhydride (0.013 mL) to a solution of 5-[2-amino-3-(3-fluoro-5-propoxy-phenyl)-1-hydroxy-propyl]-2-(3-fluoro-2-fluoromethyl-2-methyl-propoxy)-3-methyl-morpholine-4-carboxylic acid tert-butyl ester (67 mg) in dichloromethane (2 mL). Stir at room temperature for 2 hours. Concentrate under reduced pressure and subject to silica gel chromatography, eluting with a linear gradient from hexanes to ethyl acetate to afford 5-[2-acetylamino-3-(3-fluoro-5-propoxy-phenyl)-1-hydroxy-propyl]-2-(3-fluoro-2-fluoromethyl-2-methyl-propoxy)-3-methyl-morpholine-4-carboxylic acid tert-butyl ester (49 mg, 68%) MS: m/z=591 [M+H$^+$]

Dissolve 5-[2-acetylamino-3-(3-fluoro-5-propoxy-phenyl)-1-hydroxy-propyl]-2-(3-fluoro-2-fluoromethyl-2-methyl-propoxy)-3-methyl-morpholine-4-carboxylic acid tert-butyl ester (49 mg) in trifluoroacetic acid (1 mL), stir at ambient temperature for 20 minutes and concentrate under reduced pressure. Dissolve residue in DMSO and purify by reverse-phase chromatography eluting from 10% acetonitrile in 0.01M HCl to 100% acetonitrile. Collect and evaporate the appropriate fractions, then precipitate the residue by adding diethyl ether, and drying under vacuum to afford the title compound (9.5 mg).

LCMS: m/z=491 [M+H$^+$]

EXAMPLE 332

N-{(1S,2S)-1-(3-cyclopentyloxy-5-fluoro-benzyl)-2-[(3R,5S,6R)-6-(3-fluoro-2-fluoromethyl-2-methyl-propoxy)-5-methyl-morpholin-3-yl]-1-2-hydroxy-ethyl}-acetamide hydrochloride Stir a suspension of N-{(1S,2S)-1-(3-hydroxy-5-fluoro-benzyl)-2-[(3R,5S,6R)-6-(3-fluoro-2-fluoromethyl-2-methyl-propoxy)-5-methyl-morpholin-3-yl]-1-2-hydroxy-ethyl}-acetamide (211.83 µmoles; 95.00 mg), bromocyclopentane, (423.65 µmoles; 45.45 µL;) and cesium carbonate (635.48 µmoles; 207.05 g) in dimethylformamide

| EX | Compound | MS (ES) |
|---|---|---|
| 326 | N-[(1S,2S)-2-[(3R,5S,6R)-6-(3-Fluoro-2-fluoromethyl-2-methyl-propoxy)-5-methyl-morpholin-3-yl]-1-(3-fluoro-5-isobutoxy-benzyl)-2-hydroxy-ethyl]-acetamide hydrochloride | 505 [M + H]$^+$ |
| 327 | N-{(1S,2S)-2-[(3R,5S,6R)-6-(3-Fluoro-2-fluoromethyl-2-methyl-propoxy)-5-methyl-morpholin-3-yl]-1-[3-fluoro-5-(2-methyl-cyclopropylmethoxy)-benzyl]-2-hydroxy-ethyl}-acetamide hydrochloride | 517 [M + H]$^+$ |
| 328 | N-{(1S,2S)-2-[(3R,5S,6R)-6-(3-Fluoro-2-fluoromethyl-2-methyl-propoxy)-5-methyl-morpholin-3-yl]-1-[3-fluoro-5-(1-methyl-cyclopropylmethoxy)-benzyl]-2-hydroxy-ethyl}-acetamide hydrochloride | 517 [M + H]$^+$ |
| 329 | N-{(1S,2S)-1-[3-(1-Cyclopropyl-ethoxy)-5-fluoro-benzyl]-2-[(3R,5S,6R)-6-(3-fluoro-2-fluoromethyl-2-methyl-propoxy)-5-methyl-morpholin-3-yl]-2-hydroxy-ethyl}-acetamide trifluoroacetate | 517 [M + H]$^+$ |
| 330 | N-[(1S,2S)-2-[(3R,5S,6R)-6-(3-Fluoro-2-fluoromethyl-2-methyl-propoxy)-5-methyl-morpholin-3-yl]-1-(3-fluoro-5-hydroxy-benzyl)-2-hydroxy-ethyl]-acetamide trifluoroacetate | 449 [M + H]$^+$ |

(1.06 mL) in a sealed tube at 90° C. for 1 h. Add water and extract with ethyl acetate. Dry the combined organic layers over MgSO$_4$, filter, and concentrate under reduced pressure. Subject residue to silica gel chromatography, eluting with 1% to 5% 7N NH$_3$ in MeOH/dichloromethane gradient, to provide the free base of the title compound as a pale yellow solid. Add 2M HCl in diethyl ether (2 mL) to the free base and remove solvent under vacuum to provide the title compound.

MS(ES): m/z=517

The compounds of EXAMPLES 333-334 may be prepared essentially as described in EXAMPLE 332.

| EX | Compound | MS (ES) |
|---|---|---|
| 333 | N-{(1S,2S)-2-[ (3R,5S,6R)-6-(3-fluoro-2-fluoromethyl-2-methyl-propoxy)-5-methyl-morpholin-3-yl]-1-(3-fluoro-5-isopropoxy-benzyl)-2-hydroxy-ethyl}-acetamide hydrochloride | 491 [M + H] |
| 334 | N-{(1S,2S)-2-(3R,5S,6R)-[5-Ethyl-6-(3-fluoro-2-fluoromethyl-2-methyl-propoxy)-morpholin-3-yl]-1-[3-fluoro-5-(2-fluoro-ethoxy)-benzyl]-2-hydroxy-ethyl}-acetamide hydrochloride | 509 [M + H] |

EXAMPLE 335

N-{(1S,2S)-2-[(3R,5S,6R)-6-(3-Fluoro-2,2-dimethyl-propoxy)-5-methyl-morpholin-3-yl]-1-[3-fluoro-5-(2-fluoro-ethoxy)-benzyl]-2-hydroxy-ethyl}-acetamide hydrochloride The title compound may be prepared essentially as described in EXAMPLE 261.

MS(ES): m/z=476.8 [M$^+$+H]

The compounds of Formula I are inhibitors of BACE and thereby inhibit the production of A-β peptide which has been implicated in the pathology and progression of a number of neurodegenerative disorders, including Alzheimer's disease (See: Varghese, et al., *Journal of Medicinal Chemistry*, 46(22), 4625 (2003)). Methods for determining the BACE inhibitory activity of compounds are well known in the art (See: Sinha, et al., *Science*, 286, 735 (1999); Turner, et al., *Biochemistry*, 40, 10001 (2001); Horn, et al., *Journal of Medicinal Chemistry*, 46, 1799 (2003); U.S. Pat. No. 5,744,346; U.S. Pat. No. 5,942,400; WO00/17369; WO00/03819; WO 03/040096; and WO 04/024081).

In vitro Assay Procedures:

For in vitro enzymatic and cellular assays, test compounds are prepared in DMSO to make up a 10 millimolar stock solution. The stock solution is serially diluted (in a 1:3, 1:2.5, 1:2, or 1:1 dilution series) in DMSO to obtain a final compound concentration of 10 millimolar to 1 micromolar at the first highest concentration of a ten-point dilution curve in a 96-well round-bottom plate right before conducting the in vitro enzymatic and whole assays.

In vitro Protease Inhibition Assays:

BACE1 mcaFRET Assay

Serial dilutions of test compounds are prepared as described above. Two microliter of each dilution is added to each well on row A to H of a corresponding low protein binding black plate to which 50 microliter of 50 millimolar ammonium acetate, pH 4.6, 1 mM Triton X-100, 1 mg/ml Bovine Serum Albumin, and 15 micromolar of FRET substrate (sequence: (MCA)-S-E-V-N-L-D-A-E-F-R-K(Dnp)-R-R-R-R-NH$_2$) for BACE1 activity are pre-added. The content is mixed well on a plate shaker for 10 min. Fifty microliter of two hundred picomolar human BACE1(1-460): Fc (See: Vasser, et al., *Science*, 286, 735-741 (1999)) in the same reaction buffer described above is added to the plate containing substrate and test compounds to initiate the reaction. The relative fluorescence unit (RFU) of the mixture at time 0 is recorded at excitation wavelength 330 nm and emission wavelength 400 nm, after brief mixing on a plate shaker. The reaction plate is covered with aluminum foil and kept in a dark humidified oven at room temperature for 16 to 24 hours. The RFU at the end of incubation is recorded with the same excitation and emission settings. The difference of the RFU at time 0 and the end of incubation represents the activity of BACE1 under the compound treatment. The 10-point inhibition curve was plotted and fitted with the four-parameter logistic equation to obtain the EC$_{50}$ and IC$_{50}$ values. (ee: Sinha, et al., *Nature*, 402, 537-540 (2000)). The exemplified compounds of Formula I were tested essentially as described above and exhibited an IC$_{50}$ value for BACE1 of lower than 15 μM. The following exemplified compounds were tested essentially as described above and exhibited the following activity for BACE1:

| EXAMPLE | BACE1 IC$_{50}$(nM) |
|---|---|
| 10 | 270 |
| 12 | 110 |
| 67 | 2.8 |
| 135 | 78 |

BACE2 mcaFRET Assay

Serial dilutions of test compounds are prepared as described above. Two microliter of each dilution is added to each well on row A to H of a corresponding low protein binding black plate to which 50 microliter of 50 millimolar ammonium acetate, pH 4.6, 1 mM Triton X-100, 1 mg/ml Bovine Serum Albumin, and 15 micromolar of FRET substrate (sequence: (MCA)-S-E-V-N-L-D-A-E-F-R-K(Dnp)-R-R-R-R-NH$_2$) for BACE2 activity are pre-added. The content is mixed well on a plate shaker for 10 min. Fifty microliter of four hundred picomolar purified recombinant human BACE2(1-460):Fc in the same reaction buffer described above is added to the plate containing substrate and test compounds to initiate the reaction. The relative fluorescence unit (RFU) of the mixture at time 0 is recorded at excitation wavelength 330 nm and emission wavelength 400 nm, after brief mixing on a plate shaker. The reaction plate is covered with aluminum foil and kept in a dark humidified oven at room temperature for 16 to 24 hours. The RFU at the end of incubation is recorded with the same excitation and emission setting. The difference of the RFU at time 0 and the end of incubation represents the activity of BACE2 under the compound treatment. The 10-point inhibition curve was plotted and fitted with the four-parameter logistic equation to obtain the EC$_{50}$ and IC$_{50}$ values. For example, the BACE2 IC$_{50}$ value for the compound of EXAMPLE 135 is 220 nM, representing approximately a 3 fold selectivity for BACE1 inhibition.

Expression of Human BACE1 and Human BACE2.

Human (accession number: AF190725) BACE1 and human BACE2 (accession number: AF 204944) were cloned from total brain cDNA by room temperature-PCR. The nucleotide sequences corresponding to amino acid sequences #1 to 460 were inserted into the cDNA encoding human IgG$_1$ (Fc) polypeptide (Vassar et al. 1999). This fusion protein of BACE1(1-460) or BACE2(1-460) and human Fc, named huBACE1:Fc and huBACE2:Fc respectively, were constructed into the pJB02 vector. Human BACE1(1-460):Fc (huBACE1:Fc) and human BACE2(1-460):Fc (huBACE2:Fc) were transiently expressed in HEK293 cells. 250 µg cDNA of each construct was mixed with Fugene 6 and added to 1 liter HEK293 cells. Four days after the transfection, conditioned media were harvested for purification.

Purification of huBACE1:Fc and huBACE2:Fc.

Conditioned media of HEK293 cell transiently transfected with huBACE1:Fc or huBACE2:Fc cDNA were collected. Cell debris was removed by filtering the conditioned media through 0.22 µm sterile filter. 5 ml Protein A-agarose (bed volume) was added to 4 liter conditioned media. This mixture was gently stirred overnight at 4° C. The Protein A-agarose resin was collected and packed into a low-pressure chromatography column. The column washed with 20X bed volumes of PBS at flow rate 20 ml per hour. Bound huBACE1:Fc or huBACE2:Fc protein was eluted with 50 mM acetic acid, pH 3.6, at flow rate 20 ml per hour. 1 ml fractions of eluate were neutralized immediately with 0.5 ml 200 mM ammonium acetate, pH 6.5. The purity of final product was assessed by electrophoresis in 4-20% Tris-Glycine SDS-PAGE. The enzyme was stored at −80 C in small aliquots.

Whole Cell Assay for Measuring the Inhibition of Beta-Secretase Activity

The routine whole cell assay for the measurement of inhibition of beta-secretase activity utilizes the human embryonic kidney cell line HEK293p (ATCC Accession No. CRL-1573) stably expressing a human APP751 cDNA containing the naturally occurring double mutation Lys651Met52 to Asn651Leu652, commonly called the Swedish mutation (noted HEK293/APP751sw) and shown to overproduce Abeta (Citron et al., 1992, Nature 360:672-674). Human embryonic kidney HEK293p cells stably expressing wild-type human APP751 cDNA (noted HEK293/APP751 wt) are also used to assess the inhibition of beta-secretase activity. In vitro Aβ reduction assays have been described in the literature (ee: Dovey, et al., Journal of Neurochemistry, 76, 173-181 (2001); Seubert, et al., Nature, 361, 260 (1993); and Johnson-Wood, et al., Proc. Natl. Acad. Sci. USA, 94, 1550-1555 (1997))

Cells (HEK293/APP751sw or HEK293/APP751 wt, at 3×10$^4$ cells/well, containing 200 microliters culture media, DMEM containing 10% FBS) are incubated at 37 C for 4 to 6 hours in the presence/absence of inhibitors (diluted in DMSO) at the desired concentration. At the end of the incubation, conditioned media are analyzed for beta-secretase activity, for example, by analysis of Abeta peptides designated Aβ1-x. Abeta peptides are measured by a sandwich ELISA, using monoclonal 266 as a capture antibody and biotinylated 3D6 as reporting antibody. In addition, other APP cleavage fragments, such as sAPPbeta, the cleavage product of full length APP by BACE1, can be measured in conditioned medium to assess beta-secretase activity. The sAPPbeta fragments are analyzed by a sandwich ELISA, using monoclonal 8E5 antibody as a capture antibody and rabbit polyclonal 192sw or 192 wt as a reporting antibody. The concentration of Abeta or sAPPbeta released in the conditioned media following the compound treatment corresponds to the activity of BACE1 under such conditions. The 10-point inhibition curve was plotted and fitted with the four-parameter logistic equation to obtain the EC$_{50}$ and IC$_{50}$ values for the Abeta, sAPPbeta-lowering effect. The following exemplified compounds were tested essentially as described above and exhibited the following activity for Abeta lowering effect:

| EXAMPLE | IC$_{50}$(nM) |
|---------|---------------|
| 10      | 780           |
| 12      | 340           |
| 67      | 32            |
| 135     | 95            |

In vivo Inhibition of Beta-Secretase

Several animal models, including mouse, guinea pig, dog, and monkey, may be used to screen for inhibition of beta-secretase activity in vivo following compound treatment. Animals used in this invention can be wild type, transgenic, or gene knockout animals. For example, the PDAPP mouse model, prepared as described in Games et al., 1995, Nature 373:523-527, and other non-transgenic or gene knockout animals are useful to analyze in vivo inhibition of Abeta and sAPPbeta production in the presence of inhibitory compounds. Generally, 2 to 12 month old PDAPP mice, gene knockout mice or non-transgenic animals are administered compound formulated in vehicles, such as corn oil, cyclodextran, phosphate buffers, Pharmasolve, or other suitable vehicles. One to twenty-four hours following the administration of compound, animals are sacrificed, and brains as well as cerebrospinal fluid and plasma are removed for analysis of Abeta and sAPP fragments. (ee: Dovey, et al., Journal of Neurochemistry, 76, 173-181 (2001); and Johnson-Wood, et al., Proc. Natl. Acad. Sci. USA, 94, 1550-1555 (1997))

Beginning at time 0, animals are administered by oral gavage or other means of delivery, such as sub-cutaneous injection of an inhibitory compound up to 100 mg/kg in a standard formulation such as 7% Pharmasolve. A separate group of animals receive Pharmasolve alone and serve as a vehicle-control group. At the end of the test period, animals are sacrificed and brain tissues, plasma or cerebrospinal fluid are analyzed for the presence of Abeta peptide and sAPPbeta, for example, by specific sandwich ELISA assays. For some chronic studies, brain tissues of APP transgenic animals are also analyzed for the amount of beta-amyloid plaques following compound treatment, for example, by standard histochemical and immunohistochemical methodologies.

Animals (PDAPP or other APP transgenic or non-transgenic mice) administered an inhibitory compound may demonstrate the reduction of Abeta or sAPPbeta in brain tissues, plasma or cerebrospinal fluids and decrease of beta amyloid plaques in brain tissue, as compared with vehicle-treated controls. For example, 3 hours after administration of 100 mg/kg sub-cutaneous dose of the compound of EXAMPLE 135 to young PDAPP mice, Abeta peptide levels are reduced 39%, 40% and 25% in plasma, cerebrospinal fluid and brain cortex, respectively, compared to vehicle-treated mice. Animals (PDAPP or other APP transgenic mice) administered the inhibitory compounds of the invention may also show improvement in cognitive behavioral assessments for learning and memory tasks.

Oral administration of the compounds of the present invention is preferred. However, oral administration is not the only route or even the only preferred route. For example, transdermal administration may be very desirable for patients who are forgetful or petulant about taking oral medicine, and the intravenous route may be preferred as a matter of convenience or to avoid potential complications related to oral administration. Compounds of Formula I may also be administered by the percutaneous, intramuscular, intranasal or intrarectal route in particular circumstances. The route of administration may be varied in any way, limited by the physical properties of the drugs, the convenience of the patient and the caregiver, and other relevant circumstances (*Remington's Pharmaceutical Sciences,* 18th Edition, Mack Publishing Co. (1990)).

The pharmaceutical compositions are prepared in a manner well known in the pharmaceutical art. The carrier or excipient may be a solid, semi-solid, or liquid material that can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solutions, suspensions, or the like.

The compounds of the present invention may be administered orally, for example, with an inert diluent or capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations of the present invention may be determined by methods well known to the skilled artisan.

The tablets, pills, capsules, troches, and the like may also contain one or more of the following adjuvants: binders such as povidone, hydroxypropyl cellulose, microcrystalline cellulose, or gelatin; excipients or diluents such as: starch, lactose, microcrystalline cellulose or dicalcium phosphate, disintegrating agents such as: croscarmellose, crospovidone, sodium starch glycolate, corn starch and the like; lubricants such as: magnesium stearate, stearic acid, talc or hydrogenated vegetable oil; glidants such as colloidal silicon dioxide; wetting agents such as: sodium lauryl sulfate and polysorbate 80; and sweetening agents such as: sucrose, aspartame or saccharin may be added or a flavoring agent such as: peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials that modify the physical form of the dosage unit, for example, as coatings. Thus, tablets or pills may be coated with sugar, hydroxypropyl methylcellulose, polymethacrylates, or other coating agents. Syrups may contain, in addition to the present compounds, sucrose as a sweetening agent and certain preservatives, dyes and colorings and flavors. Materials used in preparing these various compositions should be pharmaceutically pure and non-toxic in the amounts used.

The compounds of Formula I are generally effective over a wide dosage range. For example, dosages per day normally fall within the range of about 0.0001 to about 30 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

In order to achieve or maintain appropriate levels of the compounds of Formula I in the brain of an afflicted mammal, it may be necessary or desirable to co-administer an effective amount of an inhibitor of P-glycoprotein (P-gp). P-gp inhibitors and the use of such compounds are known to those skilled in the art. (See: *Cancer Research,* 53, 4595 (1993); *Clin. Cancer Res.,* 2, 7 (1996); *Cancer Research,* 56, 4171 (1996), WO99/64001; and WO01/10387).

The P-gp inhibitor may be administered in any manner that achieves a sufficient degree of inhibition of P-gp to achieve or maintain sufficient levels of the compounds of Formula I for effective BACE inhibition in the brain of an afflicted mammal. As such, the P-gp inhibitor may be administered separately before, during, or after the administration of a compound of Formula I. Furthermore, if desirable, the P-gp inhibitor may be formulated with a compound of Formula I. These formulations and methods represent further embodiments of the present invention.

Many suitable P-gp inhibitors are known today and undoubtably others will be identified in the future. Suitable P-gp inhibitors include cyclosporin A, verapamil, tamoxifen, quinidine, Vitamin E-TGPS, ritonavir, megestrol acetate, progesterone, rapamycin, 10,11-methanodibenzosuberane, phenothiazines, acridine derivatives such as GF120918, FK506, VX-710, LY355979, PSC-833, GF-102,918 and other steroids.

We claim:
1. A compound of Formula I:

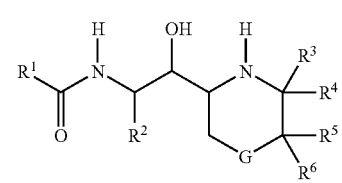

where:
$R^1$ is $C_1$-$C_8$ alkyl optionally substituted with $C_3$-$C_8$ cycloalkyl, phenyl, or furyl; $C_2$-$C_8$ alkenyl optionally substituted with $C_3$-$C_8$ cycloalkyl, phenyl, or furyl; $C_2$-$C_8$ alkynyl optionally substituted with $C_3$-$C_8$ cycloalkyl, phenyl, or furyl; or $C_3$-$C_8$ cycloalkyl, each optionally substituted up to six times with fluoro, or with up to four substituents independently selected from the group consisting of halo, cyano, methyl optionally substituted with up to three fluoro atoms, trifluoromethoxy, $C_1$-$C_6$ alkoxy, $C_3$-$C_7$ cycloalkoxy, oxo, $NR^7R^8$, and $C(O)NR^7R^7$; or $R^1$ is hydrogen; furyl; thienyl; tetrahydrofuryl; $NR^7R^8$; or $C_1$-$C_6$ alkoxy;

$R^2$ is $C_1$-$C_3$ alkyl optionally substituted with $C_3$-$C_6$ cycloalkyl; benzyl optionally monosubstituted in the phenyl ring with a substituent selected from the group consisting of halo, hydroxy, thiol, benzyloxy, $C_1$-$C_6$ alkyl optionally substituted in the alkyl chain with $C_3$-$C_8$ cycloalkyl or up to three times with fluoro, $C_1$-$C_6$ alkoxy optionally substituted in the alkyl chain with $C_3$-$C_8$ cycloalkyl or up to three times with fluoro, $C_2$-$C_6$ alkenyloxy, and $C_1$-$C_6$ alkylthio optionally substituted in the alkyl chain with $C_3$-$C_8$ cycloalkyl or up to three times with fluoro; benzyl disubstituted in the phenyl ring with a first substituent selected from the group consisting of halo, trifluoromethoxy, and $C_1$-$C_6$ alkyl optionally substituted in the alkyl chain with $C_3$-$C_8$ cycloalkyl or up to three times with fluoro, and a second substituent selected from the group consisting of halo, $C_1$-$C_6$ alkyl optionally substituted in the alkyl chain with $C_3$-$C_8$ cycloalkyl or up to three times with fluoro, $C_1$-$C_6$ alkoxy optionally substituted in the alkyl chain with $C_3$-$C_8$ cycloalkyl or up to three times with fluoro, $C_2$-$C_6$ alkenyloxy, and $C_1$-$C_6$ alkylthio optionally substituted in the alkyl chain with $C_3$-$C_8$ cycloalkyl or up to three times with fluoro; or benzyl trisubstituted in the phenyl ring with substituents independently selected from halo;

$R^3$ is hydrogen or $C_1$-$C_6$ alkyl optionally substituted with $C_3$-$C_8$ cycloalkyl or up to three times with fluoro;

$R^4$ is hydrogen or $C_1$-$C_6$ alkyl; or $R^3$ and $R^4$ taken together with the carbon atom to which they are attached form a $C_3$-$C_6$ cycloalkyl ring;

$R^5$ is hydrogen; $R^9$; or —$(CH_2)_{0-2}$—$OR^9$;

$R^6$ is hydrogen or phenyl;

G is O or $S(O)_{0-2}$;

$R^7$ is selected independently at each occurrence from the group consisting of hydrogen; $C_1$-$C_6$ alkyl; and phenyl;

$R^8$ is hydrogen; $C_1$-$C_6$ alkyl; phenyl; —$C(O)(C_1$-$C_6$ alkyl); or —$SO_2(C_1$-$C_6$ alkyl);

$R^9$ is hydrogen; $C_1$-$C_{10}$ alkyl optionally substituted with 1-6 fluorine atoms; $C_2$-$C_{10}$ acyl; $C_2$-$C_6$ alkenyl; or —$(CH_2)_{0-4}$—$R^{10}$;

$R^{10}$ is $C_3$-$C_8$ cycloalkyl; $C_3$-$C_8$ cycloalkanone; tetrahydrofuryl; tetrahydropyranyl; or phenyl each optionally substituted with one substituent selected from the group consisting of $C_3$-$C_8$ cycloalkyl, phenyl, and benzyl, up to four times with fluoro, or with one or two substituents independently selected from the group consisting of halo, $C_1$-$C_6$ alkyl optionally substituted up to three times with fluoro, $C_2$-$C_6$ acyl, $C_1$-$C_6$ alkoxy, hydroxy, and trifluoromethoxy; or $R^{10}$ is adamantyl; or a pharmaceutically acceptable salt thereof.

2. A pharmaceutical formulation comprising a compound of claim 1, in combination with a pharmaceutically acceptable carrier, diluent, or excipient.

3. A compound of Formula VII:

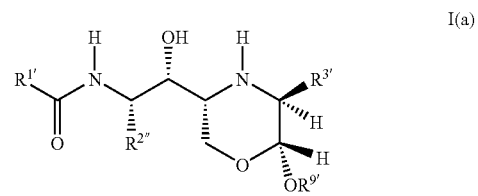

where:

$R^{2'}$ is $C_1$-$C_3$ alkyl optionally substituted with $C_3$-$C_6$ cycloalkyl; benzyl optionally monosubstituted in the phenyl ring with a substituent selected from the group consisting of halo, —$OR^{12}$, thiol, $C_1$-$C_6$ alkyl optionally substituted in the alkyl chain with $C_3$-$C_8$ cycloalkyl or up to three times with fluoro, $C_1$-$C_6$ alkoxy optionally substituted in the alkyl chain with $C_3$-$C_8$ cycloalkyl or up to three times with fluoro, $C_2$-$C_6$ alkenyloxy, and $C_1$-$C_6$ alkylthio optionally substituted in the alkyl chain with $C_3$-$C_8$ cycloalkyl or up to three times with fluoro; benzyl disubstituted in the phenyl ring with a first substituent selected from the group consisting of halo, trifluoromethoxy, and $C_1$-$C_6$ alkyl optionally substituted in the alkyl chain with $C_3$-$C_8$ cycloalkyl or up to three times with fluoro, and a second substituent selected from the group consisting of halo, —$OR^{12}$, thiol, $C_1$-$C_6$ alkyl optionally substituted in the alkyl chain with $C_3$-$C_8$ cycloalkyl or up to three times with fluoro, $C_1$-$C_6$ alkoxy optionally substituted in the alkyl chain with $C_3$-$C_8$ cycloalkyl or up to three times with fluoro, $C_2$-$C_6$ alkenyloxy, and $C_1$-$C_6$ alkylthio optionally substituted in the alkyl chain with $C_3$-$C_8$ cycloalkyl or up to three times with fluoro; or benzyl trisubstituted in the phenyl ring with substituents independently selected from halo;

$R^3$ is hydrogen or $C_1$-$C_6$ alkyl optionally substituted with $C_3$-$C_8$ cycloalkyl or up to three times with fluoro;

$R^4$ is hydrogen or $C_1$-$C_6$ alkyl; or $R^3$ and $R^4$ taken together with the carbon atom to which they are attached form a $C_3$-$C_6$ cycloalkyl ring;

$R^{5'}$ is hydroxy and $R^{6'}$ is hydrogen or $R^{5'}$ and $R^{6'}$ together with the carbon to which they are attached form a carbonyl moiety;

$R^{11}$ is a nitrogen protecting group;

$R^{11'}$ is hydrogen or a nitrogen protecting group;

$R^{12}$ is hydrogen or an oxygen protecting group; or an acid addition salt thereof.

4. A compound of Formula I(a):

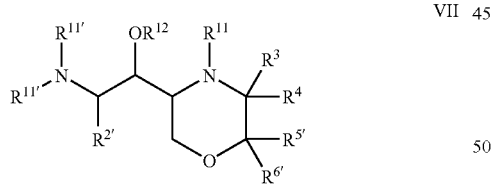

where;

$R^{1'}$ is hydrogen; benzyl; or $C_1$-$C_8$ alkyl optionally substituted with $C_1$-$C_6$ alkoxy, oxo, or up to six times with fluoro;

$R^{2''}$ is benzyl optionally monosubstituted in the 3-position of the phenyl ring with a substituent selected from the group consisting of halo, $C_1$-$C_6$ alkyl optionally substituted in the alkyl chain up to three times with fluoro, $C_1$-$C_6$ alkoxy optionally substituted in the alkyl chain up to three times with fluoro, and $C_1$-$C_6$ alkylthio optionally substituted in the alkyl chain up to three times with fluoro; or benzyl disubstituted in the phenyl ring with a first substituent selected from the group consisting of halo and trifluoromethoxy and a second substituent selected from the group consisting of halo, $C_1$-$C_6$ alkyl optionally substituted in the alkyl chain up to three times with fluoro, $C_1$-$C_6$ alkoxy optionally substituted in the alkyl chain up to three times with fluoro, or $C_1$-$C_6$ alkylthio optionally substituted in the alkyl chain up to three times with fluoro;

$R^{3'}$ is hydrogen or $C_1$-$C_4$ alkyl;

$R^{9'}$ is $C_1$-$C_{10}$ alkyl optionally substituted with 1-6 fluorine atoms; $C_1$-$C_4$ alkyl substituted with $C_1$-$C_6$ alkoxy, tetrahydrofuryl, tetrahydropyranyl, or $C_3$-$C_8$ cycloalkyl optionally substituted with up to 4 fluoro atoms; or a pharmaceutically acceptable salt thereof.

* * * * *